US011793516B2

United States Patent
Bakos et al.

(10) Patent No.: US 11,793,516 B2
(45) Date of Patent: Oct. 24, 2023

(54) SURGICAL STAPLE CARTRIDGE COMPRISING LONGITUDINAL SUPPORT BEAM

(71) Applicant: Cilag GmbH International, Zug (CH)

(72) Inventors: Gregory J. Bakos, Mason, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/211,168

(22) Filed: Mar. 24, 2021

(65) Prior Publication Data

US 2022/0304685 A1 Sep. 29, 2022

(51) Int. Cl.
| | | |
|---|---|---|
| A61B 17/072 | (2006.01) | |
| A61B 34/30 | (2016.01) | |
| A61B 17/00 | (2006.01) | |
| A61B 17/29 | (2006.01) | |

(52) U.S. Cl.
CPC .... *A61B 17/072* (2013.01); *A61B 2017/0042* (2013.01); *A61B 2017/00398* (2013.01); *A61B 2017/07264* (2013.01); *A61B 2017/07271* (2013.01); *A61B 2017/07278* (2013.01); *A61B 2017/07285* (2013.01); *A61B 2017/2927* (2013.01); *A61B 2017/2933* (2013.01); *A61B 2017/2943* (2013.01); *A61B 2017/2946* (2013.01); *A61B 2034/302* (2016.02)

(58) Field of Classification Search
CPC .................................................. A61B 17/072
See application file for complete search history.

(56) References Cited

U.S. PATENT DOCUMENTS

| | | | |
|---|---|---|---|
| 66,052 | A | 6/1867 | Smith |
| 662,587 | A | 11/1900 | Blake |
| 670,748 | A | 3/1901 | Weddeler |
| 719,487 | A | 2/1903 | Minor |

(Continued)

FOREIGN PATENT DOCUMENTS

| | | |
|---|---|---|
| AU | 2012200594 A1 | 2/2012 |
| AU | 2012203035 A1 | 6/2012 |

(Continued)

OTHER PUBLICATIONS

Design U.S. Appl. No. 29/736,648, filed Jun. 2, 2020.

(Continued)

*Primary Examiner* — Nathaniel C Chukwurah
(74) *Attorney, Agent, or Firm* — Frost Brown Todd LLP

(57) ABSTRACT

A surgical stapling assembly is disclosed. The surgical stapling assembly can include a first jaw, a second jaw, an articulation joint, a closure drive comprising a first flexible rotary drive extending through the articulation joint, and a firing drive comprising a second flexible rotary drive extending through the articulation joint and rotatable independent of the first flexible rotary drive. The surgical stapling assembly can further include a 3D-printed component. The surgical stapling assembly can be configured to form different staple shapes, such as non-planar staples and planar staples, can include an eccentrically-driven firing assembly, and/or can include a floatable component. The surgical stapling assembly can include a staple cartridge including a longitudinal support beam.

36 Claims, 99 Drawing Sheets

(56) References Cited

U.S. PATENT DOCUMENTS

| | | |
|---|---|---|
| 804,229 A | 11/1905 | Hutchinson |
| 903,739 A | 11/1908 | Lesemann |
| 951,393 A | 3/1910 | Hahn |
| 1,075,556 A | 10/1913 | Fenoughty |
| 1,082,105 A | 12/1913 | Anderson |
| 1,188,721 A | 6/1916 | Bittner |
| 1,306,107 A | 6/1919 | Elliott |
| 1,314,601 A | 9/1919 | McCaskey |
| 1,466,128 A | 8/1923 | Hallenbeck |
| 1,677,337 A | 7/1928 | Grove |
| 1,794,907 A | 3/1931 | Kelly |
| 1,849,427 A | 3/1932 | Hook |
| 1,912,783 A | 6/1933 | Meyer |
| 1,944,116 A | 1/1934 | Stratman |
| 1,954,048 A | 4/1934 | Jeffrey et al. |
| 2,028,635 A | 1/1936 | Wappler |
| 2,037,727 A | 4/1936 | La Chapelle |
| 2,120,951 A | 6/1938 | Hodgman |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,108 A | 12/1940 | Ridgway |
| 2,224,882 A | 12/1940 | Peck |
| 2,256,295 A | 9/1941 | Schmid |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Royal Lee |
| 2,420,552 A | 5/1947 | Morrill |
| 2,441,096 A | 5/1948 | Happe |
| 2,448,741 A | 9/1948 | Scott et al. |
| 2,450,527 A | 10/1948 | Smith |
| 2,491,872 A | 12/1949 | Neuman |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,724,289 A | 11/1955 | Wight |
| 2,742,955 A | 4/1956 | Dominguez |
| 2,804,848 A | 9/1957 | O'Farrell et al. |
| 2,808,482 A | 10/1957 | Zanichkowsky et al. |
| 2,825,178 A | 3/1958 | Hawkins |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,026,744 A | 3/1962 | Rouse |
| 3,032,769 A | 5/1962 | Palmer |
| 3,035,256 A | 5/1962 | Egbert |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,252,643 A | 5/1966 | Strekopytov et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,315,863 A | 4/1967 | O'Dea |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,604,561 A | 9/1971 | Mallina et al. |
| 3,608,549 A | 9/1971 | Merrill |
| 3,618,842 A | 11/1971 | Bryan |
| 3,635,394 A | 1/1972 | Natelson |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,339 A | 5/1972 | Shimizu |
| 3,661,666 A | 5/1972 | Foster et al. |
| 3,662,939 A | 5/1972 | Bryan |
| 3,685,250 A | 8/1972 | Henry et al. |
| 3,688,966 A | 9/1972 | Perkins et al. |
| 3,692,224 A | 9/1972 | Astafiev et al. |
| 3,695,646 A | 10/1972 | Mommsen |
| 3,709,221 A | 1/1973 | Riely |
| 3,717,294 A | 2/1973 | Green |
| 3,724,237 A | 4/1973 | Wood |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,822,818 A | 7/1974 | Strekopytov et al. |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,863,940 A | 2/1975 | Cummings |
| 3,883,624 A | 5/1975 | McKenzie et al. |
| 3,885,491 A | 5/1975 | Curtis |
| 3,887,393 A | 6/1975 | La Rue, Jr. |
| 3,892,228 A | 7/1975 | Mitsui |
| 3,894,174 A | 7/1975 | Cartun |
| 3,899,829 A | 8/1975 | Storm et al. |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,973,179 A | 8/1976 | Weber et al. |
| 3,981,051 A | 9/1976 | Brumlik |
| 3,999,110 A | 12/1976 | Ramstrom et al. |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,047,654 A | 9/1977 | Alvarado |
| 4,054,108 A | 10/1977 | Gill |
| 4,060,089 A | 11/1977 | Noiles |

(56) References Cited

U.S. PATENT DOCUMENTS

| | | |
|---|---|---|
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,149,461 A | 4/1979 | Simeth |
| 4,154,122 A | 5/1979 | Severin |
| 4,160,857 A | 7/1979 | Nardella et al. |
| 4,169,476 A | 10/1979 | Hiltebrandt |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,203,444 A | 5/1980 | Bonnell et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,250,817 A | 2/1981 | Michel |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,282,573 A | 8/1981 | Imai et al. |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,389,963 A | 6/1983 | Pearson |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,421,264 A | 12/1983 | Arter et al. |
| 4,423,456 A | 12/1983 | Zaidenweber |
| 4,425,915 A | 1/1984 | Ivanov |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | Digiovanni et al. |
| 4,451,743 A | 5/1984 | Suzuki et al. |
| 4,452,376 A | 6/1984 | Klieman et al. |
| 4,454,887 A | 6/1984 | Kruger |
| 4,459,519 A | 7/1984 | Erdman |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,476,864 A | 10/1984 | Tezel |
| 4,478,220 A | 10/1984 | Di Giovanni et al. |
| 4,480,641 A | 11/1984 | Failla et al. |
| 4,481,458 A | 11/1984 | Lane |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,514,477 A | 4/1985 | Kobayashi |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |

(56) References Cited

U.S. PATENT DOCUMENTS

| | | |
|---|---|---|
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,980 A | 9/1986 | Aihara |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,619,262 A | 10/1986 | Taylor |
| 4,619,391 A | 10/1986 | Sharkany et al. |
| 4,624,401 A | 11/1986 | Gassner et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,642,738 A | 2/1987 | Meller |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,651,734 A | 3/1987 | Doss et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,726,247 A | 2/1988 | Hormann |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,755,070 A | 7/1988 | Cerutti |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,788,978 A | 12/1988 | Strekopytov et al. |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,495 A | 4/1989 | Hormann |
| 4,819,853 A | 4/1989 | Green |
| 4,821,939 A | 4/1989 | Green |
| 4,827,552 A | 5/1989 | Bojar et al. |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,096 A | 5/1989 | Oh et al. |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,868,958 A | 9/1989 | Suzuki et al. |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |

(56) References Cited

U.S. PATENT DOCUMENTS

| | | |
|---|---|---|
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,950,268 A | 8/1990 | Rink |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,681 A | 10/1990 | Yang |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,976,173 A | 12/1990 | Yang |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,222 A | 4/1991 | Her |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,033,552 A | 7/1991 | Hu |
| 5,035,040 A | 7/1991 | Kerrigan et al. |
| 5,037,018 A | 8/1991 | Matsuda et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,056,953 A | 10/1991 | Marot et al. |
| 5,060,658 A | 10/1991 | Dejter, Jr. et al. |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,100,422 A | 3/1992 | Berguer et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,151,102 A | 9/1992 | Kamiyama et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |
| 5,158,567 A | 10/1992 | Green |
| D330,699 S | 11/1992 | Gill |
| 5,163,598 A | 11/1992 | Peters et al. |
| 5,164,652 A | 11/1992 | Johnson et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,181,514 A | 1/1993 | Solomon et al. |
| 5,187,422 A | 2/1993 | Izenbaard et al. |
| 5,188,102 A | 2/1993 | Idemoto et al. |
| 5,188,111 A | 2/1993 | Yates et al. |
| 5,188,126 A | 2/1993 | Fabian et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |

(56) References Cited

U.S. PATENT DOCUMENTS

| | | | |
|---|---|---|---|
| 5,222,975 | A | 6/1993 | Crainich |
| 5,222,976 | A | 6/1993 | Yoon |
| 5,223,675 | A | 6/1993 | Taft |
| D338,729 | S | 8/1993 | Sprecklemeier et al. |
| 5,234,447 | A | 8/1993 | Kaster et al. |
| 5,236,269 | A | 8/1993 | Handy |
| 5,236,424 | A | 8/1993 | Imran |
| 5,236,440 | A | 8/1993 | Hlavacek |
| 5,236,629 | A | 8/1993 | Mahabadi et al. |
| 5,239,981 | A | 8/1993 | Anapliotis |
| 5,240,163 | A | 8/1993 | Stein et al. |
| 5,242,456 | A | 9/1993 | Nash et al. |
| 5,242,457 | A | 9/1993 | Akopov et al. |
| 5,244,462 | A | 9/1993 | Delahuerga et al. |
| 5,246,156 | A | 9/1993 | Rothfuss et al. |
| 5,246,443 | A | 9/1993 | Mai |
| 5,251,801 | A | 10/1993 | Ruckdeschel et al. |
| 5,253,793 | A | 10/1993 | Green et al. |
| 5,258,007 | A | 11/1993 | Spetzler et al. |
| 5,258,008 | A | 11/1993 | Wilk |
| 5,258,009 | A | 11/1993 | Conners |
| 5,258,010 | A | 11/1993 | Green et al. |
| 5,258,012 | A | 11/1993 | Luscombe et al. |
| 5,259,366 | A | 11/1993 | Reydel et al. |
| 5,259,835 | A | 11/1993 | Clark et al. |
| 5,260,637 | A | 11/1993 | Pizzi |
| 5,261,135 | A | 11/1993 | Mitchell |
| 5,261,877 | A | 11/1993 | Fine et al. |
| 5,261,922 | A | 11/1993 | Hood |
| 5,263,629 | A | 11/1993 | Trumbull et al. |
| 5,263,937 | A | 11/1993 | Shipp |
| 5,263,973 | A | 11/1993 | Cook |
| 5,264,218 | A | 11/1993 | Rogozinski |
| 5,268,622 | A | 12/1993 | Philipp |
| 5,269,794 | A | 12/1993 | Rexroth |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,608 | A | 1/1994 | Forman et al. |
| 5,279,416 | A | 1/1994 | Malec et al. |
| 5,281,216 | A | 1/1994 | Klicek |
| 5,281,400 | A | 1/1994 | Berry, Jr. |
| 5,282,806 | A | 2/1994 | Haber et al. |
| 5,282,826 | A | 2/1994 | Quadri |
| 5,282,829 | A | 2/1994 | Hermes |
| 5,284,128 | A | 2/1994 | Hart |
| 5,285,381 | A | 2/1994 | Iskarous et al. |
| 5,285,945 | A | 2/1994 | Brinkerhoff et al. |
| 5,286,253 | A | 2/1994 | Fucci |
| 5,289,963 | A | 3/1994 | McGarry et al. |
| 5,290,271 | A | 3/1994 | Jernberg |
| 5,290,310 | A | 3/1994 | Makower et al. |
| 5,291,133 | A | 3/1994 | Gokhale et al. |
| 5,292,053 | A | 3/1994 | Bilotti et al. |
| 5,293,024 | A | 3/1994 | Sugahara et al. |
| 5,297,714 | A | 3/1994 | Kramer |
| 5,300,087 | A | 4/1994 | Knoepfler |
| 5,302,148 | A | 4/1994 | Heinz |
| 5,303,606 | A | 4/1994 | Kokinda |
| 5,304,204 | A | 4/1994 | Bregen |
| D347,474 | S | 5/1994 | Olson |
| 5,307,976 | A | 5/1994 | Olson et al. |
| 5,308,353 | A | 5/1994 | Beurrier |
| 5,308,358 | A | 5/1994 | Bond et al. |
| 5,308,576 | A | 5/1994 | Green et al. |
| 5,309,387 | A | 5/1994 | Mori et al. |
| 5,309,927 | A | 5/1994 | Welch |
| 5,312,023 | A | 5/1994 | Green et al. |
| 5,312,024 | A | 5/1994 | Grant et al. |
| 5,312,329 | A | 5/1994 | Beaty et al. |
| 5,313,935 | A | 5/1994 | Kortenbach et al. |
| 5,313,967 | A | 5/1994 | Lieber et al. |
| 5,314,424 | A | 5/1994 | Nicholas |
| 5,314,445 | A | 5/1994 | Heidmueller nee Degwitz et al. |
| 5,314,466 | A | 5/1994 | Stern et al. |
| 5,318,221 | A | 6/1994 | Green et al. |
| 5,318,589 | A | 6/1994 | Lichtman |
| 5,320,627 | A | 6/1994 | Sorensen et al. |
| D348,930 | S | 7/1994 | Olson |
| 5,326,013 | A | 7/1994 | Green et al. |
| 5,329,923 | A | 7/1994 | Lundquist |
| 5,330,486 | A | 7/1994 | Wilk |
| 5,330,487 | A | 7/1994 | Thornton et al. |
| 5,330,502 | A | 7/1994 | Hassler et al. |
| 5,331,971 | A | 7/1994 | Bales et al. |
| 5,332,142 | A | 7/1994 | Robinson et al. |
| 5,333,422 | A | 8/1994 | Warren et al. |
| 5,333,772 | A | 8/1994 | Rothfuss et al. |
| 5,333,773 | A | 8/1994 | Main et al. |
| 5,334,183 | A | 8/1994 | Wuchinich |
| 5,336,130 | A | 8/1994 | Ray |
| 5,336,229 | A | 8/1994 | Noda |
| 5,336,232 | A | 8/1994 | Green et al. |
| 5,338,317 | A | 8/1994 | Hasson et al. |
| 5,339,799 | A | 8/1994 | Kami et al. |
| 5,341,724 | A | 8/1994 | Vatel |
| 5,341,807 | A | 8/1994 | Nardella |
| 5,341,810 | A | 8/1994 | Dardel |
| 5,342,380 | A | 8/1994 | Hood |
| 5,342,381 | A | 8/1994 | Tidemand |
| 5,342,385 | A | 8/1994 | Norelli et al. |
| 5,342,395 | A | 8/1994 | Jarrett et al. |
| 5,342,396 | A | 8/1994 | Cook |
| 5,343,382 | A | 8/1994 | Hale et al. |
| 5,343,391 | A | 8/1994 | Mushabac |
| 5,344,059 | A | 9/1994 | Green et al. |
| 5,344,060 | A | 9/1994 | Gravener et al. |
| 5,344,454 | A | 9/1994 | Clarke et al. |
| 5,346,504 | A | 9/1994 | Ortiz et al. |
| 5,348,259 | A | 9/1994 | Blanco et al. |
| 5,350,104 | A | 9/1994 | Main et al. |
| 5,350,355 | A | 9/1994 | Sklar |
| 5,350,388 | A | 9/1994 | Epstein |
| 5,350,391 | A | 9/1994 | Iacovelli |
| 5,350,400 | A | 9/1994 | Esposito et al. |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,215 | A | 10/1994 | Viracola |
| 5,354,250 | A | 10/1994 | Christensen |
| 5,354,303 | A | 10/1994 | Spaeth et al. |
| 5,355,897 | A | 10/1994 | Pietrafitta et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,479 | A | 11/1994 | McGarry et al. |
| 5,368,015 | A | 11/1994 | Wilk |
| 5,368,592 | A | 11/1994 | Stern et al. |
| 5,368,599 | A | 11/1994 | Hirsch et al. |
| 5,369,565 | A | 11/1994 | Chen et al. |
| 5,370,645 | A | 12/1994 | Klicek et al. |
| 5,372,124 | A | 12/1994 | Takayama et al. |
| 5,372,596 | A | 12/1994 | Klicek et al. |
| 5,372,602 | A | 12/1994 | Burke |
| 5,374,277 | A | 12/1994 | Hassler |
| 5,375,588 | A | 12/1994 | Yoon |
| 5,376,095 | A | 12/1994 | Ortiz |
| 5,379,933 | A | 1/1995 | Green et al. |
| 5,381,649 | A | 1/1995 | Webb |

(56) References Cited

U.S. PATENT DOCUMENTS

| | | | |
|---|---|---|---|
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,874 A | 1/1995 | Jackson et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,072 A | 2/1995 | Imran |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,355 A | 6/1995 | Kulick |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,645 A | 7/1995 | Smith et al. |
| 5,431,654 A | 7/1995 | Nic |
| 5,431,666 A | 7/1995 | Sauer et al. |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,441,499 A | 8/1995 | Fritzsch |
| 5,443,197 A | 8/1995 | Malis et al. |
| 5,443,198 A | 8/1995 | Viola et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,824 A | 10/1995 | Fontayne et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,474,738 A | 12/1995 | Nichols et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,308 A | 12/1995 | Cartmell et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,377 A | 1/1996 | Smith et al. |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,164 A | 3/1996 | Ward et al. |

(56) References Cited

U.S. PATENT DOCUMENTS

| | | |
|---|---|---|
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,507,773 A | 4/1996 | Huitema et al. |
| 5,509,596 A | 4/1996 | Green et al. |
| 5,509,916 A | 4/1996 | Taylor |
| 5,509,918 A | 4/1996 | Romano |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,945 A | 8/1996 | Fritzsch |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,694 A | 10/1996 | Sauer et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,436 A | 3/1997 | Pratt et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,611,813 A | 3/1997 | Lichtman |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,979 A | 5/1997 | Mitsui et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |

(56) References Cited

U.S. PATENT DOCUMENTS

| | | |
|---|---|---|
| 5,631,973 A | 5/1997 | Green |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,637,110 A | 6/1997 | Pennybacker et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,656,917 A | 8/1997 | Theobald |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,664,404 A | 9/1997 | Ivanov et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,184 A | 10/1997 | Hassler, Jr. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,704,792 A | 1/1998 | Sobhani |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,711,960 A | 1/1998 | Shikinami |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,836 A | 2/1998 | Kliegis et al. |
| 5,715,987 A | 2/1998 | Kelley et al. |
| 5,715,988 A | 2/1998 | Palmer |
| 5,716,352 A | 2/1998 | Viola et al. |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,712 A | 3/1998 | Adair |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,736,271 A | 4/1998 | Cisar et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,746,770 A | 5/1998 | Zeitels et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,755,726 A | 5/1998 | Pratt et al. |
| 5,758,814 A | 6/1998 | Gallagher et al. |
| 5,762,255 A | 6/1998 | Chrisman et al. |
| 5,762,256 A | 6/1998 | Mastri et al. |
| 5,762,458 A | 6/1998 | Wang et al. |
| 5,765,565 A | 6/1998 | Adair |

(56) References Cited

U.S. PATENT DOCUMENTS

| | | |
|---|---|---|
| 5,766,186 A | 6/1998 | Faraz et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,640 A | 6/1998 | Jacobus et al. |
| 5,769,748 A | 6/1998 | Eyerly et al. |
| 5,769,791 A | 6/1998 | Benaron et al. |
| 5,769,892 A | 6/1998 | Kingwell |
| 5,772,099 A | 6/1998 | Gravener |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,798,752 A | 8/1998 | Buxton et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,241 A | 9/1998 | Heimberger |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,240 A | 9/1998 | Robertson |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,664 A | 2/1999 | Speier et al. |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,881,943 A | 3/1999 | Heck et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,907,664 A | 5/1999 | Wang et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,922,001 A | 7/1999 | Yoon |
| 5,922,003 A | 7/1999 | Anctil et al. |
| 5,924,864 A | 7/1999 | Loge et al. |
| 5,928,137 A | 7/1999 | Green |

(56) References Cited

U.S. PATENT DOCUMENTS

| | | |
|---|---|---|
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,013,991 A | 1/2000 | Philipp |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,019,780 A | 2/2000 | Lombardo et al. |
| 6,022,352 A | 2/2000 | Vandewalle |
| 6,023,275 A | 2/2000 | Horvitz et al. |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,126 A | 3/2000 | Hsieh |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,072,299 A | 6/2000 | Kurle et al. |
| 6,074,386 A | 6/2000 | Goble et al. |
| 6,074,401 A | 6/2000 | Gardiner et al. |
| 6,075,441 A | 6/2000 | Maloney |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,090,123 A | 7/2000 | Culp et al. |
| 6,093,186 A | 7/2000 | Goble |
| 6,094,021 A | 7/2000 | Noro et al. |
| D429,252 S | 8/2000 | Haitani et al. |
| 6,099,537 A | 8/2000 | Sugai et al. |
| 6,099,551 A | 8/2000 | Gabbay |
| 6,102,271 A | 8/2000 | Longo et al. |
| 6,102,926 A | 8/2000 | Tartaglia et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H001904 H | 10/2000 | Yates et al. |
| RE36,923 E | 10/2000 | Hiroi et al. |
| 6,126,058 A | 10/2000 | Adams et al. |
| 6,126,359 A | 10/2000 | Dittrich et al. |
| 6,126,670 A | 10/2000 | Walker et al. |

(56) References Cited

U.S. PATENT DOCUMENTS

| | | | |
|---|---|---|---|
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,186,957 B1 | 2/2001 | Milam |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,311 B1 | 3/2001 | Danek et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,211,626 B1 | 4/2001 | Lys et al. |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,235,036 B1 | 5/2001 | Gardner et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,246 B1 | 7/2001 | Pantages et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,269,997 B1 | 8/2001 | Balazs et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,317,616 B1 | 11/2001 | Glossop |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| 6,349,868 B1 | 2/2002 | Mattingly et al. |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,361,542 B1 | 3/2002 | Dimitriu et al. |
| 6,364,828 B1 | 4/2002 | Yeung et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |

(56) References Cited

U.S. PATENT DOCUMENTS

| | | |
|---|---|---|
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| 6,406,440 B1 | 6/2002 | Stefanchik |
| 6,406,472 B1 | 6/2002 | Jensen |
| 6,409,724 B1 | 6/2002 | Penny et al. |
| H002037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,656 B2 | 9/2002 | Brissette et al. |
| 6,454,781 B1 | 9/2002 | Witt et al. |
| 6,457,338 B1 | 10/2002 | Frenken |
| 6,457,625 B1 | 10/2002 | Tormala et al. |
| 6,458,077 B1 | 10/2002 | Boebel et al. |
| 6,458,142 B1 | 10/2002 | Faller et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,063 B1 | 11/2002 | Frigard |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,189 B1 | 12/2002 | Lang et al. |
| 6,500,194 B2 | 12/2002 | Benderev et al. |
| D468,749 S | 1/2003 | Friedman |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,506,399 B2 | 1/2003 | Donovan |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| D471,206 S | 3/2003 | Buzzard et al. |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,844 B2 | 4/2003 | Lee et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,569,173 B1 | 5/2003 | Blatter et al. |
| 6,572,629 B2 | 6/2003 | Kalloo et al. |
| 6,575,969 B1 | 6/2003 | Rittman, III et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,572 B1 | 7/2003 | Suzuta |

(56) References Cited

U.S. PATENT DOCUMENTS

| | | |
|---|---|---|
| 6,592,597 B2 | 7/2003 | Grant et al. |
| 6,594,552 B1 | 7/2003 | Nowlin et al. |
| 6,595,914 B2 | 7/2003 | Kato |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| 6,626,938 B1 | 9/2003 | Butaric et al. |
| H002086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,215 B1 | 4/2004 | David et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,106 B1 | 4/2004 | Charles et al. |
| 6,723,109 B2 | 4/2004 | Solingen |
| 6,726,651 B1 | 4/2004 | Robinson et al. |
| 6,726,697 B2 | 4/2004 | Nicholas et al. |
| 6,726,705 B2 | 4/2004 | Peterson et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,810 B2 | 5/2004 | Hoey et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,825 B2 | 6/2004 | Shoenman et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,763,307 B2 | 7/2004 | Berg et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,778,846 B1 | 8/2004 | Martinez et al. |
| 6,780,151 B2 | 8/2004 | Grabover et al. |
| 6,780,180 B2 | 8/2004 | Goble et al. |
| 6,783,524 B2 | 8/2004 | Anderson et al. |
| 6,784,775 B2 | 8/2004 | Mandell et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |

(56) References Cited

U.S. PATENT DOCUMENTS

| | | |
|---|---|---|
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,801,009 B2 | 10/2004 | Makaran et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,806,867 B1 | 10/2004 | Arruda et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,860,169 B2 | 3/2005 | Shinozaki |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,876,850 B2 | 4/2005 | Maeshima et al. |
| 6,877,647 B2 | 4/2005 | Green et al. |
| 6,878,106 B1 | 4/2005 | Herrmann |
| 6,882,127 B2 | 4/2005 | Konigbauer |
| 6,883,199 B1 | 4/2005 | Lundell et al. |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,244 B1 | 5/2005 | Walker et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,705 B2 | 5/2005 | Niemeyer |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,927,315 B1 | 8/2005 | Heinecke et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,949,196 B2 | 9/2005 | Schmitz et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| D511,525 S | 11/2005 | Hernandez et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |

(56) References Cited

U.S. PATENT DOCUMENTS

| | | |
|---|---|---|
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,991,146 B2 | 1/2006 | Sinisi et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 6,999,821 B2 | 2/2006 | Jenney et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,005,828 B2 | 2/2006 | Karikomi |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,213 B2 | 3/2006 | Clark et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,399 B2 | 4/2006 | Driessen |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,033,378 B2 | 4/2006 | Smith et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,038,421 B2 | 5/2006 | Trifilo |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,716 B1 | 5/2006 | Kucharczyk et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,123 B2 | 6/2006 | Gregorio et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,412 B1 | 7/2006 | Reynolds et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,081,318 B2 | 7/2006 | Lee et al. |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,363 B2 | 9/2006 | Nishizawa et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,201 B2 | 9/2006 | Truckai et al. |
| 7,112,214 B2 | 9/2006 | Peterson et al. |
| RE39,358 E | 10/2006 | Goble |
| D530,339 S | 10/2006 | Hernandez et al. |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |

(56) References Cited

U.S. PATENT DOCUMENTS

| | | |
|---|---|---|
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,846 B2 | 1/2007 | Dycus et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,160,311 B2 | 1/2007 | Blatter et al. |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,117 B2 | 1/2007 | Hellenkamp |
| 7,166,133 B2 | 1/2007 | Evans et al. |
| 7,168,604 B2 | 1/2007 | Milliman et al. |
| 7,169,146 B2 | 1/2007 | Truckai et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,197,965 B1 | 4/2007 | Anderson |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,205,959 B2 | 4/2007 | Henriksson |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,226,467 B2 | 6/2007 | Lucatero et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,273,488 B2 | 9/2007 | Nakamura et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,311,709 B2 | 12/2007 | Truckai et al. |
| 7,313,430 B2 | 12/2007 | Urquhart et al. |
| 7,314,473 B2 | 1/2008 | Jinno et al. |
| 7,320,704 B2 | 1/2008 | Lashinski et al. |

(56) References Cited

U.S. PATENT DOCUMENTS

| | | |
|---|---|---|
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,183 B2 | 2/2008 | Reddy et al. |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,398 B2 | 4/2008 | Kanazawa |
| 7,354,440 B2 | 4/2008 | Truckal et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,367,973 B2 | 5/2008 | Manzo et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| D570,868 S | 6/2008 | Hosokawa et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| D575,793 S | 8/2008 | Ording |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,430,849 B1 | 10/2008 | Coutts et al. |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| D580,942 S | 11/2008 | Oshiro et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,450,991 B2 | 11/2008 | Smith et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,455,687 B2 | 11/2008 | Saunders et al. |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,147 B2 | 1/2009 | Honeycutt et al. |
| 7,479,608 B2 | 1/2009 | Smith |
| 7,481,347 B2 | 1/2009 | Roy |
| 7,481,348 B2 | 1/2009 | Marczyk |

(56) References Cited

U.S. PATENT DOCUMENTS

| | | |
|---|---|---|
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,492,261 B2 | 2/2009 | Cambre et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,497,137 B2 | 3/2009 | Tellenbach et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,544,197 B2 | 6/2009 | Kelsch et al. |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,572,285 B2 | 8/2009 | Frey et al. |
| 7,572,298 B2 | 8/2009 | Roller et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Lio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,605,826 B2 | 10/2009 | Sauer |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| 7,618,427 B2 | 11/2009 | Ortiz et al. |
| D605,201 S | 12/2009 | Lorenz et al. |
| D606,992 S | 12/2009 | Liu et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,625,388 B2 | 12/2009 | Boukhny et al. |
| 7,625,662 B2 | 12/2009 | Vaisnys et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,484 B2 | 1/2010 | Vereschagin |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,003 B2 | 2/2010 | Lorang et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,670,337 B2 | 3/2010 | Young |
| 7,673,780 B2 | 3/2010 | Shelton, IV et al. |

(56) References Cited

U.S. PATENT DOCUMENTS

| | | |
|---|---|---|
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,678,121 B1 | 3/2010 | Knodel |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,690,547 B2 | 4/2010 | Racenet et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,706,853 B2 | 4/2010 | Hacker et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,708,768 B2 | 5/2010 | Danek et al. |
| 7,709,136 B2 | 5/2010 | Touchton et al. |
| 7,712,182 B2 | 5/2010 | Zeiler et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,735,704 B2 | 6/2010 | Bilotti |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,758,613 B2 | 7/2010 | Whitman |
| 7,762,462 B2 | 7/2010 | Gelbman |
| 7,762,998 B2 | 7/2010 | Birk et al. |
| D622,286 S | 8/2010 | Umezawa |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,614 B1 | 8/2010 | McGonagle et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,651 B2 | 8/2010 | Madhani et al. |
| 7,780,663 B2 | 8/2010 | Yates et al. |
| 7,780,685 B2 | 8/2010 | Hunt et al. |
| 7,782,382 B2 | 8/2010 | Fujimura |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |

(56) References Cited

U.S. PATENT DOCUMENTS

| | | |
|---|---|---|
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,819,894 B2 | 10/2010 | Mitsuishi et al. |
| 7,823,076 B2 | 10/2010 | Borovsky et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,829,416 B2 | 11/2010 | Kudou et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,840,253 B2 | 11/2010 | Tremblay et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,845,538 B2 | 12/2010 | Whitman |
| 7,845,912 B2 | 12/2010 | Sung et al. |
| 7,846,085 B2 | 12/2010 | Silverman et al. |
| 7,846,149 B2 | 12/2010 | Jankowski |
| 7,846,161 B2 | 12/2010 | Dumbauld et al. |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,877,869 B2 | 2/2011 | Mehdizadeh et al. |
| 7,879,063 B2 | 2/2011 | Khosravi |
| 7,879,070 B2 | 2/2011 | Ortiz et al. |
| 7,879,367 B2 | 2/2011 | Heublein et al. |
| 7,883,461 B2 | 2/2011 | Albrecht et al. |
| 7,883,465 B2 | 2/2011 | Donofrio et al. |
| 7,883,540 B2 | 2/2011 | Niwa et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,887,755 B2 | 2/2011 | Mingerink et al. |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,671 B2 | 3/2011 | Kim et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |
| 7,942,300 B2 | 5/2011 | Rethy et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |

(56) References Cited

U.S. PATENT DOCUMENTS

| | | |
|---|---|---|
| 7,946,453 B2 | 5/2011 | Voegele et al. |
| 7,947,011 B2 | 5/2011 | Birk et al. |
| 7,948,381 B2 | 5/2011 | Lindsay et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,951,166 B2 | 5/2011 | Orban, III et al. |
| 7,952,464 B2 | 5/2011 | Nikitin et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,954,688 B2 | 6/2011 | Argentine et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,508 B2 | 7/2011 | Hoag |
| 7,976,563 B2 | 7/2011 | Summerer |
| 7,979,137 B2 | 7/2011 | Tracey et al. |
| 7,980,443 B2 | 7/2011 | Scheib et al. |
| 7,981,025 B2 | 7/2011 | Pool et al. |
| 7,981,102 B2 | 7/2011 | Patel et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,835 B2 | 10/2011 | Yasuda et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,052,697 B2 | 11/2011 | Phillips |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |

(56) References Cited

U.S. PATENT DOCUMENTS

| | | |
|---|---|---|
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,114,345 B2 | 2/2012 | Dlugos, Jr. et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,157,834 B2 | 4/2012 | Conlon |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,190,238 B2 | 5/2012 | Moll et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,207,863 B2 | 6/2012 | Neubauer et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |

(56) References Cited

U.S. PATENT DOCUMENTS

| | | |
|---|---|---|
| 8,235,274 B2 | 8/2012 | Cappola |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,266,232 B2 | 9/2012 | Piper et al. |
| 8,267,300 B2 | 9/2012 | Boudreaux |
| 8,267,849 B2 | 9/2012 | Wazer et al. |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,290,883 B2 | 10/2012 | Takeuchi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| D672,784 S | 12/2012 | Clanton et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,271 B2 | 12/2012 | Humayun et al. |
| 8,323,789 B2 | 12/2012 | Rozhin et al. |
| 8,324,585 B2 | 12/2012 | McBroom et al. |
| 8,327,514 B2 | 12/2012 | Kim |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,065 B2 | 12/2012 | Shah |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | Ditizio et al. |
| D676,866 S | 2/2013 | Chaudhri |

(56) References Cited

U.S. PATENT DOCUMENTS

| | | |
|---|---|---|
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,368,327 B2 | 2/2013 | Benning et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,374,723 B2 | 2/2013 | Zhao et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,377,059 B2 | 2/2013 | Deville et al. |
| 8,381,828 B2 | 2/2013 | Whitman et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,972 B2 | 3/2013 | Kostrzewski |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,108 B2 | 3/2013 | Powell et al. |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |
| 8,403,198 B2 | 3/2013 | Sorrentino et al. |
| 8,403,832 B2 | 3/2013 | Cunningham et al. |
| 8,403,926 B2 | 3/2013 | Nobis et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| D680,646 S | 4/2013 | Hunt et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,211 B2 | 4/2013 | Baroud |
| 8,409,222 B2 | 4/2013 | Whitfield et al. |
| 8,409,223 B2 | 4/2013 | Sorrentino et al. |
| 8,409,234 B2 | 4/2013 | Stahler et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,469 B2 | 4/2013 | Diolaiti |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,419,755 B2 | 4/2013 | Deem et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,439,830 B2 | 5/2013 | McKinley et al. |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| D686,244 S | 7/2013 | Moriya et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,486,047 B2 | 7/2013 | Stopek |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,852 B2 | 7/2013 | Viola |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,673 B2 | 8/2013 | Keller |
| 8,499,966 B2 | 8/2013 | Palmer et al. |
| 8,499,992 B2 | 8/2013 | Whitman et al. |
| 8,499,993 B2 | 8/2013 | Shelton, IV et al. |
| 8,499,994 B2 | 8/2013 | D'Arcangelo |
| 8,500,721 B2 | 8/2013 | Jinno |
| 8,500,762 B2 | 8/2013 | Sholev et al. |

(56) References Cited

U.S. PATENT DOCUMENTS

| | | |
|---|---|---|
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,938 B2 | 8/2013 | Eisenhardt et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,787 B2 | 9/2013 | Ludwin et al. |
| 8,523,881 B2 | 9/2013 | Cabiri et al. |
| 8,523,882 B2 | 9/2013 | Huitema et al. |
| 8,523,900 B2 | 9/2013 | Jinno et al. |
| 8,529,588 B2 | 9/2013 | Ahlberg et al. |
| 8,529,599 B2 | 9/2013 | Holsten |
| 8,529,600 B2 | 9/2013 | Woodard, Jr. et al. |
| 8,529,819 B2 | 9/2013 | Ostapoff et al. |
| 8,531,153 B2 | 9/2013 | Baarman et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,646 B2 | 9/2013 | Mendez-Coll |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,598 B2 | 11/2013 | Razzaque et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,591,400 B2 | 11/2013 | Sugiyama |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,431 B2 | 12/2013 | Timm et al. |
| 8,617,155 B2 | 12/2013 | Johnson et al. |
| 8,620,473 B2 | 12/2013 | Diolaiti et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,467 B2 | 1/2014 | Whitman et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,656,929 B2 | 2/2014 | Miller et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |

(56) References Cited

U.S. PATENT DOCUMENTS

| | | |
|---|---|---|
| 8,672,208 B2 | 3/2014 | Hess et al. |
| 8,672,209 B2 | 3/2014 | Crainich |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,706,316 B1 | 4/2014 | Hoevenaar |
| 8,708,210 B2 | 4/2014 | Zemlok et al. |
| 8,708,211 B2 | 4/2014 | Zemlok et al. |
| 8,708,212 B2 | 4/2014 | Williams |
| 8,708,213 B2 | 4/2014 | Shelton, IV et al. |
| 8,709,012 B2 | 4/2014 | Muller |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,611 B2 | 5/2014 | Milliman |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,765,942 B2 | 7/2014 | Feraud et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,159 B2 | 8/2014 | Moriyama |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |

(56) References Cited

U.S. PATENT DOCUMENTS

| | | |
|---|---|---|
| 8,828,046 B2 | 9/2014 | Stefanchik et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,004 B2 | 9/2014 | Holsten et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,845,622 B2 | 9/2014 | Paik et al. |
| 8,851,215 B2 | 10/2014 | Goto |
| 8,851,354 B2 | 10/2014 | Swensgard et al. |
| 8,851,355 B2 | 10/2014 | Aranyi et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,547 B2 | 10/2014 | Brogna |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,869,912 B2 | 10/2014 | Ro.beta.kamp et al. |
| 8,869,913 B2 | 10/2014 | Matthias et al. |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,871,829 B2 | 10/2014 | Gerold et al. |
| 8,875,971 B2 | 11/2014 | Hall et al. |
| 8,875,972 B2 | 11/2014 | Weisenburgh, II et al. |
| 8,876,698 B2 | 11/2014 | Sakamoto et al. |
| 8,876,857 B2 | 11/2014 | Burbank |
| 8,876,858 B2 | 11/2014 | Braun |
| 8,882,660 B2 | 11/2014 | Phee et al. |
| 8,882,792 B2 | 11/2014 | Dietz et al. |
| 8,884,560 B2 | 11/2014 | Ito |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,910,847 B2 | 12/2014 | Nalagatla et al. |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,915,842 B2 | 12/2014 | Weisenburgh, II et al. |
| 8,920,368 B2 | 12/2014 | Sandhu et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,931,692 B2 | 1/2015 | Sancak |
| 8,936,614 B2 | 1/2015 | Allen, IV |
| 8,937,408 B2 | 1/2015 | Ganem et al. |
| 8,939,343 B2 | 1/2015 | Milliman et al. |
| 8,939,344 B2 | 1/2015 | Olson et al. |
| 8,939,898 B2 | 1/2015 | Omoto |
| 8,944,069 B2 | 2/2015 | Miller et al. |
| 8,945,095 B2 | 2/2015 | Blumenkranz et al. |
| 8,945,098 B2 | 2/2015 | Seibold et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,961,542 B2 | 2/2015 | Whitfield et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,984,711 B2 | 3/2015 | Ota et al. |
| 8,985,240 B2 | 3/2015 | Winnard |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |

(56) References Cited

U.S. PATENT DOCUMENTS

| | | |
|---|---|---|
| 9,000,720 B2 | 4/2015 | Stulen et al. |
| 9,002,518 B2 | 4/2015 | Manzo et al. |
| 9,004,339 B1 | 4/2015 | Park |
| 9,004,799 B1 | 4/2015 | Tibbits |
| 9,005,230 B2 | 4/2015 | Yates et al. |
| 9,005,238 B2 | 4/2015 | Desantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,014,856 B2 | 4/2015 | Manzo et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,017,849 B2 | 4/2015 | Stulen et al. |
| 9,017,851 B2 | 4/2015 | Felder et al. |
| D729,274 S | 5/2015 | Clement et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,468 B2 | 5/2015 | Scarfogliero et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,028,529 B2 | 5/2015 | Fox et al. |
| 9,030,166 B2 | 5/2015 | Kano |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,039,736 B2 | 5/2015 | Scirica et al. |
| 9,040,062 B2 | 5/2015 | Maeda et al. |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,238 B2 | 6/2015 | Orszulak |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,089 B2 | 6/2015 | Orszulak |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,070,068 B2 | 6/2015 | Coveley et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,586 B2 | 7/2015 | Hafner et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,338 B2 | 7/2015 | Smith et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,095,642 B2 | 8/2015 | Harder et al. |
| 9,096,033 B2 | 8/2015 | Holop et al. |
| 9,098,153 B2 | 8/2015 | Shen et al. |
| 9,099,863 B2 | 8/2015 | Smith et al. |
| 9,099,877 B2 | 8/2015 | Banos et al. |
| 9,099,922 B2 | 8/2015 | Toosky et al. |
| 9,101,358 B2 | 8/2015 | Kerr et al. |
| 9,101,359 B2 | 8/2015 | Smith et al. |
| 9,101,385 B2 | 8/2015 | Shelton, IV et al. |
| 9,101,475 B2 | 8/2015 | Wei et al. |
| 9,101,621 B2 | 8/2015 | Zeldis |
| 9,107,663 B2 | 8/2015 | Swensgard |
| 9,107,667 B2 | 8/2015 | Hodgkinson |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,875 B2 | 8/2015 | Viola et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,651 B2 | 9/2015 | Mandakolathur Vasudevan et al. |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D740,414 S | 10/2015 | Katsura |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,154,189 B2 | 10/2015 | Von Novak et al. |
| 9,161,753 B2 | 10/2015 | Prior |
| 9,161,769 B2 | 10/2015 | Stoddard et al. |

(56) References Cited

U.S. PATENT DOCUMENTS

| | | |
|---|---|---|
| 9,161,803 B2 | 10/2015 | Yates et al. |
| 9,161,807 B2 | 10/2015 | Garrison |
| 9,161,855 B2 | 10/2015 | Rousseau et al. |
| 9,164,271 B2 | 10/2015 | Ebata et al. |
| 9,167,960 B2 | 10/2015 | Yamaguchi et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,171,244 B2 | 10/2015 | Endou et al. |
| 9,179,832 B2 | 11/2015 | Diolaiti |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,376 B2 | 11/2015 | Almodovar |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| D746,459 S | 12/2015 | Kaercher et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,881 B2 | 12/2015 | Penna |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,504 B2 | 12/2015 | Viola et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,686 B2 | 1/2016 | Blair |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,760 B2 | 1/2016 | Shelton, IV |
| 9,226,761 B2 | 1/2016 | Burbank |
| 9,226,767 B2 | 1/2016 | Stulen et al. |
| 9,226,799 B2 | 1/2016 | Lightcap et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,241,758 B2 | 1/2016 | Franer et al. |
| 9,244,524 B2 | 1/2016 | Inoue et al. |
| D748,668 S | 2/2016 | Kim et al. |
| D749,128 S | 2/2016 | Perez et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,254,170 B2 | 2/2016 | Parihar et al. |
| 9,259,265 B2 | 2/2016 | Harris et al. |
| 9,259,268 B2 | 2/2016 | Behnke, II et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,510 B2 | 2/2016 | Dietzel et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,283,334 B2 | 3/2016 | Mantell et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,811 B2 | 4/2016 | Goldberg et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |

(56) References Cited

U.S. PATENT DOCUMENTS

| | | |
|---|---|---|
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,291 B2 | 4/2016 | Schall et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,326,824 B2 | 5/2016 | Inoue et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,339,342 B2 | 5/2016 | Prisco et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,352,071 B2 | 5/2016 | Landgrebe et al. |
| D758,433 S | 6/2016 | Lee et al. |
| D759,063 S | 6/2016 | Chen |
| 9,358,003 B2 | 6/2016 | Hail et al. |
| 9,358,004 B2 | 6/2016 | Sniffin et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,358,065 B2 | 6/2016 | Ladtkow et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,223 B2 | 6/2016 | Scirica |
| 9,364,226 B2 | 6/2016 | Zemlok et al. |
| 9,364,228 B2 | 6/2016 | Straehnz et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,361 B2 | 6/2016 | Viola et al. |
| 9,370,362 B2 | 6/2016 | Petty et al. |
| 9,370,364 B2 | 6/2016 | Smith et al. |
| 9,370,400 B2 | 6/2016 | Parihar |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,385,640 B2 | 7/2016 | Sun et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,392,885 B2 | 7/2016 | Vogler et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,393,354 B2 | 7/2016 | Freedman et al. |
| 9,396,369 B1 | 7/2016 | Whitehurst et al. |
| 9,396,669 B2 | 7/2016 | Karkanias et al. |
| 9,398,905 B2 | 7/2016 | Martin |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,402,682 B2 | 8/2016 | Worrell et al. |
| 9,402,688 B2 | 8/2016 | Min et al. |
| 9,408,604 B2 | 8/2016 | Shelton, IV et al. |
| 9,408,605 B1 | 8/2016 | Knodel et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,421,682 B2 | 8/2016 | McClaskey et al. |
| 9,427,223 B2 | 8/2016 | Park et al. |
| 9,427,231 B2 | 8/2016 | Racenet et al. |
| 9,429,204 B2 | 8/2016 | Stefan et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Overes et al. |
| 9,451,958 B2 | 9/2016 | Shelton, IV et al. |
| 9,452,020 B2 | 9/2016 | Griffiths et al. |
| D768,152 S | 10/2016 | Gutierrez et al. |
| D768,156 S | 10/2016 | Frincke |
| D768,167 S | 10/2016 | Jones et al. |
| D769,315 S | 10/2016 | Scotti |
| D769,930 S | 10/2016 | Agrawal |
| 9,461,340 B2 | 10/2016 | Li et al. |
| 9,463,012 B2 | 10/2016 | Bonutti et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |

(56) References Cited

U.S. PATENT DOCUMENTS

| | | |
|---|---|---|
| 9,474,506 B2 | 10/2016 | Magnin et al. |
| 9,474,513 B2 | 10/2016 | Ishida et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| 9,477,649 B1 | 10/2016 | Davidson et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,215 B2 | 11/2016 | Olson et al. |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,172 B2 | 11/2016 | Weisshaupt et al. |
| 9,492,189 B2 | 11/2016 | Williams et al. |
| 9,492,192 B2 | 11/2016 | To et al. |
| 9,492,237 B2 | 11/2016 | Kang et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,520 B2 | 11/2016 | Worrell et al. |
| 9,504,521 B2 | 11/2016 | Deutmeyer et al. |
| 9,504,528 B2 | 11/2016 | Ivinson et al. |
| 9,507,399 B2 | 11/2016 | Chien |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,515,366 B2 | 12/2016 | Herbsommer et al. |
| 9,517,063 B2 | 12/2016 | Swayze et al. |
| 9,517,065 B2 | 12/2016 | Simms et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,014 B2 | 12/2016 | Nishizawa et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| 9,526,921 B2 | 12/2016 | Kimball et al. |
| D776,683 S | 1/2017 | Gobinski et al. |
| D777,773 S | 1/2017 | Shi |
| 9,532,783 B2 | 1/2017 | Swayze et al. |
| 9,539,060 B2 | 1/2017 | Lightcap et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,733 B2 | 1/2017 | Knodel |
| 9,549,735 B2 | 1/2017 | Shelton, IV et al. |
| 9,549,750 B2 | 1/2017 | Shelton, IV et al. |
| 9,554,794 B2 | 1/2017 | Baber et al. |
| 9,554,796 B2 | 1/2017 | Kostrzewski |
| 9,554,803 B2 | 1/2017 | Smith et al. |
| 9,554,812 B2 | 1/2017 | Inkpen et al. |
| 9,554,854 B2 | 1/2017 | Yates et al. |
| 9,559,624 B2 | 1/2017 | Philipp |
| 9,561,013 B2 | 2/2017 | Tsuchiya |
| 9,561,029 B2 | 2/2017 | Scheib et al. |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,561,072 B2 | 2/2017 | Ko |
| 9,566,061 B2 | 2/2017 | Aronhalt et al. |
| 9,566,062 B2 | 2/2017 | Boudreaux |
| 9,566,064 B2 | 2/2017 | Williams et al. |
| 9,566,065 B2 | 2/2017 | Knodel |
| 9,566,067 B2 | 2/2017 | Milliman et al. |
| 9,572,552 B1 | 2/2017 | Bodor et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| 9,579,143 B2 | 2/2017 | Ullrich et al. |
| 9,579,158 B2 | 2/2017 | Brianza et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,078 B2 | 3/2017 | Scirica et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,079 B2 | 4/2017 | Kamei et al. |
| 9,610,080 B2 | 4/2017 | Whitfield et al. |
| 9,610,412 B2 | 4/2017 | Zemlok et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,622,746 B2 | 4/2017 | Simms et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,632 B2 | 4/2017 | Linder et al. |
| 9,629,652 B2 | 4/2017 | Mumaw et al. |
| 9,629,814 B2 | 4/2017 | Widenhouse et al. |
| D785,794 S | 5/2017 | Magno, Jr. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,091 B2 | 5/2017 | Beardsley et al. |
| 9,636,111 B2 | 5/2017 | Wenchell |
| 9,636,112 B2 | 5/2017 | Penna et al. |
| 9,636,113 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |

(56) References Cited

U.S. PATENT DOCUMENTS

| | | |
|---|---|---|
| 9,642,642 B2 | 5/2017 | Lim |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,649,190 B2 | 5/2017 | Mathies |
| 9,651,032 B2 | 5/2017 | Weaver et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,661,991 B2 | 5/2017 | Glossop |
| 9,662,108 B2 | 5/2017 | Williams |
| 9,662,110 B2 | 5/2017 | Huang et al. |
| 9,662,111 B2 | 5/2017 | Holsten et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,668,735 B2 | 6/2017 | Beetel |
| 9,675,344 B2 | 6/2017 | Combrowski et al. |
| 9,675,348 B2 | 6/2017 | Smith et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,368 B2 | 6/2017 | Guo et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,775 B2 | 7/2017 | Agarwal et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,315 B2 | 7/2017 | Chen et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,700,334 B2 | 7/2017 | Hinman et al. |
| 9,700,381 B2 | 7/2017 | Amat Girbau |
| 9,702,823 B2 | 7/2017 | Maher et al. |
| 9,706,674 B2 | 7/2017 | Collins et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,003 B2 | 7/2017 | Hoell, Jr. et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,466 B2 | 7/2017 | Kostrzewski |
| 9,713,468 B2 | 7/2017 | Harris et al. |
| 9,713,470 B2 | 7/2017 | Scirica et al. |
| 9,713,474 B2 | 7/2017 | Lorenz |
| D795,919 S | 8/2017 | Bischoff et al. |
| 9,717,497 B2 | 8/2017 | Zerkle et al. |
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,730,757 B2 | 8/2017 | Brudniok |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,298 B2 | 8/2017 | Isbell, Jr. |
| 9,737,299 B2 | 8/2017 | Yan |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,323 B2 | 8/2017 | Thapliyal et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,503 B2 | 9/2017 | Milliman |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,187 B2 | 10/2017 | Zergiebel et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |

(56) References Cited

U.S. PATENT DOCUMENTS

| | | |
|---|---|---|
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,815,118 B1 | 11/2017 | Schmitt et al. |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,235 B2 | 12/2017 | Penna et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,839,481 B2 | 12/2017 | Blumenkranz et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,850,994 B2 | 12/2017 | Schena |
| D808,989 S | 1/2018 | Ayvazian et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,366 B2 | 1/2018 | Aranyi |
| 9,861,382 B2 | 1/2018 | Smith et al. |
| 9,861,446 B2 | 1/2018 | Lang |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,867,617 B2 | 1/2018 | Ma |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,722 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,358 B2 | 2/2018 | Faller et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,117 B2 | 4/2018 | Hathaway et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |

(56) References Cited

U.S. PATENT DOCUMENTS

| | | |
|---|---|---|
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,740 B2 | 5/2018 | Krause et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| 10,004,552 B1 | 6/2018 | Kleyman et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,120 B2 | 7/2018 | Martin et al. |
| 10,022,123 B2 | 7/2018 | Williams et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,046,904 B2 | 8/2018 | Evans et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,642 B2 | 9/2018 | Marczyk et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,126 B2 | 10/2018 | Sauer |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter, III et al. |
| 10,117,650 B2 | 11/2018 | Nicholas et al. |

(56) References Cited

U.S. PATENT DOCUMENTS

| | | |
|---|---|---|
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,123,845 B2 | 11/2018 | Yeung |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,382 B2 | 11/2018 | Gladstone |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,146,423 B1 | 12/2018 | Reed et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,161,816 B2 | 12/2018 | Jackson et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,389 B2 | 1/2019 | Vendely et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,911 B2 | 2/2019 | Miller et al. |
| 10,194,912 B2 | 2/2019 | Scheib et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| D847,199 S | 4/2019 | Whitmore |
| 10,244,991 B2 | 4/2019 | Shademan et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,645 B2 | 4/2019 | Kostrzewski |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,363 B2 | 4/2019 | Worrell et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |

(56) References Cited

U.S. PATENT DOCUMENTS

| | | |
|---|---|---|
| 10,265,090 B2 | 4/2019 | Ingmanson et al. |
| 10,271,840 B2 | 4/2019 | Sapre |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,847 B2 | 4/2019 | Racenet et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,700 B2 | 5/2019 | Scheib |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |
| 10,299,790 B2 | 5/2019 | Beardsley |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| 10,303,851 B2 | 5/2019 | Nguyen et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,578 B2 | 6/2019 | Leimbach et al. |
| 10,314,579 B2 | 6/2019 | Chowaniec et al. |
| 10,314,580 B2 | 6/2019 | Scheib et al. |
| 10,314,582 B2 | 6/2019 | Shelton, IV et al. |
| 10,314,584 B2 | 6/2019 | Scirica et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,937 B2 | 7/2019 | Williams |
| 10,349,939 B2 | 7/2019 | Shelton, IV et al. |
| 10,349,941 B2 | 7/2019 | Marczyk et al. |
| 10,349,963 B2 | 7/2019 | Fiksen et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,866 B2 | 8/2019 | Wang et al. |
| 10,368,867 B2 | 8/2019 | Harris et al. |
| 10,368,892 B2 | 8/2019 | Stulen et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D859,466 S | 9/2019 | Okada et al. |
| D860,219 S | 9/2019 | Rasmussen et al. |
| D861,035 S | 9/2019 | Park et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,398,460 B2 | 9/2019 | Overmyer |
| 10,404,136 B2 | 9/2019 | Oktavec et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,405,937 B2 | 9/2019 | Black et al. |
| 10,413,155 B2 | 9/2019 | Inoue |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,551 B2 | 9/2019 | Calderoni |
| 10,420,552 B2 | 9/2019 | Shelton, IV et al. |
| 10,420,553 B2 | 9/2019 | Shelton, IV et al. |
| 10,420,554 B2 | 9/2019 | Collings et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |

(56) References Cited

U.S. PATENT DOCUMENTS

| | | |
|---|---|---|
| 10,420,560 B2 | 9/2019 | Shelton, IV et al. |
| 10,420,561 B2 | 9/2019 | Shelton, IV et al. |
| 10,420,577 B2 | 9/2019 | Chowaniec et al. |
| D861,707 S | 10/2019 | Yang |
| D862,518 S | 10/2019 | Niven et al. |
| D863,343 S | 10/2019 | Mazlish et al. |
| D864,388 S | 10/2019 | Barber |
| D865,174 S | 10/2019 | Auld et al. |
| D865,175 S | 10/2019 | Widenhouse et al. |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,426,555 B2 | 10/2019 | Crowley et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,842 B2 | 10/2019 | Amariglio et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,371 B2 | 11/2019 | Kostrzewski |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,767 B2 | 11/2019 | Gleiman et al. |
| 10,470,768 B2 | 11/2019 | Harris et al. |
| 10,470,769 B2 | 11/2019 | Shelton, IV et al. |
| 10,471,282 B2 | 11/2019 | Kirk et al. |
| 10,471,576 B2 | 11/2019 | Totsu |
| 10,471,607 B2 | 11/2019 | Butt et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,187 B2 | 11/2019 | Shelton, IV et al. |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,482,292 B2 | 11/2019 | Clouser et al. |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,917 B2 | 12/2019 | Scheib et al. |
| 10,499,918 B2 | 12/2019 | Schellin et al. |
| 10,500,000 B2 | 12/2019 | Swayze et al. |
| 10,500,004 B2 | 12/2019 | Hanuschik et al. |
| 10,500,309 B2 | 12/2019 | Shah et al. |
| 10,507,034 B2 | 12/2019 | Timm |
| 10,508,720 B2 | 12/2019 | Nicholas |
| 10,512,461 B2 | 12/2019 | Gupta et al. |
| 10,512,462 B2 | 12/2019 | Felder et al. |
| 10,512,464 B2 | 12/2019 | Park et al. |
| 10,517,590 B2 | 12/2019 | Giordano et al. |
| 10,517,592 B2 | 12/2019 | Shelton, IV et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 10,524,784 B2 | 1/2020 | Kostrzewski |
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,524,870 B2 | 1/2020 | Saraliev et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,908 B2 | 1/2020 | Mei et al. |
| 10,542,974 B2 | 1/2020 | Yates et al. |
| 10,542,976 B2 | 1/2020 | Calderoni et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,593 B2 | 2/2020 | Shelton, IV et al. |
| 10,548,600 B2 | 2/2020 | Shelton, IV et al. |
| 10,548,673 B2 | 2/2020 | Harris et al. |
| 10,561,418 B2 | 2/2020 | Richard et al. |
| 10,561,419 B2 | 2/2020 | Beardsley |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,493 B2 | 2/2020 | Blase et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| D879,808 S | 3/2020 | Harris et al. |
| D879,809 S | 3/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |

(56) References Cited

U.S. PATENT DOCUMENTS

| | | |
|---|---|---|
| 10,588,231 B2 | 3/2020 | Sgroi, Jr. et al. |
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,835 B2 | 3/2020 | Kerr et al. |
| 10,595,862 B2 | 3/2020 | Shelton, IV et al. |
| 10,595,882 B2 | 3/2020 | Parfett et al. |
| 10,595,887 B2 | 3/2020 | Shelton, IV et al. |
| 10,595,929 B2 | 3/2020 | Boudreaux et al. |
| 10,603,036 B2 | 3/2020 | Hunter et al. |
| 10,603,039 B2 | 3/2020 | Vendely et al. |
| 10,603,041 B2 | 3/2020 | Miller et al. |
| 10,603,117 B2 | 3/2020 | Schings et al. |
| 10,603,128 B2 | 3/2020 | Zergiebel et al. |
| D882,783 S | 4/2020 | Shelton, IV et al. |
| 10,610,224 B2 | 4/2020 | Shelton, IV et al. |
| 10,610,225 B2 | 4/2020 | Reed et al. |
| 10,610,236 B2 | 4/2020 | Baril |
| 10,610,313 B2 | 4/2020 | Bailey et al. |
| 10,610,346 B2 | 4/2020 | Schwartz |
| 10,617,411 B2 | 4/2020 | Williams |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,416 B2 | 4/2020 | Leimbach et al. |
| 10,617,417 B2 | 4/2020 | Baxter, III et al. |
| 10,617,418 B2 | 4/2020 | Barton et al. |
| 10,617,420 B2 | 4/2020 | Shelton, IV et al. |
| 10,617,438 B2 | 4/2020 | O'Keefe et al. |
| 10,624,616 B2 | 4/2020 | Mukherjee et al. |
| 10,624,630 B2 | 4/2020 | Deville et al. |
| 10,624,633 B2 | 4/2020 | Shelton, IV et al. |
| 10,624,634 B2 | 4/2020 | Shelton, IV et al. |
| 10,624,635 B2 | 4/2020 | Harris et al. |
| 10,624,709 B2 | 4/2020 | Remm |
| 10,624,861 B2 | 4/2020 | Widenhouse et al. |
| 10,625,062 B2 | 4/2020 | Matlock et al. |
| 10,631,857 B2 | 4/2020 | Kostrzewski |
| 10,631,858 B2 | 4/2020 | Burbank |
| 10,631,859 B2 | 4/2020 | Shelton, IV et al. |
| 10,631,860 B2 | 4/2020 | Bakos et al. |
| 10,636,104 B2 | 4/2020 | Mazar et al. |
| 10,639,018 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,089 B2 | 5/2020 | Manwaring et al. |
| 10,639,115 B2 | 5/2020 | Shelton, IV et al. |
| 10,642,633 B1 | 5/2020 | Chopra et al. |
| 10,645,905 B2 | 5/2020 | Gandola et al. |
| 10,646,220 B2 | 5/2020 | Shelton, IV et al. |
| 10,646,292 B2 | 5/2020 | Solomon et al. |
| 10,653,413 B2 | 5/2020 | Worthington et al. |
| 10,653,417 B2 | 5/2020 | Shelton, IV et al. |
| 10,653,435 B2 | 5/2020 | Shelton, IV et al. |
| 10,660,640 B2 | 5/2020 | Yates et al. |
| 10,667,408 B2 | 5/2020 | Sgroi, Jr. et al. |
| D888,953 S | 6/2020 | Baxter, III et al. |
| 10,667,808 B2 | 6/2020 | Baxter, III et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,818 B2 | 6/2020 | McLain et al. |
| 10,674,895 B2 | 6/2020 | Yeung et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,028 B2 | 6/2020 | Shelton, IV et al. |
| 10,675,035 B2 | 6/2020 | Zingman |
| 10,675,080 B2 | 6/2020 | Woloszko et al. |
| 10,675,102 B2 | 6/2020 | Forgione et al. |
| 10,677,035 B2 | 6/2020 | Balan et al. |
| 10,682,134 B2 | 6/2020 | Shelton, IV et al. |
| 10,682,136 B2 | 6/2020 | Harris et al. |
| 10,682,137 B2 | 6/2020 | Stokes et al. |
| 10,682,138 B2 | 6/2020 | Shelton, IV et al. |
| 10,682,141 B2 | 6/2020 | Moore et al. |
| 10,682,142 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,812 B2 | 6/2020 | Shelton, IV et al. |
| 10,687,813 B2 | 6/2020 | Shelton, IV et al. |
| 10,687,817 B2 | 6/2020 | Shelton, IV et al. |
| 10,687,819 B2 | 6/2020 | Stokes et al. |
| 10,687,904 B2 | 6/2020 | Harris et al. |
| 10,695,053 B2 | 6/2020 | Hess et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,062 B2 | 6/2020 | Leimbach et al. |
| 10,695,063 B2 | 6/2020 | Morgan et al. |
| 10,695,074 B2 | 6/2020 | Carusillo |
| 10,695,081 B2 | 6/2020 | Shelton, IV et al. |
| 10,695,119 B2 | 6/2020 | Smith |
| 10,695,123 B2 | 6/2020 | Allen, IV |
| 10,695,187 B2 | 6/2020 | Moskowitz et al. |
| D890,784 S | 7/2020 | Shelton, IV et al. |
| 10,702,266 B2 | 7/2020 | Parihar et al. |
| 10,702,267 B2 | 7/2020 | Hess et al. |
| 10,702,270 B2 | 7/2020 | Shelton, IV et al. |
| 10,702,271 B2 | 7/2020 | Aranyi et al. |
| 10,705,660 B2 | 7/2020 | Xiao |
| 10,709,446 B2 | 7/2020 | Harris et al. |
| 10,709,468 B2 | 7/2020 | Shelton, IV et al. |
| 10,709,469 B2 | 7/2020 | Shelton, IV et al. |
| 10,709,496 B2 | 7/2020 | Moua et al. |
| 10,716,563 B2 | 7/2020 | Shelton, IV et al. |
| 10,716,565 B2 | 7/2020 | Shelton, IV et al. |
| 10,716,568 B2 | 7/2020 | Hall et al. |
| 10,716,614 B2 | 7/2020 | Yates et al. |
| 10,717,179 B2 | 7/2020 | Koenig et al. |
| 10,722,232 B2 | 7/2020 | Yates et al. |
| 10,722,233 B2 | 7/2020 | Wellman |
| 10,722,292 B2 | 7/2020 | Arya et al. |
| 10,722,293 B2 | 7/2020 | Arya et al. |
| 10,722,317 B2 | 7/2020 | Ward et al. |
| D893,717 S | 8/2020 | Messerly et al. |
| 10,729,432 B2 | 8/2020 | Shelton, IV et al. |
| 10,729,434 B2 | 8/2020 | Harris et al. |
| 10,729,435 B2 | 8/2020 | Richard |
| 10,729,436 B2 | 8/2020 | Shelton, IV et al. |
| 10,729,443 B2 | 8/2020 | Cabrera et al. |
| 10,729,458 B2 | 8/2020 | Stoddard et al. |
| 10,729,501 B2 | 8/2020 | Leimbach et al. |
| 10,729,509 B2 | 8/2020 | Shelton, IV et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,630 B2 | 8/2020 | Huang et al. |
| 10,736,633 B2 | 8/2020 | Vendely et al. |
| 10,736,634 B2 | 8/2020 | Shelton, IV et al. |
| 10,736,636 B2 | 8/2020 | Baxter, III et al. |
| 10,736,644 B2 | 8/2020 | Windolf et al. |
| 10,736,702 B2 | 8/2020 | Harris et al. |
| 10,737,398 B2 | 8/2020 | Remirez et al. |
| 10,743,849 B2 | 8/2020 | Shelton, IV et al. |
| 10,743,850 B2 | 8/2020 | Hibner et al. |
| 10,743,851 B2 | 8/2020 | Swayze et al. |
| 10,743,868 B2 | 8/2020 | Shelton, IV et al. |
| 10,743,870 B2 | 8/2020 | Hall et al. |
| 10,743,872 B2 | 8/2020 | Leimbach et al. |
| 10,743,873 B2 | 8/2020 | Overmyer et al. |
| 10,743,874 B2 | 8/2020 | Shelton, IV et al. |
| 10,743,875 B2 | 8/2020 | Shelton, IV et al. |
| 10,743,877 B2 | 8/2020 | Shelton, IV et al. |
| 10,743,930 B2 | 8/2020 | Nagtegaal |

(56) References Cited

U.S. PATENT DOCUMENTS

| | | |
|---|---|---|
| 10,751,048 B2 | 8/2020 | Whitman et al. |
| 10,751,053 B2 | 8/2020 | Harris et al. |
| 10,751,076 B2 | 8/2020 | Laurent et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,233 B2 | 9/2020 | Scheib et al. |
| 10,758,259 B2 | 9/2020 | Demmy et al. |
| 10,765,425 B2 | 9/2020 | Yates et al. |
| 10,765,427 B2 | 9/2020 | Shelton, IV et al. |
| 10,765,429 B2 | 9/2020 | Leimbach et al. |
| 10,765,430 B2 | 9/2020 | Wixey |
| 10,765,432 B2 | 9/2020 | Moore et al. |
| 10,765,442 B2 | 9/2020 | Strobl |
| 10,772,625 B2 | 9/2020 | Shelton, IV et al. |
| 10,772,628 B2 | 9/2020 | Chen et al. |
| 10,772,629 B2 | 9/2020 | Shelton, IV et al. |
| 10,772,630 B2 | 9/2020 | Wixey |
| 10,772,631 B2 | 9/2020 | Zergiebel et al. |
| 10,772,632 B2 | 9/2020 | Kostrzewski |
| 10,772,651 B2 | 9/2020 | Shelton, IV et al. |
| 10,779,818 B2 | 9/2020 | Zemlok et al. |
| 10,779,820 B2 | 9/2020 | Harris et al. |
| 10,779,821 B2 | 9/2020 | Harris et al. |
| 10,779,822 B2 | 9/2020 | Yates et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,826 B2 | 9/2020 | Shelton, IV et al. |
| 10,779,903 B2 | 9/2020 | Wise et al. |
| 10,780,539 B2 | 9/2020 | Shelton, IV et al. |
| 10,786,248 B2 | 9/2020 | Rousseau et al. |
| 10,786,253 B2 | 9/2020 | Shelton, IV et al. |
| 10,786,255 B2 | 9/2020 | Hodgkinson et al. |
| 10,792,038 B2 | 10/2020 | Becerra et al. |
| 10,796,471 B2 | 10/2020 | Leimbach et al. |
| 10,799,240 B2 | 10/2020 | Shelton, IV et al. |
| 10,799,306 B2 | 10/2020 | Robinson et al. |
| 10,806,448 B2 | 10/2020 | Shelton, IV et al. |
| 10,806,449 B2 | 10/2020 | Shelton, IV et al. |
| 10,806,450 B2 | 10/2020 | Yates et al. |
| 10,806,451 B2 | 10/2020 | Harris et al. |
| 10,806,453 B2 | 10/2020 | Chen et al. |
| 10,806,479 B2 | 10/2020 | Shelton, IV et al. |
| 10,813,638 B2 | 10/2020 | Shelton, IV et al. |
| 10,813,639 B2 | 10/2020 | Shelton, IV et al. |
| 10,813,640 B2 | 10/2020 | Adams et al. |
| 10,813,641 B2 | 10/2020 | Setser et al. |
| 10,813,683 B2 | 10/2020 | Baxter, III et al. |
| 10,813,705 B2 | 10/2020 | Hares et al. |
| 10,813,710 B2 | 10/2020 | Grubbs |
| 10,820,939 B2 | 11/2020 | Sartor |
| 10,828,028 B2 | 11/2020 | Harris et al. |
| 10,828,030 B2 | 11/2020 | Weir et al. |
| 10,828,032 B2 | 11/2020 | Leimbach et al. |
| 10,828,033 B2 | 11/2020 | Shelton, IV et al. |
| 10,828,089 B2 | 11/2020 | Clark et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,249 B2 | 11/2020 | Schellin et al. |
| 10,835,251 B2 | 11/2020 | Shelton, IV et al. |
| 10,835,330 B2 | 11/2020 | Shelton, IV et al. |
| 10,842,357 B2 | 11/2020 | Moskowitz et al. |
| 10,842,473 B2 | 11/2020 | Scheib et al. |
| 10,842,488 B2 | 11/2020 | Swayze et al. |
| 10,842,489 B2 | 11/2020 | Shelton, IV |
| 10,842,490 B2 | 11/2020 | DiNardo et al. |
| 10,842,491 B2 | 11/2020 | Shelton, IV et al. |
| 10,842,492 B2 | 11/2020 | Shelton, IV et al. |
| D904,612 S | 12/2020 | Wynn et al. |
| D904,613 S | 12/2020 | Wynn et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,856,866 B2 | 12/2020 | Shelton, IV et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,863,981 B2 | 12/2020 | Overmyer et al. |
| 10,863,984 B2 | 12/2020 | Shelton, IV et al. |
| 10,863,986 B2 | 12/2020 | Yates et al. |
| 10,869,663 B2 | 12/2020 | Shelton, IV et al. |
| 10,869,664 B2 | 12/2020 | Shelton, IV |
| 10,869,665 B2 | 12/2020 | Shelton, IV et al. |
| 10,869,666 B2 | 12/2020 | Shelton, IV et al. |
| 10,869,669 B2 | 12/2020 | Shelton, IV et al. |
| 10,874,290 B2 | 12/2020 | Walen et al. |
| 10,874,391 B2 | 12/2020 | Shelton, IV et al. |
| 10,874,392 B2 | 12/2020 | Scirica et al. |
| 10,874,393 B2 | 12/2020 | Satti |
| 10,874,396 B2 | 12/2020 | Moore et al. |
| 10,874,399 B2 | 12/2020 | Zhang |
| 10,879,275 B2 | 12/2020 | Li et al. |
| D907,647 S | 1/2021 | Siebel et al. |
| D907,648 S | 1/2021 | Siebel et al. |
| D908,216 S | 1/2021 | Messerly et al. |
| 10,881,395 B2 | 1/2021 | Merchant et al. |
| 10,881,396 B2 | 1/2021 | Shelton, IV et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,888,318 B2 | 1/2021 | Parihar et al. |
| 10,888,321 B2 | 1/2021 | Shelton, Iv et al. |
| 10,888,322 B2 | 1/2021 | Morgan et al. |
| 10,888,323 B2 | 1/2021 | Chen et al. |
| 10,888,325 B2 | 1/2021 | Harris et al. |
| 10,888,328 B2 | 1/2021 | Shelton, IV et al. |
| 10,888,329 B2 | 1/2021 | Moore et al. |
| 10,888,330 B2 | 1/2021 | Moore et al. |
| 10,888,369 B2 | 1/2021 | Messerly et al. |
| 10,892,899 B2 | 1/2021 | Shelton, IV et al. |
| 10,893,853 B2 | 1/2021 | Shelton, IV et al. |
| 10,893,863 B2 | 1/2021 | Shelton, IV et al. |
| 10,893,864 B2 | 1/2021 | Harris et al. |
| 10,893,867 B2 | 1/2021 | Leimbach et al. |
| 10,898,183 B2 | 1/2021 | Shelton, IV et al. |
| 10,898,184 B2 | 1/2021 | Yates et al. |
| 10,898,185 B2 | 1/2021 | Overmyer et al. |
| 10,898,186 B2 | 1/2021 | Bakos et al. |
| 10,898,190 B2 | 1/2021 | Yates et al. |
| 10,898,193 B2 | 1/2021 | Shelton, IV et al. |
| 10,898,194 B2 | 1/2021 | Moore et al. |
| 10,898,195 B2 | 1/2021 | Moore et al. |
| 10,903,685 B2 | 1/2021 | Yates et al. |
| D910,847 S | 2/2021 | Shelton, IV et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,905,422 B2 | 2/2021 | Bakos et al. |
| 10,905,423 B2 | 2/2021 | Baber et al. |
| 10,905,426 B2 | 2/2021 | Moore et al. |
| 10,905,427 B2 | 2/2021 | Moore et al. |
| 10,911,515 B2 | 2/2021 | Biasi et al. |
| 10,912,559 B2 | 2/2021 | Harris et al. |
| 10,912,562 B2 | 2/2021 | Dunki-Jacobs et al. |
| 10,912,575 B2 | 2/2021 | Shelton, IV et al. |
| 10,918,364 B2 | 2/2021 | Applegate et al. |
| 10,918,380 B2 | 2/2021 | Morgan et al. |
| 10,918,385 B2 | 2/2021 | Overmyer et al. |
| 10,918,386 B2 | 2/2021 | Shelton, IV et al. |
| 10,919,156 B2 | 2/2021 | Roberts et al. |
| 10,925,600 B2 | 2/2021 | McCuen |
| 10,925,605 B2 | 2/2021 | Moore et al. |
| D914,878 S | 3/2021 | Shelton, IV et al. |
| 10,932,772 B2 | 3/2021 | Shelton, IV et al. |
| 10,932,774 B2 | 3/2021 | Shelton, IV |
| 10,932,775 B2 | 3/2021 | Shelton, IV et al. |
| 10,932,778 B2 | 3/2021 | Smith et al. |
| 10,932,779 B2 | 3/2021 | Vendely et al. |
| 10,932,784 B2 | 3/2021 | Mozdzierz et al. |

(56) References Cited

U.S. PATENT DOCUMENTS

| | | |
|---|---|---|
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,945,728 B2 | 3/2021 | Morgan et al. |
| 10,945,729 B2 | 3/2021 | Shelton, IV et al. |
| 10,945,731 B2 | 3/2021 | Baxter, III et al. |
| 10,952,708 B2 | 3/2021 | Scheib et al. |
| 10,952,726 B2 | 3/2021 | Chowaniec |
| 10,952,727 B2 | 3/2021 | Giordano et al. |
| 10,952,728 B2 | 3/2021 | Shelton, IV et al. |
| 10,952,759 B2 | 3/2021 | Messerly et al. |
| 10,952,767 B2 | 3/2021 | Kostrzewski et al. |
| 10,959,722 B2 | 3/2021 | Morgan et al. |
| 10,959,725 B2 | 3/2021 | Kerr et al. |
| 10,959,726 B2 | 3/2021 | Williams et al. |
| 10,959,727 B2 | 3/2021 | Hunter et al. |
| 10,959,731 B2 | 3/2021 | Casasanta, Jr. et al. |
| 10,959,744 B2 | 3/2021 | Shelton, IV et al. |
| 10,959,797 B2 | 3/2021 | Licht et al. |
| D917,500 S | 4/2021 | Siebel et al. |
| 10,966,627 B2 | 4/2021 | Shelton, IV et al. |
| 10,966,717 B2 | 4/2021 | Shah et al. |
| 10,966,718 B2 | 4/2021 | Shelton, IV et al. |
| 10,966,791 B2 | 4/2021 | Harris et al. |
| 10,973,515 B2 | 4/2021 | Harris et al. |
| 10,973,516 B2 | 4/2021 | Shelton, IV et al. |
| 10,973,517 B2 | 4/2021 | Wixey |
| 10,973,519 B2 | 4/2021 | Weir et al. |
| 10,973,520 B2 | 4/2021 | Shelton, IV et al. |
| 10,980,534 B2 | 4/2021 | Yates et al. |
| 10,980,535 B2 | 4/2021 | Yates et al. |
| 10,980,536 B2 | 4/2021 | Weaner et al. |
| 10,980,537 B2 | 4/2021 | Shelton, IV et al. |
| 10,980,538 B2 | 4/2021 | Nalagatla et al. |
| 10,980,539 B2 | 4/2021 | Harris et al. |
| 10,980,560 B2 | 4/2021 | Shelton, IV et al. |
| 10,983,646 B2 | 4/2021 | Yoon et al. |
| 10,987,102 B2 | 4/2021 | Gonzalez et al. |
| 10,987,178 B2 | 4/2021 | Shelton, IV et al. |
| 10,993,713 B2 | 5/2021 | Shelton, IV et al. |
| 10,993,715 B2 | 5/2021 | Shelton, IV et al. |
| 10,993,717 B2 | 5/2021 | Shelton, IV et al. |
| 11,000,274 B2 | 5/2021 | Shelton, IV et al. |
| 11,000,275 B2 | 5/2021 | Shelton, IV et al. |
| 11,000,277 B2 | 5/2021 | Giordano et al. |
| 11,005,291 B2 | 5/2021 | Calderoni |
| 11,006,951 B2 | 5/2021 | Giordano et al. |
| 11,006,955 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,511 B2 | 5/2021 | Huang et al. |
| 11,013,552 B2 | 5/2021 | Widenhouse et al. |
| 11,013,563 B2 | 5/2021 | Shelton, IV et al. |
| 11,020,016 B2 | 6/2021 | Wallace et al. |
| 11,020,113 B2 | 6/2021 | Shelton, IV et al. |
| 11,020,115 B2 | 6/2021 | Scheib et al. |
| 11,026,678 B2 | 6/2021 | Overmyer et al. |
| 11,026,680 B2 | 6/2021 | Shelton, IV et al. |
| 11,026,684 B2 | 6/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,033,267 B2 | 6/2021 | Shelton, IV et al. |
| 11,039,834 B2 | 6/2021 | Harris et al. |
| 11,039,836 B2 | 6/2021 | Shelton, IV et al. |
| 11,039,837 B2 | 6/2021 | Shelton, IV et al. |
| 11,039,849 B2 | 6/2021 | Bucciaglia et al. |
| 11,045,189 B2 | 6/2021 | Yates et al. |
| 11,045,191 B2 | 6/2021 | Shelton, IV et al. |
| 11,045,192 B2 | 6/2021 | Harris et al. |
| 11,045,196 B2 | 6/2021 | Olson et al. |
| 11,045,197 B2 | 6/2021 | Shelton, IV et al. |
| 11,045,199 B2 | 6/2021 | Mozdzierz et al. |
| 11,051,807 B2 | 7/2021 | Shelton, IV et al. |
| 11,051,810 B2 | 7/2021 | Harris et al. |
| 11,051,811 B2 | 7/2021 | Shelton, IV et al. |
| 11,051,813 B2 | 7/2021 | Shelton, IV et al. |
| 11,051,836 B2 | 7/2021 | Shelton, IV et al. |
| 11,051,840 B2 | 7/2021 | Shelton, IV et al. |
| 11,051,873 B2 | 7/2021 | Wiener et al. |
| 11,058,418 B2 | 7/2021 | Shelton, IV et al. |
| 11,058,420 B2 | 7/2021 | Shelton, IV et al. |
| 11,058,422 B2 | 7/2021 | Harris et al. |
| 11,058,423 B2 | 7/2021 | Shelton, IV et al. |
| 11,058,425 B2 | 7/2021 | Widenhouse et al. |
| 11,058,426 B2 | 7/2021 | Nalagatla et al. |
| 11,058,498 B2 | 7/2021 | Shelton, IV et al. |
| 11,064,997 B2 | 7/2021 | Shelton, IV et al. |
| 11,064,998 B2 | 7/2021 | Shelton, IV |
| 11,065,048 B2 | 7/2021 | Messerly et al. |
| 11,069,012 B2 | 7/2021 | Shelton, IV et al. |
| 11,071,542 B2 | 7/2021 | Chen et al. |
| 11,071,543 B2 | 7/2021 | Shelton, IV et al. |
| 11,071,545 B2 | 7/2021 | Baber et al. |
| 11,071,554 B2 | 7/2021 | Parfett et al. |
| 11,071,560 B2 | 7/2021 | Deck et al. |
| 11,076,853 B2 | 8/2021 | Parfett et al. |
| 11,076,854 B2 | 8/2021 | Baber et al. |
| 11,076,921 B2 | 8/2021 | Shelton, IV et al. |
| 11,076,929 B2 | 8/2021 | Shelton, IV et al. |
| 11,083,452 B2 | 8/2021 | Schmid et al. |
| 11,083,453 B2 | 8/2021 | Shelton, IV et al. |
| 11,083,454 B2 | 8/2021 | Harris et al. |
| 11,083,456 B2 | 8/2021 | Shelton, IV et al. |
| 11,083,457 B2 | 8/2021 | Shelton, IV et al. |
| 11,083,458 B2 | 8/2021 | Harris et al. |
| 11,090,045 B2 | 8/2021 | Shelton, IV |
| 11,090,046 B2 | 8/2021 | Shelton, IV et al. |
| 11,090,047 B2 | 8/2021 | Shelton, Iv et al. |
| 11,090,048 B2 | 8/2021 | Fanelli et al. |
| 11,090,075 B2 | 8/2021 | Hunter et al. |
| 11,096,688 B2 | 8/2021 | Shelton, IV et al. |
| 11,096,689 B2 | 8/2021 | Overmyer et al. |
| 11,100,631 B2 | 8/2021 | Yates et al. |
| 11,103,241 B2 | 8/2021 | Yates et al. |
| 11,103,248 B2 | 8/2021 | Shelton, IV et al. |
| 11,103,268 B2 | 8/2021 | Shelton, IV et al. |
| 11,103,269 B2 | 8/2021 | Shelton, IV et al. |
| 11,109,858 B2 | 9/2021 | Shelton, IV et al. |
| 11,109,859 B2 | 9/2021 | Overmyer et al. |
| 11,109,860 B2 | 9/2021 | Shelton, IV et al. |
| 11,109,866 B2 | 9/2021 | Shelton, IV et al. |
| 11,109,878 B2 | 9/2021 | Shelton, IV et al. |
| 11,109,925 B2 | 9/2021 | Cooper et al. |
| 11,116,485 B2 | 9/2021 | Scheib et al. |
| 11,116,502 B2 | 9/2021 | Shelton, IV et al. |
| 11,116,594 B2 | 9/2021 | Beardsley |
| 11,123,069 B2 | 9/2021 | Baxter, III et al. |
| 11,123,070 B2 | 9/2021 | Shelton, IV et al. |
| 11,129,611 B2 | 9/2021 | Shelton, IV et al. |
| 11,129,613 B2 | 9/2021 | Harris et al. |
| 11,129,615 B2 | 9/2021 | Scheib et al. |
| 11,129,616 B2 | 9/2021 | Shelton, IV et al. |
| 11,129,634 B2 | 9/2021 | Scheib et al. |
| 11,129,636 B2 | 9/2021 | Shelton, IV et al. |
| 11,129,666 B2 | 9/2021 | Messerly et al. |
| 11,129,680 B2 | 9/2021 | Shelton, IV et al. |
| 11,132,462 B2 | 9/2021 | Shelton, IV et al. |
| 11,133,106 B2 | 9/2021 | Shelton, IV et al. |
| 11,134,938 B2 | 10/2021 | Timm et al. |
| 11,134,940 B2 | 10/2021 | Shelton, IV et al. |
| 11,134,942 B2 | 10/2021 | Harris et al. |
| 11,134,943 B2 | 10/2021 | Giordano et al. |
| 11,134,944 B2 | 10/2021 | Wise et al. |
| 11,134,947 B2 | 10/2021 | Shelton, IV et al. |
| 11,135,352 B2 | 10/2021 | Shelton, IV et al. |
| 11,141,153 B2 | 10/2021 | Shelton, IV et al. |
| 11,141,155 B2 | 10/2021 | Shelton, IV |
| 11,141,156 B2 | 10/2021 | Shelton, IV |
| 11,141,159 B2 | 10/2021 | Scheib et al. |
| 11,141,160 B2 | 10/2021 | Shelton, IV et al. |

(56) References Cited

U.S. PATENT DOCUMENTS

| | | |
|---|---|---|
| 11,147,547 B2 | 10/2021 | Shelton, IV et al. |
| 11,147,549 B2 | 10/2021 | Timm et al. |
| 11,147,551 B2 | 10/2021 | Shelton, IV |
| 11,147,553 B2 | 10/2021 | Shelton, IV |
| 11,147,554 B2 | 10/2021 | Aronhalt et al. |
| 11,154,296 B2 | 10/2021 | Aronhalt et al. |
| 11,154,297 B2 | 10/2021 | Swayze et al. |
| 11,154,298 B2 | 10/2021 | Timm et al. |
| 11,154,299 B2 | 10/2021 | Shelton, IV et al. |
| 11,154,300 B2 | 10/2021 | Nalagatla et al. |
| 11,154,301 B2 | 10/2021 | Beckman et al. |
| 11,160,551 B2 | 11/2021 | Shelton, IV et al. |
| 11,160,553 B2 | 11/2021 | Simms et al. |
| 11,160,601 B2 | 11/2021 | Worrell et al. |
| 11,166,716 B2 | 11/2021 | Shelton, IV et al. |
| 11,166,717 B2 | 11/2021 | Shelton, IV et al. |
| 11,166,720 B2 | 11/2021 | Giordano et al. |
| 11,166,772 B2 | 11/2021 | Shelton, IV et al. |
| 11,166,773 B2 | 11/2021 | Ragosta et al. |
| 11,172,580 B2 | 11/2021 | Gaertner, II |
| 11,172,927 B2 | 11/2021 | Shelton, IV |
| 11,172,929 B2 | 11/2021 | Shelton, IV |
| 11,179,150 B2 | 11/2021 | Yates et al. |
| 11,179,151 B2 | 11/2021 | Shelton, IV et al. |
| 11,179,152 B2 | 11/2021 | Morgan et al. |
| 11,179,153 B2 | 11/2021 | Shelton, IV |
| 11,179,155 B2 | 11/2021 | Shelton, IV et al. |
| 11,179,208 B2 | 11/2021 | Yates et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,191,543 B2 | 12/2021 | Overmyer et al. |
| 11,191,545 B2 | 12/2021 | Vendely et al. |
| 11,197,668 B2 | 12/2021 | Shelton, IV et al. |
| 11,197,670 B2 | 12/2021 | Shelton, IV et al. |
| 11,197,671 B2 | 12/2021 | Shelton, IV et al. |
| 11,197,672 B2 | 12/2021 | Dunki-Jacobs et al. |
| 11,202,570 B2 | 12/2021 | Shelton, IV et al. |
| 11,202,631 B2 | 12/2021 | Shelton, IV et al. |
| 11,202,633 B2 | 12/2021 | Harris et al. |
| 11,207,064 B2 | 12/2021 | Shelton, IV et al. |
| 11,207,065 B2 | 12/2021 | Harris et al. |
| 11,207,067 B2 | 12/2021 | Shelton, IV et al. |
| 11,207,089 B2 | 12/2021 | Kostrzewski et al. |
| 11,207,090 B2 | 12/2021 | Shelton, IV et al. |
| 11,207,146 B2 | 12/2021 | Shelton, IV et al. |
| 11,213,293 B2 | 1/2022 | Worthington et al. |
| 11,213,294 B2 | 1/2022 | Shelton, IV et al. |
| 11,213,302 B2 | 1/2022 | Parfett et al. |
| 11,213,359 B2 | 1/2022 | Shelton, IV et al. |
| 11,219,453 B2 | 1/2022 | Shelton, IV et al. |
| 11,219,455 B2 | 1/2022 | Shelton, IV et al. |
| 11,224,423 B2 | 1/2022 | Shelton, IV et al. |
| 11,224,426 B2 | 1/2022 | Shelton, IV et al. |
| 11,224,427 B2 | 1/2022 | Shelton, IV et al. |
| 11,224,428 B2 | 1/2022 | Scott et al. |
| 11,224,454 B2 | 1/2022 | Shelton, IV et al. |
| 11,224,497 B2 | 1/2022 | Shelton, IV et al. |
| 11,229,436 B2 | 1/2022 | Shelton, IV et al. |
| 11,229,437 B2 | 1/2022 | Shelton, IV et al. |
| 11,234,698 B2 | 2/2022 | Shelton, IV et al. |
| 11,234,700 B2 | 2/2022 | Ragosta et al. |
| 11,241,229 B2 | 2/2022 | Shelton, IV et al. |
| 11,241,230 B2 | 2/2022 | Shelton, IV et al. |
| 11,241,235 B2 | 2/2022 | Shelton, IV et al. |
| 11,246,590 B2 | 2/2022 | Swayze et al. |
| 11,246,616 B2 | 2/2022 | Shelton, IV et al. |
| 11,246,618 B2 | 2/2022 | Hall et al. |
| 11,246,678 B2 | 2/2022 | Shelton, IV et al. |
| 11,253,254 B2 | 2/2022 | Kimball et al. |
| 11,253,256 B2 | 2/2022 | Harris et al. |
| 11,259,799 B2 | 3/2022 | Overmyer et al. |
| 11,259,803 B2 | 3/2022 | Shelton, IV et al. |
| 11,259,807 B2 | 3/2022 | Shelton, IV et al. |
| 11,266,406 B2 | 3/2022 | Leimbach et al. |
| 11,266,409 B2 | 3/2022 | Huitema et al. |
| 11,266,410 B2 | 3/2022 | Shelton, IV et al. |
| 11,266,468 B2 | 3/2022 | Shelton, IV et al. |
| 11,272,927 B2 | 3/2022 | Swayze et al. |
| 11,272,928 B2 | 3/2022 | Shelton, IV |
| 11,272,931 B2 | 3/2022 | Boudreaux et al. |
| 11,272,938 B2 | 3/2022 | Shelton, IV et al. |
| 11,278,279 B2 | 3/2022 | Morgan et al. |
| 11,278,280 B2 | 3/2022 | Shelton, IV et al. |
| 11,278,284 B2 | 3/2022 | Shelton, IV et al. |
| 11,284,890 B2 | 3/2022 | Nalagatla et al. |
| 11,284,891 B2 | 3/2022 | Shelton, IV et al. |
| 11,284,898 B2 | 3/2022 | Baxter, III et al. |
| 11,284,953 B2 | 3/2022 | Shelton, IV et al. |
| 11,291,440 B2 | 4/2022 | Harris et al. |
| 11,291,441 B2 | 4/2022 | Giordano et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,449 B2 | 4/2022 | Swensgard et al. |
| 11,291,451 B2 | 4/2022 | Shelton, IV |
| 11,291,465 B2 | 4/2022 | Parihar et al. |
| 11,291,510 B2 | 4/2022 | Shelton, IV et al. |
| 11,298,125 B2 | 4/2022 | Ming et al. |
| 11,298,127 B2 | 4/2022 | Shelton, IV |
| 11,298,128 B2 | 4/2022 | Messerly et al. |
| 11,298,129 B2 | 4/2022 | Bakos et al. |
| 11,298,130 B2 | 4/2022 | Bakos et al. |
| 11,298,132 B2 | 4/2022 | Shelton, IV et al. |
| 11,298,134 B2 | 4/2022 | Huitema et al. |
| 11,304,695 B2 | 4/2022 | Shelton, IV et al. |
| 11,304,696 B2 | 4/2022 | Shelton, Iv et al. |
| 11,304,697 B2 | 4/2022 | Fanelli et al. |
| 11,304,699 B2 | 4/2022 | Shelton, IV et al. |
| 11,304,704 B2 | 4/2022 | Thomas et al. |
| 11,311,290 B2 | 4/2022 | Shelton, IV et al. |
| 11,311,292 B2 | 4/2022 | Shelton, IV et al. |
| 11,311,294 B2 | 4/2022 | Swayze et al. |
| 11,311,295 B2 | 4/2022 | Wingardner et al. |
| 11,311,342 B2 | 4/2022 | Parihar et al. |
| D950,728 S | 5/2022 | Bakos et al. |
| D952,144 S | 5/2022 | Boudreaux |
| 11,317,910 B2 | 5/2022 | Miller et al. |
| 11,317,912 B2 | 5/2022 | Jenkins et al. |
| 11,317,913 B2 | 5/2022 | Shelton, IV et al. |
| 11,317,915 B2 | 5/2022 | Boudreaux et al. |
| 11,317,917 B2 | 5/2022 | Shelton, IV et al. |
| 11,317,919 B2 | 5/2022 | Shelton, IV et al. |
| 11,317,978 B2 | 5/2022 | Cameron et al. |
| 11,324,501 B2 | 5/2022 | Shelton, IV et al. |
| 11,324,506 B2 | 5/2022 | Beckman et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,691 B2 | 5/2022 | Widenhouse et al. |
| 11,337,693 B2 | 5/2022 | Hess et al. |
| 11,337,698 B2 | 5/2022 | Baxter, III et al. |
| 11,344,299 B2 | 5/2022 | Yates et al. |
| 11,344,303 B2 | 5/2022 | Shelton, IV et al. |
| 11,350,843 B2 | 6/2022 | Shelton, IV et al. |
| 11,350,916 B2 | 6/2022 | Shelton, IV et al. |
| 11,350,928 B2 | 6/2022 | Shelton, IV et al. |
| 11,350,929 B2 | 6/2022 | Giordano et al. |
| 11,350,932 B2 | 6/2022 | Shelton, IV et al. |
| 11,350,934 B2 | 6/2022 | Bakos et al. |
| 11,350,935 B2 | 6/2022 | Shelton, IV et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,364,027 B2 | 6/2022 | Harris et al. |
| 11,364,046 B2 | 6/2022 | Shelton, IV et al. |
| 11,369,368 B2 | 6/2022 | Shelton, IV et al. |
| 11,369,376 B2 | 6/2022 | Simms et al. |
| 11,369,377 B2 | 6/2022 | Boudreaux et al. |
| 11,373,755 B2 | 6/2022 | Shelton, IV et al. |
| 11,376,001 B2 | 7/2022 | Shelton, IV et al. |
| 11,376,082 B2 | 7/2022 | Shelton, IV et al. |
| 11,376,098 B2 | 7/2022 | Shelton, IV et al. |

(56) References Cited

U.S. PATENT DOCUMENTS

| | | |
|---|---|---|
| 11,382,625 B2 | 7/2022 | Huitema et al. |
| 11,382,626 B2 | 7/2022 | Shelton, IV et al. |
| 11,382,627 B2 | 7/2022 | Huitema et al. |
| 11,382,628 B2 | 7/2022 | Baxter, III et al. |
| 11,382,638 B2 | 7/2022 | Harris et al. |
| 11,382,697 B2 | 7/2022 | Shelton, IV et al. |
| 11,389,160 B2 | 7/2022 | Shelton, IV et al. |
| 11,389,162 B2 | 7/2022 | Baber et al. |
| 11,389,164 B2 | 7/2022 | Yates et al. |
| 11,395,651 B2 | 7/2022 | Shelton, IV et al. |
| 11,395,652 B2 | 7/2022 | Parihar et al. |
| 11,399,828 B2 | 8/2022 | Swayze et al. |
| 11,399,829 B2 | 8/2022 | Leimbach et al. |
| 11,399,831 B2 | 8/2022 | Overmyer et al. |
| 11,399,837 B2 | 8/2022 | Shelton, IV et al. |
| 11,406,377 B2 | 8/2022 | Schmid et al. |
| 11,406,378 B2 | 8/2022 | Baxter, III et al. |
| 11,406,380 B2 | 8/2022 | Yates et al. |
| 11,406,381 B2 | 8/2022 | Parihar et al. |
| 11,406,382 B2 | 8/2022 | Shelton, IV et al. |
| 11,406,386 B2 | 8/2022 | Baber et al. |
| 11,406,390 B2 | 8/2022 | Shelton, IV et al. |
| 11,410,259 B2 | 8/2022 | Harris et al. |
| 11,413,042 B2 | 8/2022 | Shelton, IV et al. |
| 11,413,102 B2 | 8/2022 | Shelton, IV et al. |
| 11,419,606 B2 | 8/2022 | Overmyer et al. |
| 11,419,630 B2 | 8/2022 | Yates et al. |
| 11,424,027 B2 | 8/2022 | Shelton, IV |
| 11,426,160 B2 | 8/2022 | Shelton, IV et al. |
| 11,426,167 B2 | 8/2022 | Shelton, IV et al. |
| 11,426,251 B2 | 8/2022 | Kimball et al. |
| 11,432,816 B2 | 9/2022 | Leimbach et al. |
| 11,432,885 B2 | 9/2022 | Shelton, IV et al. |
| 11,439,391 B2 | 9/2022 | Bruns et al. |
| 11,439,470 B2 | 9/2022 | Spivey et al. |
| 11,446,029 B2 | 9/2022 | Shelton, IV et al. |
| 11,446,034 B2 | 9/2022 | Shelton, IV et al. |
| 11,452,528 B2 | 9/2022 | Leimbach et al. |
| D966,512 S | 10/2022 | Shelton, IV et al. |
| D967,421 S | 10/2022 | Shelton, IV et al. |
| 11,457,918 B2 | 10/2022 | Shelton, IV et al. |
| 11,464,511 B2 | 10/2022 | Timm et al. |
| 11,464,512 B2 | 10/2022 | Shelton, IV et al. |
| 11,464,513 B2 | 10/2022 | Shelton, IV et al. |
| 11,464,514 B2 | 10/2022 | Yates et al. |
| 11,464,601 B2 | 10/2022 | Shelton, IV et al. |
| 11,471,155 B2 | 10/2022 | Shelton, IV et al. |
| 11,471,156 B2 | 10/2022 | Shelton, IV et al. |
| 11,471,157 B2 | 10/2022 | Baxter, III et al. |
| 11,478,241 B2 | 10/2022 | Shelton, IV et al. |
| 11,478,244 B2 | 10/2022 | DiNardo et al. |
| D971,232 S | 11/2022 | Siebel et al. |
| 11,484,307 B2 | 11/2022 | Hall et al. |
| 11,484,309 B2 | 11/2022 | Harris et al. |
| 11,484,311 B2 | 11/2022 | Shelton, IV et al. |
| 11,484,312 B2 | 11/2022 | Shelton, IV et al. |
| 11,490,889 B2 | 11/2022 | Overmyer et al. |
| 11,497,488 B2 | 11/2022 | Leimbach et al. |
| 11,497,489 B2 | 11/2022 | Baxter, III et al. |
| 11,497,492 B2 | 11/2022 | Shelton, IV |
| 11,497,499 B2 | 11/2022 | Shelton, IV et al. |
| 11,504,116 B2 | 11/2022 | Schmid et al. |
| 11,504,119 B2 | 11/2022 | Shelton, IV et al. |
| 11,504,122 B2 | 11/2022 | Shelton, IV et al. |
| 11,504,192 B2 | 11/2022 | Shelton, IV et al. |
| 11,510,671 B2 | 11/2022 | Shelton, IV et al. |
| 11,510,741 B2 | 11/2022 | Shelton, IV et al. |
| 11,517,304 B2 | 12/2022 | Yates et al. |
| 11,517,306 B2 | 12/2022 | Miller et al. |
| 11,517,309 B2 | 12/2022 | Bakos et al. |
| 11,517,311 B2 | 12/2022 | Lytle, IV et al. |
| 11,517,315 B2 | 12/2022 | Huitema et al. |
| 11,517,325 B2 | 12/2022 | Shelton, IV et al. |
| 11,517,390 B2 | 12/2022 | Baxter, III |
| 11,523,821 B2 | 12/2022 | Harris et al. |
| 11,523,822 B2 | 12/2022 | Shelton, IV et al. |
| 11,523,823 B2 | 12/2022 | Hunter et al. |
| 11,529,137 B2 | 12/2022 | Shelton, IV et al. |
| 11,529,138 B2 | 12/2022 | Jaworek et al. |
| 11,529,139 B2 | 12/2022 | Shelton, IV et al. |
| 11,529,140 B2 | 12/2022 | Shelton, IV et al. |
| 11,529,142 B2 | 12/2022 | Leimbach et al. |
| 11,534,162 B2 | 12/2022 | Shelton, IV |
| 11,534,259 B2 | 12/2022 | Leimbach et al. |
| D974,560 S | 1/2023 | Shelton, IV et al. |
| D975,278 S | 1/2023 | Shelton, IV et al. |
| D975,850 S | 1/2023 | Shelton, IV et al. |
| D975,851 S | 1/2023 | Shelton, IV et al. |
| 11,540,824 B2 | 1/2023 | Shelton, IV et al. |
| 11,540,829 B2 | 1/2023 | Shelton, IV et al. |
| 11,547,403 B2 | 1/2023 | Shelton, IV et al. |
| 11,547,404 B2 | 1/2023 | Shelton, IV et al. |
| 11,553,911 B2 | 1/2023 | Shelton, IV et al. |
| 11,553,916 B2 | 1/2023 | Vendely et al. |
| 11,553,919 B2 | 1/2023 | Shelton, IV et al. |
| 11,553,971 B2 | 1/2023 | Shelton, IV et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0030219 A1 | 10/2001 | Green et al. |
| 2001/0034530 A1 | 10/2001 | Malackowski et al. |
| 2001/0045442 A1 | 11/2001 | Whitman |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0023126 A1 | 2/2002 | Flavin |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0054158 A1 | 5/2002 | Asami |
| 2002/0082612 A1 | 6/2002 | Moll et al. |
| 2002/0087048 A1 | 7/2002 | Brock et al. |
| 2002/0087148 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0111621 A1 | 8/2002 | Wallace et al. |
| 2002/0111624 A1 | 8/2002 | Witt et al. |
| 2002/0116063 A1 | 8/2002 | Giannetti et al. |
| 2002/0117533 A1 | 8/2002 | Milliman et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0138086 A1 | 9/2002 | Sixto et al. |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0161277 A1 | 10/2002 | Boone et al. |
| 2002/0177848 A1 | 11/2002 | Truckai et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0018323 A1 | 1/2003 | Wallace et al. |
| 2003/0028236 A1 | 2/2003 | Gillick et al. |
| 2003/0040670 A1 | 2/2003 | Govari |
| 2003/0045835 A1 | 3/2003 | Anderson et al. |
| 2003/0047230 A1 | 3/2003 | Kim |
| 2003/0047582 A1 | 3/2003 | Sonnenschein et al. |
| 2003/0050628 A1 | 3/2003 | Whitman et al. |
| 2003/0050654 A1 | 3/2003 | Whitman et al. |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0105475 A1 | 6/2003 | Sancoff et al. |

(56) References Cited

U.S. PATENT DOCUMENTS

| | | |
|---|---|---|
| 2003/0114851 A1 | 6/2003 | Truckai et al. |
| 2003/0121586 A1 | 7/2003 | Mitra et al. |
| 2003/0135204 A1 | 7/2003 | Lee et al. |
| 2003/0139741 A1 | 7/2003 | Goble et al. |
| 2003/0144660 A1 | 7/2003 | Mollenauer |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0163029 A1 | 8/2003 | Sonnenschein et al. |
| 2003/0163085 A1 | 8/2003 | Tanner et al. |
| 2003/0164172 A1 | 9/2003 | Chumas et al. |
| 2003/0181800 A1 | 9/2003 | Bonutti |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034287 A1 | 2/2004 | Hickle |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092992 A1 | 5/2004 | Adams et al. |
| 2004/0093020 A1 | 5/2004 | Sinton |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0231870 A1 | 11/2004 | McCormick et al. |
| 2004/0232201 A1 | 11/2004 | Wenchell et al. |
| 2004/0236352 A1 | 11/2004 | Wang et al. |
| 2004/0239582 A1 | 12/2004 | Seymour |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254680 A1 | 12/2004 | Sunaoshi |
| 2004/0260315 A1 | 12/2004 | Deli et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0023325 A1 | 2/2005 | Gresham et al. |
| 2005/0032511 A1 | 2/2005 | Malone et al. |
| 2005/0033352 A1 | 2/2005 | Zepf et al. |
| 2005/0044489 A1 | 2/2005 | Yamagami et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0067548 A1 | 3/2005 | Inoue |
| 2005/0070929 A1 | 3/2005 | Dalessandro et al. |
| 2005/0075561 A1 | 4/2005 | Golden |
| 2005/0079088 A1 | 4/2005 | Wirth et al. |
| 2005/0080342 A1 | 4/2005 | Gilreath et al. |
| 2005/0085693 A1 | 4/2005 | Belson et al. |
| 2005/0085838 A1 | 4/2005 | Thompson et al. |
| 2005/0090709 A1 | 4/2005 | Okada et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0120836 A1 | 6/2005 | Anderson |
| 2005/0124855 A1 | 6/2005 | Jaffe et al. |
| 2005/0125897 A1 | 6/2005 | Wyslucha et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0145672 A1 | 7/2005 | Schwemberger et al. |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0191936 A1 | 9/2005 | Marine et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0242950 A1 | 11/2005 | Lindsay et al. |
| 2005/0245965 A1 | 11/2005 | Orban, III et al. |

(56) References Cited

U.S. PATENT DOCUMENTS

| | | |
|---|---|---|
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0256546 A1 | 11/2005 | Vaisnys et al. |
| 2005/0258963 A1 | 11/2005 | Rodriguez et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0267464 A1 | 12/2005 | Truckai et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |
| 2006/0008787 A1 | 1/2006 | Hayman et al. |
| 2006/0011698 A1 | 1/2006 | Okada et al. |
| 2006/0015009 A1 | 1/2006 | Jaffe et al. |
| 2006/0020167 A1 | 1/2006 | Sitzmann |
| 2006/0020258 A1 | 1/2006 | Strauss et al. |
| 2006/0020272 A1 | 1/2006 | Gildenberg |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0226957 A1 | 10/2006 | Miller et al. |
| 2006/0235368 A1 | 10/2006 | Oz |
| 2006/0241666 A1 | 10/2006 | Briggs et al. |
| 2006/0244460 A1 | 11/2006 | Weaver |
| 2006/0247584 A1 | 11/2006 | Sheetz et al. |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289600 A1 | 12/2006 | Wales et al. |
| 2006/0289602 A1 | 12/2006 | Wales et al. |
| 2006/0291981 A1 | 12/2006 | Viola et al. |
| 2007/0005045 A1 | 1/2007 | Mintz et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043338 A1 | 2/2007 | Moll et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0055305 A1 | 3/2007 | Schnyder et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0103437 A1 | 5/2007 | Rosenberg |
| 2007/0106113 A1 | 5/2007 | Ravo |
| 2007/0106317 A1 | 5/2007 | Shelton et al. |
| 2007/0118115 A1 | 5/2007 | Artale et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0152829 A1 | 7/2007 | Lindsay et al. |
| 2007/0155010 A1 | 7/2007 | Farnsworth et al. |
| 2007/0162056 A1 | 7/2007 | Gerbi et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0173872 A1 | 7/2007 | Neuenfeldt |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0191915 A1 | 8/2007 | Strother et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0221701 A1 | 9/2007 | Ortiz et al. |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0244496 A1 | 10/2007 | Hellenkamp |
| 2007/0246505 A1 | 10/2007 | Pace-Floridia et al. |
| 2007/0260132 A1 | 11/2007 | Sterling |
| 2007/0260242 A1 | 11/2007 | Dycus et al. |
| 2007/0262592 A1 | 11/2007 | Hwang et al. |
| 2007/0270660 A1 | 11/2007 | Caylor et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |

(56) References Cited

U.S. PATENT DOCUMENTS

| | | |
|---|---|---|
| 2007/0290027 A1 | 12/2007 | Maatta et al. |
| 2007/0296286 A1 | 12/2007 | Avenell |
| 2008/0000941 A1 | 1/2008 | Sonnenschein et al. |
| 2008/0003196 A1 | 1/2008 | Jonn et al. |
| 2008/0007237 A1 | 1/2008 | Nagashima et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0046000 A1 | 2/2008 | Lee et al. |
| 2008/0051833 A1 | 2/2008 | Gramuglia et al. |
| 2008/0064920 A1 | 3/2008 | Bakos et al. |
| 2008/0064921 A1 | 3/2008 | Larkin et al. |
| 2008/0065153 A1 | 3/2008 | Allard et al. |
| 2008/0069736 A1 | 3/2008 | Mingerink et al. |
| 2008/0071328 A1 | 3/2008 | Haubrich et al. |
| 2008/0077158 A1 | 3/2008 | Haider et al. |
| 2008/0078802 A1 | 4/2008 | Hess et al. |
| 2008/0081948 A1 | 4/2008 | Weisenburgh et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0083811 A1 | 4/2008 | Marczyk |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0126984 A1 | 5/2008 | Fleishman et al. |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0149682 A1 | 6/2008 | Uhm |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0208058 A1 | 8/2008 | Sabata et al. |
| 2008/0216704 A1 | 9/2008 | Eisenbeis et al. |
| 2008/0234709 A1 | 9/2008 | Houser |
| 2008/0234866 A1 | 9/2008 | Kishi et al. |
| 2008/0242939 A1 | 10/2008 | Johnston |
| 2008/0243088 A1 | 10/2008 | Evans |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0255420 A1 | 10/2008 | Lee et al. |
| 2008/0255421 A1 | 10/2008 | Hegeman et al. |
| 2008/0255663 A1 | 10/2008 | Akpek et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0281332 A1 | 11/2008 | Taylor |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0296347 A1 | 12/2008 | Shelton, IV et al. |
| 2008/0297287 A1 | 12/2008 | Shachar et al. |
| 2008/0298784 A1 | 12/2008 | Kastner |
| 2008/0308504 A1 | 12/2008 | Hallan et al. |
| 2008/0308602 A1 | 12/2008 | Timm et al. |
| 2008/0308603 A1 | 12/2008 | Shelton et al. |
| 2008/0308607 A1 | 12/2008 | Timm et al. |
| 2008/0308807 A1 | 12/2008 | Yamazaki et al. |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0007014 A1 | 1/2009 | Coomer et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0110533 A1 | 4/2009 | Jinno |
| 2009/0112234 A1 | 4/2009 | Crainich et al. |
| 2009/0114701 A1 | 5/2009 | Zemlok et al. |
| 2009/0118762 A1 | 5/2009 | Crainch et al. |
| 2009/0119011 A1 | 5/2009 | Kondo et al. |
| 2009/0120994 A1 | 5/2009 | Murray et al. |
| 2009/0131819 A1 | 5/2009 | Ritchie et al. |
| 2009/0132400 A1 | 5/2009 | Conway |
| 2009/0135280 A1 | 5/2009 | Johnston et al. |
| 2009/0138003 A1 | 5/2009 | Deville et al. |
| 2009/0143797 A1 | 6/2009 | Smith et al. |
| 2009/0143855 A1 | 6/2009 | Weber et al. |
| 2009/0149871 A9 | 6/2009 | Kagan et al. |
| 2009/0167548 A1 | 7/2009 | Sugahara |
| 2009/0171147 A1 | 7/2009 | Lee et al. |
| 2009/0177218 A1 | 7/2009 | Young et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0204126 A1 | 8/2009 | Le |
| 2009/0204925 A1 | 8/2009 | Bhat et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0248100 A1 | 10/2009 | Vaisnys et al. |
| 2009/0253959 A1 | 10/2009 | Yoshie et al. |
| 2009/0255974 A1 | 10/2009 | Viola |
| 2009/0261141 A1 | 10/2009 | Stratton et al. |

(56) References Cited

U.S. PATENT DOCUMENTS

| | | |
|---|---|---|
| 2009/0262078 A1 | 10/2009 | Pizzi |
| 2009/0270895 A1 | 10/2009 | Churchill et al. |
| 2009/0273353 A1 | 11/2009 | Kroh et al. |
| 2009/0277288 A1 | 11/2009 | Doepker et al. |
| 2009/0278406 A1 | 11/2009 | Hoffman |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0325859 A1 | 12/2009 | Ameer et al. |
| 2010/0002013 A1 | 1/2010 | Kagaya |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016853 A1 | 1/2010 | Burbank |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0030239 A1 | 2/2010 | Viola et al. |
| 2010/0032179 A1 | 2/2010 | Hanspers et al. |
| 2010/0036370 A1 | 2/2010 | Mirel et al. |
| 2010/0036441 A1 | 2/2010 | Procter |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069833 A1 | 3/2010 | Wenderow et al. |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094312 A1 | 4/2010 | Ruiz Morales et al. |
| 2010/0094340 A1 | 4/2010 | Stopek et al. |
| 2010/0094400 A1 | 4/2010 | Bolduc et al. |
| 2010/0100123 A1 | 4/2010 | Bennett |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0125786 A1 | 5/2010 | Ozawa et al. |
| 2010/0133317 A1 | 6/2010 | Shelton, IV et al. |
| 2010/0137990 A1 | 6/2010 | Apatsidis et al. |
| 2010/0138659 A1 | 6/2010 | Carmichael et al. |
| 2010/0145146 A1 | 6/2010 | Melder |
| 2010/0147921 A1 | 6/2010 | Olson |
| 2010/0147922 A1 | 6/2010 | Olson |
| 2010/0159435 A1 | 6/2010 | Mueller et al. |
| 2010/0168741 A1 | 7/2010 | Sanai et al. |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0194541 A1 | 8/2010 | Stevenson et al. |
| 2010/0198159 A1 | 8/2010 | Voss et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0228250 A1 | 9/2010 | Brogna |
| 2010/0234687 A1 | 9/2010 | Azarbarzin et al. |
| 2010/0241137 A1 | 9/2010 | Doyle et al. |
| 2010/0245102 A1 | 9/2010 | Yokoi |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0291184 A1 | 11/2010 | Clark et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0325568 A1 | 12/2010 | Pedersen et al. |
| 2010/0327041 A1 | 12/2010 | Milliman et al. |
| 2010/0331856 A1 | 12/2010 | Carlson et al. |
| 2011/0006101 A1 | 1/2011 | Hall et al. |
| 2011/0009694 A1 | 1/2011 | Schultz et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0028991 A1 | 2/2011 | Ikeda et al. |
| 2011/0029270 A1 | 2/2011 | Mueglitz |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0056717 A1 | 3/2011 | Herisse |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0095067 A1 | 4/2011 | Ohdaira |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0118708 A1 | 5/2011 | Burbank et al. |
| 2011/0118754 A1 | 5/2011 | Dachs, II et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0220381 A1 | 9/2011 | Friese et al. |
| 2011/0224543 A1 | 9/2011 | Johnson et al. |
| 2011/0225105 A1 | 9/2011 | Scholer et al. |
| 2011/0230713 A1 | 9/2011 | Kleemann et al. |
| 2011/0235168 A1 | 9/2011 | Sander |
| 2011/0238044 A1 | 9/2011 | Main et al. |
| 2011/0241597 A1 | 10/2011 | Zhu et al. |
| 2011/0251606 A1 | 10/2011 | Kerr |
| 2011/0256266 A1 | 10/2011 | Orme et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278035 A1 | 11/2011 | Chen |
| 2011/0278343 A1 | 11/2011 | Knodel et al. |
| 2011/0279268 A1 | 11/2011 | Konishi et al. |
| 2011/0285507 A1 | 11/2011 | Nelson |
| 2011/0290856 A1 | 12/2011 | Shelton, IV et al. |
| 2011/0290858 A1 | 12/2011 | Whitman et al. |
| 2011/0292258 A1 | 12/2011 | Adler et al. |
| 2011/0293690 A1 | 12/2011 | Griffin et al. |
| 2011/0295295 A1 | 12/2011 | Shelton, IV et al. |
| 2011/0295299 A1 | 12/2011 | Braithwaite et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0008880 A1 | 1/2012 | Toth |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |

(56) References Cited

U.S. PATENT DOCUMENTS

| | | |
|---|---|---|
| 2012/0029550 A1 | 2/2012 | Forsell |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080491 A1 | 4/2012 | Shelton, IV et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0143175 A1 | 6/2012 | Hermann et al. |
| 2012/0171539 A1 | 7/2012 | Rejman et al. |
| 2012/0175398 A1 | 7/2012 | Sandborn et al. |
| 2012/0190964 A1 | 7/2012 | Hyde et al. |
| 2012/0197239 A1 | 8/2012 | Smith et al. |
| 2012/0197272 A1 | 8/2012 | Oray et al. |
| 2012/0203213 A1 | 8/2012 | Kimball et al. |
| 2012/0211542 A1 | 8/2012 | Racenet |
| 2012/0220990 A1 | 8/2012 | McKenzie et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0241494 A1 | 9/2012 | Marczyk |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0256494 A1 | 10/2012 | Kesler et al. |
| 2012/0271327 A1 | 10/2012 | West et al. |
| 2012/0283707 A1 | 11/2012 | Giordano et al. |
| 2012/0286019 A1 | 11/2012 | Hueil et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0296316 A1 | 11/2012 | Imuta |
| 2012/0296342 A1 | 11/2012 | Haglund Wendelschafer |
| 2012/0298722 A1 | 11/2012 | Hess et al. |
| 2012/0301498 A1 | 11/2012 | Altreuter et al. |
| 2012/0310254 A1 | 12/2012 | Manzo et al. |
| 2012/0316424 A1 | 12/2012 | Stopek |
| 2012/0330329 A1 | 12/2012 | Harris et al. |
| 2013/0006227 A1 | 1/2013 | Takash I No |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0069088 A1 | 3/2013 | Speck et al. |
| 2013/0075447 A1 | 3/2013 | Weisenburgh, II et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0106352 A1 | 5/2013 | Nagamine |
| 2013/0112729 A1 | 5/2013 | Beardsley et al. |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153639 A1 | 6/2013 | Hodgkinson et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172713 A1 | 7/2013 | Kirschenman |
| 2013/0172878 A1 | 7/2013 | Smith |
| 2013/0175315 A1 | 7/2013 | Milliman |
| 2013/0175317 A1 | 7/2013 | Yates et al. |
| 2013/0183769 A1 | 7/2013 | Tajima |
| 2013/0211244 A1 | 8/2013 | Nathaniel |
| 2013/0214025 A1 | 8/2013 | Zemlok et al. |
| 2013/0215449 A1 | 8/2013 | Yamasaki |
| 2013/0231681 A1 | 9/2013 | Robinson et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267950 A1 | 10/2013 | Rosa et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0284792 A1 | 10/2013 | Ma |
| 2013/0289565 A1 | 10/2013 | Hassler, Jr. |
| 2013/0293353 A1 | 11/2013 | McPherson et al. |
| 2013/0303845 A1 | 11/2013 | Skula et al. |
| 2013/0306704 A1 | 11/2013 | Balbierz et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0002322 A1 | 1/2014 | Kanome et al. |
| 2014/0005550 A1 | 1/2014 | Lu et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0008289 A1 | 1/2014 | Williams et al. |
| 2014/0014704 A1 | 1/2014 | Onukuri et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0022283 A1 | 1/2014 | Chan et al. |
| 2014/0039549 A1 | 2/2014 | Belsky et al. |
| 2014/0041191 A1 | 2/2014 | Knodel |
| 2014/0048580 A1 | 2/2014 | Merchant et al. |
| 2014/0069240 A1 | 3/2014 | Dauvin et al. |
| 2014/0078715 A1 | 3/2014 | Pickard et al. |
| 2014/0081176 A1 | 3/2014 | Hassan |
| 2014/0088614 A1 | 3/2014 | Blumenkranz |
| 2014/0094681 A1 | 4/2014 | Valentine et al. |
| 2014/0100558 A1 | 4/2014 | Schmitz et al. |
| 2014/0107697 A1 | 4/2014 | Patani et al. |
| 2014/0110453 A1 | 4/2014 | Wingardner et al. |
| 2014/0115229 A1 | 4/2014 | Kothamasu et al. |
| 2014/0131418 A1 | 5/2014 | Kostrzewski |
| 2014/0131419 A1 | 5/2014 | Bettuchi |
| 2014/0135832 A1 | 5/2014 | Park et al. |
| 2014/0151433 A1 | 6/2014 | Shelton, IV et al. |
| 2014/0155916 A1 | 6/2014 | Hodgkinson et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |

(56) References Cited

U.S. PATENT DOCUMENTS

| | | |
|---|---|---|
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0183244 A1 | 7/2014 | Duque et al. |
| 2014/0188091 A1 | 7/2014 | Vidal et al. |
| 2014/0188101 A1 | 7/2014 | Bales, Jr. et al. |
| 2014/0188159 A1 | 7/2014 | Steege |
| 2014/0207124 A1 | 7/2014 | Aldridge et al. |
| 2014/0209658 A1 | 7/2014 | Skalla et al. |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0262408 A1 | 9/2014 | Woodard |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0287703 A1 | 9/2014 | Herbsommer et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0358163 A1 | 12/2014 | Farin et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0001272 A1 | 1/2015 | Sniffin et al. |
| 2015/0002089 A1 | 1/2015 | Rejman et al. |
| 2015/0022012 A1 | 1/2015 | Kim et al. |
| 2015/0025549 A1 | 1/2015 | Kilroy et al. |
| 2015/0025571 A1 | 1/2015 | Suzuki et al. |
| 2015/0034697 A1 | 2/2015 | Mastri et al. |
| 2015/0039010 A1 | 2/2015 | Beardsley et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060516 A1 | 3/2015 | Collings et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0067582 A1 | 3/2015 | Donnelly et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076211 A1 | 3/2015 | Irka et al. |
| 2015/0080883 A1 | 3/2015 | Haverkost et al. |
| 2015/0082624 A1 | 3/2015 | Craig et al. |
| 2015/0083781 A1 | 3/2015 | Giordano et al. |
| 2015/0087952 A1 | 3/2015 | Albert et al. |
| 2015/0088127 A1 | 3/2015 | Craig et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |
| 2015/0127021 A1 | 5/2015 | Harris et al. |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209045 A1 | 7/2015 | Hodgkinson et al. |
| 2015/0216605 A1 | 8/2015 | Baldwin |
| 2015/0222212 A1 | 8/2015 | Iwata |
| 2015/0223868 A1 | 8/2015 | Brandt et al. |
| 2015/0230697 A1 | 8/2015 | Phee et al. |
| 2015/0230794 A1 | 8/2015 | Wellman et al. |
| 2015/0230861 A1 | 8/2015 | Woloszko et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272606 A1 | 10/2015 | Nobis |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297824 A1 | 10/2015 | Cabiri et al. |
| 2015/0303417 A1 | 10/2015 | Koeder et al. |
| 2015/0305743 A1 | 10/2015 | Casasanta et al. |
| 2015/0313594 A1 | 11/2015 | Shelton, IV et al. |
| 2015/0324317 A1 | 11/2015 | Collins et al. |
| 2015/0352699 A1 | 12/2015 | Sakai et al. |
| 2015/0366585 A1 | 12/2015 | Lemay et al. |
| 2015/0367497 A1 | 12/2015 | Ito et al. |
| 2015/0372265 A1 | 12/2015 | Morisaku et al. |
| 2015/0374372 A1 | 12/2015 | Zergiebel et al. |
| 2015/0374378 A1 | 12/2015 | Giordano et al. |
| 2016/0000437 A1 | 1/2016 | Giordano et al. |
| 2016/0000452 A1 | 1/2016 | Yates et al. |
| 2016/0000453 A1 | 1/2016 | Yates et al. |
| 2016/0029998 A1 | 2/2016 | Brister et al. |
| 2016/0030042 A1 | 2/2016 | Heinrich et al. |
| 2016/0030043 A1 | 2/2016 | Fanelli et al. |
| 2016/0030076 A1 | 2/2016 | Faller et al. |
| 2016/0051316 A1 | 2/2016 | Boudreaux |
| 2016/0066913 A1 | 3/2016 | Swayze et al. |
| 2016/0069449 A1 | 3/2016 | Kanai et al. |
| 2016/0074035 A1 | 3/2016 | Whitman et al. |
| 2016/0074040 A1 | 3/2016 | Widenhouse et al. |
| 2016/0082161 A1 | 3/2016 | Zilberman et al. |
| 2016/0118201 A1 | 4/2016 | Nicholas et al. |
| 2016/0132026 A1 | 5/2016 | Wingardner et al. |
| 2016/0135835 A1 | 5/2016 | Onuma |
| 2016/0135895 A1 | 5/2016 | Faasse et al. |
| 2016/0139666 A1 | 5/2016 | Rubin et al. |
| 2016/0174969 A1 | 6/2016 | Kerr et al. |
| 2016/0174983 A1 | 6/2016 | Shelton, IV et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192927 A1 | 7/2016 | Kostrzewski |
| 2016/0192960 A1 | 7/2016 | Bueno et al. |
| 2016/0199063 A1 | 7/2016 | Mandakolathur Vasudevan et al. |
| 2016/0199956 A1 | 7/2016 | Shelton, IV et al. |
| 2016/0220150 A1 | 8/2016 | Sharonov |
| 2016/0235494 A1 | 8/2016 | Shelton, IV et al. |
| 2016/0242783 A1 | 8/2016 | Shelton, IV et al. |
| 2016/0242855 A1 | 8/2016 | Fichtinger et al. |
| 2016/0249910 A1 | 9/2016 | Shelton, IV et al. |
| 2016/0249922 A1 | 9/2016 | Morgan et al. |
| 2016/0249929 A1 | 9/2016 | Cappola et al. |
| 2016/0256159 A1 | 9/2016 | Pinjala et al. |
| 2016/0256184 A1 | 9/2016 | Shelton, IV et al. |
| 2016/0256221 A1 | 9/2016 | Smith |
| 2016/0256229 A1 | 9/2016 | Morgan et al. |
| 2016/0262745 A1 | 9/2016 | Morgan et al. |
| 2016/0262921 A1 | 9/2016 | Balbierz et al. |
| 2016/0270781 A1 | 9/2016 | Scirica |

(56) References Cited

U.S. PATENT DOCUMENTS

| | | |
|---|---|---|
| 2016/0287265 A1 | 10/2016 | MacDonald et al. |
| 2016/0287279 A1 | 10/2016 | Bovay et al. |
| 2016/0302820 A1 | 10/2016 | Hibner et al. |
| 2016/0310143 A1 | 10/2016 | Bettuchi |
| 2016/0314716 A1 | 10/2016 | Grubbs |
| 2016/0314717 A1 | 10/2016 | Grubbs |
| 2016/0345972 A1 | 12/2016 | Beardsley et al. |
| 2016/0367122 A1 | 12/2016 | Ichimura et al. |
| 2016/0374669 A1 | 12/2016 | Overmyer et al. |
| 2016/0374716 A1 | 12/2016 | Kessler |
| 2017/0007234 A1 | 1/2017 | Chin et al. |
| 2017/0007244 A1 | 1/2017 | Shelton, IV et al. |
| 2017/0007245 A1 | 1/2017 | Shelton, IV et al. |
| 2017/0007347 A1 | 1/2017 | Jaworek et al. |
| 2017/0020616 A1 | 1/2017 | Vale et al. |
| 2017/0055819 A1 | 3/2017 | Hansen et al. |
| 2017/0055980 A1 | 3/2017 | Vendely et al. |
| 2017/0056008 A1 | 3/2017 | Shelton, IV et al. |
| 2017/0056016 A1 | 3/2017 | Barton et al. |
| 2017/0056018 A1 | 3/2017 | Zeiner et al. |
| 2017/0066054 A1 | 3/2017 | Birky |
| 2017/0079642 A1 | 3/2017 | Overmyer et al. |
| 2017/0086829 A1 | 3/2017 | Vendely et al. |
| 2017/0086830 A1 | 3/2017 | Yates et al. |
| 2017/0086842 A1 | 3/2017 | Shelton, IV et al. |
| 2017/0086930 A1 | 3/2017 | Thompson et al. |
| 2017/0086932 A1 | 3/2017 | Auld et al. |
| 2017/0095922 A1 | 4/2017 | Licht et al. |
| 2017/0105727 A1 | 4/2017 | Scheib et al. |
| 2017/0105733 A1 | 4/2017 | Scheib et al. |
| 2017/0105786 A1 | 4/2017 | Scheib et al. |
| 2017/0106302 A1 | 4/2017 | Cummings et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0168187 A1 | 6/2017 | Calderoni et al. |
| 2017/0172382 A1 | 6/2017 | Nir et al. |
| 2017/0172549 A1 | 6/2017 | Smaby et al. |
| 2017/0172662 A1 | 6/2017 | Panescu et al. |
| 2017/0182195 A1 | 6/2017 | Wagner |
| 2017/0182211 A1 | 6/2017 | Raxworthy et al. |
| 2017/0196558 A1 | 7/2017 | Morgan et al. |
| 2017/0196649 A1 | 7/2017 | Yates et al. |
| 2017/0202607 A1 | 7/2017 | Shelton, IV et al. |
| 2017/0202770 A1 | 7/2017 | Friedrich et al. |
| 2017/0224332 A1 | 8/2017 | Hunter et al. |
| 2017/0231628 A1 | 8/2017 | Shelton, IV et al. |
| 2017/0231629 A1 | 8/2017 | Stopek et al. |
| 2017/0238962 A1 | 8/2017 | Hansen et al. |
| 2017/0242455 A1 | 8/2017 | Dickens |
| 2017/0245949 A1 | 8/2017 | Randle |
| 2017/0249431 A1 | 8/2017 | Shelton, IV et al. |
| 2017/0252060 A1 | 9/2017 | Ellingson et al. |
| 2017/0255799 A1 | 9/2017 | Zhao et al. |
| 2017/0262110 A1 | 9/2017 | Polishchuk et al. |
| 2017/0265774 A1 | 9/2017 | Johnson et al. |
| 2017/0281186 A1 | 10/2017 | Shelton, IV et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0312042 A1 | 11/2017 | Giordano et al. |
| 2017/0319047 A1 | 11/2017 | Poulsen et al. |
| 2017/0319201 A1 | 11/2017 | Morgan et al. |
| 2017/0333034 A1 | 11/2017 | Morgan et al. |
| 2017/0333035 A1 | 11/2017 | Morgan et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0358052 A1 | 12/2017 | Yuan |
| 2017/0360441 A1 | 12/2017 | Sgroi |
| 2017/0367695 A1 | 12/2017 | Shelton, IV et al. |
| 2018/0042610 A1 | 2/2018 | Sgroi, Jr. |
| 2018/0042689 A1 | 2/2018 | Mozdzierz et al. |
| 2018/0049738 A1 | 2/2018 | Meloul et al. |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0067004 A1 | 3/2018 | Sgroi, Jr. |
| 2018/0085117 A1 | 3/2018 | Shelton, IV et al. |
| 2018/0085120 A1 | 3/2018 | Viola |
| 2018/0092710 A1 | 4/2018 | Bosisio et al. |
| 2018/0114591 A1 | 4/2018 | Pribanic et al. |
| 2018/0116658 A1 | 5/2018 | Aronhalt, IV et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125594 A1 | 5/2018 | Beardsley |
| 2018/0132849 A1 | 5/2018 | Miller et al. |
| 2018/0132850 A1 | 5/2018 | Leimbach et al. |
| 2018/0132926 A1 | 5/2018 | Asher et al. |
| 2018/0132952 A1 | 5/2018 | Spivey et al. |
| 2018/0133521 A1 | 5/2018 | Frushour et al. |
| 2018/0140299 A1 | 5/2018 | Weaner et al. |
| 2018/0146960 A1 | 5/2018 | Shelton, IV et al. |
| 2018/0153542 A1 | 6/2018 | Shelton, IV et al. |
| 2018/0153634 A1 | 6/2018 | Zemlok et al. |
| 2018/0161034 A1 | 6/2018 | Scheib et al. |
| 2018/0168572 A1 | 6/2018 | Burbank |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0168754 A1 | 6/2018 | Overmyer |
| 2018/0228490 A1 | 8/2018 | Richard et al. |
| 2018/0231475 A1 | 8/2018 | Brown et al. |
| 2018/0235609 A1 | 8/2018 | Harris et al. |
| 2018/0235617 A1 | 8/2018 | Shelton, IV et al. |
| 2018/0235618 A1 | 8/2018 | Kostrzewski |
| 2018/0235626 A1 | 8/2018 | Shelton, IV et al. |
| 2018/0236181 A1 | 8/2018 | Marlin et al. |
| 2018/0242970 A1 | 8/2018 | Mozdzierz |
| 2018/0250002 A1 | 9/2018 | Eschbach |
| 2018/0271604 A1 | 9/2018 | Grout et al. |
| 2018/0273597 A1 | 9/2018 | Stimson |
| 2018/0280073 A1 | 10/2018 | Sanai et al. |
| 2018/0289371 A1 | 10/2018 | Wang et al. |
| 2018/0296216 A1 | 10/2018 | Shelton, IV et al. |
| 2018/0296290 A1 | 10/2018 | Namiki et al. |
| 2018/0317905 A1 | 11/2018 | Olson et al. |
| 2018/0317915 A1 | 11/2018 | McDonald, II |
| 2018/0325514 A1 | 11/2018 | Harris et al. |
| 2018/0333169 A1 | 11/2018 | Leimbach et al. |
| 2018/0360446 A1 | 12/2018 | Shelton, IV et al. |
| 2018/0360456 A1 | 12/2018 | Shelton, IV et al. |
| 2018/0368066 A1 | 12/2018 | Howell et al. |
| 2018/0368839 A1 | 12/2018 | Shelton, IV et al. |
| 2018/0368841 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2018/0372806 A1 | 12/2018 | Laughery et al. |
| 2018/0375165 A1 | 12/2018 | Shelton, IV et al. |
| 2019/0000457 A1 | 1/2019 | Shelton, IV et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000469 A1 | 1/2019 | Shelton, IV et al. |

(56) References Cited

U.S. PATENT DOCUMENTS

| | | |
|---|---|---|
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000481 A1 | 1/2019 | Harris et al. |
| 2019/0000535 A1 | 1/2019 | Messerly et al. |
| 2019/0000536 A1 | 1/2019 | Yates et al. |
| 2019/0008515 A1 | 1/2019 | Beardsley et al. |
| 2019/0015102 A1 | 1/2019 | Baber et al. |
| 2019/0015165 A1 | 1/2019 | Giordano et al. |
| 2019/0017311 A1 | 1/2019 | McGettrick et al. |
| 2019/0021733 A1 | 1/2019 | Burbank |
| 2019/0029682 A1 | 1/2019 | Huitema et al. |
| 2019/0029701 A1 | 1/2019 | Shelton, IV et al. |
| 2019/0038281 A1 | 2/2019 | Shelton, IV et al. |
| 2019/0038283 A1 | 2/2019 | Shelton, IV et al. |
| 2019/0038285 A1 | 2/2019 | Mozdzierz |
| 2019/0059986 A1 | 2/2019 | Shelton, IV et al. |
| 2019/0076143 A1 | 3/2019 | Smith |
| 2019/0090871 A1 | 3/2019 | Shelton, IV et al. |
| 2019/0091183 A1 | 3/2019 | Tomat et al. |
| 2019/0104919 A1 | 4/2019 | Shelton, IV et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105039 A1 | 4/2019 | Morgan et al. |
| 2019/0105044 A1 | 4/2019 | Shelton, IV et al. |
| 2019/0110779 A1 | 4/2019 | Gardner et al. |
| 2019/0110791 A1 | 4/2019 | Shelton, IV et al. |
| 2019/0117224 A1 | 4/2019 | Setser et al. |
| 2019/0125320 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125342 A1 | 5/2019 | Beardsley et al. |
| 2019/0125344 A1 | 5/2019 | Dinardo et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125476 A1 | 5/2019 | Shelton, IV et al. |
| 2019/0133422 A1 | 5/2019 | Nakamura |
| 2019/0133577 A1 | 5/2019 | Weadock et al. |
| 2019/0138770 A1 | 5/2019 | Compaijen et al. |
| 2019/0150925 A1 | 5/2019 | Marczyk et al. |
| 2019/0151029 A1 | 5/2019 | Robinson |
| 2019/0175847 A1 | 6/2019 | Pocreva, III et al. |
| 2019/0183491 A1 | 6/2019 | Shelton, IV et al. |
| 2019/0183502 A1 | 6/2019 | Shelton, IV et al. |
| 2019/0183594 A1 | 6/2019 | Shelton, IV et al. |
| 2019/0192141 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192151 A1 | 6/2019 | Shelton, IV et al. |
| 2019/0192153 A1 | 6/2019 | Shelton, IV et al. |
| 2019/0192155 A1 | 6/2019 | Shelton, IV et al. |
| 2019/0192157 A1 | 6/2019 | Scott et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200989 A1 | 7/2019 | Burbank et al. |
| 2019/0200998 A1 | 7/2019 | Shelton, IV et al. |
| 2019/0201020 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201034 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201079 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0261982 A1 | 8/2019 | Holsten |
| 2019/0261983 A1 | 8/2019 | Granger et al. |
| 2019/0261984 A1 | 8/2019 | Nelson et al. |
| 2019/0261987 A1 | 8/2019 | Viola et al. |
| 2019/0269400 A1 | 9/2019 | Mandakolathur Vasudevan et al. |
| 2019/0269402 A1 | 9/2019 | Murray et al. |
| 2019/0269428 A1 | 9/2019 | Allen et al. |
| 2019/0274685 A1 | 9/2019 | Olson et al. |
| 2019/0282233 A1 | 9/2019 | Burbank et al. |
| 2019/0290264 A1 | 9/2019 | Morgan et al. |
| 2019/0290266 A1 | 9/2019 | Scheib et al. |
| 2019/0290267 A1 | 9/2019 | Baxter, III et al. |
| 2019/0290297 A1 | 9/2019 | Haider et al. |
| 2019/0298350 A1 | 10/2019 | Shelton, IV et al. |
| 2019/0298353 A1 | 10/2019 | Shelton, IV et al. |
| 2019/0298356 A1* | 10/2019 | Shelton, IV ...... A61B 17/07207 |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0298381 A1 | 10/2019 | Kreidler et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307456 A1 | 10/2019 | Shelton, IV et al. |
| 2019/0314015 A1 | 10/2019 | Shelton, IV et al. |
| 2019/0321040 A1 | 10/2019 | Shelton, IV |
| 2019/0321062 A1 | 10/2019 | Williams |
| 2019/0328387 A1 | 10/2019 | Overmyer et al. |
| 2019/0343515 A1 | 11/2019 | Morgan et al. |
| 2019/0357909 A1 | 11/2019 | Huitema et al. |
| 2019/0388091 A1 | 12/2019 | Eschbach et al. |
| 2020/0000531 A1 | 1/2020 | Giordano et al. |
| 2020/0008802 A1 | 1/2020 | Aronhalt et al. |
| 2020/0008809 A1 | 1/2020 | Shelton, IV et al. |
| 2020/0008827 A1 | 1/2020 | Dearden et al. |
| 2020/0015817 A1 | 1/2020 | Harris et al. |
| 2020/0015819 A1 | 1/2020 | Shelton, IV et al. |
| 2020/0015915 A1 | 1/2020 | Swayze et al. |
| 2020/0037939 A1 | 2/2020 | Castagna et al. |
| 2020/0038016 A1 | 2/2020 | Shelton, IV et al. |
| 2020/0038018 A1 | 2/2020 | Shelton, IV et al. |

(56) References Cited

U.S. PATENT DOCUMENTS

| | | |
|---|---|---|
| 2020/0038020 A1 | 2/2020 | Yates et al. |
| 2020/0046355 A1 | 2/2020 | Harris et al. |
| 2020/0046356 A1 | 2/2020 | Baxter, III et al. |
| 2020/0054320 A1 | 2/2020 | Harris et al. |
| 2020/0054321 A1 | 2/2020 | Harris et al. |
| 2020/0054329 A1 | 2/2020 | Shelton, IV et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060523 A1 | 2/2020 | Matsuda et al. |
| 2020/0060713 A1 | 2/2020 | Leimbach et al. |
| 2020/0061385 A1 | 2/2020 | Schwarz et al. |
| 2020/0085431 A1 | 3/2020 | Swayze et al. |
| 2020/0085435 A1 | 3/2020 | Shelton, IV et al. |
| 2020/0085518 A1 | 3/2020 | Giordano et al. |
| 2020/0093484 A1 | 3/2020 | Shelton, IV et al. |
| 2020/0093506 A1 | 3/2020 | Leimbach et al. |
| 2020/0093550 A1 | 3/2020 | Spivey et al. |
| 2020/0100783 A1 | 4/2020 | Yates et al. |
| 2020/0107829 A1 | 4/2020 | Shelton, IV et al. |
| 2020/0114505 A1 | 4/2020 | Kikuchi |
| 2020/0138436 A1 | 5/2020 | Yates et al. |
| 2020/0138534 A1 | 5/2020 | Garcia Kilroy et al. |
| 2020/0146741 A1 | 5/2020 | Long et al. |
| 2020/0187943 A1 | 6/2020 | Shelton, IV et al. |
| 2020/0197027 A1 | 6/2020 | Hershberger et al. |
| 2020/0205810 A1 | 7/2020 | Posey et al. |
| 2020/0205811 A1 | 7/2020 | Posey et al. |
| 2020/0205823 A1 | 7/2020 | Vendely et al. |
| 2020/0214706 A1 | 7/2020 | Vendely et al. |
| 2020/0214731 A1 | 7/2020 | Shelton, IV et al. |
| 2020/0229814 A1 | 7/2020 | Amariglio et al. |
| 2020/0237371 A1 | 7/2020 | Huitema et al. |
| 2020/0253605 A1 | 8/2020 | Swayze et al. |
| 2020/0261086 A1 | 8/2020 | Zeiner et al. |
| 2020/0261106 A1 | 8/2020 | Hess et al. |
| 2020/0268377 A1 | 8/2020 | Schmid et al. |
| 2020/0275927 A1 | 9/2020 | Shelton, IV et al. |
| 2020/0275930 A1 | 9/2020 | Harris et al. |
| 2020/0280219 A1 | 9/2020 | Laughery et al. |
| 2020/0281585 A1 | 9/2020 | Timm et al. |
| 2020/0289112 A1 | 9/2020 | Whitfield et al. |
| 2020/0297341 A1 | 9/2020 | Yates et al. |
| 2020/0297346 A1 | 9/2020 | Shelton, IV et al. |
| 2020/0305862 A1 | 10/2020 | Yates et al. |
| 2020/0305863 A1 | 10/2020 | Yates et al. |
| 2020/0305864 A1 | 10/2020 | Yates et al. |
| 2020/0305870 A1 | 10/2020 | Shelton, IV |
| 2020/0305872 A1 | 10/2020 | Weidner et al. |
| 2020/0305874 A1 | 10/2020 | Huitema et al. |
| 2020/0315612 A1 | 10/2020 | Shelton, IV et al. |
| 2020/0315623 A1 | 10/2020 | Eisinger et al. |
| 2020/0315983 A1 | 10/2020 | Widenhouse et al. |
| 2020/0323526 A1 | 10/2020 | Huang et al. |
| 2020/0330092 A1 | 10/2020 | Shelton, IV et al. |
| 2020/0330093 A1 | 10/2020 | Shelton, IV et al. |
| 2020/0330096 A1 | 10/2020 | Shelton, IV et al. |
| 2020/0330181 A1 | 10/2020 | Junger et al. |
| 2020/0337693 A1 | 10/2020 | Shelton, IV et al. |
| 2020/0337791 A1 | 10/2020 | Shelton, IV et al. |
| 2020/0345346 A1 | 11/2020 | Shelton, IV et al. |
| 2020/0345349 A1 | 11/2020 | Kimball et al. |
| 2020/0345352 A1 | 11/2020 | Shelton, IV et al. |
| 2020/0345353 A1 | 11/2020 | Leimbach et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345363 A1 | 11/2020 | Shelton, IV et al. |
| 2020/0345435 A1 | 11/2020 | Traina |
| 2020/0352562 A1 | 11/2020 | Timm et al. |
| 2020/0367886 A1 | 11/2020 | Shelton, IV et al. |
| 2020/0375585 A1 | 12/2020 | Swayze et al. |
| 2020/0375597 A1 | 12/2020 | Shelton, IV et al. |
| 2020/0390444 A1 | 12/2020 | Harris et al. |
| 2020/0397430 A1 | 12/2020 | Patel et al. |
| 2020/0405292 A1 | 12/2020 | Shelton, IV et al. |
| 2020/0405293 A1 | 12/2020 | Shelton, IV et al. |
| 2020/0405296 A1 | 12/2020 | Shelton, IV et al. |
| 2020/0405302 A1 | 12/2020 | Shelton, IV et al. |
| 2020/0405304 A1 | 12/2020 | Mozdzierz et al. |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405316 A1 | 12/2020 | Shelton, IV et al. |
| 2020/0405341 A1 | 12/2020 | Hess et al. |
| 2020/0405403 A1 | 12/2020 | Shelton, IV et al. |
| 2020/0405404 A1 | 12/2020 | Shelton, IV et al. |
| 2020/0405410 A1 | 12/2020 | Shelton, IV |
| 2020/0405439 A1 | 12/2020 | Shelton, IV et al. |
| 2020/0410177 A1 | 12/2020 | Shelton, IV |
| 2021/0000466 A1 | 1/2021 | Leimbach et al. |
| 2021/0000467 A1 | 1/2021 | Shelton, IV et al. |
| 2021/0015480 A1 | 1/2021 | Shelton, IV et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059670 A1 | 3/2021 | Overmyer et al. |
| 2021/0059672 A1 | 3/2021 | Giordano et al. |
| 2021/0059673 A1 | 3/2021 | Shelton, IV et al. |
| 2021/0068820 A1 | 3/2021 | Parihar et al. |
| 2021/0068829 A1 | 3/2021 | Miller et al. |
| 2021/0068832 A1 | 3/2021 | Yates et al. |
| 2021/0068835 A1 | 3/2021 | Shelton, IV et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085318 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0093321 A1 | 4/2021 | Auld et al. |
| 2021/0093323 A1 | 4/2021 | Scirica et al. |
| 2021/0100541 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0128153 A1 | 5/2021 | Sgroi |
| 2021/0137522 A1 | 5/2021 | Shelton, IV et al. |
| 2021/0153866 A1 | 5/2021 | Knapp et al. |
| 2021/0177401 A1 | 6/2021 | Abramek et al. |
| 2021/0186492 A1 | 6/2021 | Shelton, IV et al. |
| 2021/0186493 A1 | 6/2021 | Shelton, IV et al. |
| 2021/0186495 A1 | 6/2021 | Shelton, Iv et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0204941 A1 | 7/2021 | Dewaele et al. |
| 2021/0204951 A1 | 7/2021 | Sgroi et al. |
| 2021/0212671 A1 | 7/2021 | Ramadan et al. |
| 2021/0212691 A1 | 7/2021 | Smith et al. |
| 2021/0212776 A1 | 7/2021 | Schmitt et al. |
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244411 A1 | 8/2021 | Smith et al. |
| 2021/0244412 A1 | 8/2021 | Vendely et al. |
| 2021/0259681 A1 | 8/2021 | Shelton, IV et al. |
| 2021/0259687 A1 | 8/2021 | Gonzalez et al. |

(56) References Cited

U.S. PATENT DOCUMENTS

| | | |
|---|---|---|
| 2021/0259986 A1 | 8/2021 | Widenhouse et al. |
| 2021/0259987 A1 | 8/2021 | Widenhouse et al. |
| 2021/0267589 A1 | 9/2021 | Swayze et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275175 A1 | 9/2021 | Vadali et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282774 A1 | 9/2021 | Shelton, IV et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0290322 A1 | 9/2021 | Traina |
| 2021/0298745 A1 | 9/2021 | Leimbach et al. |
| 2021/0298746 A1 | 9/2021 | Leimbach et al. |
| 2021/0307744 A1 | 10/2021 | Walcott et al. |
| 2021/0307748 A1 | 10/2021 | Harris et al. |
| 2021/0315566 A1 | 10/2021 | Yates et al. |
| 2021/0315570 A1 | 10/2021 | Shelton, IV |
| 2021/0315571 A1 | 10/2021 | Swayze et al. |
| 2021/0315573 A1 | 10/2021 | Shelton, IV et al. |
| 2021/0315574 A1 | 10/2021 | Shelton, IV et al. |
| 2021/0315576 A1 | 10/2021 | Shelton, IV et al. |
| 2021/0315577 A1 | 10/2021 | Shelton, IV et al. |
| 2021/0322009 A1 | 10/2021 | Huang et al. |
| 2021/0330321 A1 | 10/2021 | Leimbach et al. |
| 2021/0338233 A1 | 11/2021 | Shelton, IV et al. |
| 2021/0338234 A1 | 11/2021 | Shelton, IV et al. |
| 2021/0338260 A1 | 11/2021 | Le Rolland et al. |
| 2021/0353284 A1 | 11/2021 | Yang et al. |
| 2021/0369271 A1 | 12/2021 | Schings et al. |
| 2021/0369273 A1 | 12/2021 | Yates et al. |
| 2021/0378669 A1 | 12/2021 | Shelton, IV et al. |
| 2021/0393260 A1 | 12/2021 | Shelton, IV et al. |
| 2021/0393261 A1 | 12/2021 | Harris et al. |
| 2021/0393262 A1 | 12/2021 | Shelton, IV et al. |
| 2021/0393268 A1 | 12/2021 | Shelton, IV et al. |
| 2021/0393366 A1 | 12/2021 | Shelton, IV et al. |
| 2022/0000478 A1 | 1/2022 | Shelton, IV et al. |
| 2022/0000479 A1 | 1/2022 | Shelton, IV et al. |
| 2022/0015760 A1 | 1/2022 | Beardsley et al. |
| 2022/0031313 A1 | 2/2022 | Bakos et al. |
| 2022/0031314 A1 | 2/2022 | Bakos et al. |
| 2022/0031315 A1 | 2/2022 | Bakos et al. |
| 2022/0031319 A1 | 2/2022 | Witte et al. |
| 2022/0031320 A1 | 2/2022 | Hall et al. |
| 2022/0031322 A1 | 2/2022 | Parks |
| 2022/0031323 A1 | 2/2022 | Witte |
| 2022/0031324 A1 | 2/2022 | Hall et al. |
| 2022/0031345 A1 | 2/2022 | Witte |
| 2022/0031346 A1 | 2/2022 | Parks |
| 2022/0031350 A1 | 2/2022 | Witte |
| 2022/0031351 A1 | 2/2022 | Moubarak et al. |
| 2022/0049593 A1 | 2/2022 | Groover et al. |
| 2022/0054125 A1 | 2/2022 | Ji et al. |
| 2022/0054130 A1 | 2/2022 | Overmyer et al. |
| 2022/0061836 A1 | 3/2022 | Parihar et al. |
| 2022/0061843 A1 | 3/2022 | Vendely et al. |
| 2022/0061845 A1 | 3/2022 | Shelton, IV et al. |
| 2022/0061862 A1 | 3/2022 | Shelton, IV et al. |
| 2022/0071630 A1 | 3/2022 | Swayze et al. |
| 2022/0071631 A1 | 3/2022 | Harris et al. |
| 2022/0071632 A1 | 3/2022 | Patel et al. |
| 2022/0071635 A1 | 3/2022 | Shelton, IV et al. |
| 2022/0079580 A1 | 3/2022 | Vendely et al. |
| 2022/0079586 A1 | 3/2022 | Shelton, IV et al. |
| 2022/0079588 A1 | 3/2022 | Harris et al. |
| 2022/0079589 A1 | 3/2022 | Harris et al. |
| 2022/0079590 A1 | 3/2022 | Harris et al. |
| 2022/0079595 A1 | 3/2022 | Huitema et al. |
| 2022/0079596 A1 | 3/2022 | Huitema et al. |
| 2022/0087676 A1 | 3/2022 | Shelton, IV et al. |
| 2022/0104816 A1 | 4/2022 | Fernandes et al. |
| 2022/0117602 A1 | 4/2022 | Wise et al. |
| 2022/0133299 A1 | 5/2022 | Baxter, III |
| 2022/0133300 A1 | 5/2022 | Leimbach et al. |
| 2022/0133301 A1 | 5/2022 | Leimbach |
| 2022/0133302 A1 | 5/2022 | Zerkle et al. |
| 2022/0133303 A1 | 5/2022 | Huang |
| 2022/0133304 A1 | 5/2022 | Leimbach et al. |
| 2022/0133310 A1 | 5/2022 | Ross |
| 2022/0133311 A1 | 5/2022 | Huang |
| 2022/0133312 A1 | 5/2022 | Huang |
| 2022/0142643 A1 | 5/2022 | Shelton, IV et al. |
| 2022/0151611 A1 | 5/2022 | Shelton, IV et al. |
| 2022/0151613 A1 | 5/2022 | Vendely et al. |
| 2022/0151614 A1 | 5/2022 | Vendely et al. |
| 2022/0151615 A1 | 5/2022 | Shelton, IV et al. |
| 2022/0151616 A1 | 5/2022 | Shelton, IV et al. |
| 2022/0160358 A1 | 5/2022 | Wixey |
| 2022/0167968 A1 | 6/2022 | Worthington et al. |
| 2022/0167970 A1 | 6/2022 | Aronhalt et al. |
| 2022/0167971 A1 | 6/2022 | Shelton, IV et al. |
| 2022/0167972 A1 | 6/2022 | Shelton, IV et al. |
| 2022/0167973 A1 | 6/2022 | Shelton, IV et al. |
| 2022/0167974 A1 | 6/2022 | Shelton, IV et al. |
| 2022/0167975 A1 | 6/2022 | Shelton, IV et al. |
| 2022/0167977 A1 | 6/2022 | Shelton, IV et al. |
| 2022/0167979 A1 | 6/2022 | Yates et al. |
| 2022/0167980 A1 | 6/2022 | Shelton, IV et al. |
| 2022/0167981 A1 | 6/2022 | Shelton, IV et al. |
| 2022/0167982 A1 | 6/2022 | Shelton, IV et al. |
| 2022/0167983 A1 | 6/2022 | Shelton, IV et al. |
| 2022/0167984 A1 | 6/2022 | Shelton, IV et al. |
| 2022/0167995 A1 | 6/2022 | Parfett et al. |
| 2022/0168038 A1 | 6/2022 | Shelton, IV et al. |
| 2022/0175370 A1 | 6/2022 | Shelton, IV et al. |
| 2022/0175371 A1 | 6/2022 | Hess et al. |
| 2022/0175372 A1 | 6/2022 | Shelton, IV et al. |
| 2022/0175375 A1 | 6/2022 | Harris et al. |
| 2022/0175378 A1 | 6/2022 | Leimbach et al. |
| 2022/0175381 A1 | 6/2022 | Scheib et al. |
| 2022/0183685 A1 | 6/2022 | Shelton, IV et al. |
| 2022/0211367 A1 | 7/2022 | Schmid et al. |
| 2022/0218332 A1 | 7/2022 | Shelton, IV et al. |
| 2022/0218333 A1 | 7/2022 | Parihar et al. |
| 2022/0218334 A1 | 7/2022 | Parihar et al. |
| 2022/0218336 A1 | 7/2022 | Timm et al. |
| 2022/0218337 A1 | 7/2022 | Timm et al. |
| 2022/0218338 A1 | 7/2022 | Shelton, IV et al. |
| 2022/0218340 A1 | 7/2022 | Harris et al. |
| 2022/0218344 A1 | 7/2022 | Leimbach et al. |
| 2022/0218345 A1 | 7/2022 | Shelton, IV et al. |
| 2022/0218346 A1 | 7/2022 | Shelton, IV et al. |
| 2022/0218347 A1 | 7/2022 | Shelton, IV et al. |
| 2022/0218348 A1 | 7/2022 | Swensgard et al. |
| 2022/0218349 A1 | 7/2022 | Shelton, IV et al. |
| 2022/0218350 A1 | 7/2022 | Shelton, IV et al. |
| 2022/0218351 A1 | 7/2022 | Shelton, IV et al. |
| 2022/0218376 A1 | 7/2022 | Shelton, IV et al. |
| 2022/0218378 A1 | 7/2022 | Shelton, IV et al. |
| 2022/0218381 A1 | 7/2022 | Leimbach et al. |
| 2022/0218382 A1 | 7/2022 | Leimbach et al. |
| 2022/0225980 A1 | 7/2022 | Shelton, IV et al. |
| 2022/0225982 A1 | 7/2022 | Yates et al. |
| 2022/0225986 A1 | 7/2022 | Shelton, IV et al. |
| 2022/0225992 A1 | 7/2022 | Smith et al. |
| 2022/0225993 A1 | 7/2022 | Huitema et al. |
| 2022/0225994 A1 | 7/2022 | Setser et al. |
| 2022/0226012 A1 | 7/2022 | Shelton, IV et al. |
| 2022/0226013 A1 | 7/2022 | Hall et al. |
| 2022/0233184 A1 | 7/2022 | Parihar et al. |
| 2022/0233185 A1 | 7/2022 | Parihar et al. |
| 2022/0233186 A1 | 7/2022 | Timm et al. |
| 2022/0233187 A1 | 7/2022 | Timm et al. |
| 2022/0233188 A1 | 7/2022 | Timm et al. |

(56) References Cited

U.S. PATENT DOCUMENTS

| | | | |
|---|---|---|---|
| 2022/0233194 A1 | 7/2022 | Baxter, III et al. |
| 2022/0233195 A1 | 7/2022 | Shelton, IV et al. |
| 2022/0233257 A1 | 7/2022 | Shelton, IV et al. |
| 2022/0240927 A1 | 8/2022 | Timm et al. |
| 2022/0240928 A1 | 8/2022 | Timm et al. |
| 2022/0240929 A1 | 8/2022 | Timm et al. |
| 2022/0240930 A1 | 8/2022 | Yates et al. |
| 2022/0240936 A1 | 8/2022 | Huitema et al. |
| 2022/0240937 A1 | 8/2022 | Shelton, IV et al. |
| 2022/0249095 A1 | 8/2022 | Shelton, IV et al. |
| 2022/0265272 A1 | 8/2022 | Li et al. |
| 2022/0273291 A1 | 9/2022 | Shelton, IV et al. |
| 2022/0273292 A1 | 9/2022 | Shelton, IV et al. |
| 2022/0273293 A1 | 9/2022 | Shelton, IV et al. |
| 2022/0273294 A1 | 9/2022 | Creamer et al. |
| 2022/0273299 A1 | 9/2022 | Shelton, IV et al. |
| 2022/0273300 A1 | 9/2022 | Shelton, IV et al. |
| 2022/0273301 A1 | 9/2022 | Creamer et al. |
| 2022/0273302 A1 | 9/2022 | Shelton, IV et al. |
| 2022/0273303 A1 | 9/2022 | Creamer et al. |
| 2022/0273304 A1 | 9/2022 | Shelton, IV et al. |
| 2022/0273305 A1 | 9/2022 | Shelton, IV et al. |
| 2022/0273306 A1 | 9/2022 | Shelton, IV et al. |
| 2022/0273307 A1 | 9/2022 | Shelton, IV et al. |
| 2022/0273308 A1 | 9/2022 | Shelton, IV et al. |
| 2022/0278438 A1 | 9/2022 | Shelton, IV et al. |
| 2022/0287711 A1 | 9/2022 | Ming et al. |
| 2022/0296230 A1 | 9/2022 | Adams et al. |
| 2022/0296231 A1 | 9/2022 | Adams et al. |
| 2022/0296232 A1 | 9/2022 | Adams et al. |
| 2022/0296233 A1 | 9/2022 | Morgan et al. |
| 2022/0296234 A1 | 9/2022 | Shelton, IV et al. |
| 2022/0296235 A1 | 9/2022 | Morgan et al. |
| 2022/0296236 A1 | 9/2022 | Bakos et al. |
| 2022/0296237 A1 | 9/2022 | Bakos et al. |
| 2022/0304679 A1 | 9/2022 | Bakos et al. |
| 2022/0304680 A1 | 9/2022 | Shelton, IV et al. |
| 2022/0304681 A1 | 9/2022 | Shelton, IV et al. |
| 2022/0304682 A1 | 9/2022 | Shelton, IV et al. |
| 2022/0304683 A1 | 9/2022 | Shelton, IV et al. |
| 2022/0304684 A1 | 9/2022 | Bakos et al. |
| 2022/0304686 A1 | 9/2022 | Shelton, IV et al. |
| 2022/0304687 A1 | 9/2022 | Shelton, IV et al. |
| 2022/0304688 A1 | 9/2022 | Shelton, IV et al. |
| 2022/0304689 A1 | 9/2022 | Shelton, IV |
| 2022/0304690 A1 | 9/2022 | Baxter, III et al. |
| 2022/0304714 A1 | 9/2022 | Shelton, IV et al. |
| 2022/0304715 A1 | 9/2022 | Shelton, IV |
| 2022/0313253 A1 | 10/2022 | Shelton, IV et al. |
| 2022/0313263 A1 | 10/2022 | Huitema et al. |
| 2022/0313619 A1 | 10/2022 | Schmid et al. |
| 2022/0323067 A1 | 10/2022 | Overmyer et al. |
| 2022/0323070 A1 | 10/2022 | Ross et al. |
| 2022/0330940 A1 | 10/2022 | Shelton, IV et al. |
| 2022/0338870 A1 | 10/2022 | Swayze et al. |
| 2022/0346774 A1 | 11/2022 | Hess et al. |
| 2022/0346775 A1 | 11/2022 | Hess et al. |

FOREIGN PATENT DOCUMENTS

| | | | |
|---|---|---|---|
| AU | 2012268848 A1 | 1/2013 |
| AU | 2011218702 B2 | 6/2013 |
| AU | 2012200178 B2 | 7/2013 |
| BR | 112013007744 A2 | 6/2016 |
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 1777406 A | 5/2006 |
| CN | 2785249 Y | 5/2006 |
| CN | 2796654 Y | 7/2006 |
| CN | 2868212 Y | 2/2007 |
| CN | 200942099 Y | 9/2007 |
| CN | 200984209 Y | 12/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101188900 A | 5/2008 |
| CN | 101203085 A | 6/2008 |
| CN | 101273908 A | 10/2008 |
| CN | 101378791 A | 3/2009 |
| CN | 101507635 A | 8/2009 |
| CN | 101522120 A | 9/2009 |
| CN | 101669833 A | 3/2010 |
| CN | 101716090 A | 6/2010 |
| CN | 101721236 A | 6/2010 |
| CN | 101756727 A | 6/2010 |
| CN | 101828940 A | 9/2010 |
| CN | 101856250 A | 10/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 102217961 A | 10/2011 |
| CN | 102217963 A | 10/2011 |
| CN | 102243850 A | 11/2011 |
| CN | 102247182 A | 11/2011 |
| CN | 102247183 A | 11/2011 |
| CN | 101779977 B | 12/2011 |
| CN | 102309352 A | 1/2012 |
| CN | 101912284 B | 7/2012 |
| CN | 102125450 B | 7/2012 |
| CN | 202313537 U | 7/2012 |
| CN | 202397539 U | 8/2012 |
| CN | 202426586 U | 9/2012 |
| CN | 102743201 A | 10/2012 |
| CN | 202489990 U | 10/2012 |
| CN | 102228387 B | 11/2012 |
| CN | 102835977 A | 12/2012 |
| CN | 202568350 U | 12/2012 |
| CN | 103037781 A | 4/2013 |
| CN | 103083053 A | 5/2013 |
| CN | 103391037 A | 11/2013 |
| CN | 203328751 U | 12/2013 |
| CN | 103505264 A | 1/2014 |
| CN | 103584893 A | 2/2014 |
| CN | 103635150 A | 3/2014 |
| CN | 103690212 A | 4/2014 |
| CN | 203564285 U | 4/2014 |
| CN | 203564287 U | 4/2014 |
| CN | 203597997 U | 5/2014 |
| CN | 103829981 A | 6/2014 |
| CN | 103829983 A | 6/2014 |
| CN | 103908313 A | 7/2014 |
| CN | 203693685 U | 7/2014 |
| CN | 203736251 U | 7/2014 |
| CN | 103981635 A | 8/2014 |
| CN | 104027145 A | 9/2014 |
| CN | 203815517 U | 9/2014 |
| CN | 102783741 B | 10/2014 |
| CN | 102973300 B | 10/2014 |
| CN | 204092074 U | 1/2015 |
| CN | 104337556 A | 2/2015 |
| CN | 204158440 U | 2/2015 |
| CN | 204158441 U | 2/2015 |
| CN | 102469995 B | 3/2015 |
| CN | 104422849 A | 3/2015 |
| CN | 104586463 A | 5/2015 |
| CN | 204520822 U | 8/2015 |
| CN | 204636451 U | 9/2015 |
| CN | 103860225 B | 3/2016 |

(56) References Cited

FOREIGN PATENT DOCUMENTS

| | | |
|---|---|---|
| CN | 103750872 B | 5/2016 |
| CN | 105919642 A | 9/2016 |
| CN | 103648410 B | 10/2016 |
| CN | 105997173 A | 10/2016 |
| CN | 106344091 A | 1/2017 |
| CN | 104921730 B | 9/2017 |
| CN | 104349800 B | 11/2017 |
| CN | 107635483 A | 1/2018 |
| CN | 208625784 U | 3/2019 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004041871 A1 | 3/2006 |
| DE | 102004063606 A1 | 7/2006 |
| DE | 202007003114 U1 | 6/2007 |
| DE | 102010013150 A1 | 9/2011 |
| DE | 102012213322 A1 | 1/2014 |
| DE | 102013101158 A1 | 8/2014 |
| EM | 002220467-0008 | 4/2013 |
| EP | 0000756 A1 | 2/1979 |
| EP | 0122046 A1 | 10/1984 |
| EP | 0129442 B1 | 11/1987 |
| EP | 0251444 A1 | 1/1988 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0516544 B1 | 3/1996 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1064882 A1 | 1/2001 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1558161 A1 | 8/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 2153793 A2 | 2/2010 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2529671 A2 | 12/2012 |
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2789299 A1 | 10/2014 |
| EP | 2842500 A1 | 3/2015 |
| EP | 2853220 A1 | 4/2015 |
| EP | 2878274 A1 | 6/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 3120781 A2 | 1/2017 |
| EP | 3135225 A2 | 3/2017 |
| EP | 2789299 B1 | 5/2017 |
| EP | 3225190 A2 | 10/2017 |
| EP | 3235445 A1 | 10/2017 |
| EP | 3326548 A1 | 5/2018 |
| EP | 3363378 A1 | 8/2018 |
| EP | 3409216 A1 | 12/2018 |
| EP | 3476334 A1 | 5/2019 |
| EP | 3275378 B1 | 7/2019 |
| EP | 3505095 A1 | 7/2019 |
| EP | 3791810 A1 | 3/2021 |
| ES | 1070456 U | 9/2009 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |

(56) References Cited

FOREIGN PATENT DOCUMENTS

| | | |
|---|---|---|
| JP | S60113007 A | 6/1985 |
| JP | S62170011 U | 10/1987 |
| JP | S6333137 A | 2/1988 |
| JP | S63270040 A | 11/1988 |
| JP | S63318824 A | 12/1988 |
| JP | H0129503 B2 | 6/1989 |
| JP | H02106189 A | 4/1990 |
| JP | H0378514 U | 8/1991 |
| JP | H0385009 U | 8/1991 |
| JP | H0489041 A | 3/1992 |
| JP | H04215747 A | 8/1992 |
| JP | J04131860 U | 12/1992 |
| JP | H0584252 A | 4/1993 |
| JP | H0512325 A | 5/1993 |
| JP | H05226945 A | 9/1993 |
| JP | H0630945 A | 2/1994 |
| JP | H0636757 A | 2/1994 |
| JP | H06237937 A | 8/1994 |
| JP | H06304176 A | 11/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H0950795 A | 2/1997 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000210299 A | 8/2000 |
| JP | 2000271141 A | 10/2000 |
| JP | 2000287987 A | 10/2000 |
| JP | 2000325303 A | 11/2000 |
| JP | 2001-69758 A | 3/2001 |
| JP | 2001087272 A | 4/2001 |
| JP | 2001208655 A | 8/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006291180 A | 10/2006 |
| JP | 2006346445 A | 12/2006 |
| JP | 2007-97252 A | 4/2007 |
| JP | 2007289715 A | 11/2007 |
| JP | 2007304057 A | 11/2007 |
| JP | 2007306710 A | 11/2007 |
| JP | D1322057 | 2/2008 |
| JP | 2008154804 A | 7/2008 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | D1383743 | 2/2010 |
| JP | 2010065594 A | 3/2010 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |
| JP | 2011200665 A | 10/2011 |
| JP | D1432094 | 12/2011 |
| JP | 1433631 S | 2/2012 |
| JP | 2012115542 A | 6/2012 |
| JP | 2012143283 A | 8/2012 |
| JP | 5154710 B1 | 2/2013 |
| JP | 2013099551 A | 5/2013 |
| JP | 2013126430 A | 6/2013 |
| JP | D1481426 | 9/2013 |
| JP | 2013541982 A | 11/2013 |
| JP | 2013541983 A | 11/2013 |
| JP | 2013541997 A | 11/2013 |
| JP | 2014018667 A | 2/2014 |
| JP | D1492363 | 2/2014 |
| JP | 2014121599 A | 7/2014 |
| JP | 2014171879 A | 9/2014 |
| JP | 1517663 S | 2/2015 |
| JP | 2015512725 A | 4/2015 |
| JP | 2015513956 A | 5/2015 |
| JP | 2015513958 A | 5/2015 |
| JP | 2015514471 A | 5/2015 |
| JP | 2015516838 A | 6/2015 |
| JP | 2015521524 A | 7/2015 |
| JP | 2015521525 A | 7/2015 |
| JP | 2016007800 A | 1/2016 |
| JP | 2016508792 A | 3/2016 |
| JP | 2016512057 A | 4/2016 |
| JP | 2016530949 A | 10/2016 |
| JP | 2017513563 A | 6/2017 |
| JP | 1601498 S | 4/2018 |
| JP | 2019513530 A | 5/2019 |
| JP | 2020501797 A | 1/2020 |
| JP | D1677030 S | 1/2021 |
| JP | D1696539 S | 10/2021 |
| KR | 20100110134 A | 10/2010 |
| KR | 20110003229 A | 1/2011 |
| KR | 300631507 | 3/2012 |
| KR | 300747646 | 6/2014 |
| KR | 20180053811 A | 5/2018 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2104671 C1 | 2/1998 |
| RU | 2110965 C1 | 5/1998 |

(56) References Cited

FOREIGN PATENT DOCUMENTS

| | | |
|---|---|---|
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1042742 A1 | 9/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9308754 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0036690 A2 | 6/2000 |
| WO | WO-0053112 A2 | 9/2000 |
| WO | WO-0024448 A2 | 10/2000 |
| WO | WO-0057796 A1 | 10/2000 |
| WO | WO-0105702 A1 | 1/2001 |
| WO | WO-0154594 A | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A | 12/2001 |
| WO | WO-0219932 A1 | 3/2002 |
| WO | WO-0226143 A | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2014175894 A1 | 10/2014 |
| WO | WO-2015032797 A1 | 3/2015 |
| WO | WO-2015076780 A1 | 5/2015 |
| WO | WO-2015137040 A1 | 9/2015 |
| WO | WO-2015138760 A1 | 9/2015 |
| WO | WO-2015187107 A1 | 12/2015 |
| WO | WO-2016100682 A1 | 6/2016 |
| WO | WO-2016107448 A1 | 7/2016 |
| WO | WO 2016/182933 A1 | 11/2016 |
| WO | WO-2018011664 A1 | 1/2018 |
| WO | WO-2019036490 A1 | 2/2019 |
| WO | WO-2019130087 A1 | 7/2019 |
| WO | WO-2019130089 A1 | 7/2019 |
| WO | WO-2019208902 A1 | 10/2019 |
| WO | WO-2021189234 A1 | 9/2021 |

OTHER PUBLICATIONS

Design U.S. Appl. No. 29/736,649, filed Jun. 2, 2020.
Design U.S. Appl. No. 29/736,651, filed Jun. 2, 2020.
Design U.S. Appl. No. 29/736,652, filed Jun. 2, 2020.
Design U.S. Appl. No. 29/736,653, filed Jun. 2, 2020.
Design U.S. Appl. No. 29/736,654, filed Jun. 2, 2020.
Design U.S. Appl. No. 29/736,655, filed Jun. 2, 2020.
U.S. Appl. No. 16/720,766, filed Dec. 19, 2019.
"ATM-MPLS Network Interworking Version 2.0, of-aic-0178.001" ATM Standard, the ATM Forum Technical Committee, published Aug. 2003.
"Council Directive 93/42/EEC of Jun. 14, 1993, Concerning Medical Devices," Official Journal of the European Communities, L&C. Ligislation and Competition, S, No. L 169, Jun. 14, 1993, pp. 1-43.
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
A.V. Kasture and S.G. Wadodkar, Pharmaceutical Chemistry-Ii: Second Year Diploma in Pharmacy, Nirali Prakashan, p. 339, 2007.
Adeeb, et al., "An Inductive Link-Based Wireless Power Transfer System for Biomedical. Applications," Research Article, Nov. 14, 2011, pp. 1-12, vol. 2012, Article ID 879294, Hindawi Publishing Corporation.
Allegro MicroSystems, LLC, Automotive Full Bridge Mosfet Driver, A3941-Ds, Rev. 5, 21 pp., http://www.allegromicro.com/~/media/Files/Datasheets/A3941-Datasheet.ashx?la=en.
Anonymous, Analog Devices Wiki, Chapter 11: the Current Mirror, Aug. 20, 2017, 22 pages. https://wiki.analog.com/university/courses/electronics/text/chapter-11?rev=1503222341.
Anonymous: "Sense & Control Application Note Current Sensing Using Linear Hall Sensors," Feb. 3, 2009, pp. 1-18. Retrieved from

(56) References Cited

OTHER PUBLICATIONS the Internet: URL: http://www.infineon.com/dgdl/Current_Sensing_Rev.1.1.pdf?fileld=db3a304332d040720132d9395 03e5f17 [retrieved on Oct. 18, 2016].
Arjo Loeve et al., Scopes Too Flexible . . . and Too Stiff, 2010, IEEE Pulse, Nov./Dec. 2010 (Year: 2010), 16 pages.
Arrow Sign Icon Next Button, by Blan-k, shutterstock.com [online], published on or before Aug. 6, 2014, [retrieved on Jun. 4, 2019], retrieved from the Internet [Url:https://www.shutterstock.com/de/image-vector/arrow-sign-icon-next-button-navigation-207700303?irgwc=1&utm . . . see PDF in file for full URL] (Year: 2014).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?Cretry=1&Sretry=0; [online] accessed: Sep. 22, 2008 (2 pp.).
Biomedical Coatings, Fort Wayne Metals, Research Products Corporation, obtained online at www.fwmetals.com on Jun. 21, 2010 (1 page).
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Breedveld et al., "A New, Easily Miniaturized Sterrable Endoscope," IEEE Engineering in Medicine and Biology Magazine (Nov./Dec. 2005).
Byrne et al., "Molecular Imprinting Within Hydrogels," Advanced Drug Delivery Reviews, 54 (2002) pp. 149-161.
C.C. Thompson et al., "Peroral Endoscopic Reduction of Dilated Gastrojejunal Anastomosis After Roux-en-Y Gastric Bypass: a Possible New Option for Patients with Weight Regain," Surg Endosc (2006) vol. 20., pp. 1744-1748.
Chen et al., "Elastomeric Biomaterials for Tissue Engineering," Progress in Polymer Science 38 (2013), pp. 584-671.
Covidien "iDrive™ Ultra Powered Stapling System, a Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Curved Tip Reload with Tri-Staple™ Technology," (2012), 2 pages.
Covidien Brochure, "Endo GIA™ Reloads with Tri-Staple™ Technology and Endo Gia™Ultra Universal Staplers," (2010), 2 pages.
Covidien Brochure, "Endo GIA™Reloads with Tri-Staple™Technology," (2010), 1 page.
Covidien Brochure, "Endo GIA™ Reloads with Tri-Staple™ Technology," (2010), 2 pages.
Covidien Brochure, "Endo GIA™ Black Reload with Tri-Staple™ Technology," (2012), 2 pages.
Covidien Brochure, "Endo GIA™ Ultra Universal Stapler," (2010), 2 pages.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Data Sheet of LM4F230H5QR, 2007.
Datasheet for Panasonic TK Relays Ultra Low Profile 2 a Polarized Relay, Copyright Matsushita Electric Works, Ltd. (Known of at least as early as Aug. 17, 2010), 5 pages.
Disclosed Anonymously, "Motor-Driven Surgical Stapler Improvements," Research Disclosure Database No. 526041, Published: Feb. 2008.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Fischer, Martin H, "Colloid-Chemical Studies on Soaps", the Chemical Engineer, pp. 184-193, Aug. 1919.
Foot and Ankle: Core Knowledge in Orthopaedics; by DiGiovanni MD, Elsevier; (p. 27, left column, heading "Materials for Soft Orthoses", 7th bullet point); (Year: 2007).
Forum discussion regarding "SPEED IS FASTER", published on Oct. 1, 2014 and retrieved on Nov. 8, 2019 from URL https://english.stackexchange.com/questions/199018/how-is-that-correct-speed-is-faster-or-prices-are-cheaper (Year: 2014).
Gao et al., "Mechanical Signature Enhancement of Response Vibrations in the Time Lag Domain," Fifth International Congress on Sound and Vibration, Dec. 15-18, 1997, pp. 1-8.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
http://ninpgan.net/publications/51-100/89.pdf; 2004, Ning Pan, on Uniqueness of Fibrous Materials, Design & Nature II. Eds: Colins, M. And Brebbia, C. Wit Press, Boston, 493-504.
IEEE Std 802.03.2012 (Revision of IEEE Std 802.Mar. 2008, published Dec. 28, 2012.
Indian Standard: Automotive Vehicles—Brakes and Braking Systems (IS 11852-1:2001), Mar. 1, 2001.
Jauchem, J.R., "Effects of low-level radio-frequency (3 kHz to 300 GHz) enery on human cardiovascular, reproductive, immune, and other systems: a review of the recent literatured," Int. J. Hyg. Environ. Health 211 (2008) 1-29.
Jeong et al., "Thermosensitive Sol-Gel Reversible Hydrogels," Advanced Drug Delivery Reviews, 54 (2002) pp. 37-51.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Makerbot, 10 Advantages of 3D Printing, 2020 (retrieved via the wayback machine), Makerbot.com (Year: 2020).
Matsuda, "Thermodynamics of Formation of Porous Polymeric Membrane from Solutions," Polymer Journal, vol. 23, No. 5, pp. 435-444 (1991).

(56) References Cited

OTHER PUBLICATIONS

Miyata et al., "Biomolecule-Sensitive Hydrogels," Advanced Drug Delivery Reviews, 54 (2002) pp. 79-98.
Molina, "Low Level Reader Protocol (LLRP)," Oct. 13, 2010, pp. 1-198.
Mouser Electronics, "LM317 3-Terminal Adjustable Regulator with Overcurrent/Overtemperature Self Protection", 30 Sep. 2016 (Sep. 30, 2016), XP0555246104, Retrieved from the Internet: URL: http://www.mousercom/ds/2/405/1m317m-440423.pdf, pp. 1-9.
Mouser Electronics, "LM317M 3-Terminal Adjustable Regulator with Overcurrent/Overtemperature Self Protection", 31 Mar. 2014 (Mar. 31, 2014), XP0555246104, Retrieved from the Internet: URL: http://www.mousercom/ds/2/405/1m317m-440423.pdf, pp. 1-8.
NF Monographs: Sodium Stearate, U.S. Pharmacopeia, http://www.pharmacopeia.cn/v29240/usp29nf24s0_m77360.html, accessed May 23, 2016.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Pitt et al., "Attachment of Hyaluronan to Metallic Surfaces," J. Biomed. Mater. Res. 68A: pp. 95106, 2004.
Pushing Pixels (GIF), published on dribble.com, 2013.
Qiu et al., "Environment-Sensitive Hydrogels for Drug Delivery," Advanced Drug Delivery Reviews, 53 (2001) pp. 321-339.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Rotary Systems: Sealed Slip Ring Categories, Rotary Systems, 22 May 2017, retrieved from the internet: http://web.archive.org/we/20170522174710/http:/rotarysystems.com: 80/slip-rings/sealed/, retrieved on Aug. 12, 2020, pp. 1-2.
Sandvik, "Welding Handbook," https://www.metingss/wp-content/uploads/2018/05/welding-handbook.pdf, retrieved on Jun. 22, 2020. pp. 5-6.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Schroeter, John, "Demystifying UHF GEN 2 RFID, HF RFID," Online Article, Jun. 2, 2008,. pp. 1-3, <https://www.edn.com/design/industrial-control/4019123/Demystifying-Uhf-Gen-2-. Rfid-Hf-Rfid>.
Seils et al., Covidien Summary: Clinical Study "UCONN Biodynamics: Final Report on Results," (2 pages).
Serial Communication Protocol; Michael Lemmon Feb. 1, 2009; http://www3.nd.eduhlemmon/courses/ee224/web-manual/web-manual/lab12/node2.html; Wayback Machine to Apr. 29, 2012.
Slow Safety Sign, shutterstock.com [online], published on or before 2017-05-09, [retrieved on May 31, 2019], retrieved from the https://www.shutterstock.com/image-victor/slow-safety-sign-twodimensional-turtle-symbolizing- . . . see Pdf in file for full URL] (Year: 2017).
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
Solorio et al., "Gelatin Microspheres Crosslinked with Genipin for Local Delivery of Growth Factors," J. Tissue Eng. Regen. Med. (2010), 4(7): pp. 514-523.
Texas Instruments: "Current Recirculation and Decay Modes," Application Report SLVA321—Mar. 2009; Retrieved from the Internet: Url:http://www.ti.com/lit/an/sIva321/sIva321 [retrieved. on Apr. 25, 2017], 7 pages.
The Sodem Aseptic Battery Transfer Kit, Sodem Systems, 2000, 3 pages.
Trendafilova et al., "Vibration-based Methods for Structural and Machinery Fault Diagnosis Based on Nonlinear Dynamics Tools," In: Fault Diagnosis in Robotic and Industrial Systems, IConcept Press Ltd, 2012, pp. 1-29.
Tutorial overview of inductively coupled RFID Systems, UPM, May 2003, pp. 1-7, UPM Rafsec,<htto://cdn.mobiusconsultino.com/papers/rfidsystems.pdf>.
U.S. Appl. No. 62/798,651, filed Jan. 30, 2019.
U.S. Appl. No. 62/840,602, filed Apr. 30, 2019.
V.K. Ahluwalia and Madhuri Goyal, A Textbook of Organic Chemistry, Section 19.11.3, p. 356, 2000.
Van Meer et al., "A Disposable Plastic Compact Wrist for Smart Minimally Invasive Surgical Tools," LAAS/CNRS (Aug. 2005).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Yan et al, Comparison of the effects of Mg—6Zn and Ti—3AI-2.5V alloys on TGF-β/TNF-α/VEGF/b-FGF in the healing of the intestinal track in vivo, Biomed. Mater. 9 (2014), 11 pages.
Yan et al., "Comparison of the effects of Mg-6Zn and titanium on intestinal tract in vivo," J Mater Sci: Mater Med (2013), 11 pages.
Yang et al.; "4D printing reconfigurable, deployable and mechanically tunable metamaterials," Material Horizions, vol. 6, pp. 1244-1250 (2019).
Young, "Microcellular foams via phase separation," Journal of Vacuum Science & Technology a 4(3), (May/Jun. 1986).
Youtube.com; video by Fibran (retrieved from URL https://www.youtube.com/watch?v=vN2Qjt51gFQ); (Year: 2018).
International Search Report and Written Opinion dated Jul. 8, 2022 for Application No. PCT/IB2022/052521, 13 pgs.

\* cited by examiner

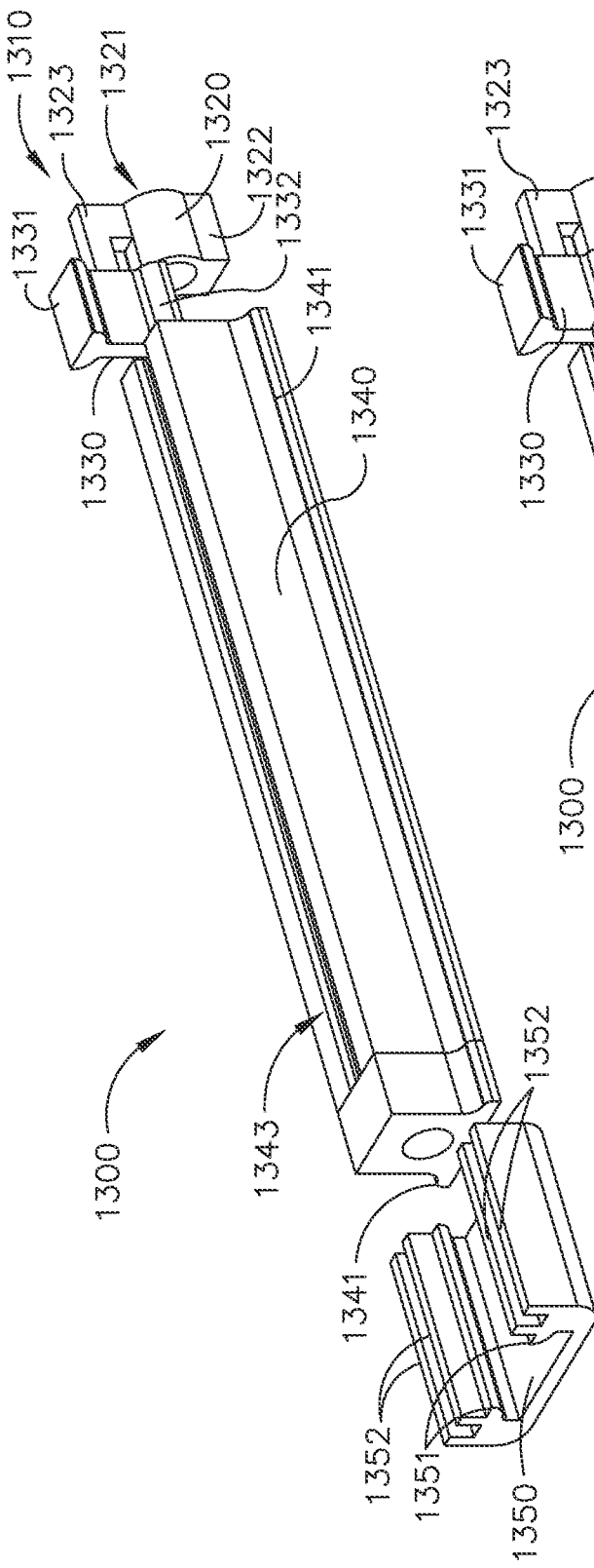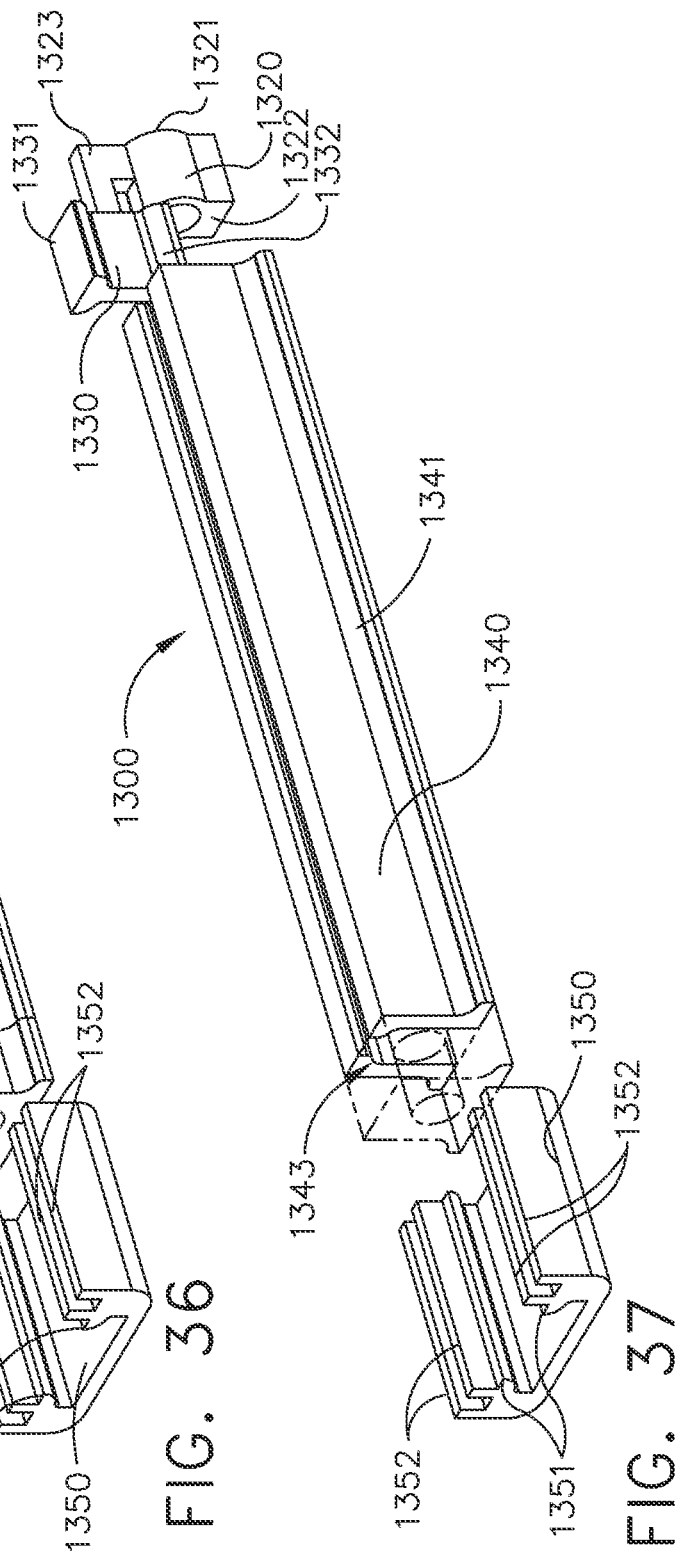

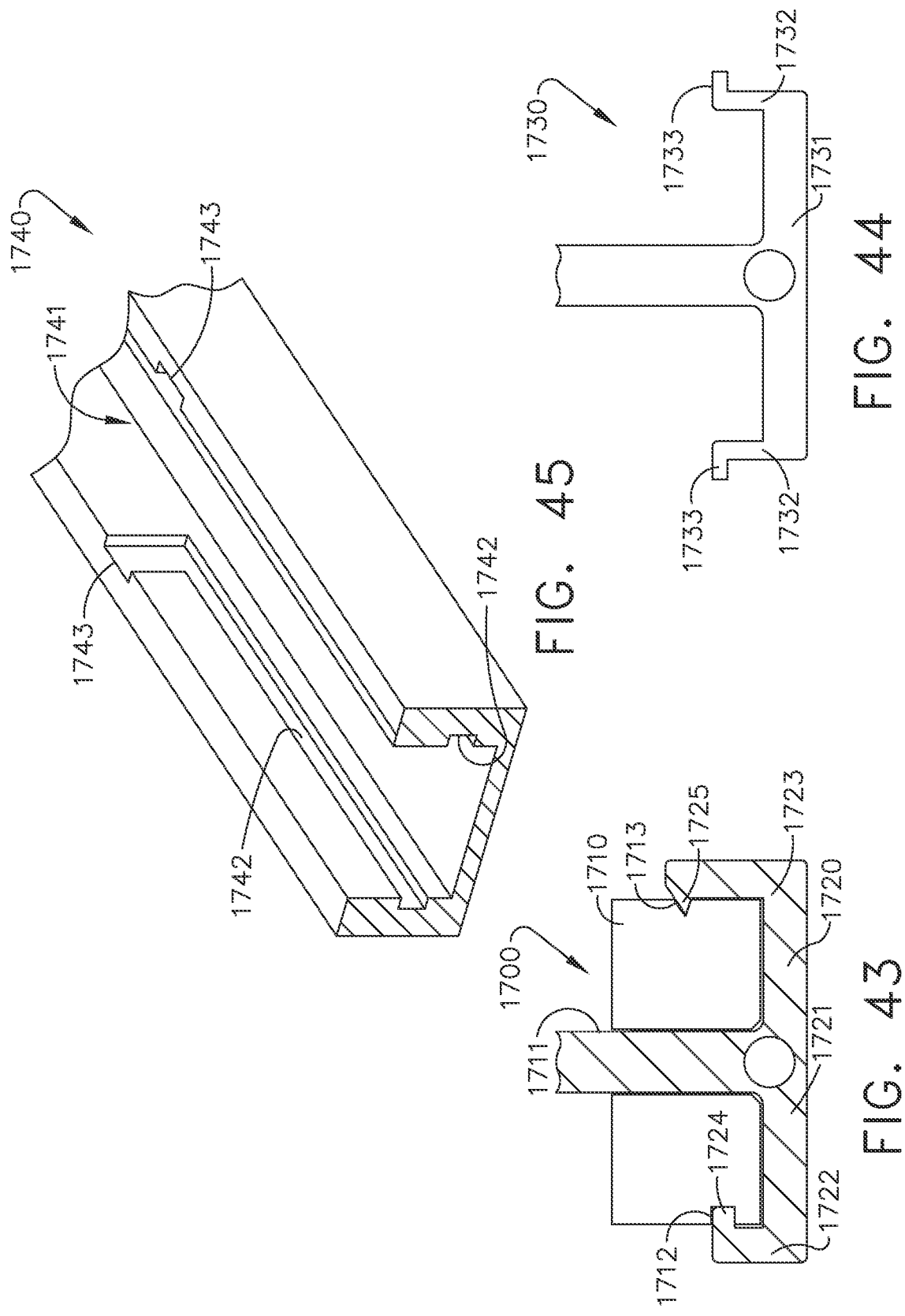

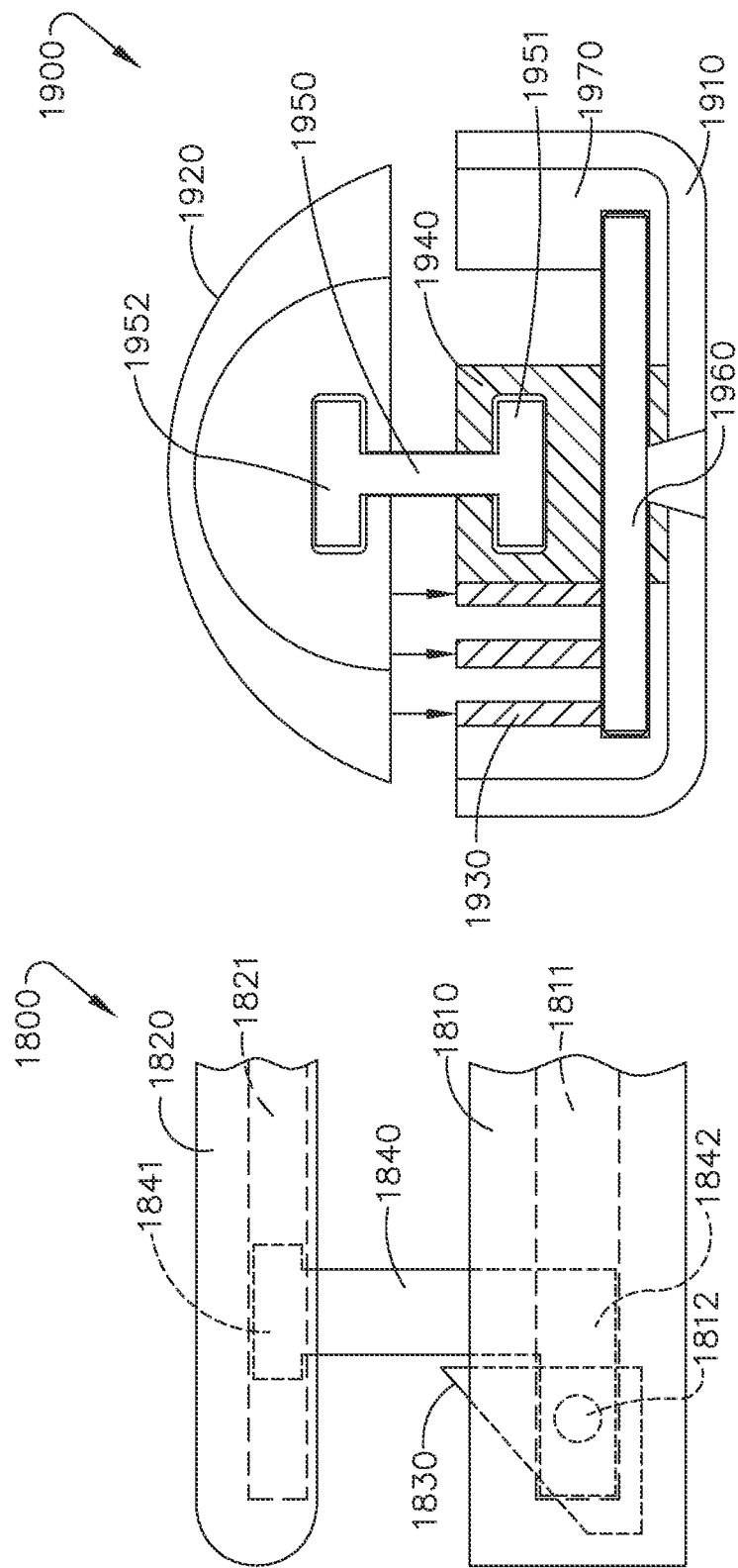

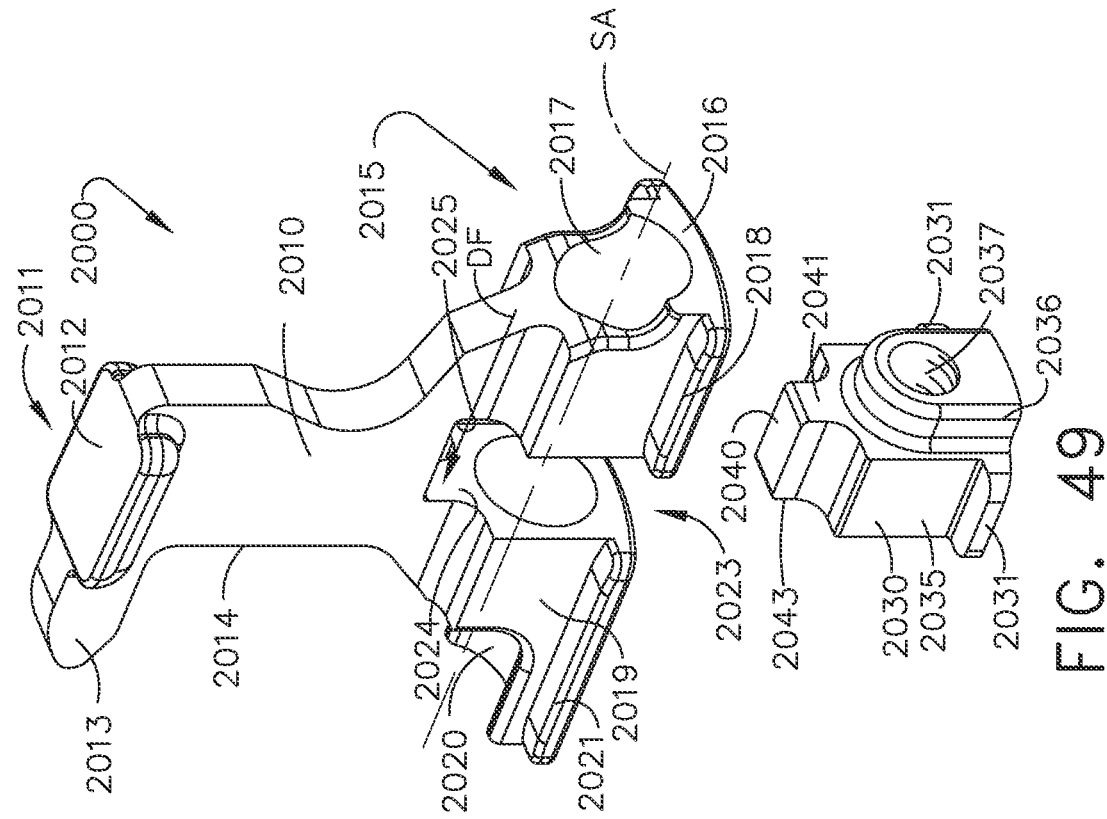
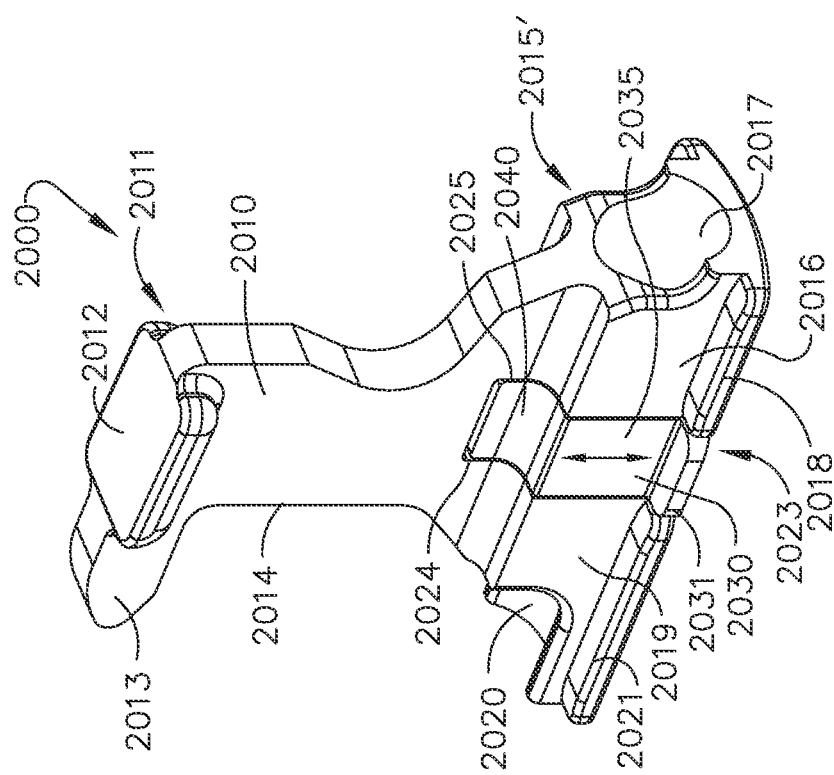
FIG. 49
FIG. 48

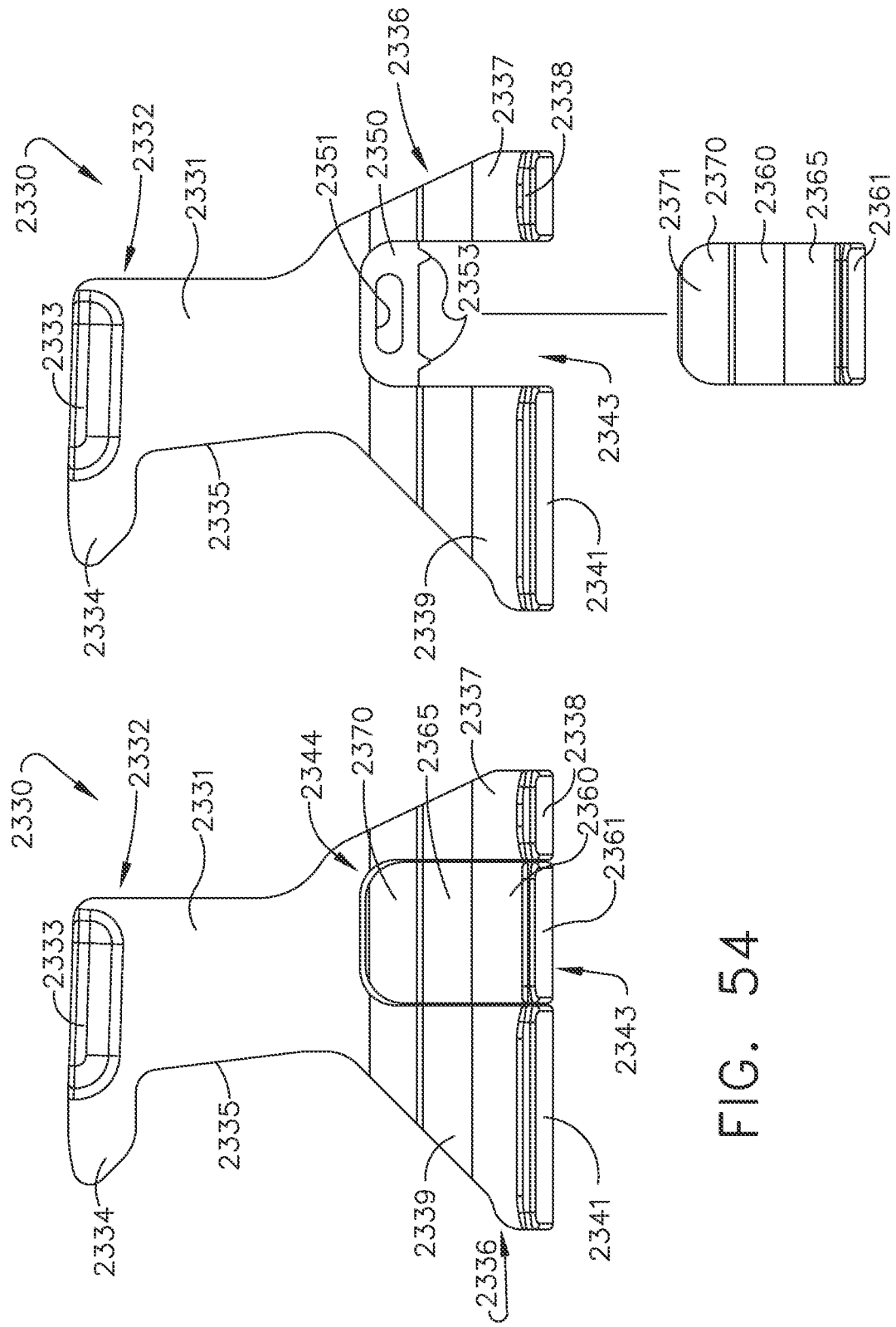

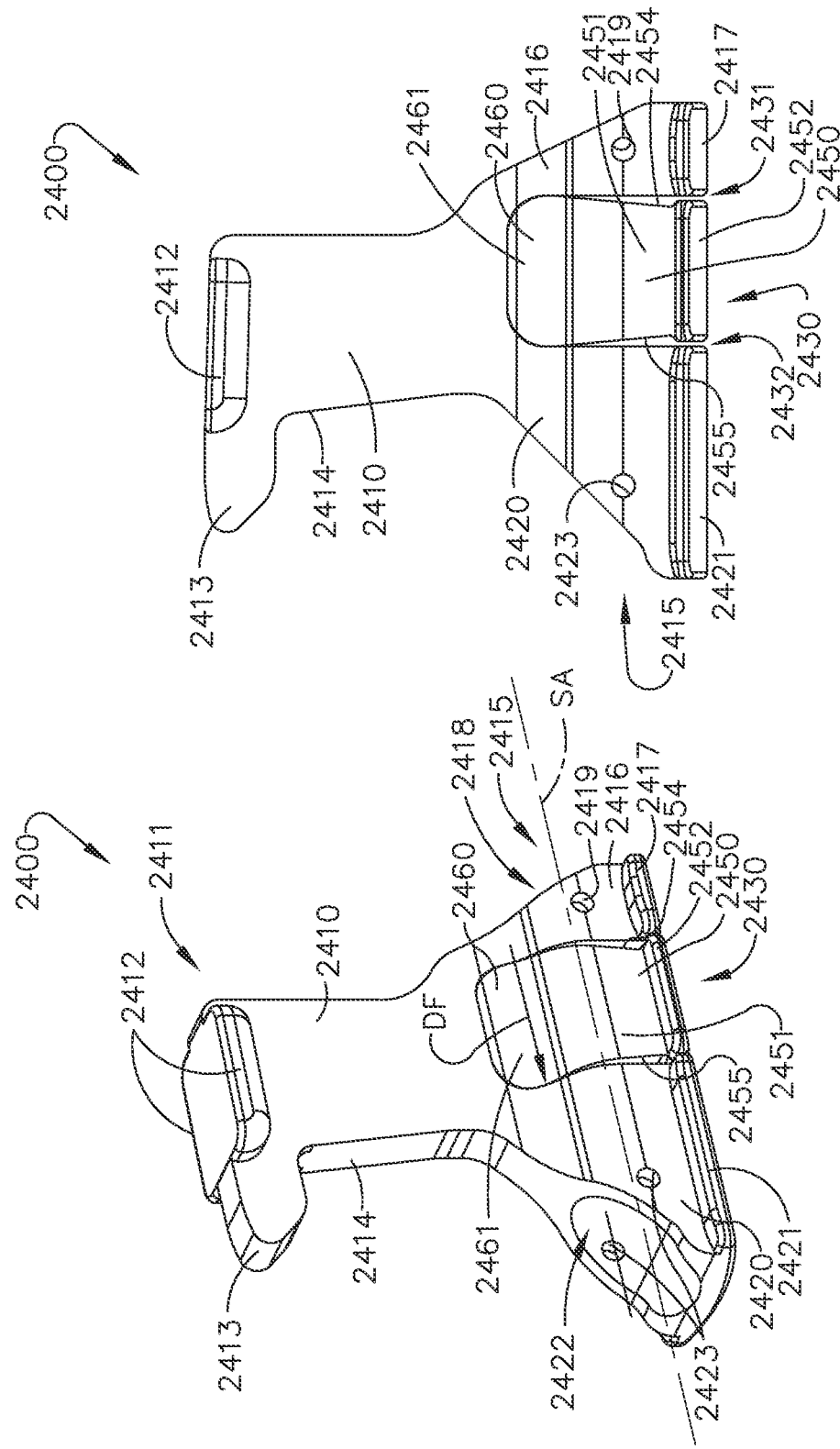

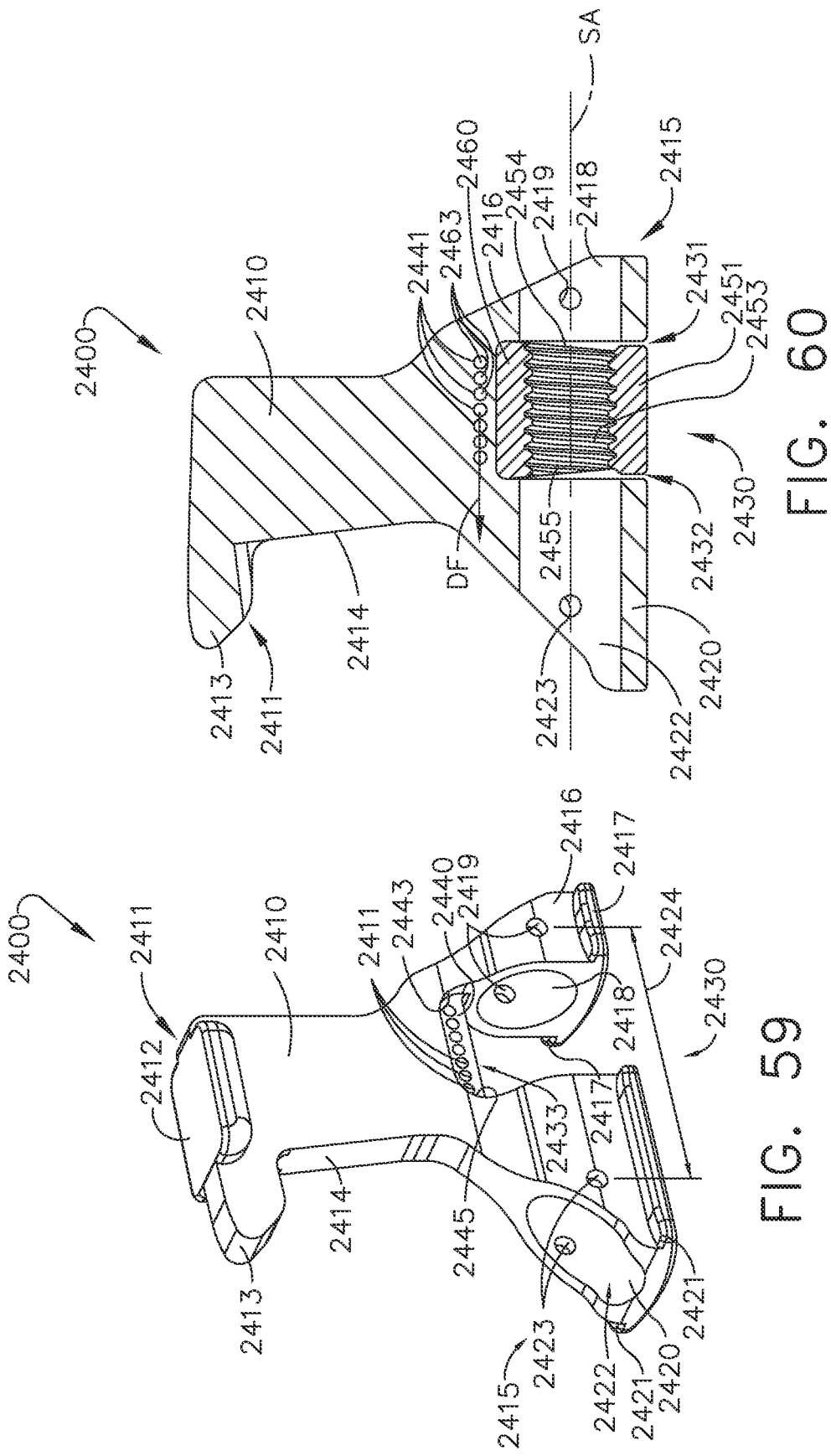

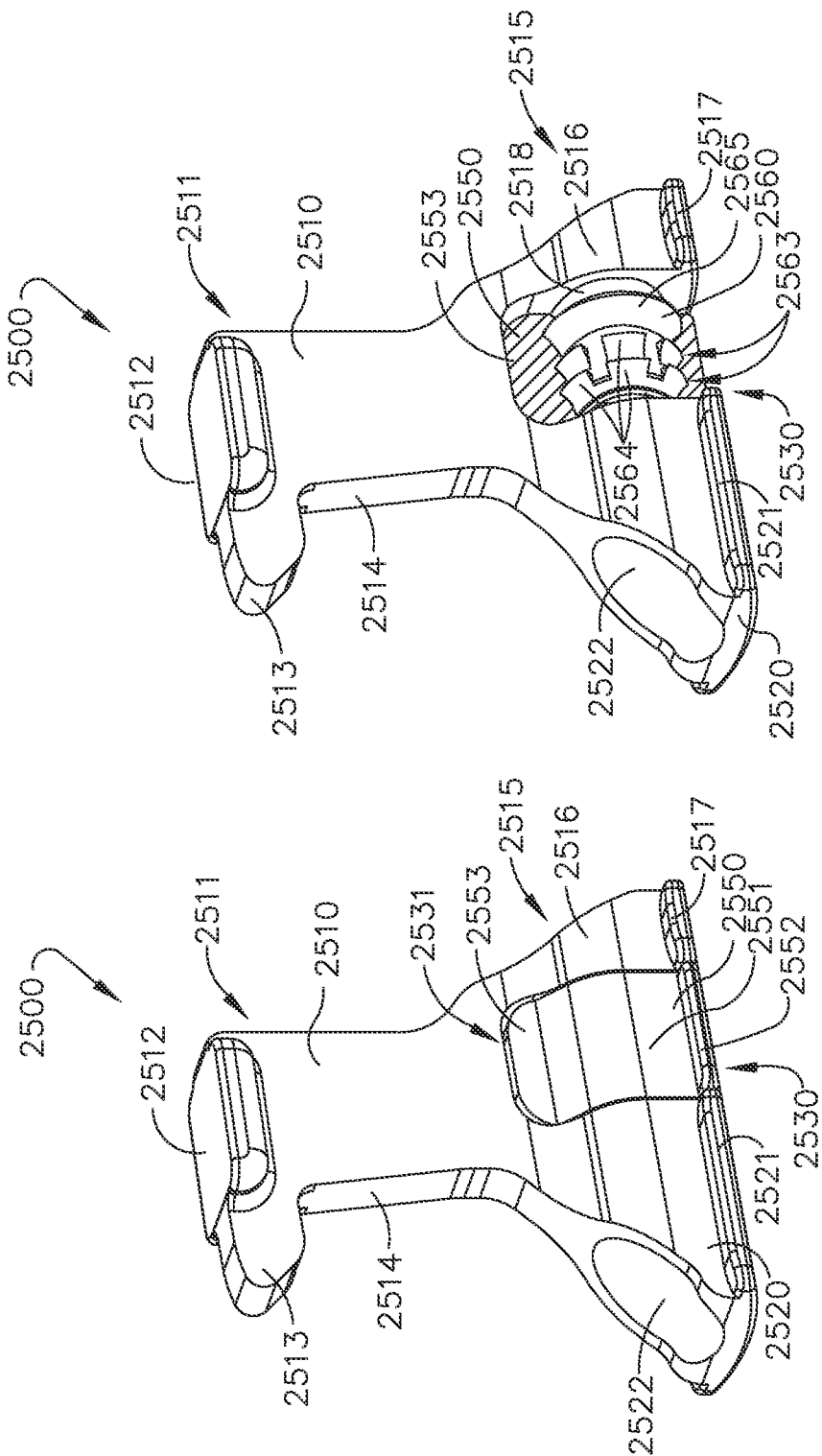

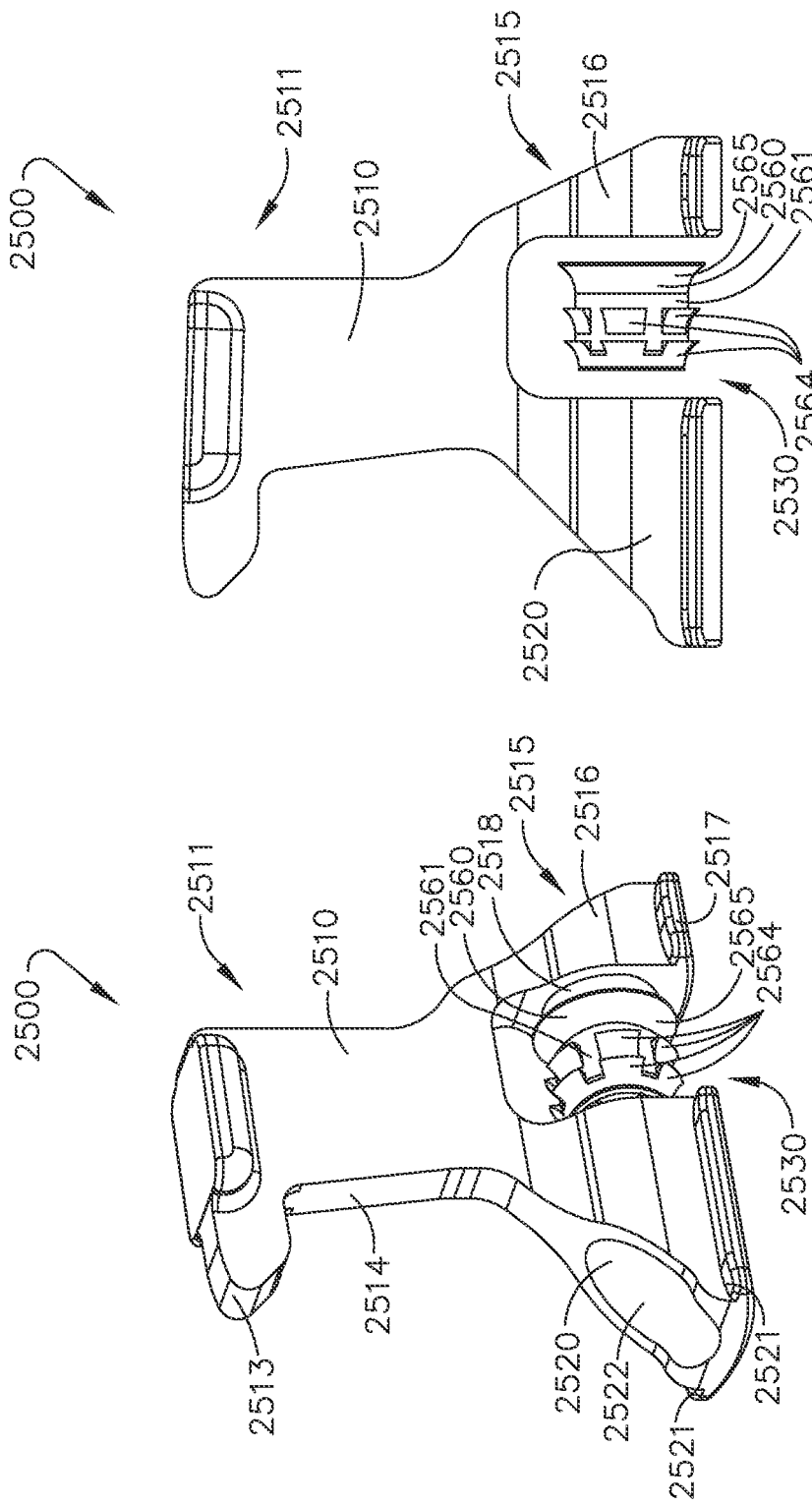

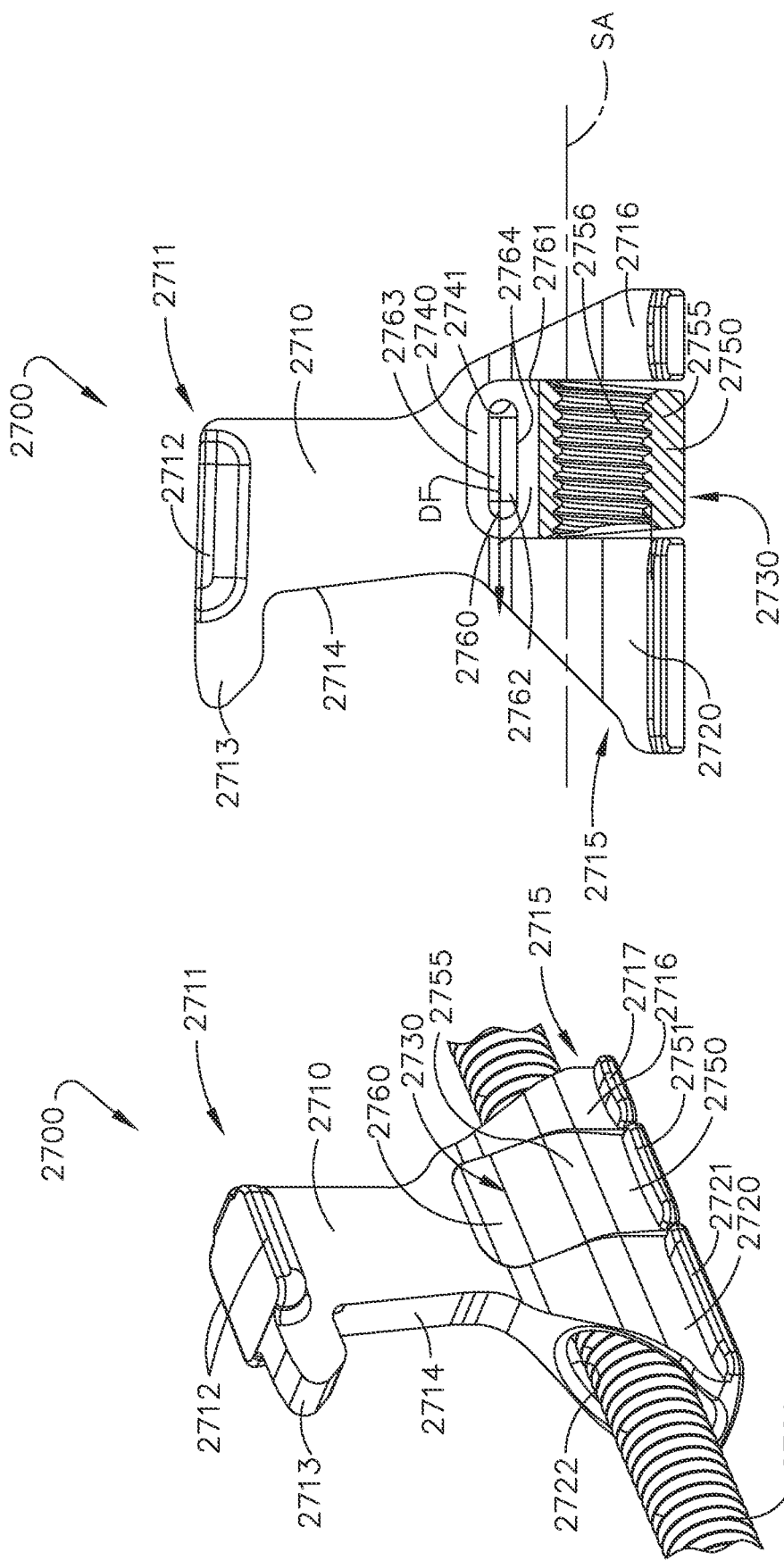

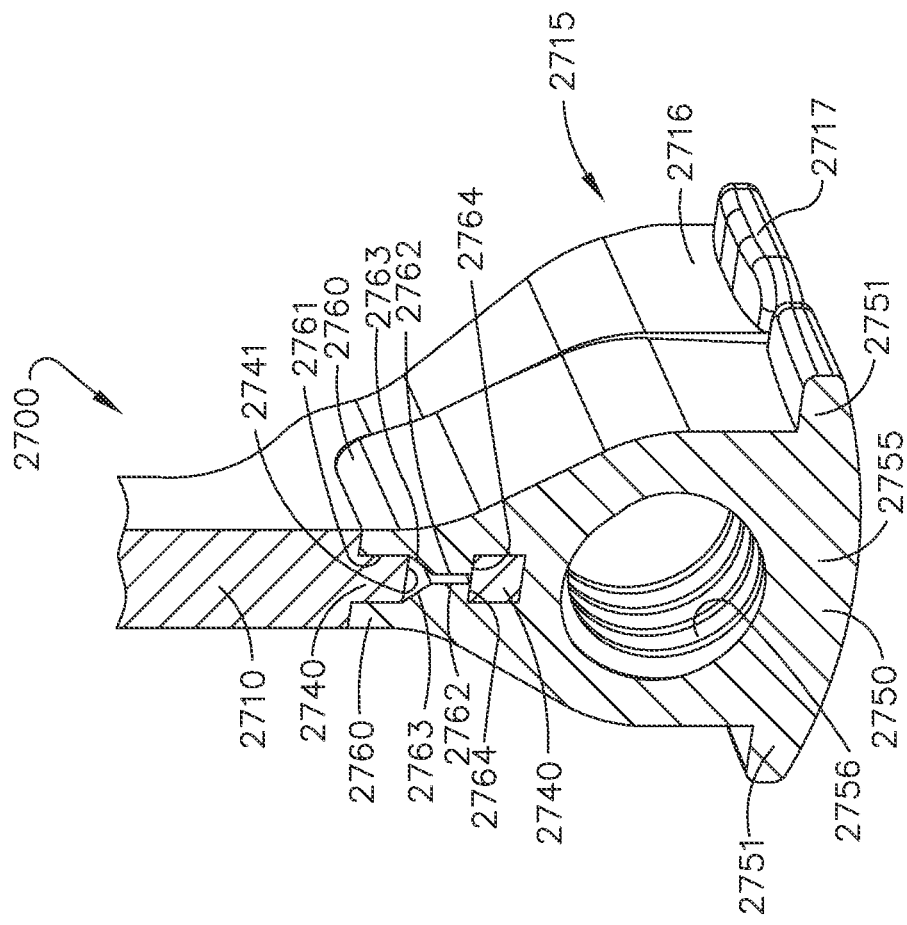
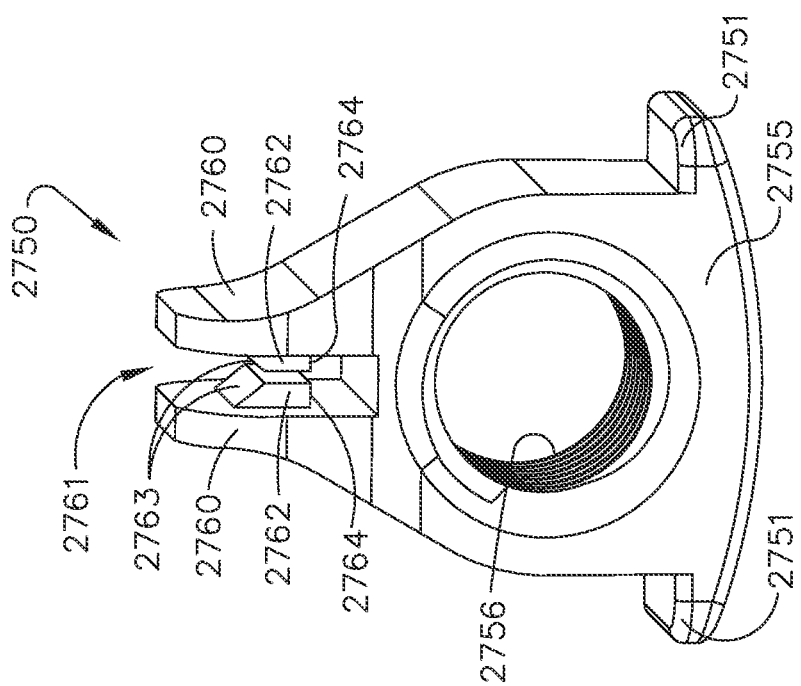

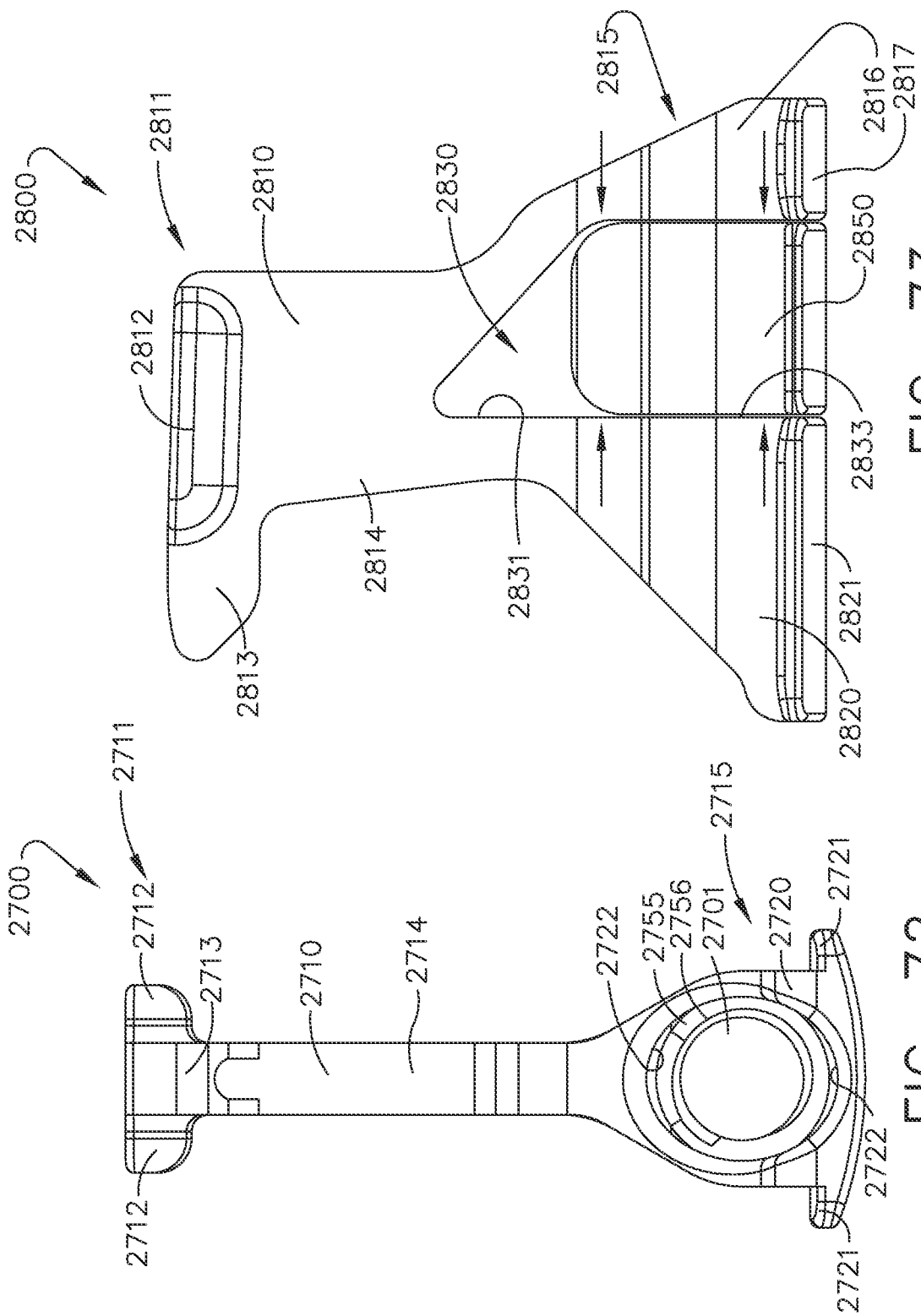

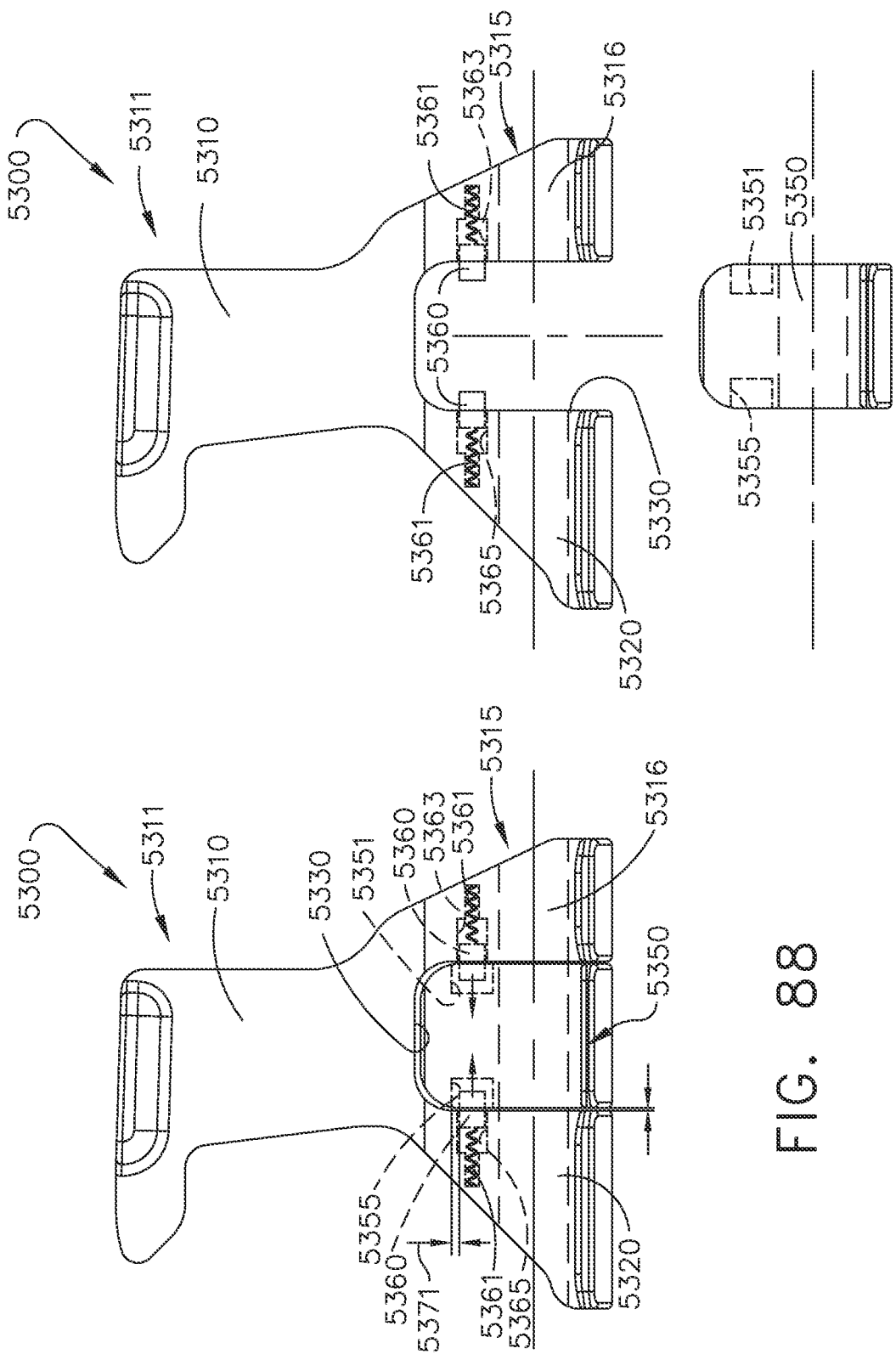

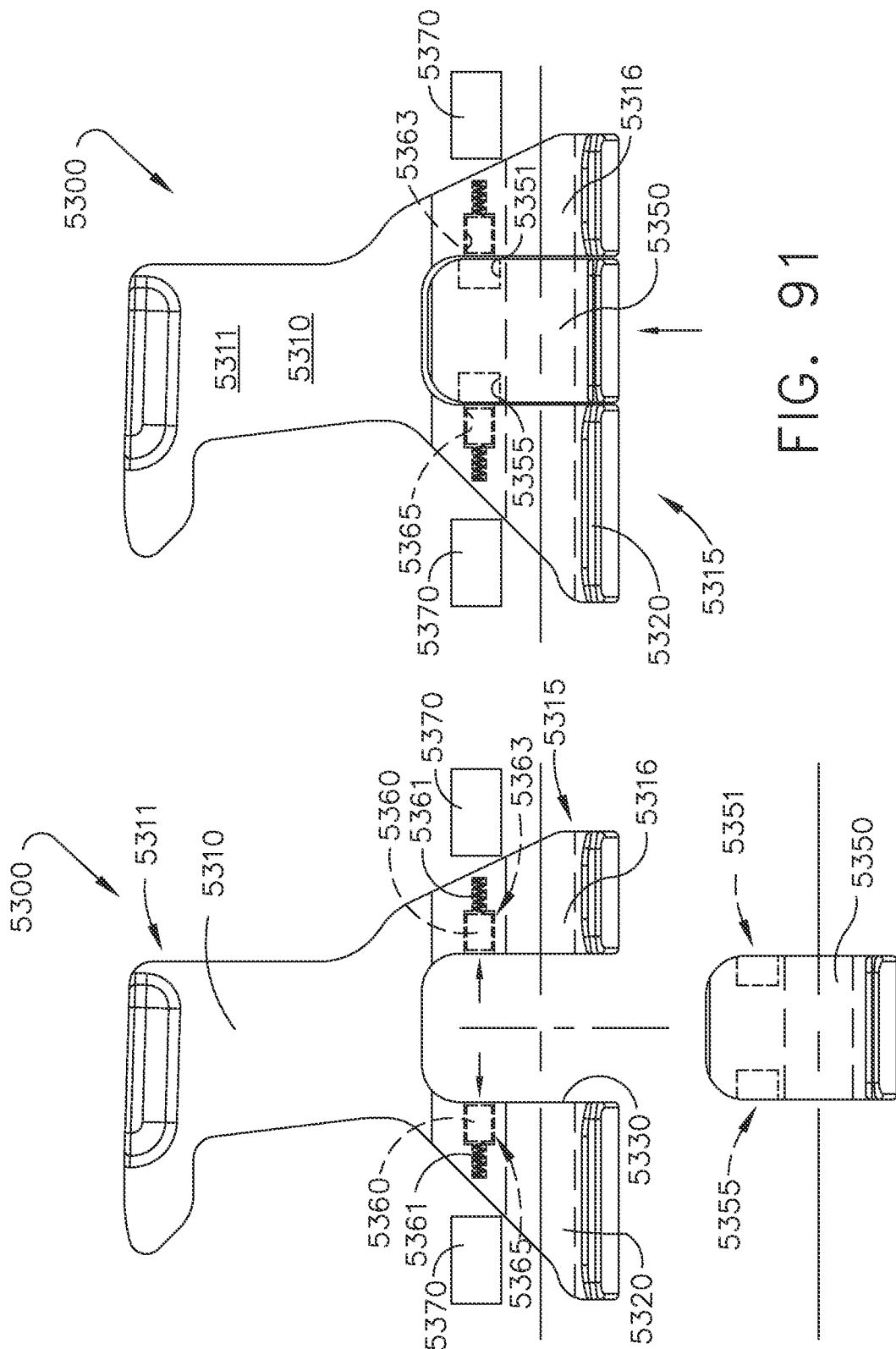

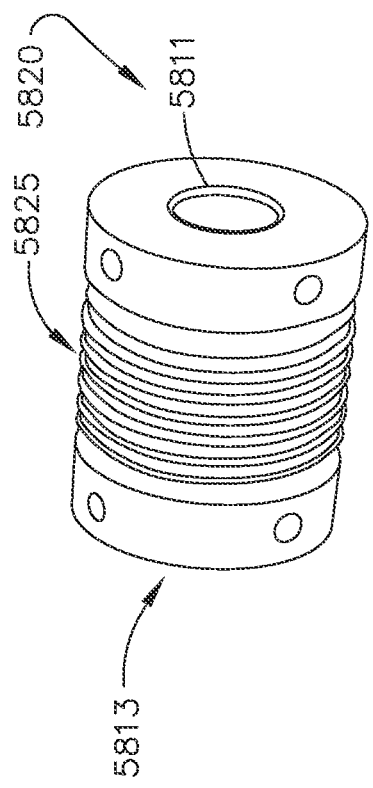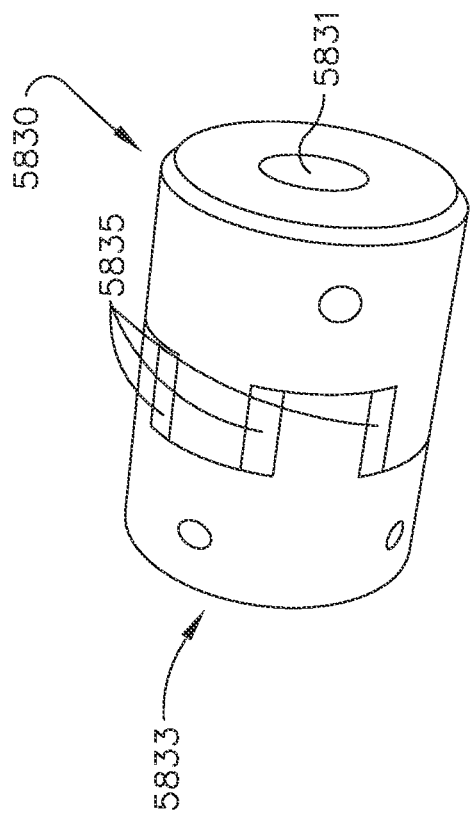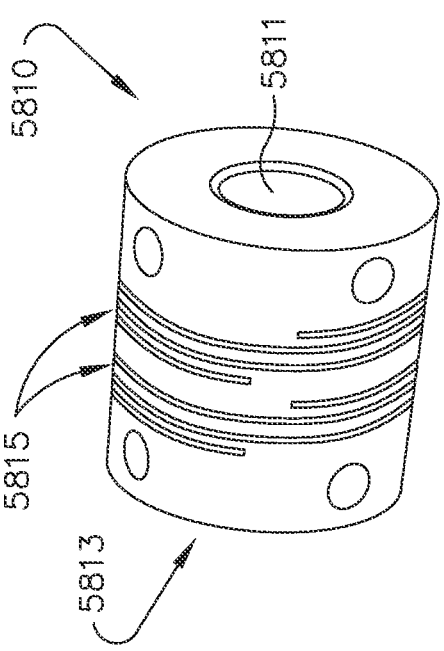

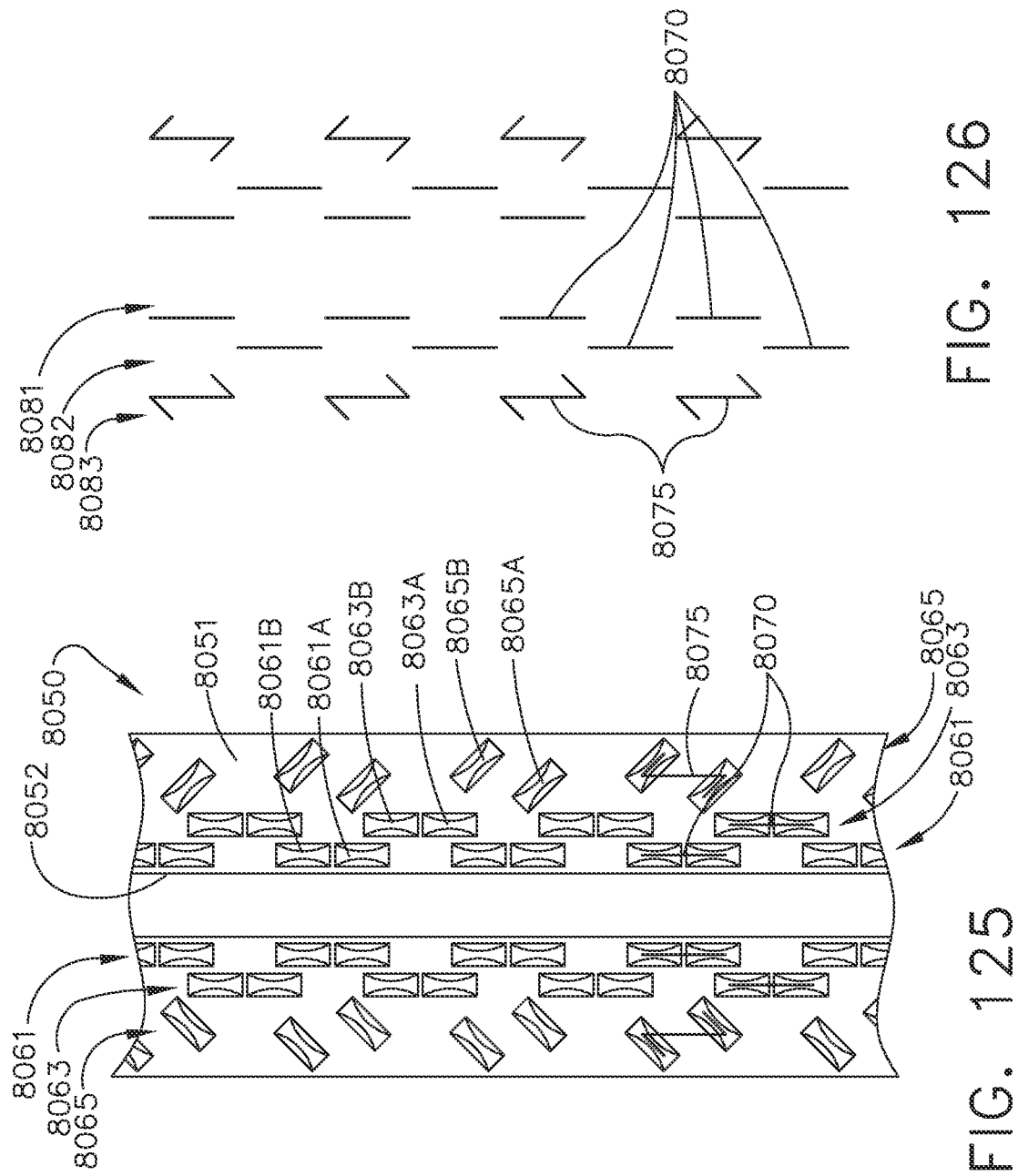

SURGICAL STAPLE CARTRIDGE COMPRISING LONGITUDINAL SUPPORT BEAM

BACKGROUND

The present invention relates to surgical instruments and, in various arrangements, to surgical stapling and cutting instruments, end effectors, and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 36 is an exploded perspective view of a portions of a stapling assembly including a support beam, a firing member assembly, and a sled, in accordance with at least one aspect of the present disclosure.

FIG. 37 is an exploded perspective view of the portions of the stapling assembly of FIG. 33, wherein a distal end of the support beam is shown in hidden lines to show the profile of a longitudinal channel of the support beam, in accordance with at least one aspect of the present disclosure.

FIG. 43 is a cross-sectional elevation view of portions of a stapling assembly including a sled and a cartridge support, in accordance with at least one aspect of the present disclosure.

FIG. 44 is an elevation view of a sled configured to fit within guide slots of a staple cartridge or cartridge support of a stapling assembly, in accordance with at least one aspect of the present disclosure.

FIG. 45 is a cross-sectional perspective view of a portion of a cartridge support configured to receive a sled therein, in accordance with at least one aspect of the present disclosure.

FIG. 46 is a schematic of portions of a stapling assembly including an anvil, a firing member, a cartridge jaw, and a sled pinned to the firing member, in accordance with at least one aspect of the present disclosure.

FIG. 47 is a cross-sectional view of a stapling assembly comprising a cartridge channel and an anvil, in accordance with at least one aspect of the present disclosure.

FIG. 48 is a perspective view of a firing member assembly comprising a primary body portion and a drive nut, in accordance with at least one aspect of the present disclosure.

FIG. 49 is an exploded perspective view of the firing member assembly of FIG. 48, in accordance with at least one aspect of the present disclosure.

FIG. 54 is an elevation view of the firing member assembly of FIG. 53, in accordance with at least one aspect of the present disclosure.

FIG. 55 is an exploded elevation view of the firing member assembly of FIG. 53, in accordance with at least one aspect of the present disclosure.

FIG. 57 is a perspective view of a firing member assembly comprising a primary body portion and a drive nut, in accordance with at least one aspect of the present disclosure.

FIG. 58 is an elevation view of the firing member assembly of FIG. 57, in accordance with at least one aspect of the present disclosure.

FIG. 59 is a perspective view of the primary body portion of the firing member assembly of FIG. 57, in accordance with at least one aspect of the present disclosure.

FIG. 60 is a cross-sectional elevation view of the firing member assembly of FIG. 57, in accordance with at least one aspect of the present disclosure.

FIG. 62 is a perspective view of a firing member assembly comprising a primary body portion and a drive nut assembly comprising an internal drive nut and an external drive portion, in accordance with at least one aspect of the present disclosure.

FIG. 63 is a perspective view of the firing member assembly of FIG. 62, wherein a portion of the external drive portion of the drive nut is cutaway for illustrative purposes to expose the internal drive nut, in accordance with at least one aspect of the present disclosure.

FIG. 64 is a perspective view of the primary body portion and internal drive nut of the firing member assembly of FIG. 62, in accordance with at least one aspect of the present disclosure.

FIG. 65 is an elevation view of the primary body portion and the internal drive nut of the firing member assembly of FIG. 62, in accordance with at least one aspect of the present disclosure.

FIG. 68 is a perspective view of a firing member assembly threadably coupled with a firing drive screw, wherein the firing member assembly comprises a primary body portion and a drive nut, in accordance with at least one aspect of the present disclosure.

FIG. 69 is a partial cross-sectional elevation view of the firing member assembly of FIG. 68, wherein the drive nut is cross-sectioned through a vertical plane, in accordance with at least one aspect of the present disclosure.

FIG. 70 is a perspective view of the drive nut of the firing member assembly of FIG. 68, in accordance with at least one aspect of the present disclosure.

FIG. 71 is a perspective, cross-sectional view of the firing member assembly of FIG. 68, in accordance with at least one aspect of the present disclosure.

FIG. 72 is an elevation view of the firing member assembly of FIG. 68, in accordance with at least one aspect of the present disclosure.

FIG. 73 is an elevation view of a firing member assembly comprising a primary body portion and a drive nut, in accordance with at least one aspect of the present disclosure.

FIG. 88 is an elevation view of a firing member assembly comprising a primary body portion and a drive nut floatably mounted within the primary body portion, in accordance with at least one aspect of the present disclosure.

FIG. 89 is an elevation view of the firing member assembly of FIG. 88 pre-assembly, in accordance with at least one aspect of the present disclosure.

FIG. 90 is an elevation view of the firing member assembly of FIG. 88 mid-assembly, in accordance with at least one aspect of the present disclosure.

FIG. 91 is an elevation view of the firing member assembly of FIG. 88 partially assembled, in accordance with at least one aspect of the present disclosure.

FIG. 98 is a perspective view of a shaft coupling for use with a drive system of a surgical stapling assembly, in accordance with at least one aspect of the present disclosure.

FIG. 99 is a perspective view of a shaft coupling for use with a drive system of a surgical stapling assembly, in accordance with at least one aspect of the present disclosure.

FIG. 100 is a perspective view of a shaft coupling for use with a drive system of a surgical stapling assembly, in accordance with at least one aspect of the present disclosure.

FIG. 106 is a cross-sectional elevation view of a drive assembly mounted to a channel flange with a locking member, wherein FIG. 106 illustrates the drive assembly in a pre-assembled configuration, in accordance with at least one aspect of the present disclosure.

FIG. 107 is a cross-sectional elevation view of the drive assembly and the channel flange of FIG. 106, wherein FIG. 107 illustrates the drive assembly in an assembled configuration, in accordance with at least one aspect of the present disclosure.

FIG. 119 is a perspective view of the firing member of FIG. 118, in accordance with at least one aspect of the present disclosure.

FIG. 120 is a cross-sectional elevation view of the firing drive assembly of FIG. 118, wherein the bailout is illustrated in an unactuated configuration, in accordance with at least one aspect of the present disclosure.

FIG. 121 is a cross-sectional elevation view of the firing drive assembly of FIG. 118 taken through a housing component of the bailout, wherein the bailout is illustrated in the unactuated configuration, in accordance with at least one aspect of the present disclosure.

FIG. 122 is a cross-sectional elevation view of the firing drive assembly of FIG. 118, wherein the bailout is illustrated in an actuated configuration, in accordance with at least one aspect of the present disclosure.

FIG. 123 is a cross-sectional elevation view of the firing drive assembly of FIG. 118 taken through a housing component of the bailout, wherein the bailout is illustrated in the actuated configuration, in accordance with at least one aspect of the present disclosure.

FIG. 124 is a perspective view of a surgical stapling assembly, in accordance with at least one aspect of the present disclosure.

FIG. 125 is a plan view of an anvil surface of an anvil of the surgical stapling assembly of FIG. 124, in accordance with at least one aspect of the present disclosure.

FIG. 126 is a plan view of formed staple lines of the surgical stapling assembly of FIG. 124, in accordance with at least one aspect of the present disclosure.

FIG. 127 is an end elevation view and a side elevation view of a planar formed staple, in accordance with at least one aspect of the present disclosure.

FIG. 128 is an end elevation view and a side elevation view of a non-planar formed staple, in accordance with at least one aspect of the present disclosure.

FIG. 129 is a cross-sectional elevation view of an anvil comprising a plurality of staple forming pocket rows, in accordance with at least one aspect of the present disclosure.

FIG. 130 is an elevation view of a sled for use with a staple cartridge, in accordance with at least one aspect of the present disclosure.

Figure 131:
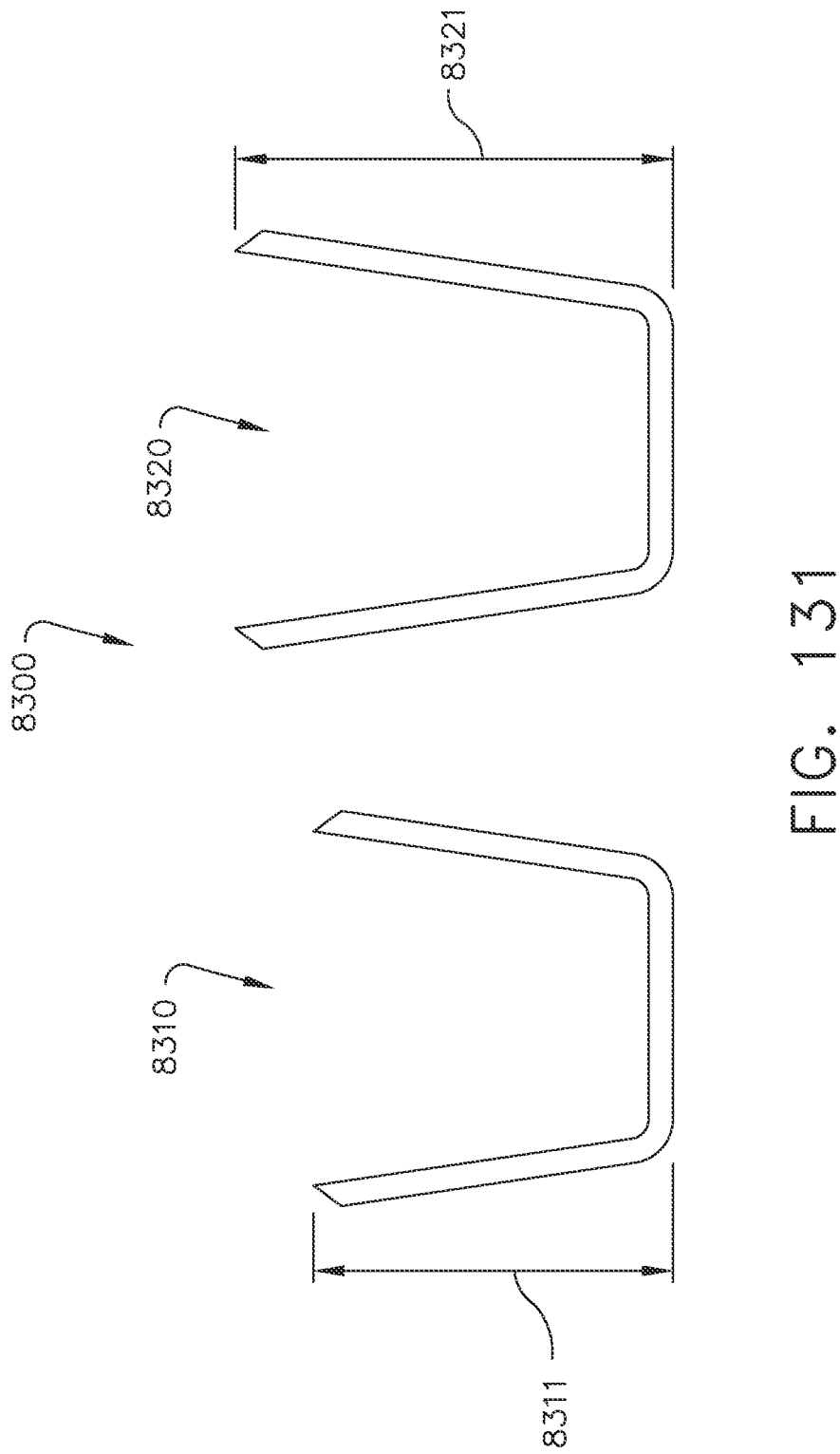

FIG. 131 is an elevation view of a first staple and a second staple for use with a surgical stapling assembly, in accordance with at least one aspect of the present disclosure.

Figure 132:
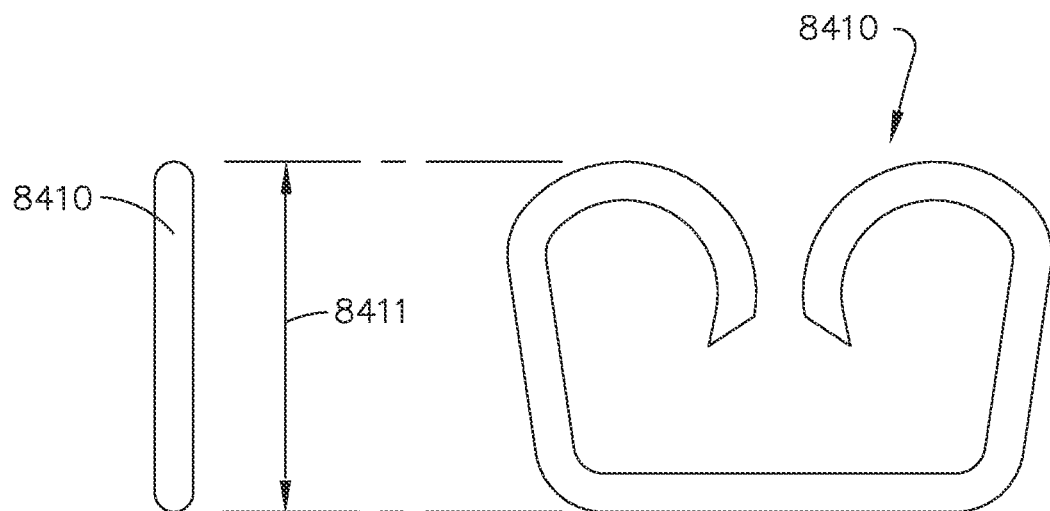

FIG. 132 is an end elevation view and a side elevation view of a planar formed staple, in accordance with at least one aspect of the present disclosure.

Figure 133:
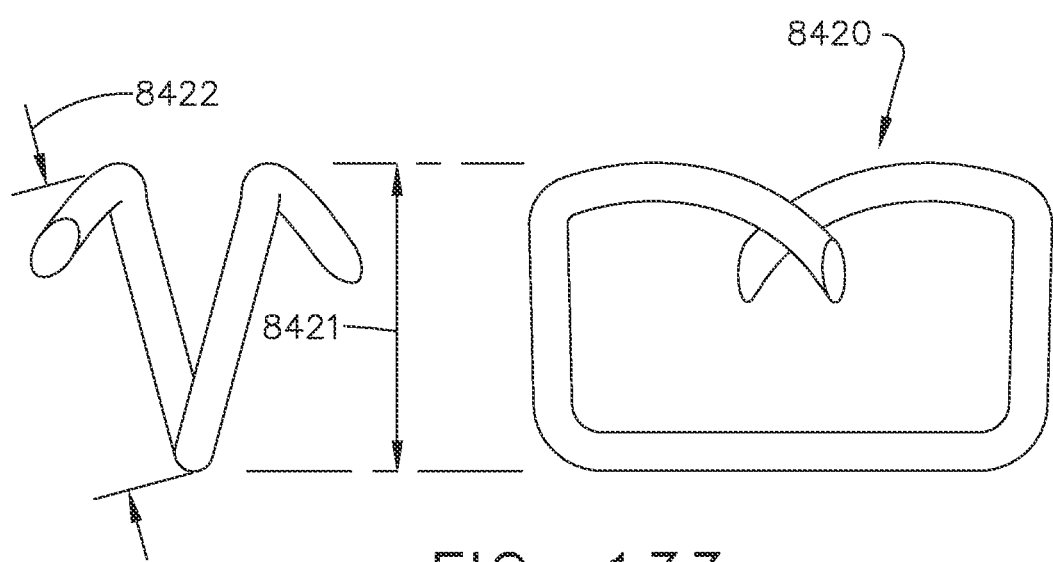

FIG. 133 is an end elevation view and a side elevation view of a non-planar formed staple, in accordance with at least one aspect of the present disclosure.

Figure 134:
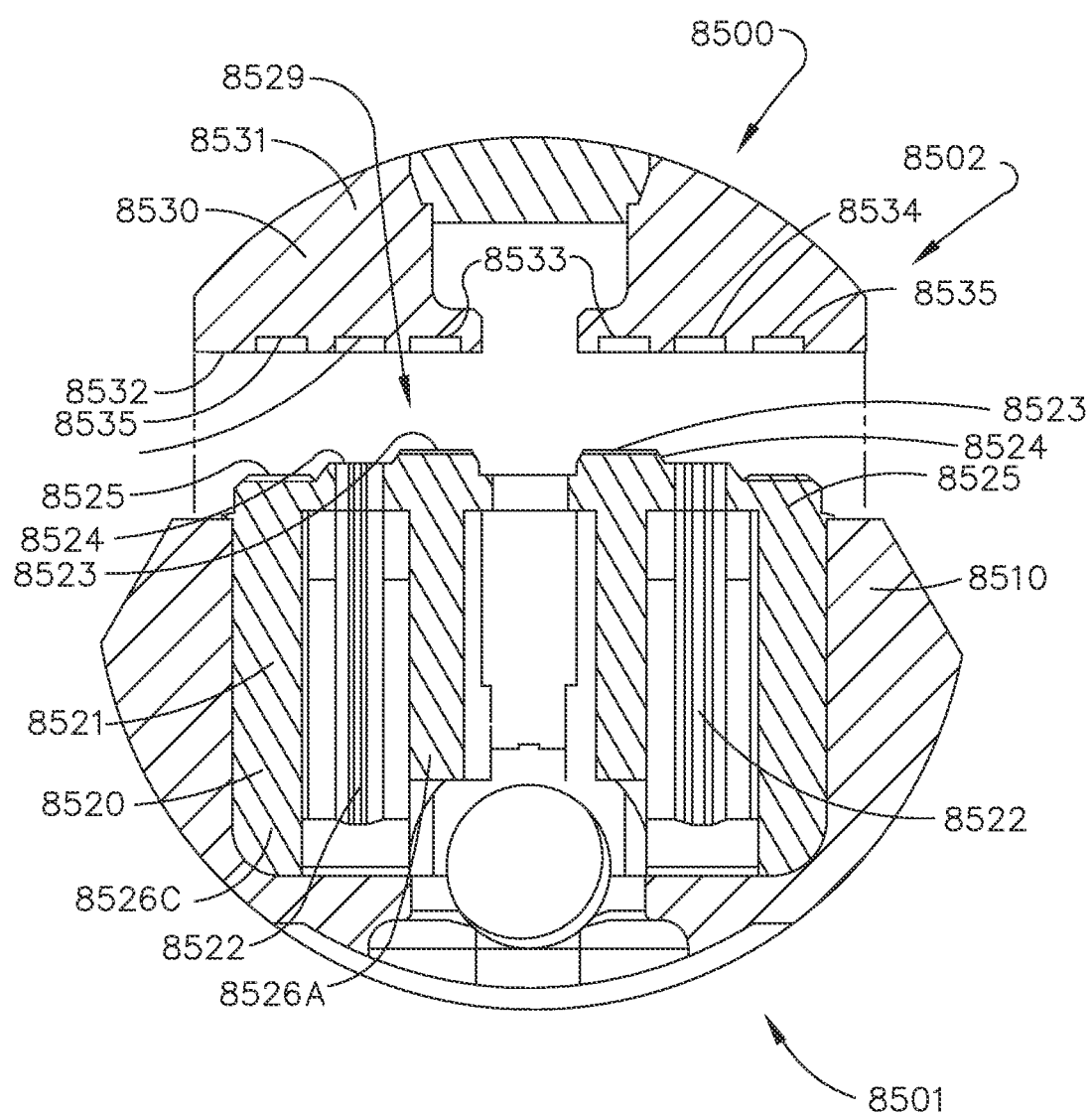

FIG. 134 is a cross-sectional elevation view of a surgical stapling assembly, in accordance with at least one aspect of the present disclosure.

Figure 135:
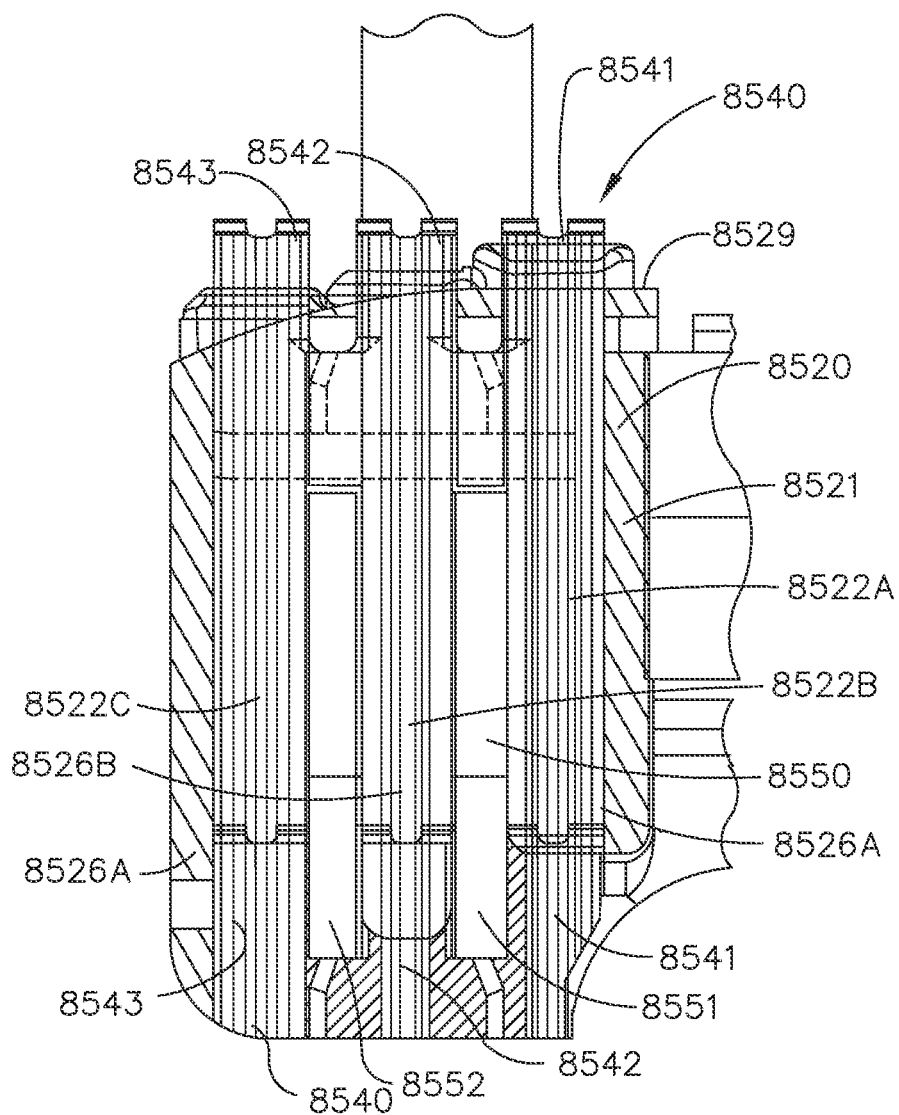

FIG. 135 is a partial cross-sectional elevation view of the surgical stapling assembly of FIG. 134, in accordance with at least one aspect of the present disclosure.

Figure 136:
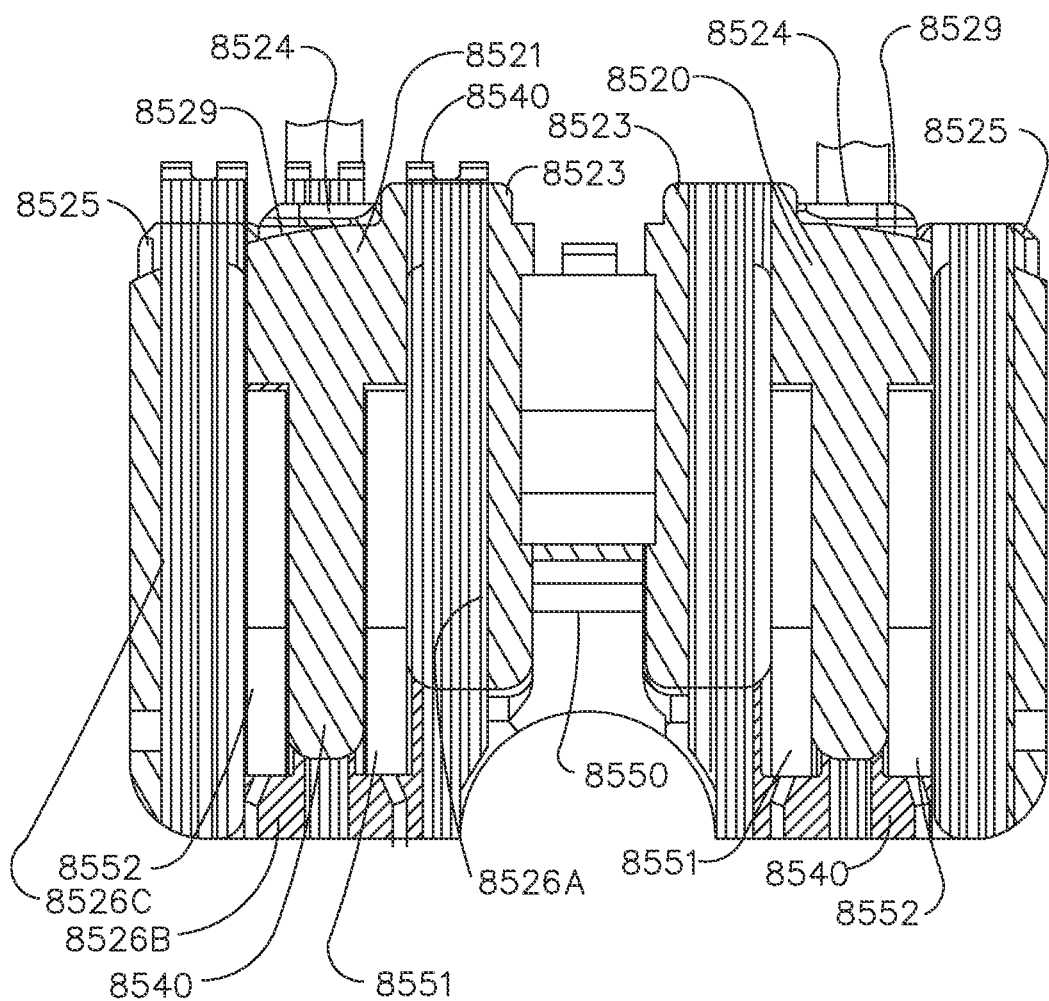

FIG. 136 is a cross-sectional elevation view of a staple cartridge and staple drivers of the surgical stapling assembly of FIG. 134, in accordance with at least one aspect of the present disclosure.

Figure 137:
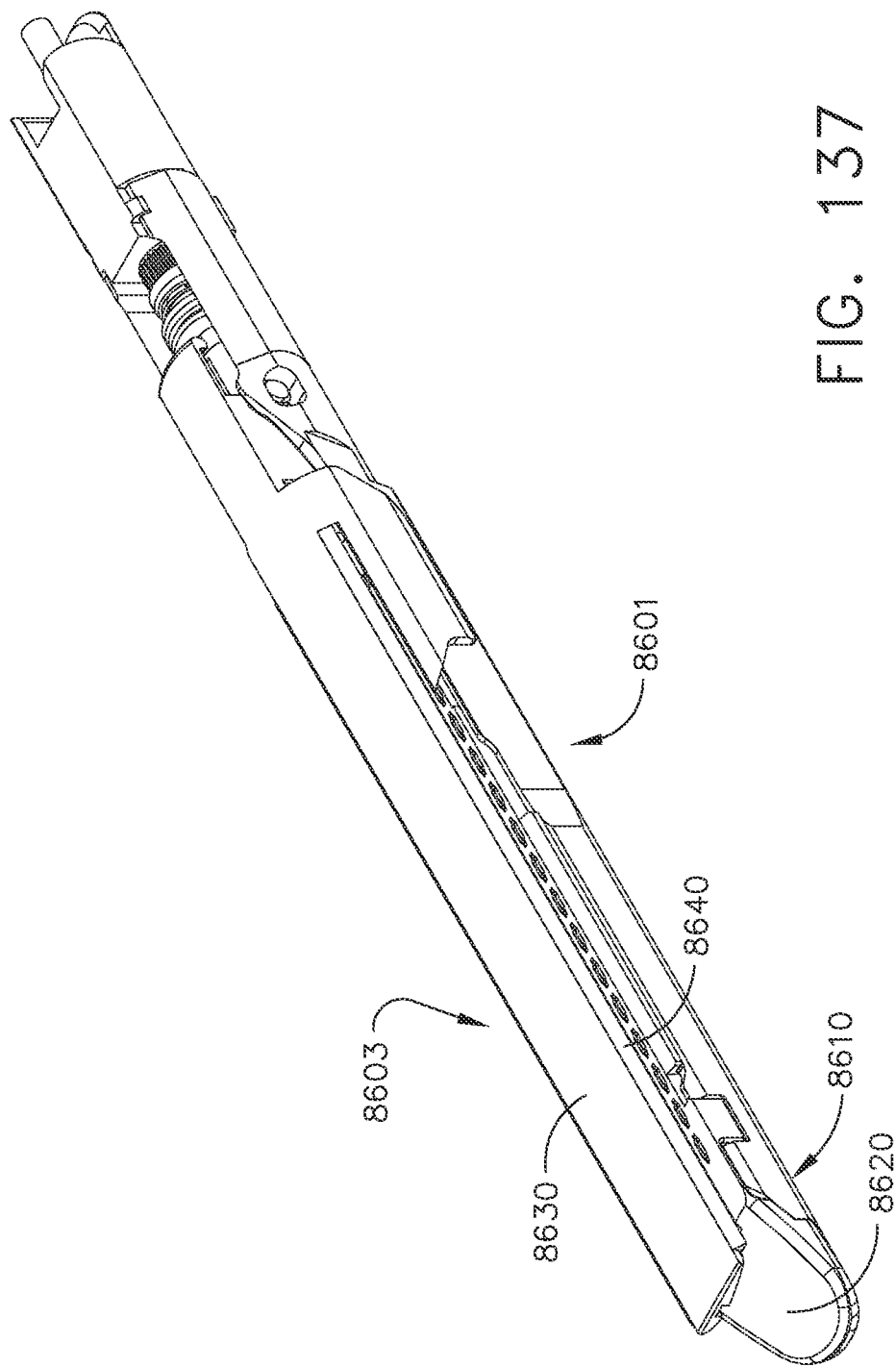

FIG. 137 is a perspective view of a surgical stapling assembly comprising a replaceable staple cartridge and a replaceable anvil plate, in accordance with at least one aspect of the present disclosure.

Figure 138:
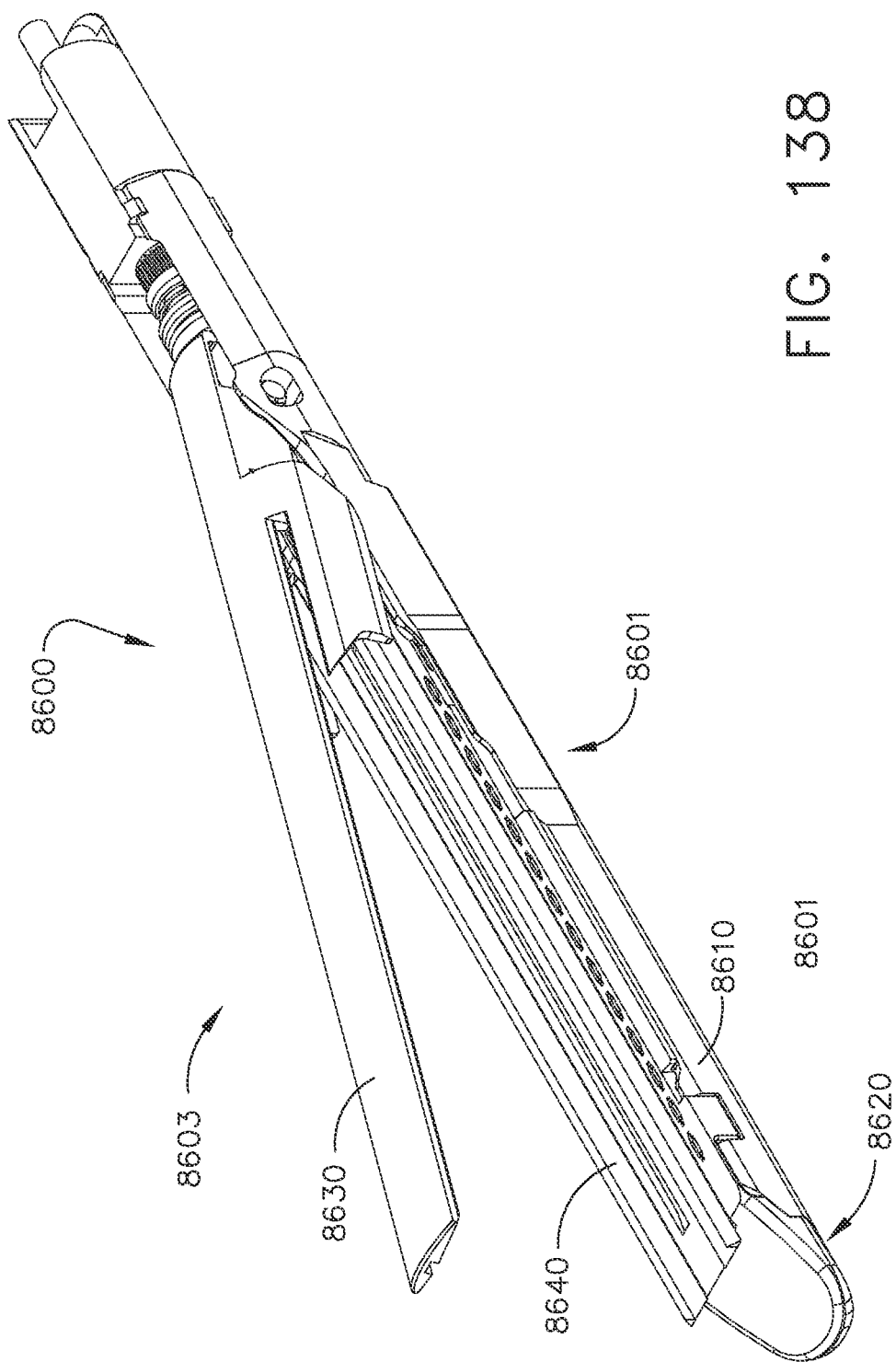

FIG. 138 is a perspective view of the surgical stapling assembly of FIG. 137 illustrated in an unclamped configuration, wherein the anvil plate is not attached to an anvil jaw of the surgical stapling assembly, in accordance with at least one aspect of the present disclosure.

Figure 139:
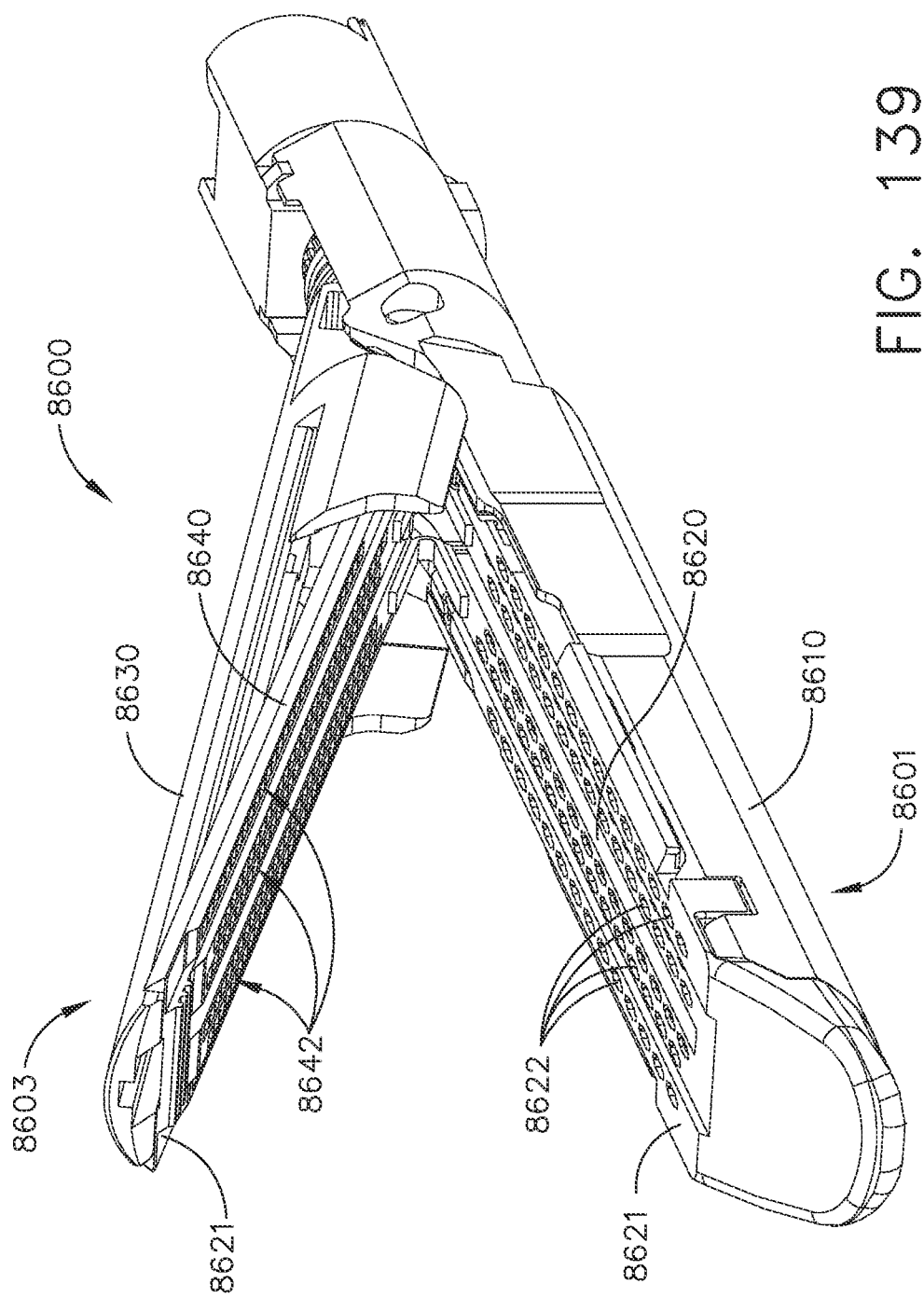

FIG. 139 is a perspective view of the surgical stapling assembly of FIG. 137, wherein the anvil plate is partially attached to the anvil jaw, in accordance with at least one aspect of the present disclosure.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. patent applications that were filed on Mar. 24, 2021, and which are each herein incorporated by reference in their respective entireties:

U.S. patent application Ser. No. 17/211,145, entitled METHOD OF USING A POWERED STAPLING DEVICE, now U.S. Patent Application Publication No. 2022/0304679;

U.S. patent application Ser. No. 17/211,161, entitled SURGICAL STAPLING ASSEMBLY COMPRISING NONPLANAR STAPLES AND PLANAR STAPLES, now U.S. Patent Application Publication No. 2022/0304684;

U.S. patent application Ser. No. 17/211,172, entitled ROTARY-DRIVEN SURGICAL STAPLING ASSEMBLY COMPRISING ECCENTRICALLY DRIVEN FIRING MEMBER, now U.S. Patent Application Publication No. 2022/0304686;

U.S. patent application Ser. No. 17/211,175, entitled ROTARY-DRIVEN SURGICAL STAPLING ASSEMBLY COMPRISING A FLOATABLE COMPONENT, now U.S. Patent Application Publication No. 2022/0304687;

U.S. patent application Ser. No. 17/211,182, entitled DRIVERS FOR FASTENER CARTRIDGE ASSEMBLIES HAVING ROTARY DRIVE SCREWS, now U.S. Patent Application Publication No. 2022/0304680;

U.S. patent application Ser. No. 17/211,189, entitled MATING FEATURES BETWEEN DRIVERS AND UNDERSIDE OF A CARTRIDGE DECK, now U.S. Patent Application Publication No. 2022/0304681;

U.S. patent application Ser. No. 17/211,192, entitled LEVERAGING SURFACES FOR CARTRIDGE INSTALLATION, now U.S. Patent Application Publication No. 2022/0304690;

U.S. patent application Ser. No. 17/211,197, entitled FASTENER CARTRIDGE WITH NON-REPEATING FASTENER ROWS, now U.S. Patent Application Publication No. 2022/0304682;

U.S. patent application Ser. No. 17/211,207, entitled FIRING MEMBERS HAVING FLEXIBLE PORTIONS FOR ADAPTING TO A LOAD DURING A SURGICAL FIRING STROKE, now U.S. Patent Application Publication No. 2022/0304688;

U.S. patent application Ser. No. 17/211,210, entitled STAPLING ASSEMBLY COMPONENTS HAVING METAL SUBSTRATES AND PLASTIC BODIES, , now U.S. Patent Application Publication No. 2022/0304689;

U.S. patent application Ser. No. 17/211,222, entitled MULTI-AXIS PIVOT JOINTS FOR SURGICAL INSTRUMENTS AND METHODS FOR MANUFACTURING SAME, now U.S. Patent Application Publication No. 2022/0304714;

U.S. patent application Ser. No. 17/211,230, entitled JOINT ARRANGEMENTS FOR MULTI-PLANAR ALIGNMENT AND SUPPORT OF OPERATIONAL DRIVE SHAFTS IN ARTICULATABLE SURGICAL INSTRUMENTS, now U.S. Patent Application Publication No. 2022/0304715; and U.S. patent application Ser. No. 17/211,242, entitled SURGICAL INSTRUMENT ARTICULATION JOINT ARRANGEMENTS COMPRISING MULTIPLE MOVING LINKAGE FEATURES, now U.S. Patent Application Publication No. 2022/0304683.

Applicant of the present application owns the following U.S. patent applications and U.S. patents that were filed on Dec. 19, 2017 and which are each herein incorporated by reference in their respective entireties:

U.S. Pat. No. 10,835,330, entitled METHOD FOR DETERMINING THE POSITION OF A ROTATABLE JAW OF A SURGICAL INSTRUMENT ATTACHMENT ASSEMBLY;

U.S. Pat. No. 10,716,565, entitled SURGICAL INSTRUMENTS WITH DUAL ARTICULATION DRIVERS;

U.S. patent application Ser. No. 15/847,325, entitled SURGICAL TOOLS CONFIGURED FOR INTERCHANGEABLE USE WITH DIFFERENT CONTROLLER INTERFACES, now U.S. Patent Application Publication No. 2019/0183491;

U.S. Pat. No. 10,729,509, entitled SURGICAL INSTRUMENT COMPRISING CLOSURE AND FIRING LOCKING MECHANISM;

U.S. patent application Ser. No. 15/847,315, entitled ROBOTIC ATTACHMENT COMPRISING EXTERIOR DRIVE ACTUATOR, now U.S. Patent application Publication No. 2019/0183594; and U.S. Design Pat. No. D910,847, entitled SURGICAL INSTRUMENT ASSEMBLY.

Applicant of the present application owns the following U.S. patent applications and U.S. patents that were filed on Jun. 28, 2017 and which are each herein incorporated by reference in their respective entireties:

U.S. patent application Ser. No. 15/635,693, entitled SURGICAL INSTRUMENT COMPRISING AN OFFSET ARTICULATION JOINT, now U.S. Patent application Publication No. 2019/0000466;

U.S. patent application Ser. No. 15/635,729, entitled SURGICAL INSTRUMENT COMPRISING AN ARTICULATION SYSTEM RATIO, now U.S. Patent application Publication No. 2019/0000467;

U.S. patent application Ser. No. 15/635,785, entitled SURGICAL INSTRUMENT COMPRISING AN ARTICULATION SYSTEM RATIO, now U.S. Patent application Publication No. 2019/0000469;

U.S. patent application Ser. No. 15/635,808, entitled SURGICAL INSTRUMENT COMPRISING FIRING MEMBER SUPPORTS, now U.S. Patent application Publication No. 2019/0000471;

U.S. patent application Ser. No. 15/635,837, entitled SURGICAL INSTRUMENT COMPRISING AN ARTICULATION SYSTEM LOCKABLE TO A FRAME, now U.S. Patent application Publication No. 2019/0000472;

U.S. Pat. No. 10,779,824, entitled SURGICAL INSTRUMENT COMPRISING AN ARTICULATION SYSTEM LOCKABLE BY A CLOSURE SYSTEM;

U.S. patent application Ser. No. 15/636,029, entitled SURGICAL INSTRUMENT COMPRISING A SHAFT INCLUDING A HOUSING ARRANGEMENT, now U.S. Patent application Publication No. 2019/0000477;

U.S. patent application Ser. No. 15/635,958, entitled SURGICAL INSTRUMENT COMPRISING SELECTIVELY ACTUATABLE ROTATABLE COUPLERS, now U.S. Patent application Publication No. 2019/0000474;

U.S. patent application Ser. No. 15/635,981, entitled SURGICAL STAPLING INSTRUMENTS COMPRISING SHORTENED STAPLE CARTRIDGE NOSES, now U.S. Patent application Publication No. 2019/0000475;

U.S. patent application Ser. No. 15/636,009, entitled SURGICAL INSTRUMENT COMPRISING A SHAFT INCLUDING A CLOSURE TUBE PROFILE, now U.S. Patent application Publication No. 2019/0000476;

U.S. Pat. No. 10,765,427, entitled METHOD FOR ARTICULATING A SURGICAL INSTRUMENT;

U.S. patent application Ser. No. 15/635,530, entitled SURGICAL INSTRUMENTS WITH ARTICULATABLE END EFFECTOR WITH AXIALLY SHORTENED ARTICULATION JOINT CONFIGURATIONS, now U.S. Patent application Publication No. 2019/0000457;

U.S. Pat. No. 10,588,633, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING;

U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS, now U.S. Patent application Publication No. 2019/0000459;

U.S. Pat. No. 10,786,253, entitled SURGICAL END EFFECTORS WITH IMPROVED JAW APERTURE ARRANGEMENTS;

U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT AXIS, now U.S. Patent application Publication No. 2019/0000461;

U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW, now U.S. Patent application Publication No. 2019/0000462;

U.S. Pat. No. 10,758,232, entitled SURGICAL INSTRUMENT WITH POSITIVE JAW OPENING FEATURES;

U.S. Pat. No. 10,639,037, entitled SURGICAL INSTRUMENT WITH AXIALLY MOVABLE CLOSURE MEMBER;

U.S. Pat. No. 10,695,057, entitled SURGICAL INSTRUMENT LOCKOUT ARRANGEMENT;

U.S. Design Pat. No. D851,762, entitled ANVIL;

U.S. Design Pat. No. D854,151, entitled SURGICAL INSTRUMENT SHAFT; and

U.S. Design Pat. No. D869,655, entitled SURGICAL FASTENER CARTRIDGE.

Applicant of the present application owns the following U.S. patent applications and U.S. patents that were filed on Jun. 27, 2017 and which are each herein incorporated by reference in their respective entireties:

U.S. patent application Ser. No. 15/634,024, entitled SURGICAL ANVIL MANUFACTURING METHODS, now U.S. Patent application Publication No. 2018/0368839;

U.S. Pat. No. 10,772,629, entitled SURGICAL ANVIL ARRANGEMENTS;

U.S. patent application Ser. No. 15/634,046, entitled SURGICAL ANVIL ARRANGEMENTS, now U.S. Patent application Publication No. 2018/0368841;

U.S. Pat. No. 10,856,869, entitled SURGICAL ANVIL ARRANGEMENTS;

U.S. patent application Ser. No. 15/634,068, entitled SURGICAL FIRING MEMBER ARRANGEMENTS, now U.S. Patent application Publication No. 2018/0368843;

U.S. patent application Ser. No. 15/634,076, entitled STAPLE FORMING POCKET ARRANGEMENTS, now U.S. Patent application Publication No. 2018/0368844;

U.S. patent application Ser. No. 15/634,090, entitled STAPLE FORMING POCKET ARRANGEMENTS, now U.S. Patent application Publication No. 2018/0368845;

U.S. patent application Ser. No. 15/634,099, entitled SURGICAL END EFFECTORS AND ANVILS, now U.S. Patent application Publication No. 2018/0368846; and U.S. Pat. No. 10,631,859, entitled ARTICULATION SYSTEMS FOR SURGICAL INSTRUMENTS.

Applicant of the present application owns the following U.S. patent applications that were filed on Jun. 2, 2020 and which are each herein incorporated by reference in their respective entireties:

U.S. Design patent application Serial No. 29/736,648, entitled STAPLE CARTRIDGE;

U.S. Design patent application Serial No. 29/736,649, entitled STAPLE CARTRIDGE;

U.S. Design patent application Serial No. 29/736,651, entitled STAPLE CARTRIDGE;

U.S. Design patent application Serial No. 29/736,652, entitled STAPLE CARTRIDGE;

U.S. Design patent application Serial No. 29/736,653, entitled STAPLE CARTRIDGE;

U.S. Design patent application Serial No. 29/736,654, entitled STAPLE CARTRIDGE; and U.S. Design patent application Serial No. 29/736,655, entitled STAPLE CARTRIDGE.

Applicant of the present application owns the following U.S. Design patent applications and U.S. patents that were filed on Nov. 14, 2016, and which are each herein incorporated by reference in their respective entireties:

U.S. patent application Ser. No. 15/350,621, now U.S. Patent application Publication No. 2018/0132849, entitled STAPLE FORMING POCKET CONFIGURATIONS FOR CIRCULAR STAPLER ANVIL;

U.S. patent application Ser. No. 15/350,624, now U.S. Patent application Publication No. 2018/0132854, entitled CIRCULAR SURGICAL STAPLER WITH ANGULARLY ASYMMETRIC DECK FEATURES;

U.S. Design Pat. No. D833,608, titled STAPLING HEAD FEATURE FOR SURGICAL STAPLER; and U.S. Design Pat. No. D830,550, titled SURGICAL STAPLER.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical device. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical device are used in many orientations and positions, and these terms are not intended to be limiting and/or absolute. In the following description, terms such as "first," "second," "top," "bottom," "up," "down," and the like are words of convenience and are not to be construed as limiting terms.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various surgical devices disclosed herein can be inserted into a body in any way, such as through a natural orifice, through an incision or puncture hole formed in tissue, etc. The working portions or end effector portions of the surgical devices can be inserted directly into a patient's body or can be inserted through an access device that has a working channel through which the end effector and elongate shaft of a surgical device can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue to be stapled. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples are contemplated.

The staples are supported by staple drivers in the cartridge body. The drivers are movable between a first, or unfired, position and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent a proximal end of the cartridge body and a distal position adjacent a distal end of the cartridge body. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected into the tissue ahead of the knife transecting the tissue.

FIGS. 1-8 depict a surgical stapling instrument 10 configured to clamp, staple, and cut tissue of a patient. The surgical stapling instrument 10 comprises a handle 20, a shaft assembly 100 attached to the handle 20, and an end effector 200. To cut and staple tissue of a patient, the end effector 200 comprises a cartridge jaw 201 and an anvil jaw 203. The anvil jaw 203 is pivotable relative to the cartridge jaw 203 to clamp tissue between the anvil jaw 203 and the cartridge jaw 203. Once tissue is clamped between the jaws 201, 203, the surgical stapling instrument 10 may be actuated to advance a firing member through the jaws 201, 203 to staple and cut tissue with the end effector 200 as discussed in greater detail below.

Discussed in greater detail below, the end effector 200 is articulatable by way of an articulation region 110 of the shaft assembly 100. Such articulation provides a user of the surgical stapling instrument 10 with the ability to position and/or maneuver the end effector 200 near the target tissue more accurately.

The handle 20 comprises a housing 21 configured to house various mechanical and electrical components and a handle portion 22 extending from the housing 21. The handle portion 22 is configured to fit in the palm of a user and/or be gripped and/or held by a user using the surgical stapling instrument 10. The handle 20 further comprises various actuators and/or triggers configured to be actuated by a user to operate one or more functions of the surgical stapling instrument 10. The handle 20 comprises a closure trigger 24, a firing trigger 25, and at least one articulation actuator 26. When actuated by a user, the closure trigger 24 is configured to clamp tissue with the end effector 200 by moving the anvil jaw 203 toward the cartridge jaw 201. When actuated by a user, the firing trigger 25 is configured to cut and staple tissue with the end effector 200 by advancing a firing member to eject staples and cut tissue with a knife. When actuated by a user, the articulation actuator 26 is configured to articulate the end effector 200 relative to the shaft assembly 100 by way of the articulation region 110. The triggers and actuators of the surgical stapling instrument 10 can either trigger one or more motors within the handle 20 to actuate various function of the surgical stapling instrument 10 and/or manually drive various drive shafts and components to actuate various function of the surgical stapling instrument 10.

The handle 20 further comprises a nozzle assembly 30 configured to support the shaft assembly 100 therein. The nozzle assembly 30 comprises an actuation wheel 31 configured to be rotated by a user to rotate the shaft assembly 100 and end effector 200 about a longitudinal axis LA relative to the handle 20. Such a mechanism permits the user of the surgical stapling instrument 10 to rotate only the shaft assembly 100 and/or end effector 200 without having to rotate the entire handle 20.

The handle 20 further comprises a battery 23 configured to provide power to various electronic components, sensors, and/or motors of the surgical stapling instrument 10. Embodiments are envisioned where the surgical stapling instrument 10 is directly connected to a power source. Embodiments are also envisioned where the surgical stapling instrument 10 is entirely manual or, non-powered, for example. Embodiments are further envisioned where articulation of the end effector, clamping and unclamping of the jaws, firing of the end effector staple and cut tissue, and shaft and/or end effector rotation are all powered systems.

In at least one instance, the shaft assembly 100 and the end effector 200 may be modular and removable from the handle 20. In at least one instance, the end effector 200 may be modular in that the end effector 200 can be removed from the shaft assembly 100 and replaced with a different end effector. In at least one instance, the shaft assembly 100 and/or the end effector 200 is employable in a surgical robotic environment. Such an embodiment would provide powered inputs from a surgical robotic interface to actuate each function of the end effector 200. Examples of such surgical robots and surgical tools are further described in U.S. Patent application Publication No. 2020/0138534, titled ROBOTIC SURGICAL SYSTEM, which published on May 7, 2020, which is incorporated by reference herein in its entirety.

In at least one instance, the shaft assembly 100 and the end effector 200 are configured to be used with a surgical robot. In such an instance, the shaft assembly 100 and the end effector 200 are configured to be coupled to a surgical robot comprising a plurality of output drives. The plurality of output drives of the surgical robot are configured to mate with the drive systems of the shaft assembly 100 and end effector 200. In such an instance, the surgical robot can actuate the various different functions of the end effector 200 such as, for example, articulating the end effector about multiple different articulation joints, rotating the shaft assembly 100 and/or end effector 200 about its longitudinal axis, clamping the end effector 200 to clamp tissue between the jaws of the end effector 200, and/or firing the end effector 200 to cut and/or staple tissue.

The shaft assembly 100 is configured to house various drive system components and/or electronic components of the surgical stapling instrument 10 so that the end effector 200 and shaft assembly 100 may be inserted through a trocar for laparoscopic surgery. The various drive system components are configured to be actuated by the various triggers and actuators of the handle 20. Such components can include drive shafts for articulation, drive shafts for clamping and unclamping the end effector 200, and/or drive shafts for firing the end effector 200. Such drive shafts may be rotated by a drive system in the handle 20 or a surgical robotic interface in the instance where the shaft assembly 100 is connected to the same. In various aspects, a stapling end effector can include two independently rotatable drive members—one for grasping tissue and one for firing staples, for example. The stapling end effector can further include an articulation joint, and the rotary motions can be transmitted through the articulation joint. In various aspects, the stapling end effector can include one or more 3D printed assemblies, which can be incorporated into an articulation, grasping, or firing systems.

Such drive shafts may be actuated by a drive system in the handle 20 or a surgical robotic interface in the instance where the shaft assembly 100 is connected to the same. Such drive shafts may comprise linear actuation, rotary actuation, or a combination thereof. A combination of rotary actuation and linear actuation may employ a series of rack gears and/or drive screws, for example.

In at least one instance, the shaft assembly 100 is also configured to house electrical leads for various sensors and/or motors, for example, positioned within the shaft assembly 100 and/or end effector 200, for example.

The shaft assembly 100 comprises an outer shaft 101 extending from the nozzle assembly 30 to the articulation region 110 comprising dual articulation joints, discussed in greater detail below. The articulation region 110 allows the end effector 200 to be articulated relative to the outer shaft 101 in two distinct planes about two separate axes AA1, AA2.

Figure 1:
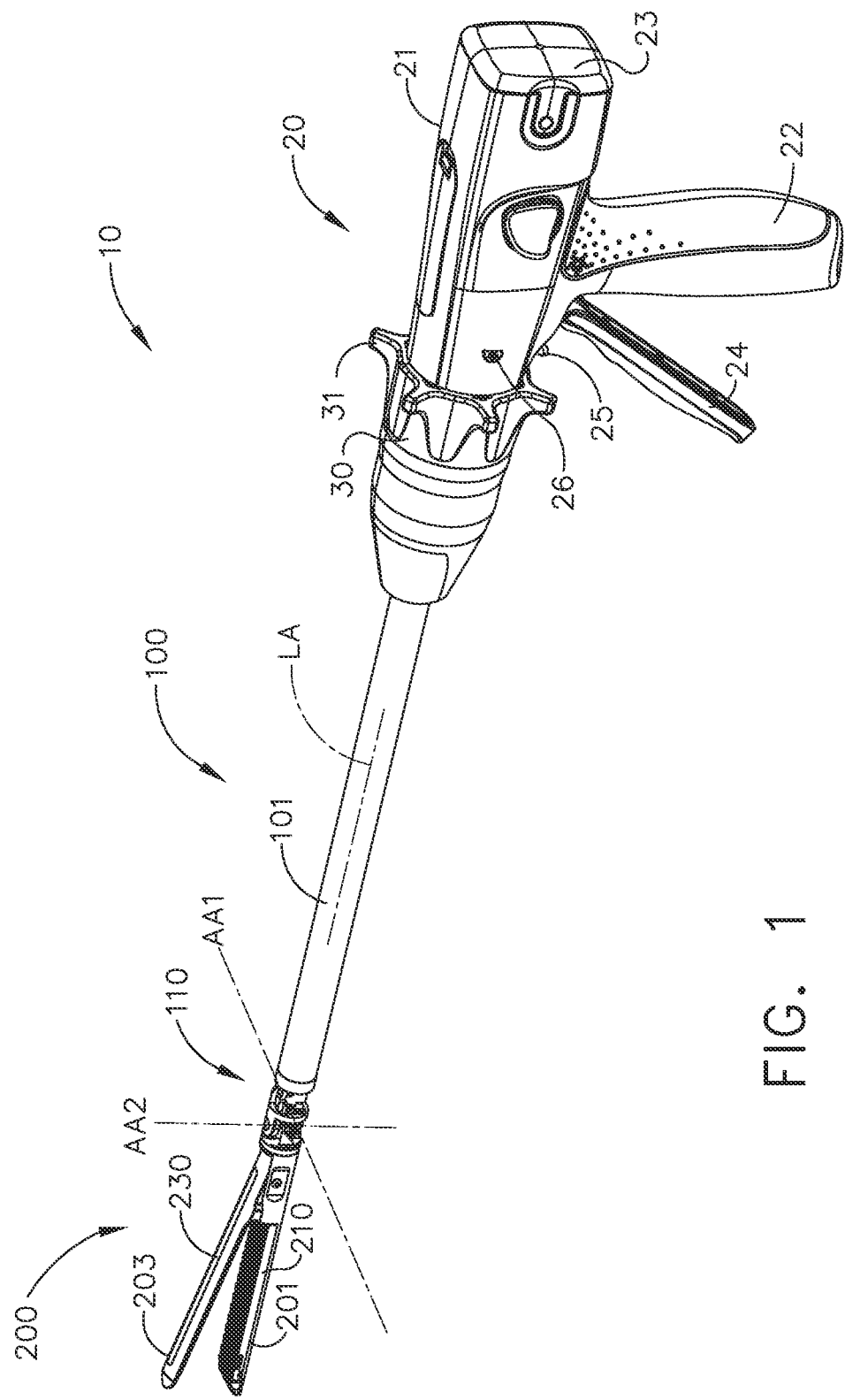
FIG. 1 is a perspective view of a surgical stapling instrument comprising a handle, a shaft assembly, and an end effector, in accordance with at least one aspect of the present disclosure.
Figure 2:
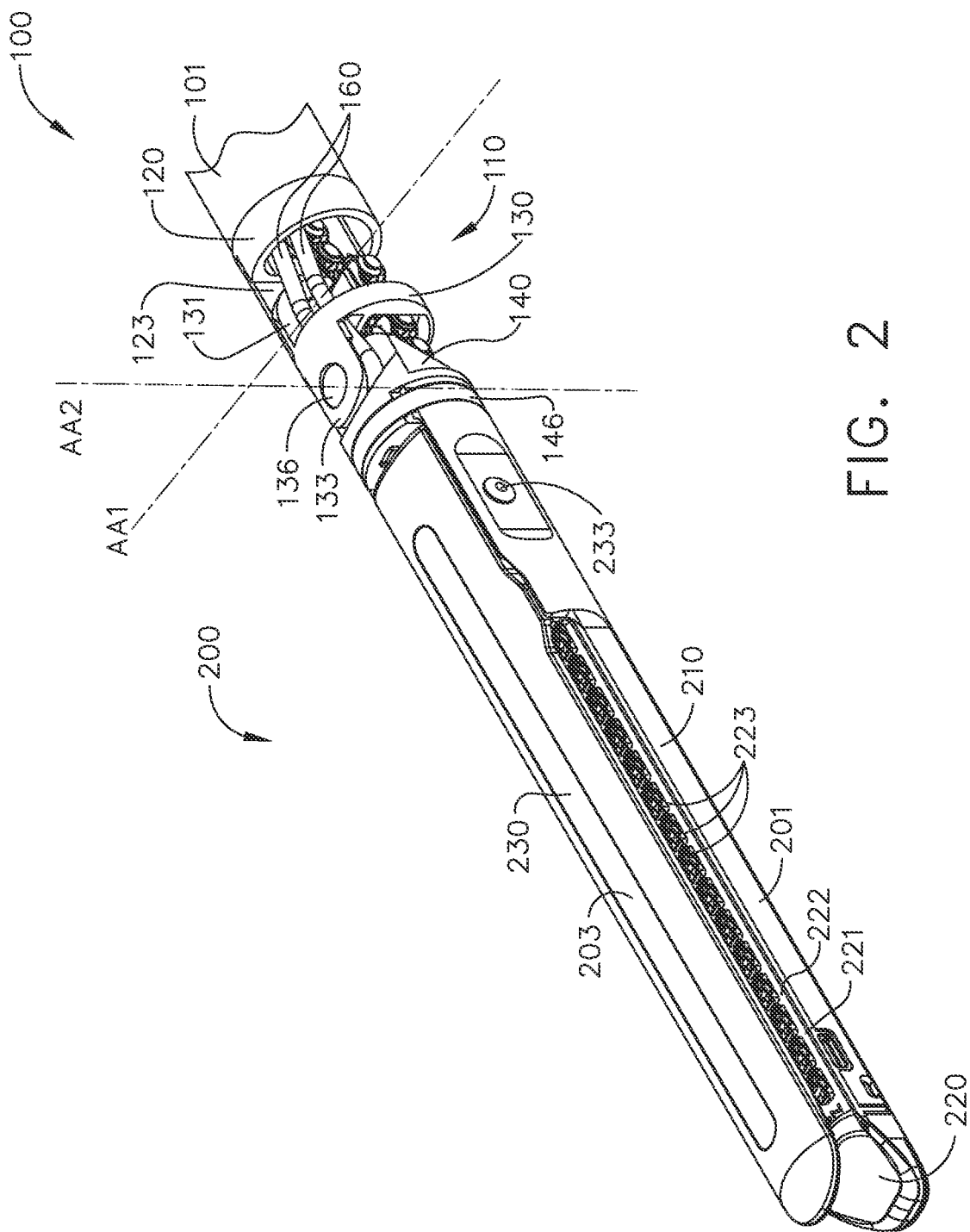
FIG. 2 is a perspective view of the end effector and a portion of the shaft assembly of the surgical stapling instrument of FIG. 1, wherein the end effector is illustrated in a straight, or non-articulated, configuration, in accordance with at least one aspect of the present disclosure.
Figure 3:
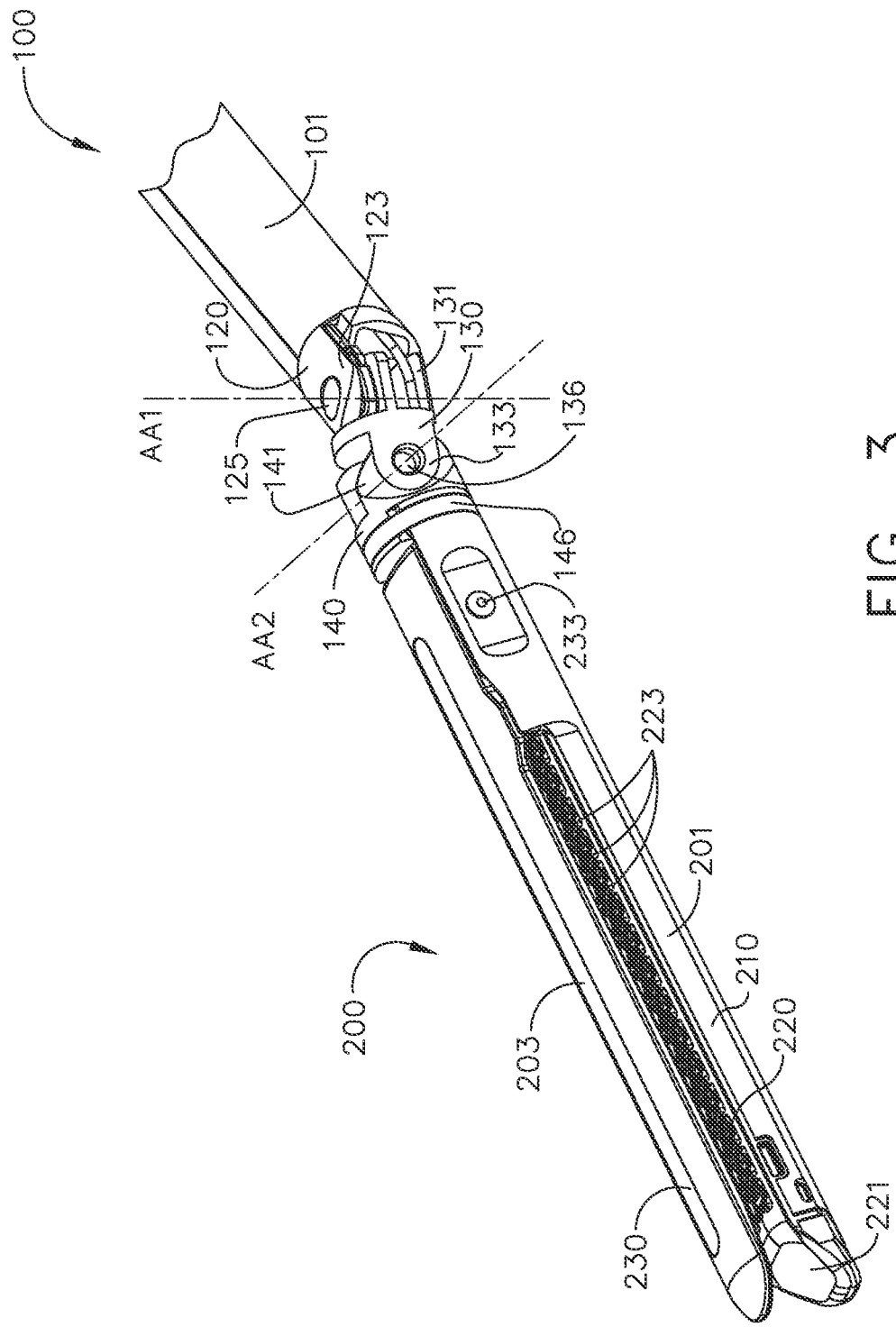
FIG. 3 is a perspective view of the end effector and a portion of the shaft assembly of the surgical stapling instrument of FIG. 1, wherein the end effector is illustrated in an articulated configuration, in accordance with at least one aspect of the present disclosure.
Figure 4:
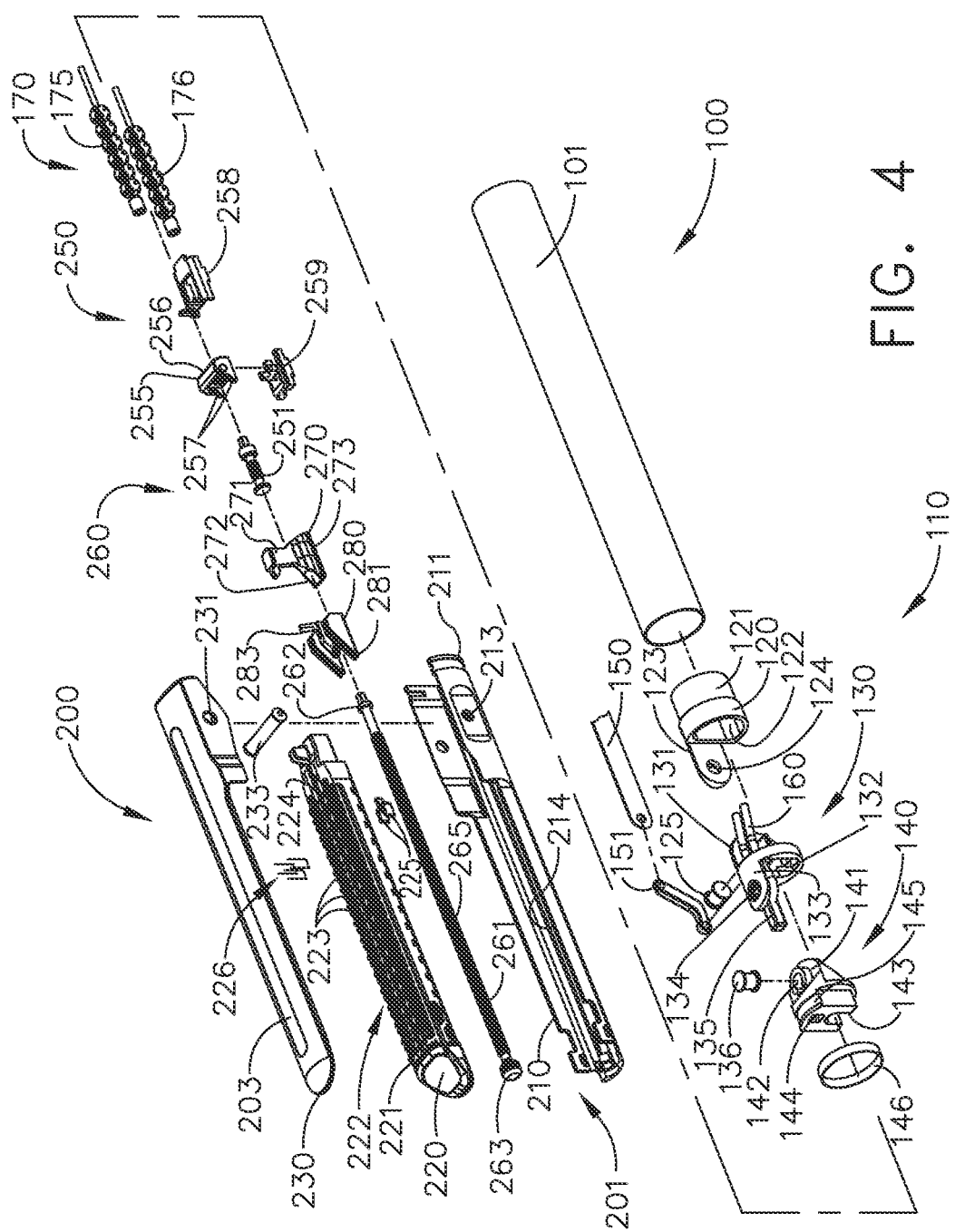
FIG. 4 is an exploded perspective view of the end effector and a portion of the shaft assembly of the surgical stapling instrument of FIG. 1, in accordance with at least one aspect of the present disclosure.
Figure 5:
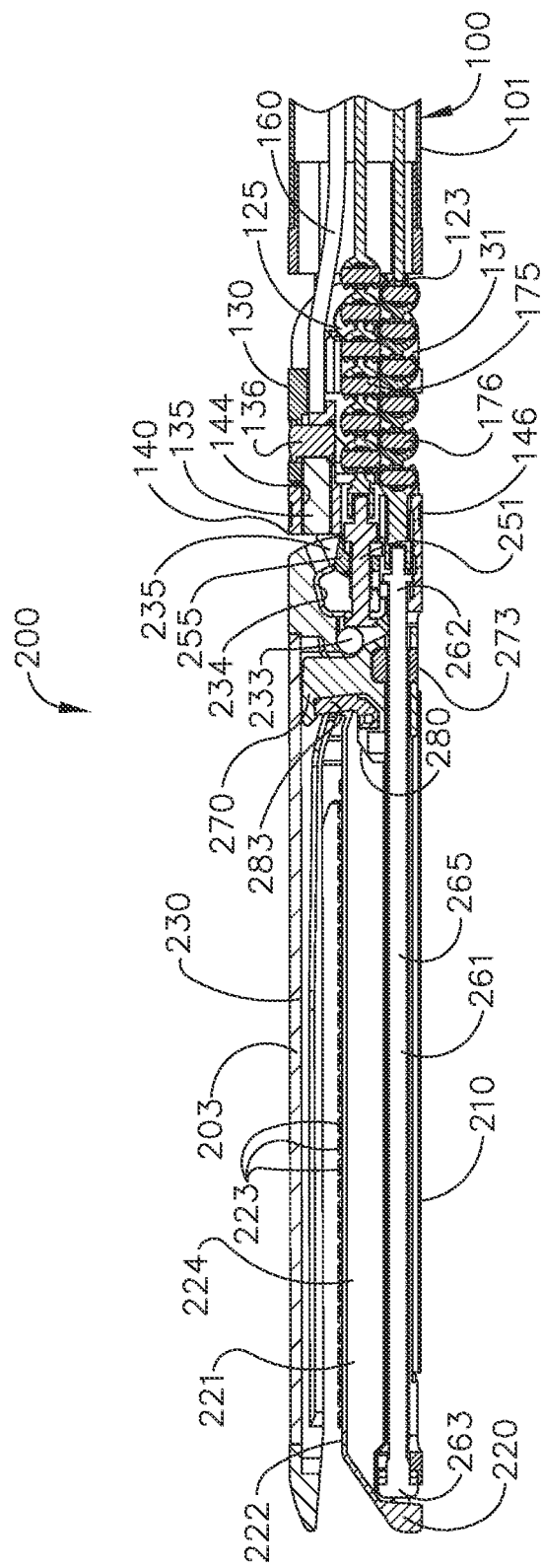
FIG. 5 is a cross-sectional elevation view of the end effector and a portion of the shaft assembly of the surgical stapling instrument of FIG. 1, wherein the end effector is illustrated in an unfired, clamped configuration, in accordance with at least one aspect of the present disclosure.
Figure 6:
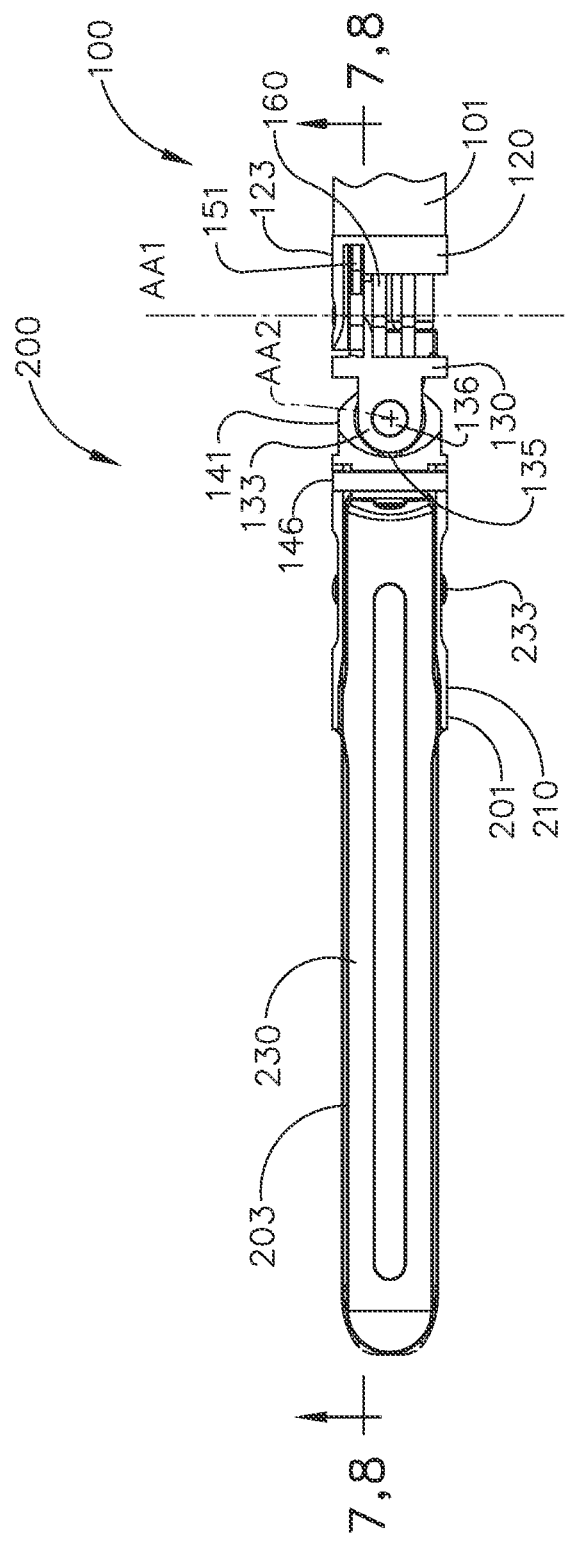
FIG. 6 is a plan view of the end effector and a portion of the shaft assembly of the surgical stapling instrument of FIG. 1, in accordance with at least one aspect of the present disclosure.
Figure 7:
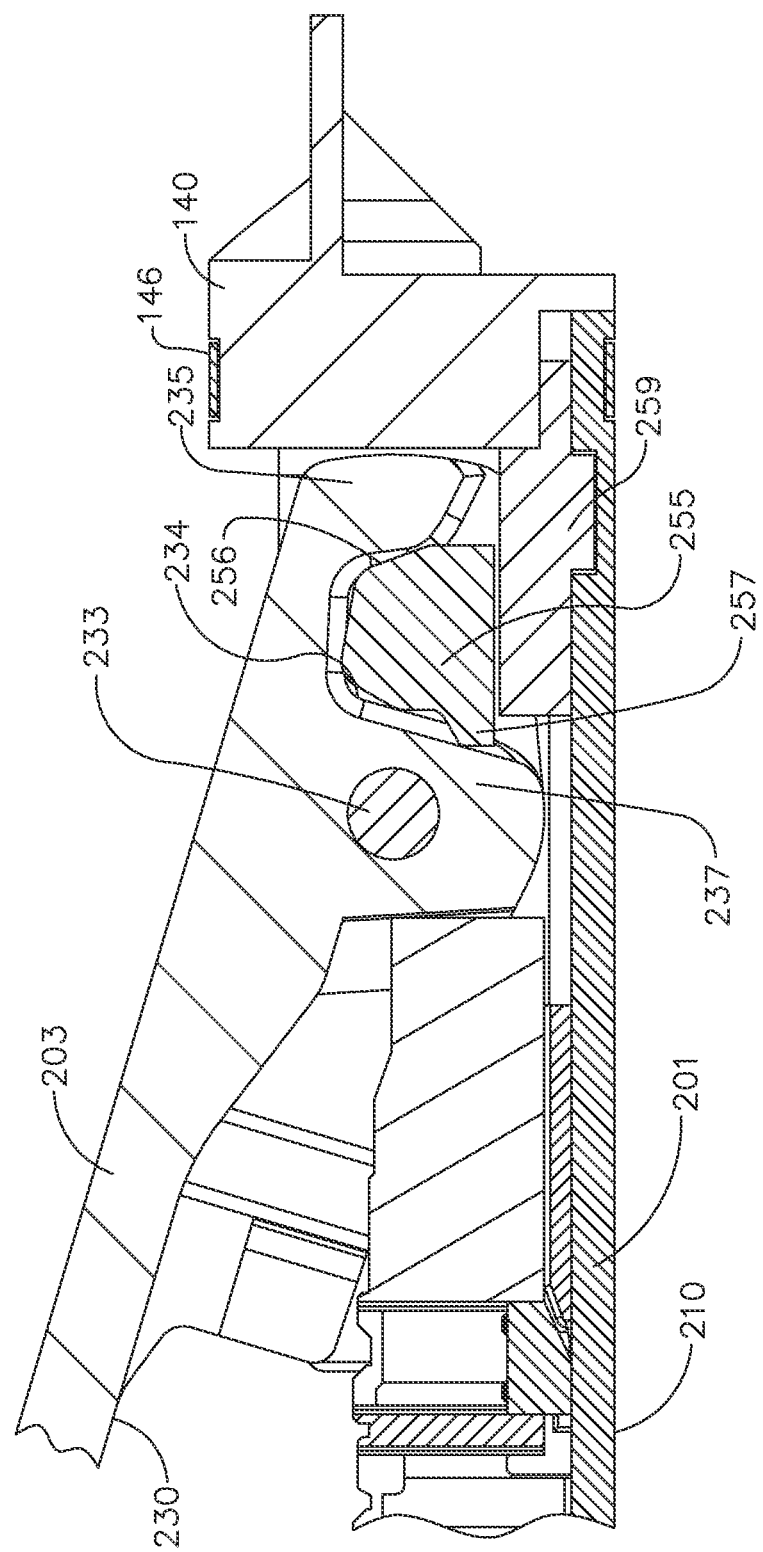
FIG. 7 is a cross-sectional elevation view of the end effector and a portion of the shaft assembly of FIG. 1 taken along section line 7-7 in FIG. 6, wherein the end effector is illustrated in an open configuration, in accordance with at least one aspect of the present disclosure.

Referring now primarily to FIG. 4, articulation of the end effector 200 will now be described. The articulation region 110 comprises two distinct articulation joints and two articulation actuators 150, 160. This allows the end effector 200 to be articulated in two different planes about two different axes AA1, AA2 independently of each other. The articulation region 110 comprises a proximal joint shaft component 120, an intermediate joint shaft component 130, and a distal joint shaft component 140. The proximal joint shaft component 120 is attached to a distal end of the shaft assembly 100, the intermediate joint shaft component 130 is pivotally connected to the proximal joint shaft component 120 and the distal joint shaft component 140, and the distal joint shaft component 140 is fixedly attached to the end effector 200 by way of a retention ring 146. Discussed in greater detail below, this arrangement provides articulation of the end effector 200 relative to the shaft assembly 100 about axis AA1 and axis AA2 independently of each other.

The proximal joint shaft component 120 comprises a proximal annular portion 121 fixedly fitted within the outer shaft 101. The proximal joint shaft component 120 also includes a hollow passage 122 to allow various drive system components to pass therethrough, and further includes an articulation tab 123 comprising a pin hole 124 configured to receive articulation pin 125. The articulation pin 125 pivotally connects the proximal joint shaft component 120 to a proximal articulation tab 131 of the intermediate joint shaft component 130. To articulate the end effector 200 about axis AA1, the articulation actuator 150 is actuated linearly either in a distal direction or a proximal direction. Such an actuator may comprise a bar or rod made of any suitable material such as metal and/or plastic, for example. The articulation actuator 150 is pivotally mounted to an articulation crosslink 151. The articulation crosslink 151 is pivotally mounted to the intermediate joint shaft component 130 off-axis relative to the articulation pin 125 so that when the articulation actuator 150 is actuated, a torque is applied to the intermediate joint shaft component 130 off-axis relative to the articulation pin 125 by the articulation crosslink 151 to cause the intermediate joint shaft component 130 and, thus, the end effector 200, to pivot about axis AA1 relative to the proximal joint shaft component 120.

The intermediate joint shaft component 130 is pivotally connected to the proximal joint shaft component 120 by way of the articulation pin 125 which defines axis AA1. Specifically, the intermediate joint shaft component 130 comprises a proximal articulation tab 131 that is pivotally connected to the proximal joint shaft component 120 by way of the articulation pin 125. The intermediate joint shaft component 130 further comprises a hollow passage 132 configured to allow various drive system components to pass therethrough and a distal articulation tab 133. The distal articulation tab 133 comprises a pin hole 134 configured to receive another articulation pin 136, which defines axis AA2, and a distally-protruding key 135.

To articulate the end effector 200 about axis AA2, the articulation cable 160 is actuated to apply an articulation torque to a proximal tab 141 of the distal joint shaft component 140 by way of the key 135. The articulation cable 160 is fixed to the key 135 such that, as the cable 160 is rotated, the key 135 is pivoted relative to the intermediate joint shaft component 130. The key 135 is fitted within a key hole 144 of the distal joint shaft component 140. Notably, the key 135 is not fixed to the intermediate joint shaft component 130 and the key 135 can be rotated relative to the intermediate joint shaft component 130. The articulation cable 160 also contacts the proximal tab 141 around the pin hole 142. This provides an additional torque moment from the articulation cable 160 to the distal joint shaft component 140. The articulation pin 136 is received within the pin hole 142 to pivotally couple the intermediate joint shaft component 130 and the distal joint shaft component 140.

In at least one instance, the articulation cable 160 is only able to be pulled in a proximal direction. In such an instance, only one side of the articulation cable 160 would be pulled proximally to articulate the end effector 200 in the desired direction. In at least one instance, the articulation cable 160 is pushed and pulled antagonistically. In other words, the cable 160 can comprise a rigid construction such that one side of the articulation cable 160 is pushed distally while the other side of the articulation cable 160 is pulled proximally. Such an arrangement can allow the articulation forces to be divided between the pushed half of the cable 160 and the pulled half of the cable 160. In at least one instance, the push-pull arrangement allows greater articulation forces to be transmitted to the corresponding articulation joint. Such forces may be necessary in an arrangement with two articulation joints. For example, if the proximal articulation joint is fully articulated, more force may be required of the articulation actuator meant to articulate the distal articulation joint owing to the stretching and/or lengthened distance that the articulation actuator for the distal articulation joint must travel.

The distal joint shaft component 140 further comprises a cutout 143 to allow various drive components to pass therethrough. The retention ring 146 secures a channel 210 of the cartridge jaw 201 to the distal joint shaft component 140 thereby fixing the end effector assembly 200 to a distal end of the articulation region 110.

As discussed above, the anvil jaw 201 is movable relative to the cartridge jaw 203 to clamp and unclamp tissue with the end effector 200. Operation of this function of the end effector 200 will now be described. The cartridge jaw 201 comprises the channel 210 and a staple cartridge 220 configured to be received within a cavity 214 of the channel 210. The channel 210 further comprises an annular groove 211 configured to receive the retention ring 146 and a pair of pivot holes 213 configured to receive a jaw-coupling pin 233. The jaw coupling pin 233 permits the anvil jaw 203 to be pivoted relative to the cartridge jaw 201.

The anvil jaw 203 comprises an anvil body 230 and a pair of pivot holes 231. The pivot holes 231 in the proximal portion of the anvil jaw 203 are configured to receive the jaw-coupling pin 233 thereby pivotally coupling the anvil jaw 203 to the cartridge jaw 201. To open and close the anvil jaw 203 relative to the cartridge jaw 201, a closure drive 250 is provided.

The closure drive 250 is actuated by a flexible drive segment 175 comprised of universally-movable joints arranged or formed end-to-end. In various instances, the flexible drive segment 175 can includes serial 3D-printed universal joints, which are printed all together as a single continuous system. Discussed in greater detail below, the flexible drive segment 175 is driven by an input shaft traversing through the shaft assembly 100. The flexible drive segment 175 transmits rotary actuation motions through the dual articulation joints. The closure drive 250 comprises a closure screw 251 and a closure wedge 255 threadably coupled to the closure screw 251. The closure wedge 255 is configured to positively cam the anvil jaw 203 open and closed. The closure screw 251 is supported by a first support body 258 and a second support body 259 secured within the channel 210.

To move the anvil jaw 203 between a clamped position (FIG. 8) and an unclamped position (FIG. 7), a closure drive shaft is actuated to actuate the flexible drive segment 175. The flexible drive segment 175 is configured to rotate the closure screw 251, which displaces the closure wedge 255. For example, the closure wedge 255 is threadably coupled to the closure screw 251 and rotational travel of the closure wedge 255 with the staple cartridge 220 is restrained. The closure screw 251 drives the closure wedge 255 proximally or distally depending on which direction the closure screw 251 is rotated.

To clamp the end effector 200 from an unclamped position (FIG. 7), the closure wedge 255 is moved proximally. As the closure wedge 255 is moved proximally, a proximal cam surface 256 of the closure wedge 255 contacts a corresponding cam surface 234 defined in a proximal end 235 of the anvil body 230. As the cam surface 256 contacts the cam surface 234, a force is applied to the proximal end 235 of the anvil body 230 causing the anvil body 230 to rotate into the clamped position (FIG. 8) about the pin 233.

To open or unclamp the end effector 200 from a clamped position (FIG. 8), the closure wedge 255 is moved distally by rotating the closure screw 251 in a direction opposite to the direction that causes the closure wedge 255 to move proximally. As the closure wedge 255 is moved distally, a pair of nubs 257 extending from a distal end of the closure wedge 255 contact the cam surface 234 near a downwardly extending tab 237 of the anvil body 230. As the nubs 257 contact the cam surface 234 near the tab 237, a force is applied to the anvil body 230 to rotate the anvil body 230 into the open position (FIG. 7) about the pin 233.

Figure 8:
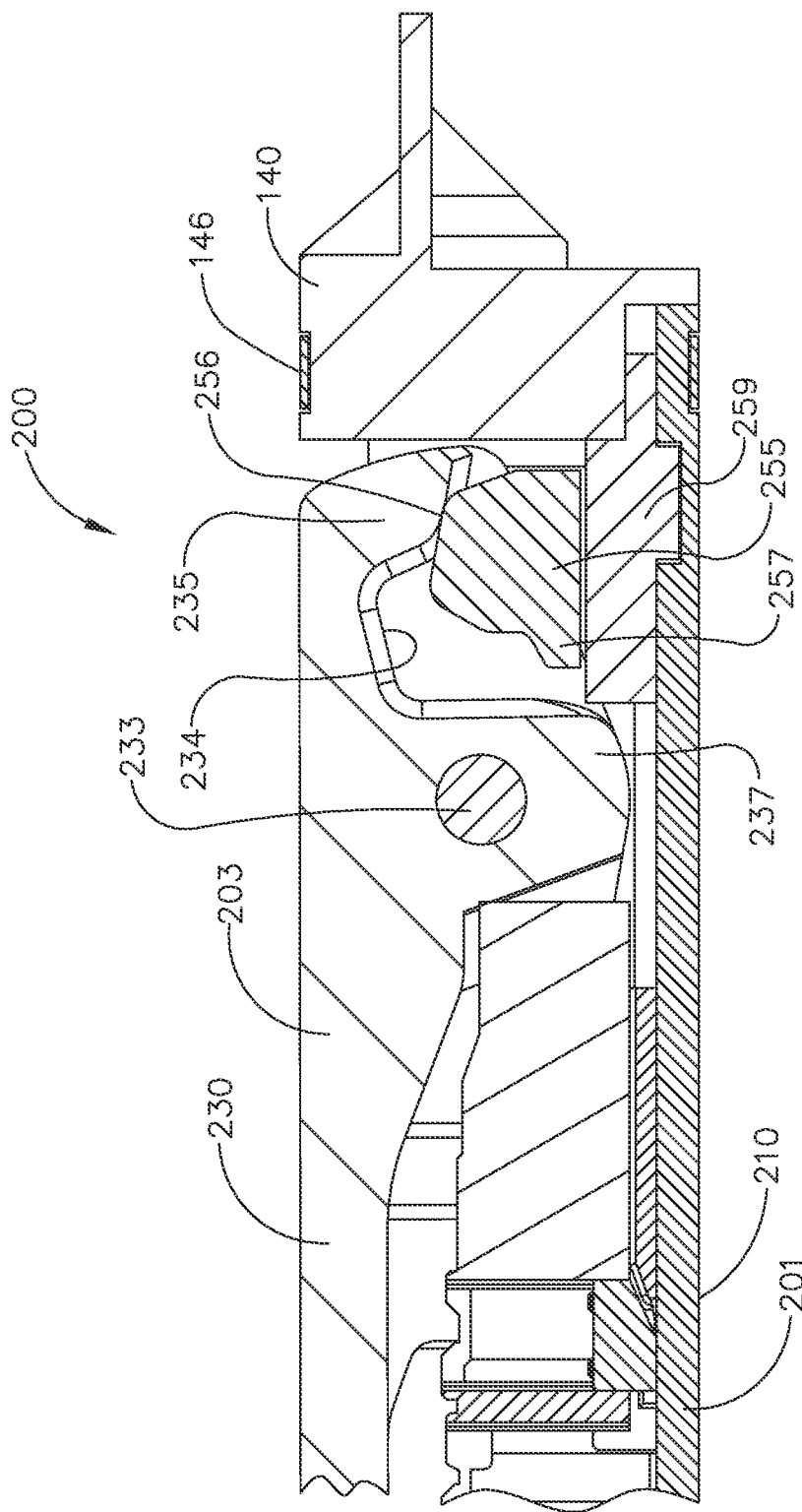
FIG. 8 is a cross-sectional elevation view of the end effector and a portion of the shaft assembly of FIG. 1 taken along section line 8-8 in FIG. 6, wherein the end effector is illustrated in a clamped configuration, in accordance with at least one aspect of the present disclosure.

In at least one instance, the profile of the cam surface 234 corresponds to the profile of the cam surface 256. For example, the cam surface 234 and the cam surface 256 may match such that a maximum cam force is applied to the anvil body 230 to cause the desired rotation of the anvil body 230. As can be seen in FIG. 8, for example, the cam surface 234 defined by the proximal end 235 of the anvil body 230 comprises a ramped section similar to that of the upper ramped section of the cam surface 256.

As discussed above, the surgical stapling instrument 10 may be actuated to advance a firing member through the jaws 201, 203 to staple and cut tissue with the end effector 200. The function of deploying staples 226 from the staple cartridge 220 and cutting tissue with knife 283 will now be described. The staple cartridge 220 comprises a cartridge body 221, a plurality of staple drivers 225, and a plurality of staples 226 removably stored within the cartridge body 221. The cartridge body 221 comprises a deck surface 222, a plurality of staple cavities 223 arranged in longitudinal rows defined in the cartridge body 221, and a longitudinal slot 224 bifurcating the cartridge body 221. The knife 283 is configured to be driven through the longitudinal slot 224 to cut tissue clamped between the anvil body 230 and the deck surface 221.

The deck surface 221 comprises a laterally-contoured tissue-supporting surface. In various aspects, the contour of the deck surface 221 can form a peak along a central portion of the cartridge body 221. Such a peak can overlay a longitudinally-extending firing screw 261 that extends through the central portion of the cartridge body 221, which is further described herein. The increased height along the peak can be associated with a smaller tissue gap along a firing path of the knife 283 in various instances. In certain aspects of the present disclosure, driver heights, formed staple heights, staple pocket extension heights, and/or staple overdrive distances can also vary laterally along the deck surface 221. Laterally-variable staple formation (e.g. a combination of 2D staples and 3D staples) is also contemplated and further described herein.

The staple drivers 225 are configured to be lifted by a sled 280 as the sled 280 is pushed distally through the staple cartridge 220 to eject the staples 226 supported by the staple drivers 225 in the staple cavities 223. The sled 280 comprises ramps 281 to contact the staple drivers 225. The sled 280 also includes the knife 283. The sled 280 is configured to be pushed by a firing member 270.

To deploy the staples 226 and cut tissue with the knife 283, the end effector 200 comprises a firing drive 260. The firing drive 260 is actuated by a flexible drive shaft 176. Discussed in greater detail below, the flexible drive shaft 176 is driven by an input shaft traversing through the shaft assembly 100. The flexible drive shaft 176 transmits rotary actuation motions through the dual articulation joints. The firing drive 260 comprises a firing screw 261 configured to be rotated by the flexible drive shaft 176. The firing screw 261 comprises journals supported within bearings in the support member 259 and the channel 210. In various instances, the firing screw 261 can float relative to the channel 210, as further described herein. The firing screw 261 comprises a proximal end 262 supported within the support member 259 and the channel 210, a distal end 263 supported within the channel 210, and threads 265 extending along a portion of the length of the firing screw 261.

The firing member 270 is threadably coupled to the firing screw 261 such that as the firing screw 261 is rotated, the firing member 270 is advanced distally or retracted proximally along the firing screw 261. Specifically, the firing member 270 comprises a body portion 271 comprising a hollow passage 272 defined therein. The firing screw 261 is configured to be received within the hollow passage 272 and is configured to be threadably coupled with a threaded component 273 of the firing member 270. Thus, as the firing screw 261 is rotated, the threaded component 273 applies a linear force to the body portion 271 to advance the firing member 270 distally or retract the firing member 270 proximally. As the firing member 270 is advanced distally, the firing member 270 pushes the sled 280. Distal movement of the sled 280 causes the ejection of the staples 223 by engaging the plurality of staple drivers 225, as further described herein. The driver 225 is a triple driver, which is configured to simultaneously fire multiple staples 223. The driver 225 can comprise lateral asymmetries, as further described herein, to maximum the width of the sled rails and accommodate the firing screw 261 down the center of the cartridge 220 in various instances.

At a point during firing of the end effector 200, a user may retract the firing member 270 to allow unclamping of the jaws 201, 203. In at least one instance, the full retraction of the firing member 270 is required to open the jaws 201, 203 where upper and lower camming members are provided on the body portion 271 which can only be disengaged from the jaws 201, 203 once the firing member 270 is fully retracted.

In various instances, the firing member 270 can be a hybrid construction of plastic and metal portions as further described herein. In various instances, the threaded component 273 can be a metal component, for example, which is incorporated into the firing member body 271 with insert molding or over molding.

The firing member 270 can also be referred to an I-beam in certain instances. The firing member 270 can include a complex 3D-printed geometry comprising a lattice pattern of spaces therein. In various instances, 3D printing can allow the firing member or a portion thereof to act as a spring and allows a portion to more readily flex, which can improve the force distribution and/or tolerances during a firing stroke, for example.

Figure 9:
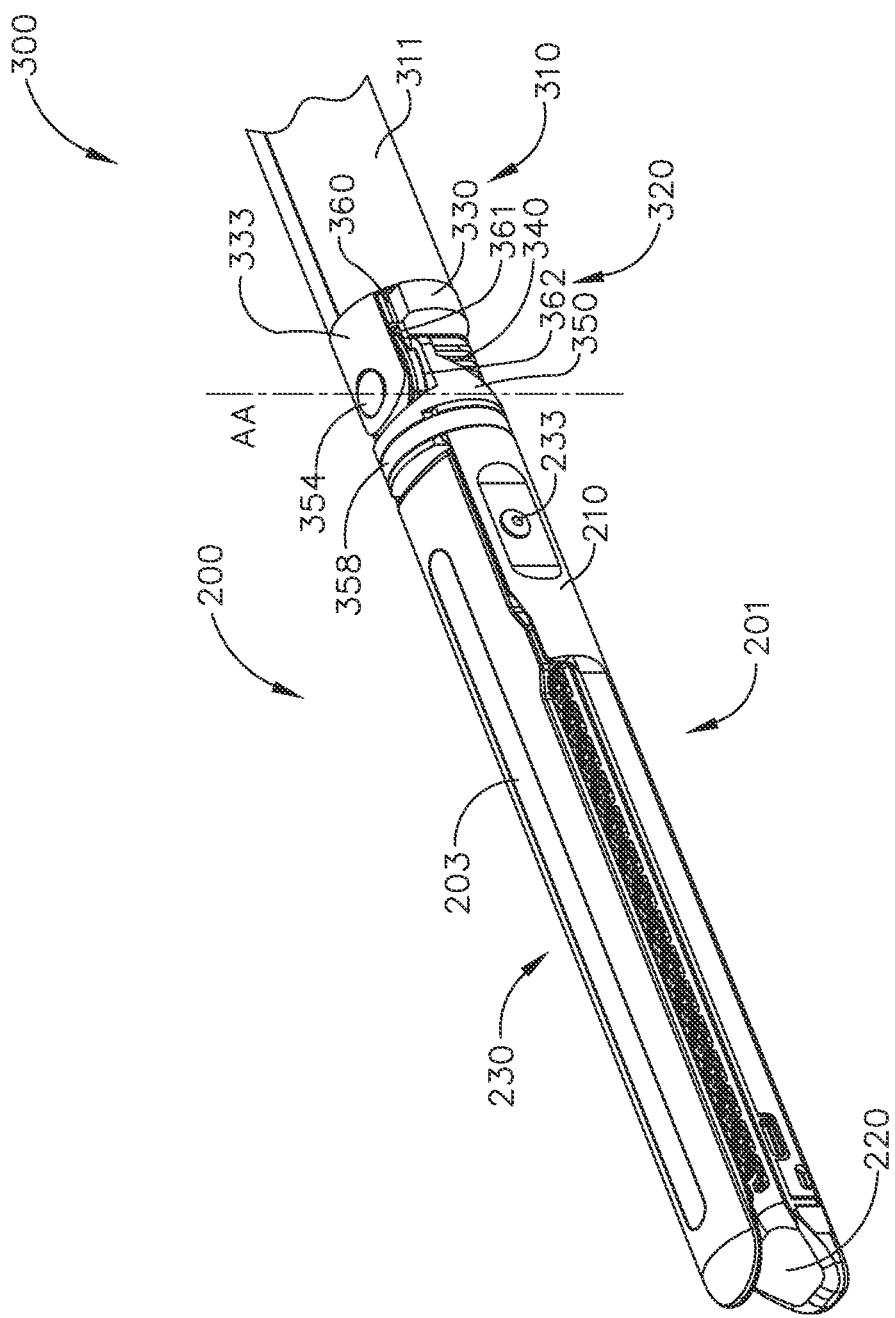
FIG. 9 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 10:
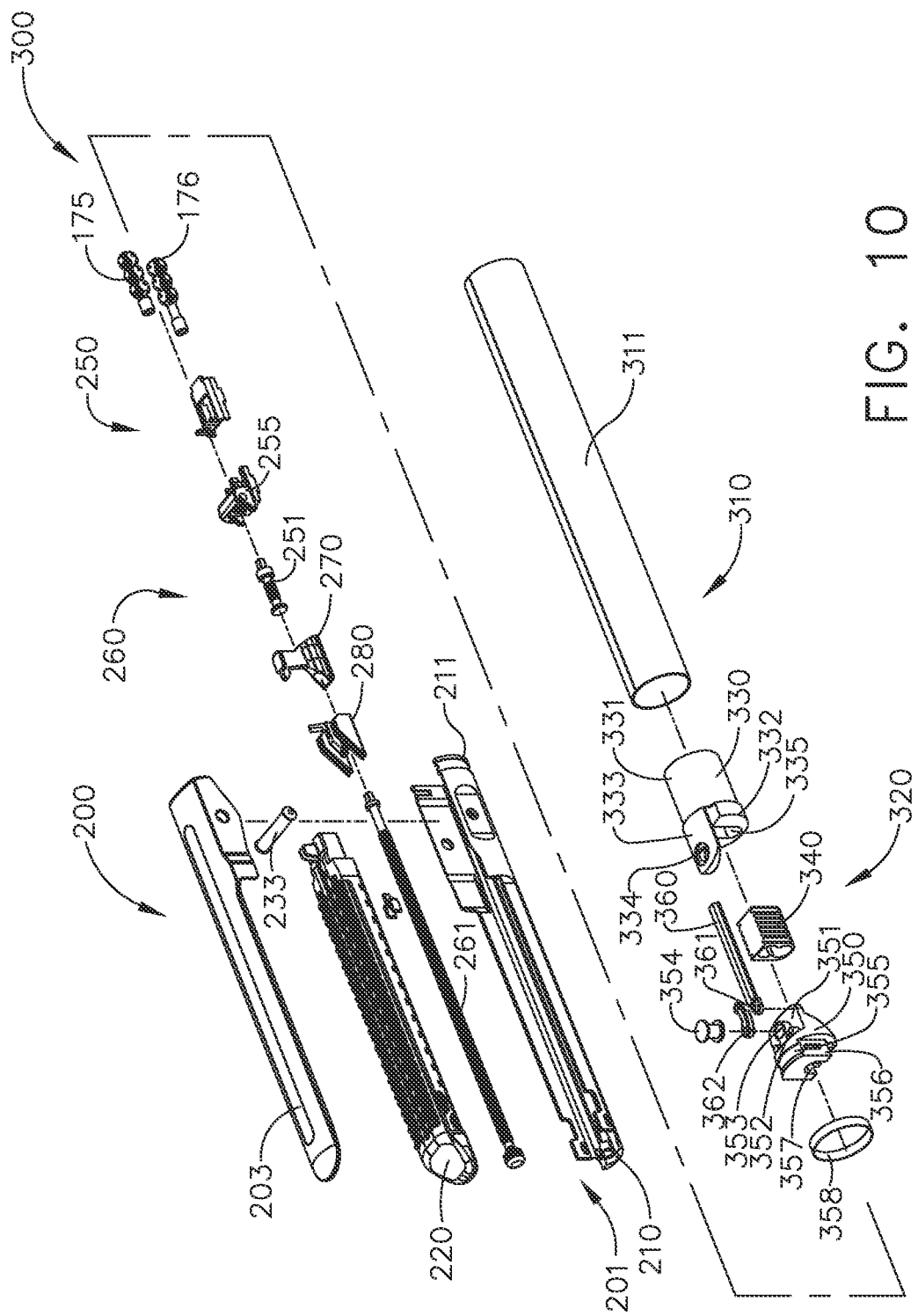
FIG. 10 is an exploded perspective view of the surgical stapling assembly of FIG. 9, in accordance with at least one aspect of the present disclosure.
Figure 11:
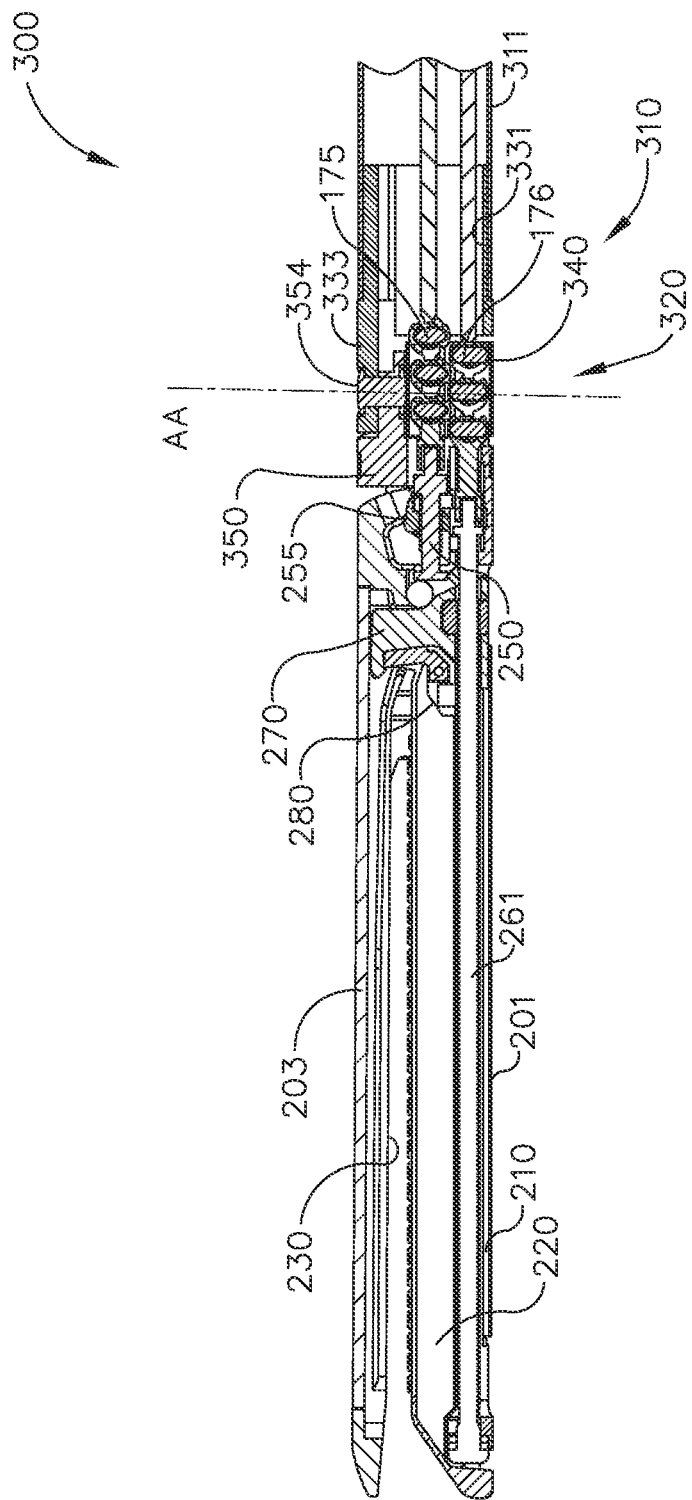
FIG. 11 is a cross-sectional elevation view of the surgical stapling assembly of FIG. 9, wherein the end effector is illustrated in an unfired, clamped configuration, in accordance with at least one aspect of the present disclosure.

FIGS. 9-11 depict a surgical stapling assembly 300 comprising a shaft assembly 310 and the end effector 200 of FIGS. 1-8 attached to the shaft assembly 310. The shaft assembly 310 may be similar in many respects to various other shaft assemblies discussed herein; however, the shaft assembly 310 comprises a single articulation joint and an articulation bar configured to articulate the end effector 200 about the single articulation joint. The surgical stapling assembly 300 is configured to cut and staple tissue. The surgical stapling assembly 300 may be attached to a surgical instrument handle and/or surgical robotic interface. The surgical instrument handle and/or surgical robotic interface can be configured to actuate various functions of the surgical stapling assembly 300. The shaft assembly 310 comprises an articulation joint 320. Discussed in greater detail below, the end effector 200 is configured to be articulated relative to an outer shaft 311 of the shaft assembly 310 about axis AA.

The shaft assembly 310 comprises the outer shaft 311, a first shaft joint component 330, and a second shaft joint component 350 pivotally coupled to the first shaft joint component 330 by way of an articulation pin 354. The first shaft joint component 330 comprises a proximal tube portion 331 configured to fit within the inner diameter of the outer shaft 311. Such a fit may comprise a press fit, for example. However, any suitable attachment means can be used. The first shaft joint component 330 also includes a distal portion 332. The distal portion 332 comprises an articulation tab 333 comprising a pin hole 334 defined therein and a hollow passage 335 through which various drive components of the surgical stapling assembly 300 can pass. Such drive components can include articulation actuators, closure actuators, and/or firing actuators for example.

The first shaft joint component 330 is pivotally connected to the second shaft joint component 350 by way of the articulation pin 354. The articulation pin 354 is also received within a pin hole 353 of a proximally-extending articulation tab 351 of the second shaft joint component 350. The pin hole 353 is axially aligned with the pin hole 334. The articulation pin 354 allows the second shaft joint component 350 to be articulated relative to the first shaft joint component 330 about the articulation axis AA. The second shaft joint component 350 further comprises a pin protrusion 352 extending from the proximal-extending articulation tab 351. Discussed in greater detail below, the pin protrusion 352 is configured to be pivotally coupled to an articulation drive system. The second shaft joint component 350 further comprises a distal portion 355 comprising an annular groove 356 configured to receive a retention ring 358. The distal portion 355 also includes a hollow passage 357 through which various drive components of the surgical stapling assembly 300 can pass. The retention ring 358 is configured to hold the first jaw 201 to the second shaft joint component 350 by fitting within the annular groove 211 of the cartridge channel 210 and the annular groove 356 of the second shaft joint component 350.

To articulate the end effector 200 about the articulation axis AA, an articulation bar 360 is provided. The articulation bar 360 may be actuated by any suitable means such as, for example, by a robotic or motorized input and/or a manual handle trigger. The articulation bar 360 may be actuated in a proximal direction and a distal direction, for example. Embodiments are envisioned where the articulation system comprises rotary driven actuation in addition to or, in lieu of, linear actuation. The articulation bar 360 extends through the outer shaft 311. The articulation bar 360 comprises a distal end 361 pivotally coupled to an articulation link 362. The articulation link 362 is pivotally coupled to the pin protrusion 352 extending from the proximally-extending articulation tab 351 off center with respect to the articulation axis AA. Such off-center coupling of the articulation link 362 allows the articulation bar 360 to apply a force to the second joint shaft component 350 to rotate the second shaft joint component 350 and, thus, the end effector 200, relative to the first joint shaft component 330. The articulation bar 360 can be advanced distally to rotate the end effector 200 in a first direction about the articulation axis AA and retracted proximally to rotate the end effector 200 in a second direction opposite the first direction about the articulation axis AA.

The shaft assembly 310 further comprises an articulation component support structure 340 positioned within the articulation joint 320. Such a support structure can provide support to various drive components configured to pass through the articulation joint 320 to the end effector 200 as the end effector 200 is articulated. The support structure 340 may also serve to isolate the drive components from tissue remnants during use.

Figure 12:
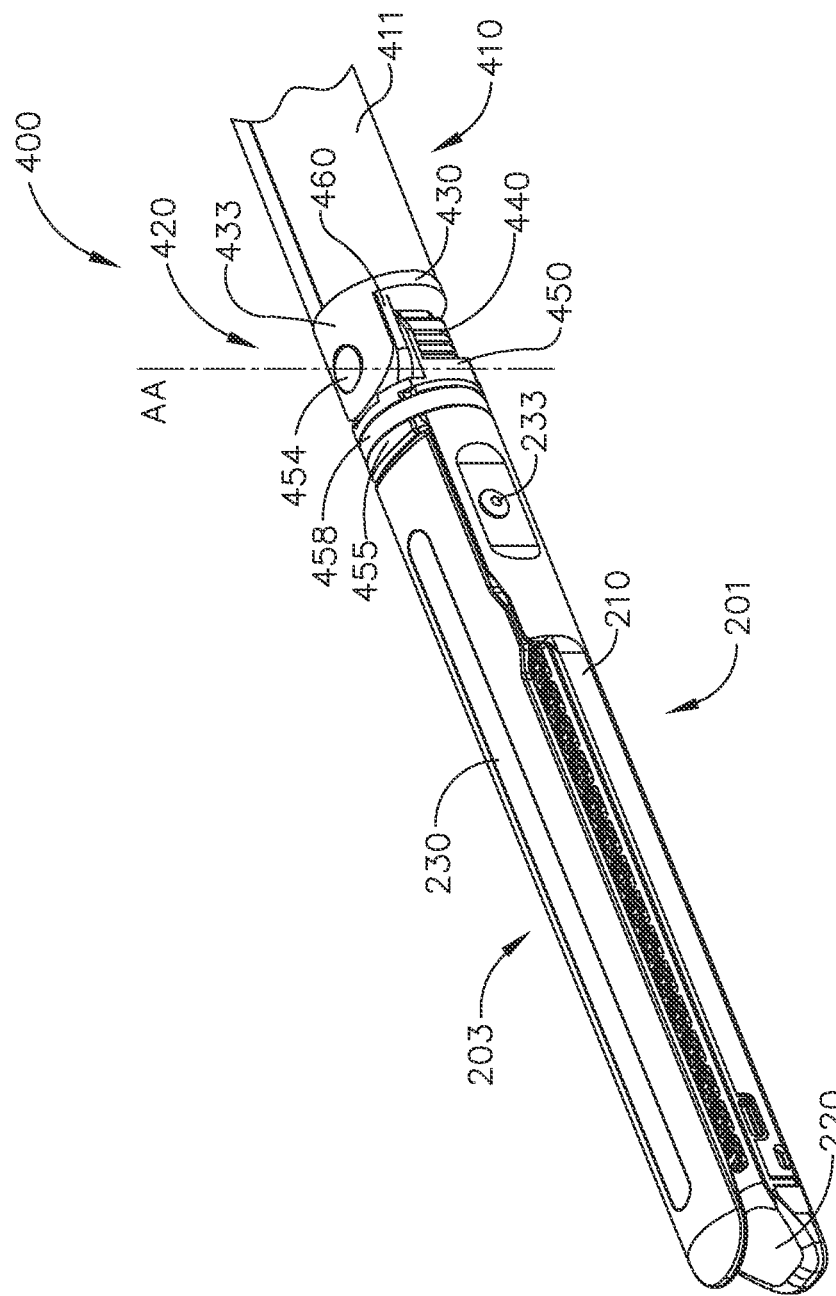
FIG. 12 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 13:
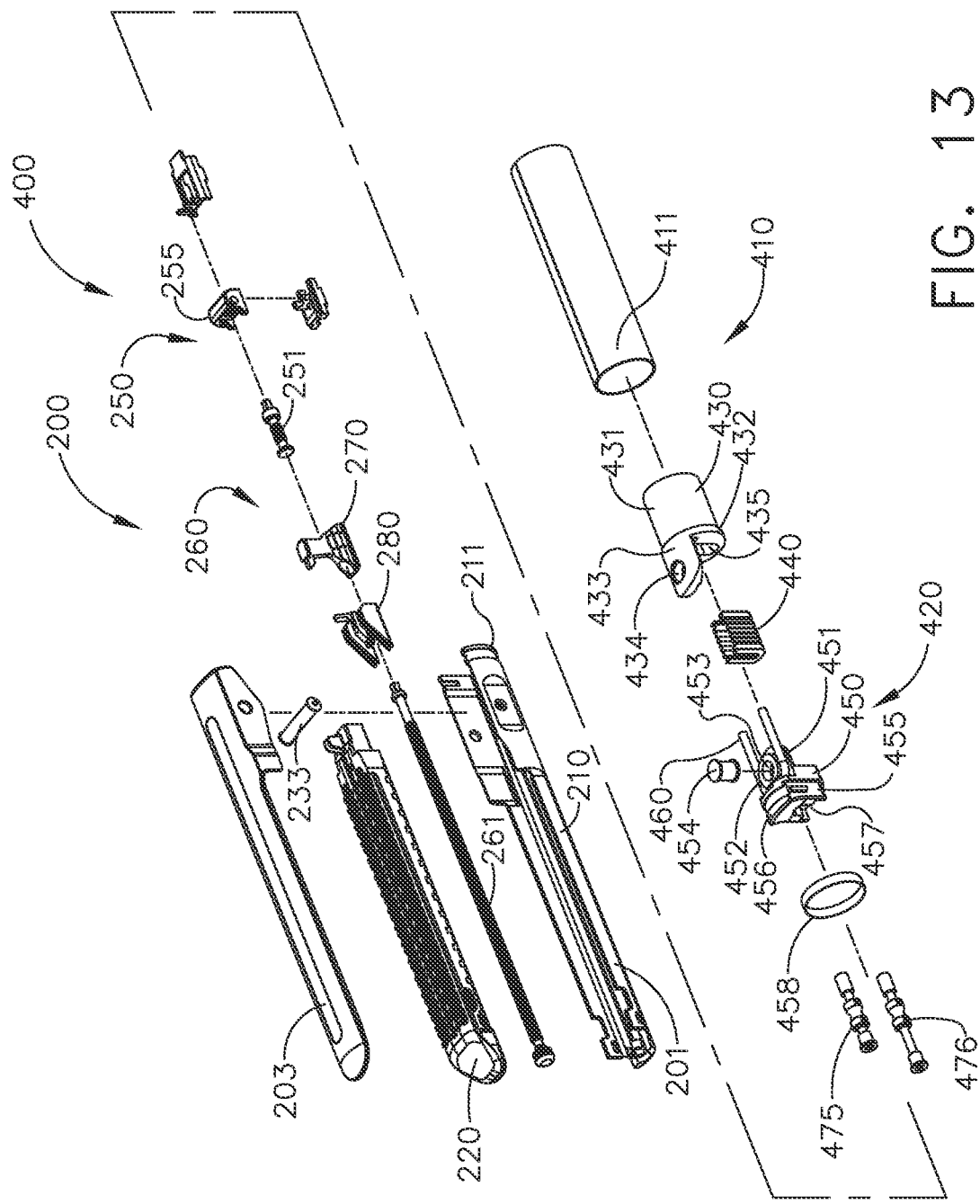
FIG. 13 is an exploded perspective view of the surgical stapling assembly of FIG. 12, in accordance with at least one aspect of the present disclosure.
Figure 14:
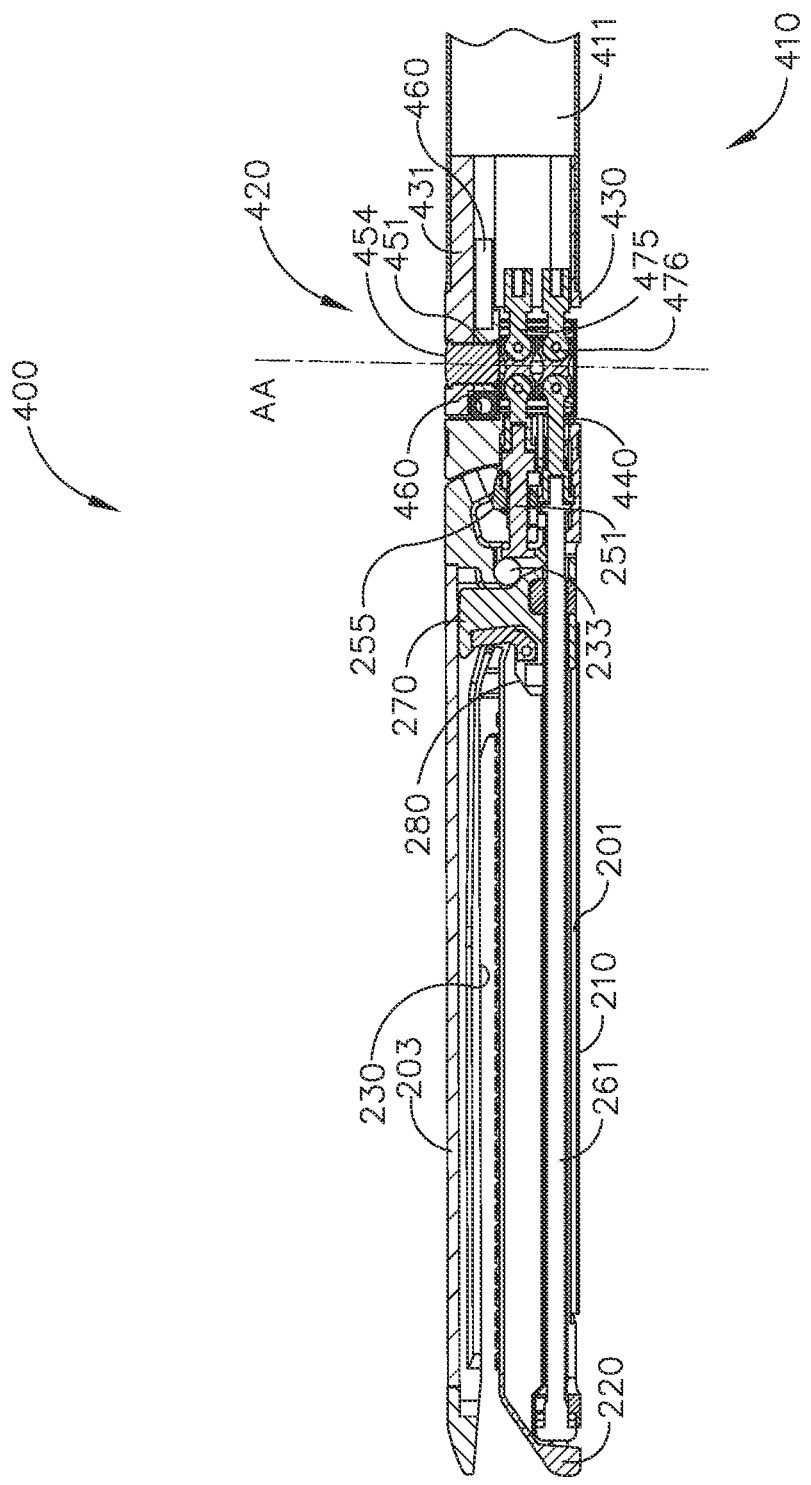
FIG. 14 is a cross-sectional elevation view of the surgical stapling assembly of FIG. 12, wherein the end effector is illustrated in an unfired, clamped configuration, in accordance with at least one aspect of the present disclosure.

FIGS. 12-14 depict a surgical stapling assembly 400 comprising a shaft assembly 410 and the end effector 200 of FIGS. 1-8 attached to the shaft assembly 410. The shaft assembly 410 may be similar in many respects to various other shaft assemblies discussed herein; however, the shaft assembly 410 comprises a single articulation joint and an articulation cable configured to articulate the end effector 200 about the single articulation joint. The surgical stapling assembly 400 is configured to cut and staple tissue. The surgical stapling assembly 400 may be attached to a surgical instrument handle and/or surgical robotic interface. The surgical instrument handle and/or surgical robotic interface can be configured to actuate various functions of the surgical stapling assembly 400. The shaft assembly 410 comprises an articulation joint 420. Discussed in greater detail below, the end effector 200 is configured to be articulated relative to an outer shaft 411 of the shaft assembly 310 about an axis AA.

The shaft assembly 410 comprises the outer shaft 411, a first shaft joint component 430, and a second shaft joint component 450 pivotally coupled to the first shaft joint component 430 by way of an articulation pin 454. The first shaft joint component 430 comprises a proximal tube portion 431 configured to fit within the inner diameter of the outer shaft 411. Such a fit may comprise a press fit, for example. However, any suitable attachment means can be used. The first shaft joint component 430 also includes a distal portion 432, which comprises an articulation tab 433 comprising a pin hole 434 defined therein. The distal portion 432 further defines a hollow passage 435 through which various drive components of the surgical stapling assembly 400 can pass. Such drive components can include articulation actuators, closure actuators, and/or firing actuators, for example.

The first shaft joint component 430 is pivotally connected to the second shaft joint component 450 by way of the articulation pin 454. The articulation pin 454 is also received within a pin hole 453 of a proximally-extending articulation tab 451 of the second shaft joint component 450. The articulation pin 454 allows the second shaft joint component 450 to be articulated relative to the first shaft joint component 430 about the articulation axis AA. The second shaft joint component 450 further comprises a drive ring structure 452. The drive ring structure 452 extends from the proximally-extending articulation tab 451 and further defines a portion of the pin hole 453. Discussed in greater detail below, the drive ring structure 452 is configured to be engaged by an articulation drive system. The second shaft joint component 450 further comprises a distal portion 455 comprising an annular groove 456 configured to receive a retention ring 458. A hollow passage 457 through the distal portion 455 is configured to receive various drive components of the surgical stapling assembly 400 therethrough. The retention ring 458 is configured to hold the first jaw 201 to the second shaft joint component 450 by fitting within the annular groove 211 of the cartridge channel 210 and the annular groove 456 of the second shaft joint component 450.

To articulate the end effector 200 about the articulation axis AA, an articulation cable 460 is provided. The articulation cable 460 may be actuated by any suitable means such as, for example, by a robotic input and/or a manual trigger on a handle of a handheld surgical instrument. The articulation cable 460 may comprise an antagonistic actuation profile. In other words, as a first side of the articulation cable 460 is pulled proximally a second side of the articulation cable 460 is allowed to advance distally like a pulley system. Similarly, as the second side is pulled proximally, the first side is allowed to advance distally. The articulation cable 460 extends through the outer shaft 411. The articulation cable 460 is positioned around the drive ring structure 452 and frictionally retained thereon to permit rotation of the second shaft joint component 450 as the articulation cable 460 is actuated. As the articulation cable 460 is actuated, the articulation cable 460 is configured to apply a rotational torque to the drive ring structure 452 of the second joint shaft component 450 and, thus, the end effector 200. Such torque is configured to cause the second joint shaft component 450 to rotate, or pivot, relative to the first joint shaft component 430 thereby articulating the end effector 200 relative to the outer shaft 411. A first side of the articulation cable 460 can pulled to rotate the end effector 200 in a first direction about the articulation axis AA and a second side of the articulation cable 460 can be pulled to rotate the end effector 200 in a second direction opposite the first direction about the articulation axis AA.

The shaft assembly 410 further comprises an articulation component support structure 440 positioned within the articulation joint 420. Such a support structure 440 can provide support to various drive components configured to pass through the articulation joint 420 to the end effector 200 as the end effector 200 is articulated. The support structure 440 may also serve to isolate the drive components from tissue remnants during use.

The surgical stapling assembly 400 further comprises a closure drive shaft segment 475 and a firing drive shaft segment 476 each configured to transmit rotary motion through the articulation joint 420 to the end effector 200. The drive shaft segments 475, 476 are configured to passively expand and contract longitudinally as the end effector 200 is articulated. For example, articulation can cause expansion and contraction of the drive shaft segments 475, 476 to account for the respective longitudinal stretching of or contracting of the length of the drive shafts owing to articulation of the end effector 200 relative to the shaft assembly 410. During expansion and contraction of the drive shaft segments 475, 476, the drive shaft segments 475, 476 maintain rotary driving engagement with corresponding input shafts extending through the outer shaft 411 and output shafts in the end effector 200. In at least one instance, the output shafts comprise the closure screw 251, which is configured to effect grasping, closing, or tissue manipulation with the jaws 201, 203, and the firing screw 261, which is configured to effect clamping of the jaws 201, 203 and firing of the firing member 270.

Figure 15:
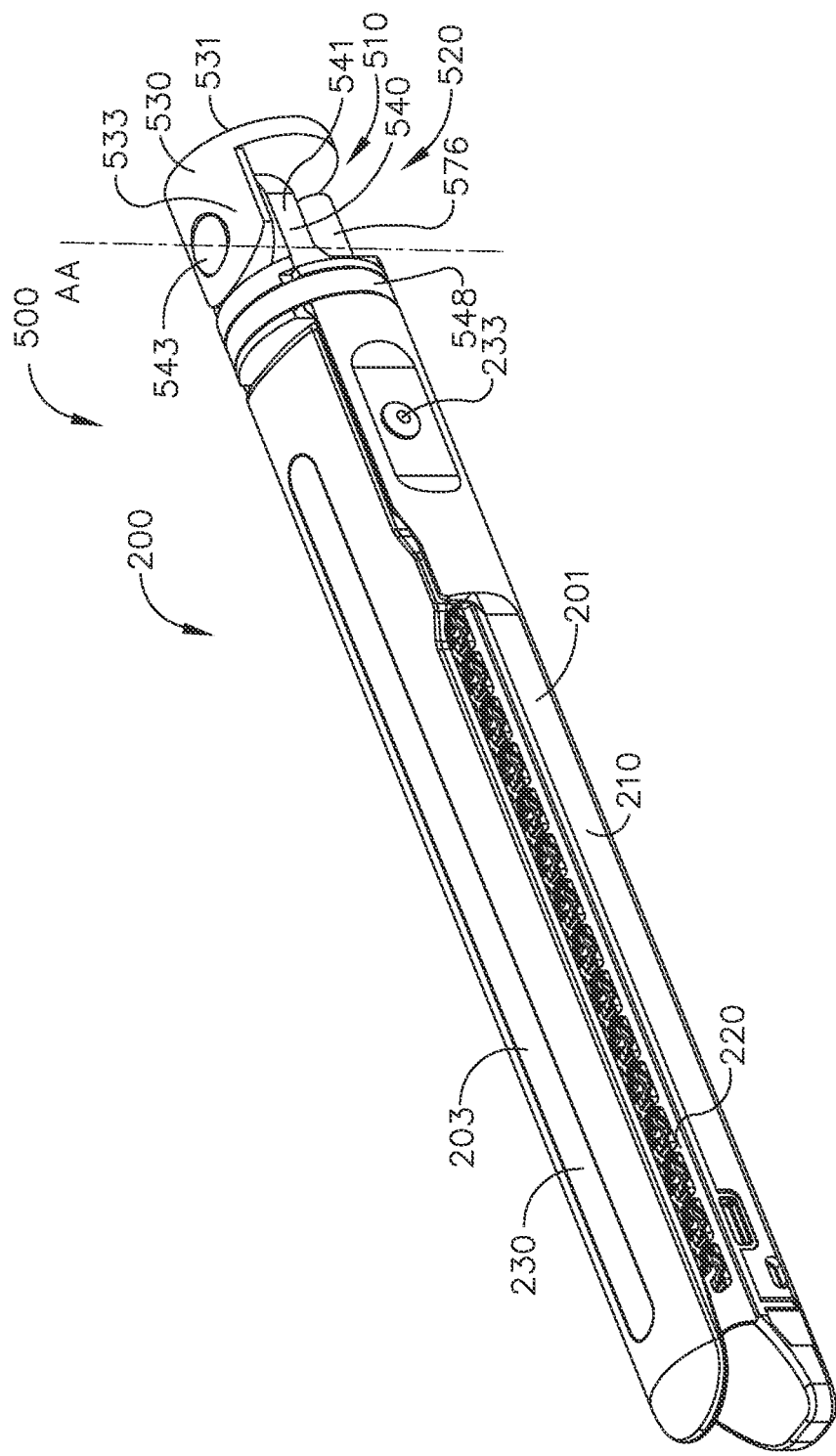
FIG. 15 is a perspective view of a surgical stapling assembly comprising a shaft assembly and the end effector of FIG. 1, wherein the end effector is attached to the shaft assembly by way of an articulation joint, in accordance with at least one aspect of the present disclosure.
Figure 16:
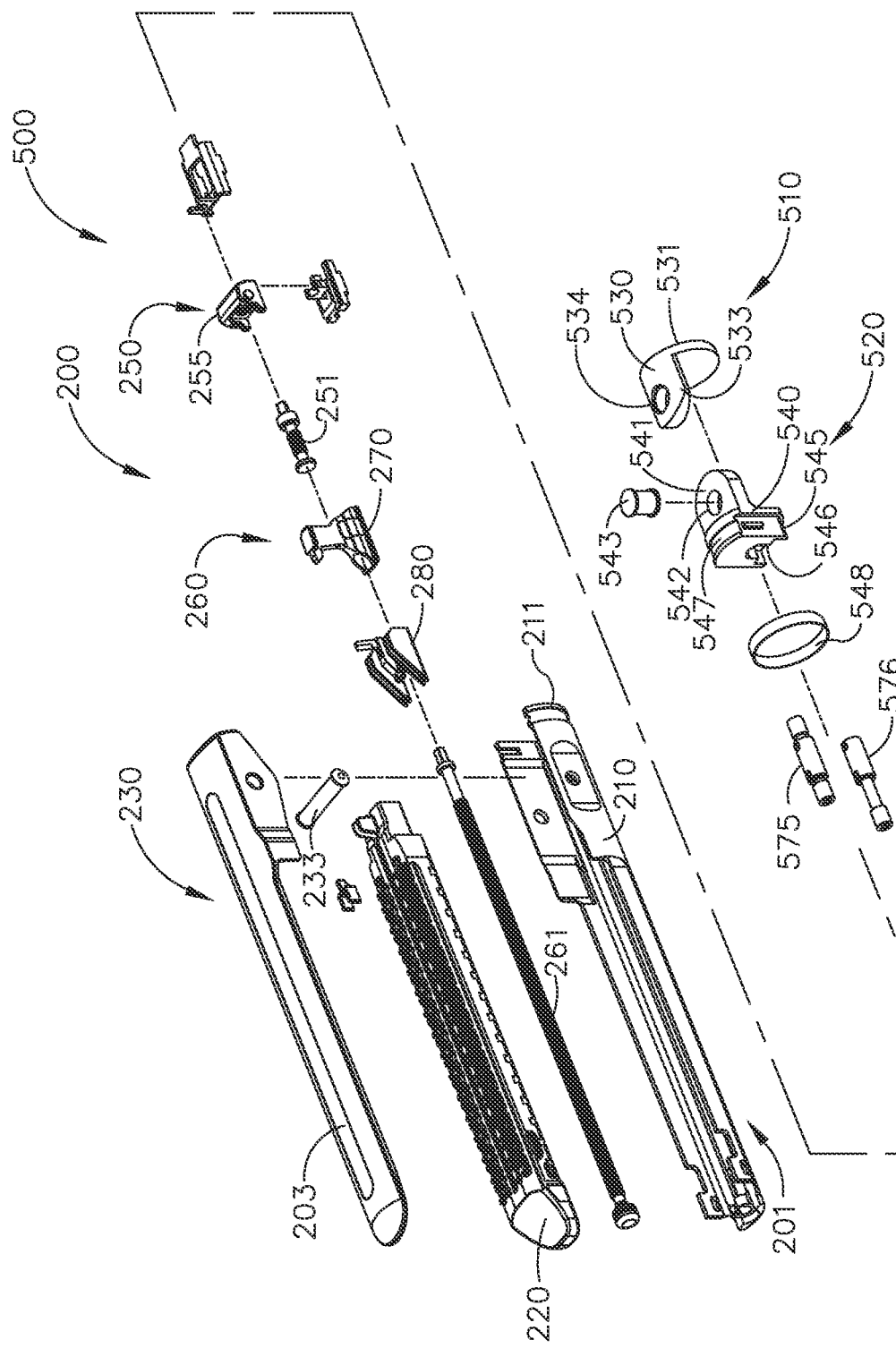
FIG. 16 is an exploded perspective view of the surgical stapling assembly of FIG. 15, in accordance with at least one aspect of the present disclosure.
Figure 17:
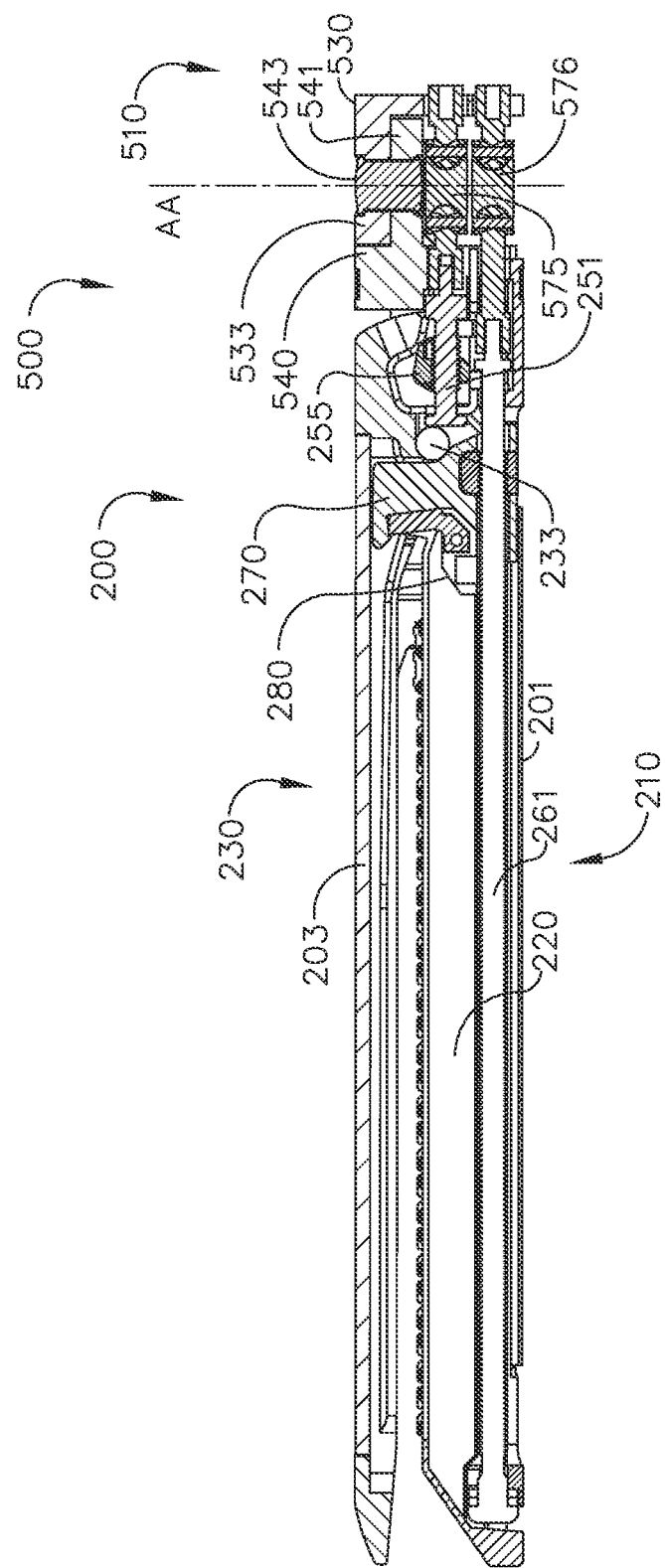
FIG. 17 is a cross-sectional elevation view of the surgical stapling assembly of FIG. 15, wherein the end effector is illustrated in an unfired, clamped configuration, in accordance with at least one aspect of the present disclosure.

FIGS. 15-17 depict a surgical stapling assembly 500 comprising a shaft assembly 510 and the end effector 200 of FIGS. 1-8 attached to the shaft assembly 510. The shaft assembly 510 may be similar in many respects to various other shaft assemblies discussed herein; however, the shaft assembly 510 comprises a single articulation joint and drive shaft segments configured to passively expand and contract. The surgical stapling assembly 500 is configured to cut and staple tissue. The surgical stapling assembly 500 may be attached to a surgical instrument handle and/or surgical robotic interface. The surgical instrument handle and/or surgical robotic interface can be configured to actuate various functions of the surgical stapling assembly 500. The shaft assembly 510 comprises an articulation joint 520. Discussed in greater detail below, the end effector 200 is configured to be articulated about an axis AA.

The shaft assembly 510 comprises a first shaft joint component 530 and a second shaft joint component 540 pivotally coupled to the first shaft joint component 530 by way of an articulation pin 543. The first shaft joint component 530 is configured to be attached to a shaft of a surgical instrument assembly and/or a surgical robotic interface. The first shaft joint component 530 comprises a proximal portion 531 and an articulation tab 533 comprising a pin hole 534 defined therein. In at least one instance, the first shaft joint component 530 comprises a hollow passage through which various drive components of the surgical stapling assembly 400 can pass. Such drive components can include articulation actuators, closure actuators, and/or firing actuators for example.

The first shaft joint component 530 is pivotally connected to the second shaft joint component 540 by way of the articulation pin 543. The articulation pin 543 is also received within a pin hole 542 of a proximally-extending articulation tab 541 of the second shaft joint component 540. The articulation pin 543 allows the second shaft joint component 540 to be articulated relative to the first shaft joint component 530 about the articulation axis AA. The second shaft joint component 540 further comprises a distal portion 545 comprising an annular groove 547 configured to receive a retention ring 548 and a hollow passage 546 through which various drive components of the surgical stapling assembly 500 can pass. The retention ring 548 is configured to hold the first jaw 201 to the second shaft joint component 540 by fitting within the annular groove 211 of the cartridge channel 210 and the annular groove 547 of the second shaft joint component 540.

Any suitable articulation drive system can be used to articulate the end effector 200 about axis AA. In at least one instance, the end effector 200 is passively articulated. In such an instance, the end effector 200 may be pressed against tissue, for example, to apply a force to the end effector 200 and cause the end effector 200 to articulate about an articulation axis. In at least one instance, the end effector 200 further comprises a spring configured to apply a neutral biasing force to the second shaft joint segment 540, for example, to cause the end effector 200 to be biased toward an unarticulated configuration.

The surgical stapling assembly 500 further comprises a closure drive shaft segment 575 and a firing drive shaft segment 576 each configured to transmit rotary motion through the articulation joint 520 to the end effector 200. The drive shaft segments 575, 576 are configured to passively expand and contract longitudinally as the end effector 200 is articulated. Articulation causes the drive shaft segments 575, 576 to expand and contract to account for the longitudinal stretching of or contracting of the length of the drive shafts owing to articulation of the end effector 200. During expansion and contraction of the drive shaft segments 575, 576, the drive shaft segments 575, 576 maintain rotary driving engagement with corresponding input shafts and output shafts in the end effector 200. In at least one instance, the output shafts comprise the closure screw 251 and the firing screw 261, which are further described herein.

Figure 18:
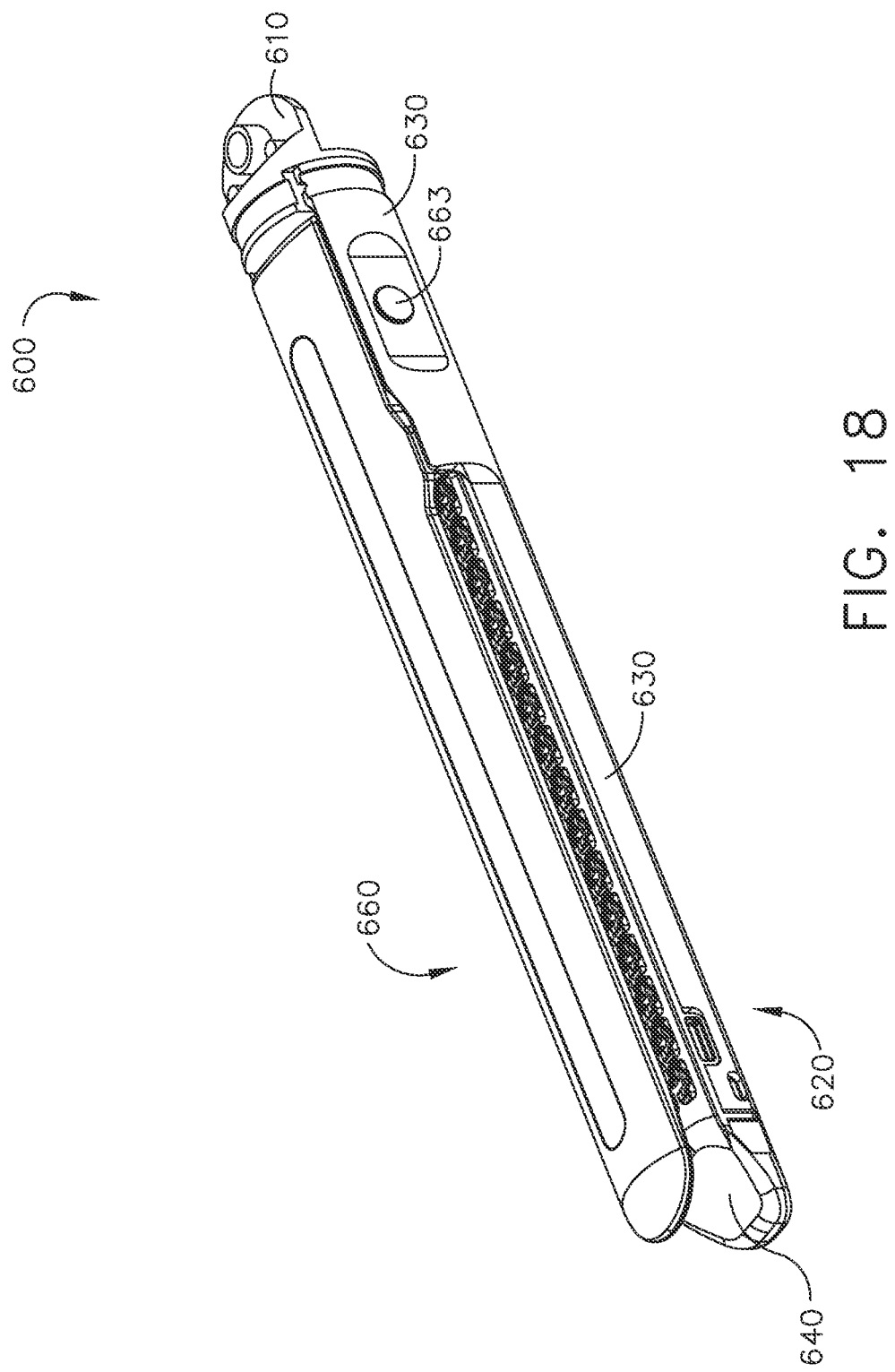
FIG. 18 is a perspective view of a surgical end effector assembly comprising the end effector of FIG. 1 and a flexible firing drive system, in accordance with at least one aspect of the present disclosure.
Figure 19:
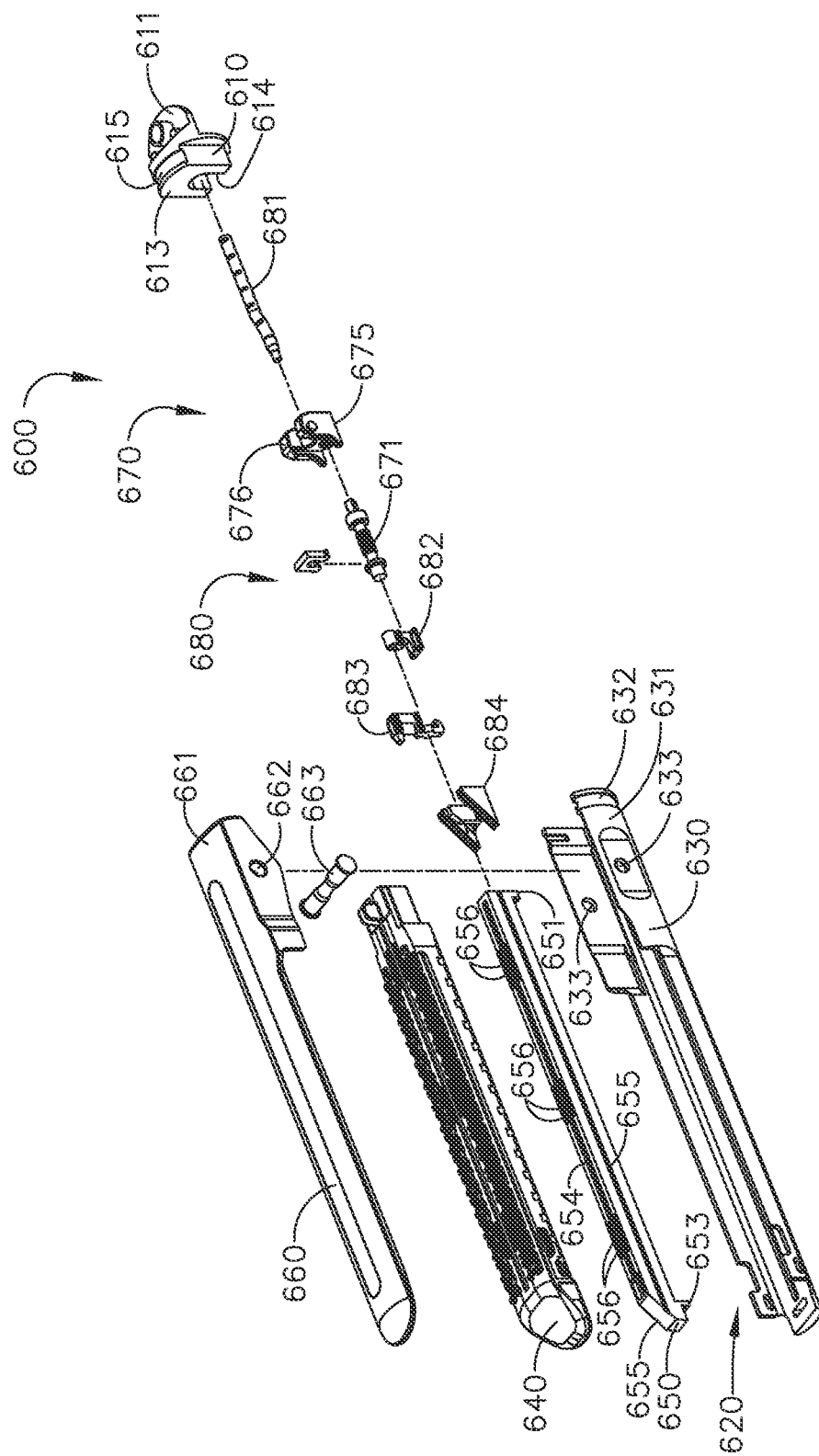
FIG. 19 is an exploded perspective view of the surgical stapling assembly of FIG. 18, in accordance with at least one aspect of the present disclosure.
Figure 20:
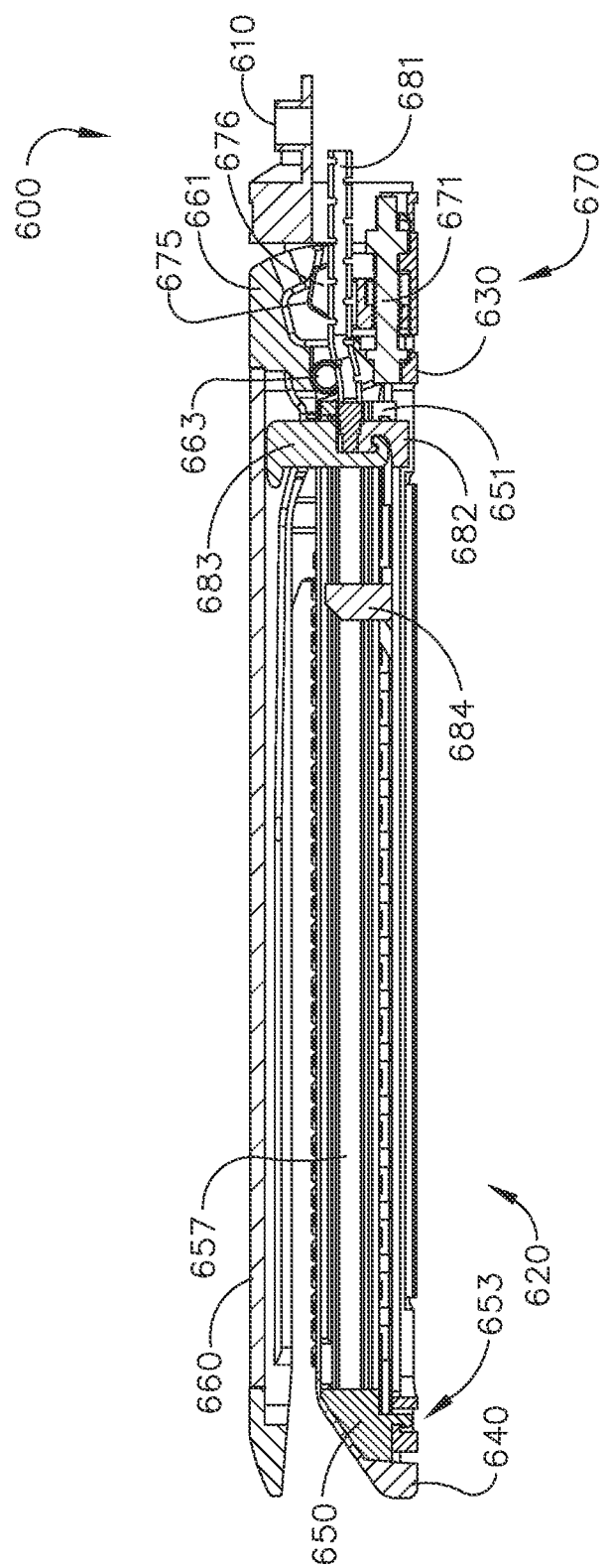
FIG. 20 is a cross-sectional elevation view of the surgical end effector assembly of FIG. 18, wherein the surgical end effector assembly is illustrated in an unfired, clamped configuration, in accordance with at least one aspect of the present disclosure.

FIGS. 18-20 depict a surgical stapling end effector assembly 600 comprising a shaft portion 610 and an end effector 600. The end effector assembly 600 is similar in many respects to various other end effector assemblies disclosed herein; however, the end effector assembly 600 comprises a multi-component firing member driven by a flexible firing shaft. The end effector assembly 600 is configured to cut and staple tissue. The end effector assembly 600 may be attached to a surgical instrument handle and/or surgical robotic interface by way of a proximal tab 611 of the shaft portion 610. The surgical instrument handle and/or surgical robotic interface can be configured to actuate various functions of the end effector assembly 600. The end effector assembly 600 comprises a cartridge channel jaw 620 and an anvil jaw 660 pivotally mounted to the cartridge channel jaw 620 to clamp tissue between the cartridge channel jaw 620 and the anvil jaw 660.

The cartridge channel jaw 620 comprises a channel 630 comprising a proximal end 631, a staple cartridge 640 configured to store a plurality of staples therein and configured to be received within the channel 630, and a support brace 650 fitted within the staple cartridge 640. The staple cartridge 640 and the support brace 650 are configured to be assembled together prior to installing the staple cartridge 640 into the channel 630. Discussed in greater detail below, the support brace 650 is configured to further support a firing member assembly as the firing member assembly is advanced through the end effector assembly 600.

The anvil jaw 660 is configured to form staples ejected from the staple cartridge 640. The anvil jaw 660 comprises a proximal end 661 comprising a pair of pin holes 662 defined therein configured to receive a coupling pin 663. The anvil jaw 660 is pivotable about the coupling pin 663 between an unclamped position and a fully clamped position. The coupling pin 663 is also received within a pair of pin holes 633 defined in the proximal end 631 of the channel 630. The coupling pin 663 serves to pivotally mount the anvil jaw 660 to the channel 630. In at least one instance, the channel 630 is mounted to the shaft portion 610 by way of a retention ring, or band, that fits around an annular groove 632 of the channel 630 and annular groove 615 of the shaft portion 610. The retention ring, or band, is configured to hold the channel 630 to the shaft portion 610.

The end effector assembly 600 comprises a closure drive 670 configured to grasp tissue between the anvil jaw 660 and the cartridge channel jaw 620 by pivoting the anvil jaw 660 relative to the channel 630. The end effector assembly 600 also includes a firing drive 680 configured to clamp, staple, and cut tissue by deploying a plurality of staples from the staple cartridge 640. The closure drive 670 comprises a closure screw 671 positioned within the channel 630 and a closure wedge 675 threadably coupled to the closure screw 671. As the closure screw 671 is rotated, the closure wedge 675 is advanced distally or retracted proximally to open or close the anvil jaw 660, respectively. The closure drive 670 may be actuated by any suitable means. For example, a rotary drive shaft may extend through the shaft portion 610 from an actuation interface, for example, to rotate the closure screw 671. Other examples of suitable rotary drive shafts are further described herein.

The firing drive 680 comprises a flexible drive shaft 681 that is configured to be moved linearly through the end effector assembly 600. The flexible drive shaft 681 may be actuated by a robotic input and/or a manually-actuated drive shaft of a handle assembly, for example. The flexible drive shaft 681 is configured to extend through a hollow passage 614 of a distal end 613 of the shaft portion 610 and is flexible so that the end effector assembly 600 may be articulated relative to a shaft from which the end effector 600 extends. The flexible drive shaft 681 extends through a clearance slot 676 defined in the closure wedge 675 and is fixedly attached to a lower firing member 682. The lower firing member 682 is configured to be reused with different staple cartridges.

The staple cartridge 640 comprises a disposable upper firing member 683 configured to hookingly engage or, latch, onto the lower firing member 682 such that the lower firing member 582 can push or, drive, the upper firing member 683 through the staple cartridge 640 and support brace 650. In other words, the firing actuation involves a two-part firing member—a disposable upper firing member 683 incorporated into the cartridge 640 and a reusable lower firing member 682 incorporated into the firing drive 680, which can be coupled together when the cartridge 640 is seated in the elongate channel 630. The two-part firing member is further described herein.

The upper firing member 683 comprises an upper flange configured to engage and position the anvil jaw 660, a knife edge configured to cut tissue, and a latch portion configured to hookingly engage the lower firing member 682. The staple cartridge 640 further comprises a sled 684 configured to engage staple drivers positioned within the staple cartridge 640 to eject staples from the staple cartridge 640. Because a knife and cutting edge are incorporated into the disposable upper firing member 683 of the staple cartridge 640, a new and/or fresh cutting edge can be supplied with each staple cartridge loaded into the end effector assembly 600.

The lower firing member 682 and the upper firing member 683 are configured to move through the support brace 650 such that the vertical loads associated with the firing sequence are configured to be distributed through the support brace 650, the staple cartridge 640, the channel 630, and the anvil jaw 660. The support brace 650 may be comprised of a metal material, for example, to be inserted within the staple cartridge 640. The support brace 650 comprises key rails 655 configured to fit within corresponding key slots defined in a longitudinal slot of the staple cartridge 640. The support brace 650 further comprises a longitudinal slot 653 configured to receive the knife of the upper firing member 683, a cylindrical passage 657 configured to receive a portion of the upper firing member 683, a portion of the lower firing member 682, and the flexible drive shaft 681. The support brace 650 further comprises vertical key extensions 656 configured to be received within corresponding key holes in the cartridge deck. Such extensions may be visible through the cartridge deck when the support brace 650 is installed within the staple cartridge 640. In at least one instance, the support brace 650 is configured to be inserted into the staple cartridge 640 from the bottom of the staple cartridge 640 facing the channel 630.

The support brace 650 further comprises a proximal tab 651 and a distal tab 653, which are both configured to be engaged with the channel 630. The tabs 651, 653 are configured to distribute at least some of the forces transmitted through the assembly 600 by the firing drive 680 and corresponding components. The distal tab 651 may serve to block the upper and lower firing members 683, 682 from being pushed through a distal end of the support brace 650 by sharing and/or redistributing the load applied to the support brace 650 by the firing drive 680 with the channel 630.

When the staple cartridge 640 is replaced so that the end effector assembly 600 can be reused, the staple cartridge 640 is removed from the channel jaw 630. Removing the staple cartridge 640 from the channel jaw 630 removes the upper firing member 683, the sled 684, the support brace 650, and the staple cartridge 640. A fresh knife can be provided with a replacement staple cartridge.

Figure 21:
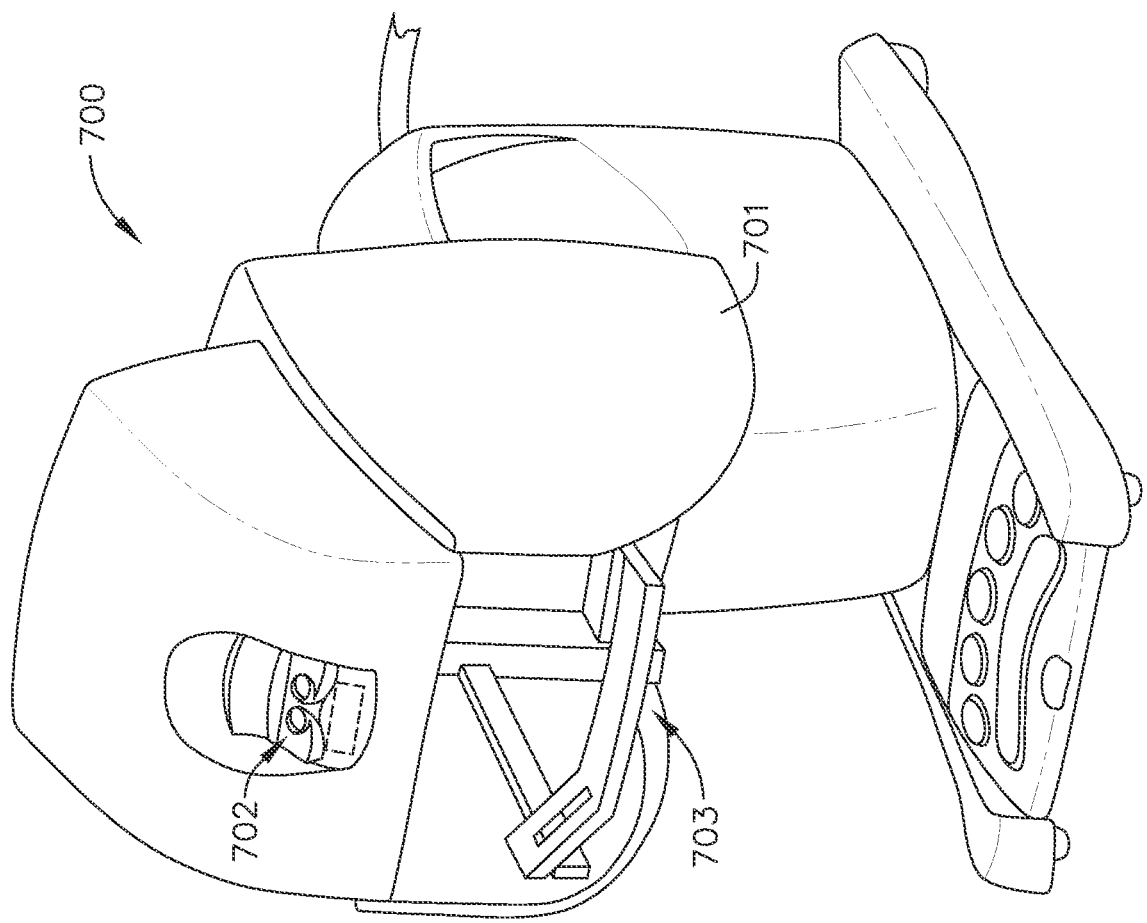
FIG. 21 is a perspective view of robotic controller, in accordance with at least one aspect of the present disclosure.
Figure 22:
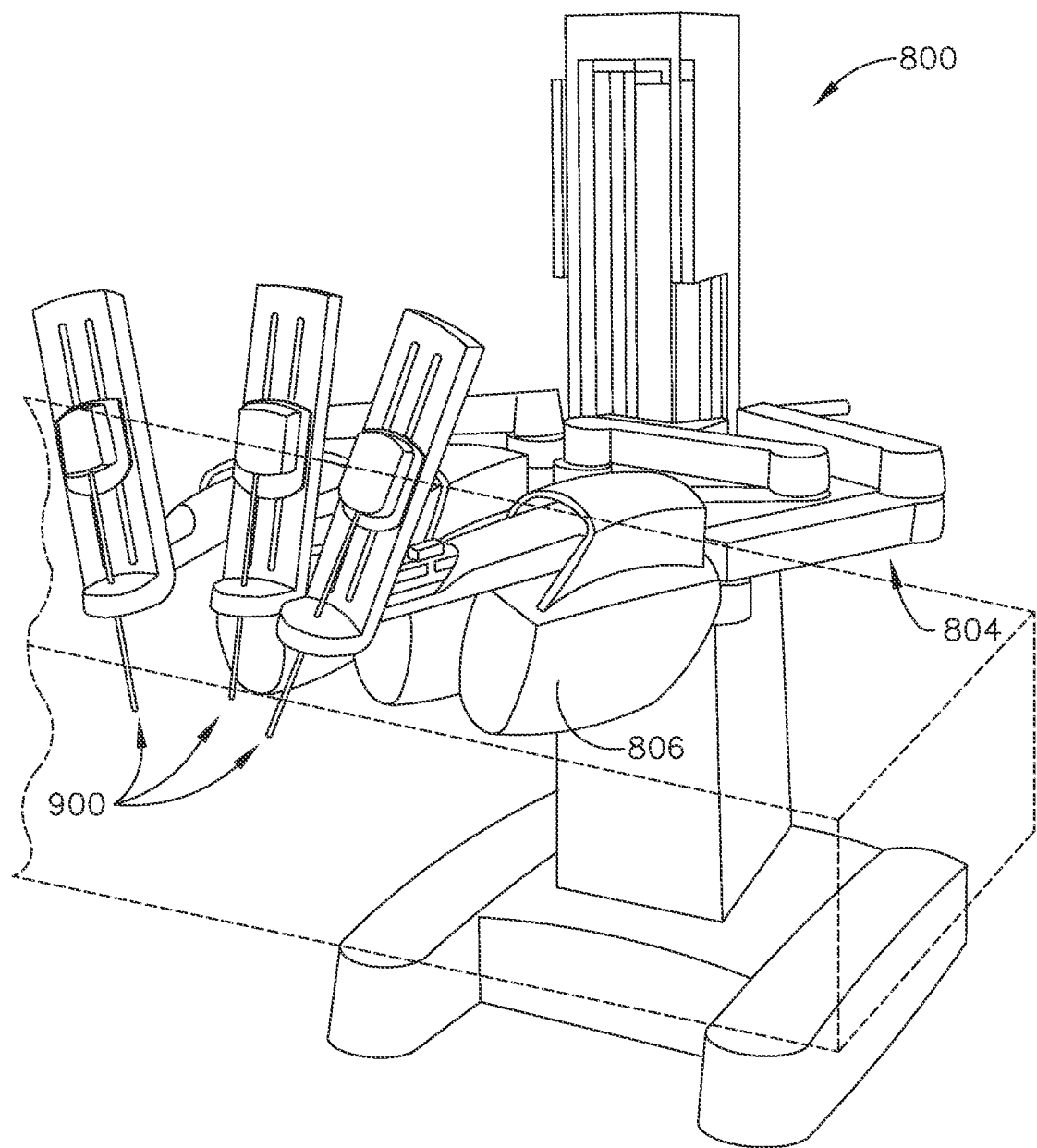
FIG. 22 is a perspective view of a robotic arm cart for a robotic surgical system, depicting manipulators on the robotic arm cart operably supporting surgical tools, in accordance with at least one aspect of the present disclosure.
Figure 23:
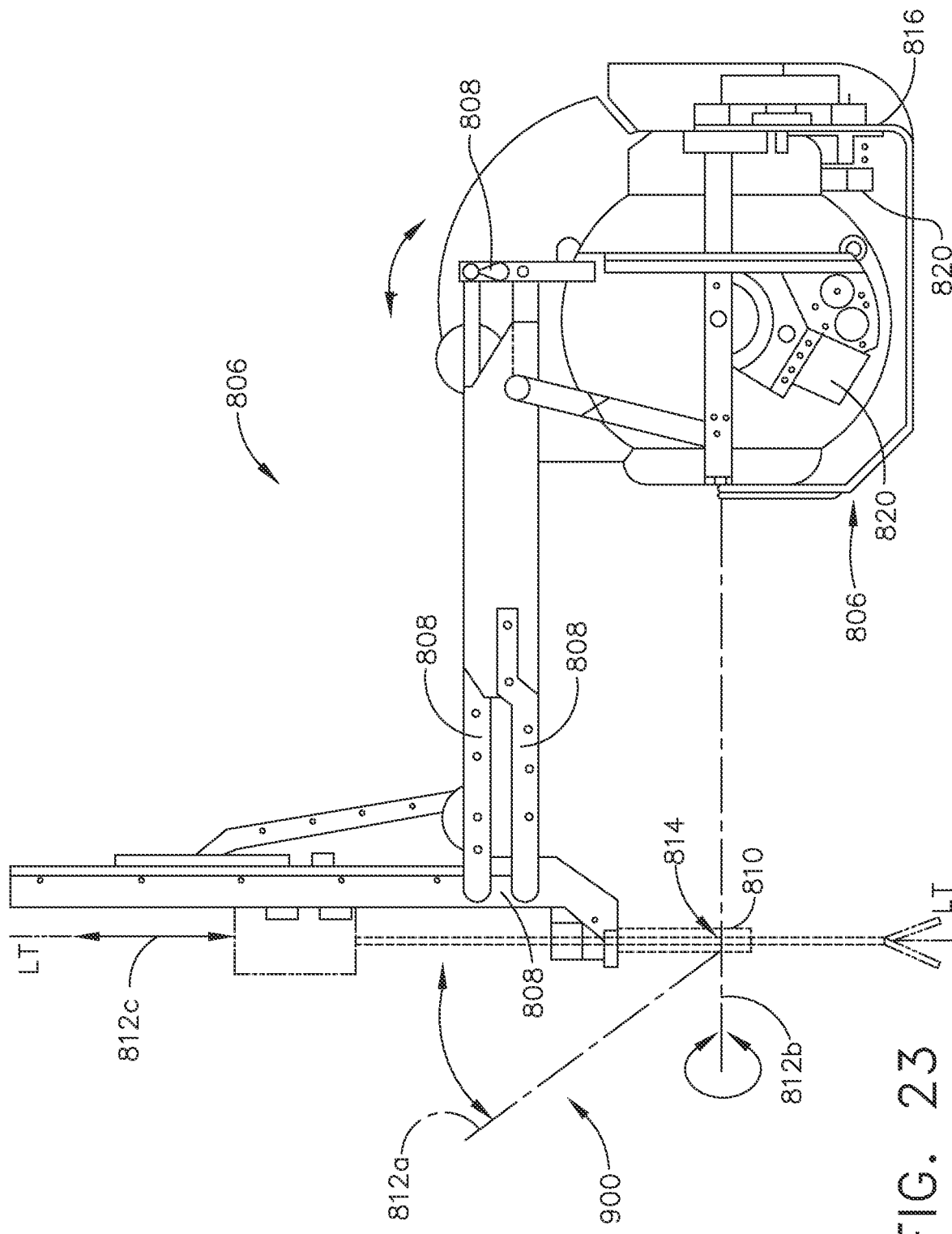
FIG. 23 is a side view of a manipulator of the surgical arm cart of FIG. 22 and a surgical grasping tool, in accordance with at least one aspect of the present disclosure.
Figure 24:
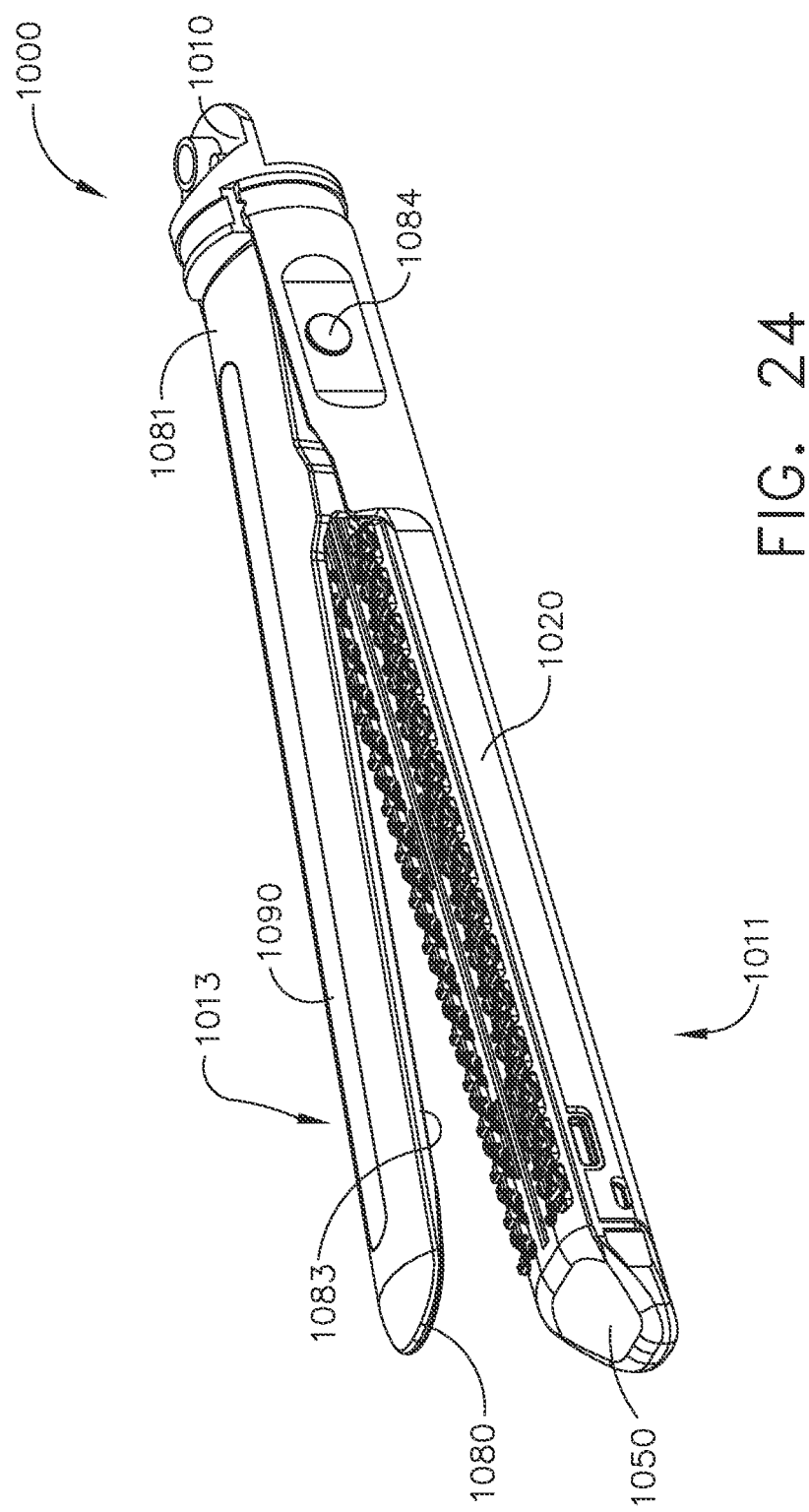
FIG. 24 is a perspective view of an end effector assembly comprising an anvil, a channel, and a staple cartridge, in accordance with at least one aspect of the present disclosure.

Various embodiments disclosed herein may be employed in connection with a robotic system 700. An exemplary robotic system is depicted in FIGS. 21-23, for example. FIG. 21 depicts a master controller 701 that may be used in connection with a surgical robot, such as the robotic arm slave cart 800 depicted in FIG. 22, for example. Master controller 701 and robotic arm slave cart 800, as well as their respective components and control systems are collectively referred to herein as a robotic system 700. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. As is known, the master controller 701 generally includes controllers (generally represented as 703 in FIG. 21) which are grasped by the surgeon and manipulated in space while the surgeon views the procedure via a stereo display 702. The controllers 701 generally comprise manual input devices which preferably move with multiple degrees of freedom, and which often further have an actuatable handle, trigger, or actuator for actuating tools (for example, for closing grasping jaws, applying an electrical potential to an electrode, or the like).

As can be seen in FIG. 22, in one form, the robotic arm cart 800 may be configured to actuate one or more surgical tools, generally designated as 900. Various robotic surgery systems and methods employing master controller and robotic arm cart arrangements are disclosed in U.S. Pat. No. 6,132,368, entitled MULTI-COMPONENT TELEPRESENCE SYSTEM AND METHOD, the entire disclosure of which is hereby incorporated by reference herein.

In various forms, the robotic arm cart 800 includes a base 702 from which, in the illustrated embodiment, surgical tools 900 may be supported. In various forms, the surgical tool(s) 900 may be supported by a series of manually articulatable linkages, generally referred to as set-up joints 804, and a robotic manipulator 806. In various embodiments, the linkage and joint arrangement may facilitate rotation of a surgical tool around a point in space, as more fully described in U.S. Pat. No. 5,817,084, entitled REMOTE CENTER POSITIONING DEVICE WITH FLEXIBLE DRIVE, the entire disclosure of which is hereby incorporated by reference herein. The parallelogram arrangement constrains rotation to pivoting about an axis 812a, sometimes called the pitch axis. The links supporting the parallelogram linkage are pivotally mounted to set-up joints 804 (FIG. 22) so that the surgical tool further rotates about an axis 812b, sometimes called the yaw axis. The pitch and yaw axes 812a, 812b intersect at the remote center 814, which is aligned along an elongate shaft of the surgical tool 900. The surgical tool 900 may have further degrees of driven freedom as supported by the manipulator 806, including sliding motion of the surgical tool 900 along the longitudinal axis "LT-LT". As the surgical tool 900 slides along the tool axis LT-LT relative to manipulator 806 (arrow 812c), the remote center 814 remains fixed relative to the base 816 of the manipulator 806. Hence, the entire manipulator is generally moved to re-position the remote center 814. Linkage 808 of manipulator 806 may be driven by a series of motors 820. These motors actively move linkage 808 in response to commands from a processor of a control system. The motors 820 may also be employed to manipulate the surgical tool 900. Alternative joint structures and set up arrangements are also contemplated. Examples of other joint and set up arrangements, for example, are disclosed in U.S. Pat. No. 5,878,193, entitled AUTOMATED ENDOSCOPE SYSTEM FOR OPTIMAL POSITIONING, the entire disclosure of which is hereby incorporated by reference herein.

While the data communication between a robotic component and the processor of the robotic surgical system is primarily described herein with reference to communication between the surgical tool and the master controller 701, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 21-23 and described in the aforementioned references.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

Various surgical instruments employ a variety of different drive shaft arrangements that serve to transmit drive motions from a corresponding source of drive motions that is supported in a handle of the surgical instrument or other portion of an automated or robotically controlled system. These drive shaft arrangements must be able to accommodate significant articulated orientations of the end effector while effectively transmitting such drive motions across the articulation joint of the surgical instrument. In addition, due to the above-mentioned size constraints dictated by the sizes of trocars through which the instrument shafts must be inserted, these drive shaft components must occupy as little space as possible within the shaft. To accommodate such requirements, many drive shaft arrangements comprise several movable elements that are coupled together in series. The small sizes (e.g., 4 mm diameter) and numbers of components lead to difficult and lengthy assembly procedures that add to the cost and complexity of the device.

As further described herein, a powered stapling device can include two independently rotatable drive members: a first rotary drive member configured to effect closing of the jaws of the end effector and a second rotary drive member configured to effect firing of a staple cartridge installed in the end effector. The first and second rotary drive members are flexible and configured to extend through at least one articulation joint. In such instances, the first and second rotary drive members can transmit rotary actuation motions through the articulation joint(s) when in a non-flexed configuration and when in a flexed configuration. Exemplary rotary drive members are further described herein.

The powered stapling assembly further comprises a first jaw, a second jaw, a closure drive comprising the first rotary drive member extending through the articulation joint, and a firing drive comprising the second rotary drive member extending through the articulation joint. The second rotary drive member can be rotatable independent of the first rotary drive member. The closure drive can be activated by a closure trigger, for example, whereupon an actuation of the closure drive effects a rotation of the first rotary drive member, which transmits a rotary motion through the articulation joint to a closure screw. The closure drive further comprises a closure wedge threadably coupled to the closure screw, wherein the closure wedge is configured to engage the first jaw to move the first jaw from an open position to a closed position upon rotation of the first rotary drive member.

The firing drive can be activated by a firing trigger, for example, which is separate from the closure trigger. The rotation of the second rotary drive member is separate from the rotation of the first rotary drive member, and a closure motion is separate and distinct from a firing motion. Activation of the firing drive effects a rotation of the second rotary drive member, which transmits a rotary motion through the articulation joint to a firing screw. The firing drive further comprises a firing member threadably coupled to the firing screw, wherein the firing member is configured to camming engage the first jaw and the second jaw and to move a cutting member and/or a staple-firing sled upon rotation of the second rotary drive member.

In various instances, at least one component in the powered stapling device can be a 3D-printed component. 3D-printed components can be incorporated into an articulation system, a closure/grasping system, and/or a firing system, as further described herein. 3D printing technology can be utilized to improve component capabilities in certain instances. For example, 3D printing can allow the printed component to exhibit metamaterial properties, such that the 3D-printed components exhibits greater structural strength and stiffness while allowing precision in the forming of small detailed features and optimizing other properties of the component such as selective flexibility and/or lubrication, for example. Exemplary 3D-printed components for the powered stapling device are further described herein and include the flexible rotatable drive member(s), e.g. serial 3D-printed universal joints, the firing member or I-beam, and/or the staple cartridge and/or sub-components thereof. In one instance, the staple cartridge can be a composite plastic-metal 3D-printed component. 3D printing of various components and considerations therefor are further described herein.

A method of stapling with such surgical stapling assemblies is also contemplated. The method can include obtaining the surgical stapling assembly and activating, by the closure trigger, the closure drive, wherein the closure wedge is configured to engage the first jaw to move the first jaw from an open position to a closed position upon a rotation of the first rotary drive member. The method can further includes activating, by the firing trigger, the firing drive, wherein the firing member is configured to camming engage the first jaw and the second jaw and to advance a cutting member and a staple-firing sled during a firing motion upon a rotation of the second rotary drive member. Various applications of 3D-printed components in such assemblies are further described herein.

FIGS. 24-33 depict an end effector assembly 1000 for stapling tissue. The end effector assembly 1000 is similar to the end effector assembly 600; however, the end effector assembly 1000 and the accompanying description comprise further details than the end effector assembly 600. The end effector assembly 1000 comprises a shaft portion 1010 and end effector comprising a first jaw 1011 and a second jaw 1013 movable relative to the first jaw 1011. The end effector assembly 1000 is configured to cut and staple tissue captured between the jaws 1011, 1013. The end effector assembly 1000 may be attached to a surgical instrument handle and/or surgical robotic interface by way of the shaft portion 1010. The surgical instrument handle and/or surgical robotic interface can be configured to actuate various functions of the end effector assembly 1000. The first jaw 1011 comprises a cartridge channel 1020 and the second jaw 1013 comprises an anvil 1080 pivotally mounted to the cartridge channel 1020 by way of pin 1084 to clamp tissue between the jaws 1011, 1013.

The end effector assembly 1000 further comprises a replaceable staple cartridge 1050 configured to be installed within the cartridge channel 1020 and a support beam 1100 positioned within the staple cartridge 1050. Discussed in greater detail below, the support beam 1100 is configured to provide additional internal support to the end effector assembly 1100 within the staple cartridge 1050. The staple cartridge 1050 comprises a cartridge body 1055 comprising a proximal end 1051, a distal end 1053, and a cartridge deck 1056. The cartridge body 1055 further comprises a plurality of staple cavities 1057 arranged in longitudinal rows defined in the deck 1056, and a longitudinal slot 1059 defined in the deck 1056 and configured to receive a portion of a firing member assembly discussed in greater detail below.

The replaceable staple cartridge 1050 is configured to removably store a plurality of staples within the staple cavities 1057. The staples are configured to be ejected from the staple cartridge and against an anvil surface 1083 of the anvil 1080 to form the staples and staple tissue captured between the deck 1056 and the anvil surface 1083. To eject the staples, a sled 1070 is pushed from a proximal end 1051 of the staple cartridge 1050 toward a distal end 1053 of the staple cartridge 1050 by the firing member assembly. As the sled 1070 translates longitudinally within the staple cartridge 1050, the sled 1070 is configured to contact and lift a plurality of staple drivers supporting the staples within the staple cartridge 1050 and form the staples against the anvil surface 1083.

Figure 25:
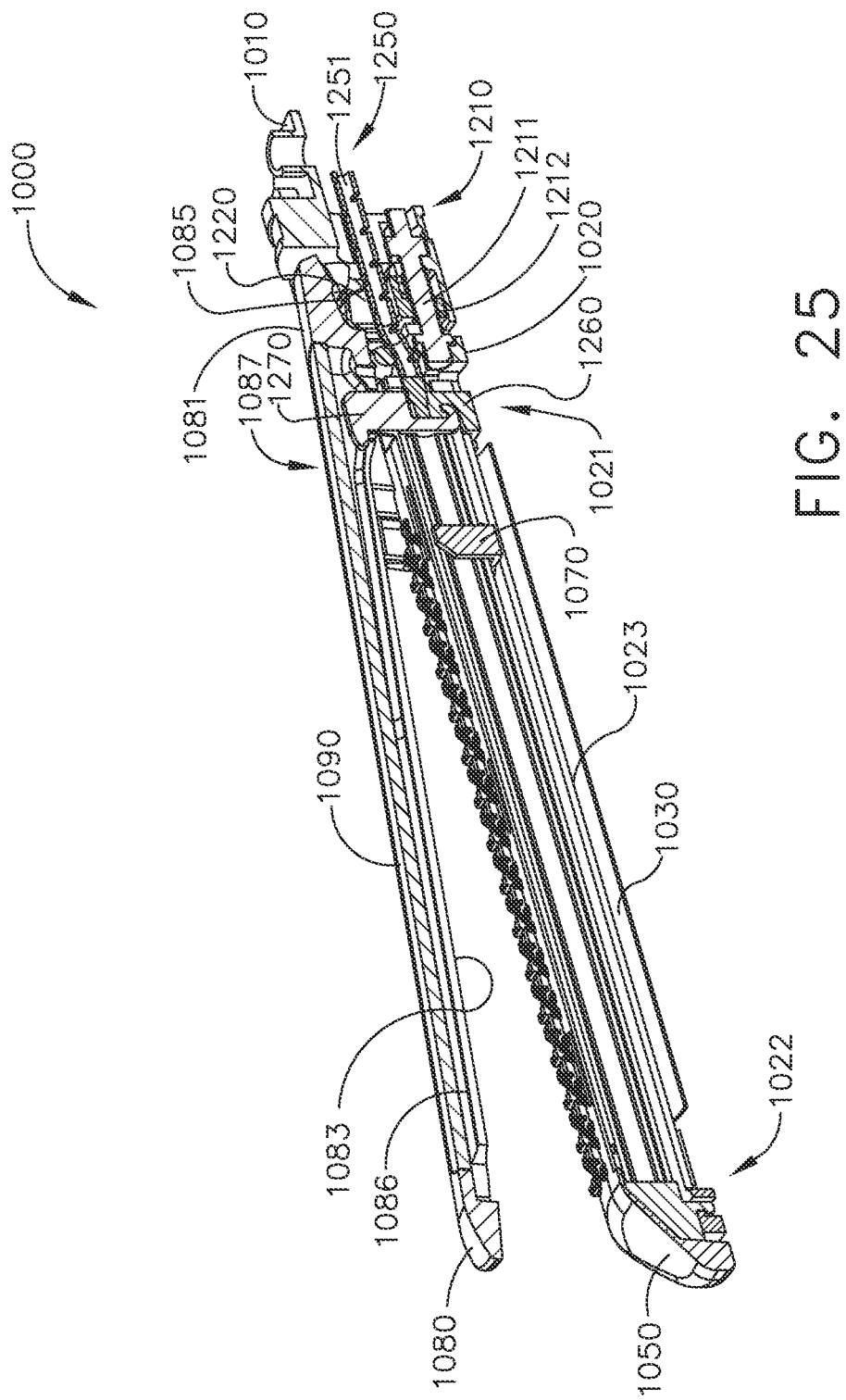
FIG. 25 is a cross-sectional perspective view of the end effector assembly of FIG. 24, in accordance with at least one aspect of the present disclosure.
Figure 26:
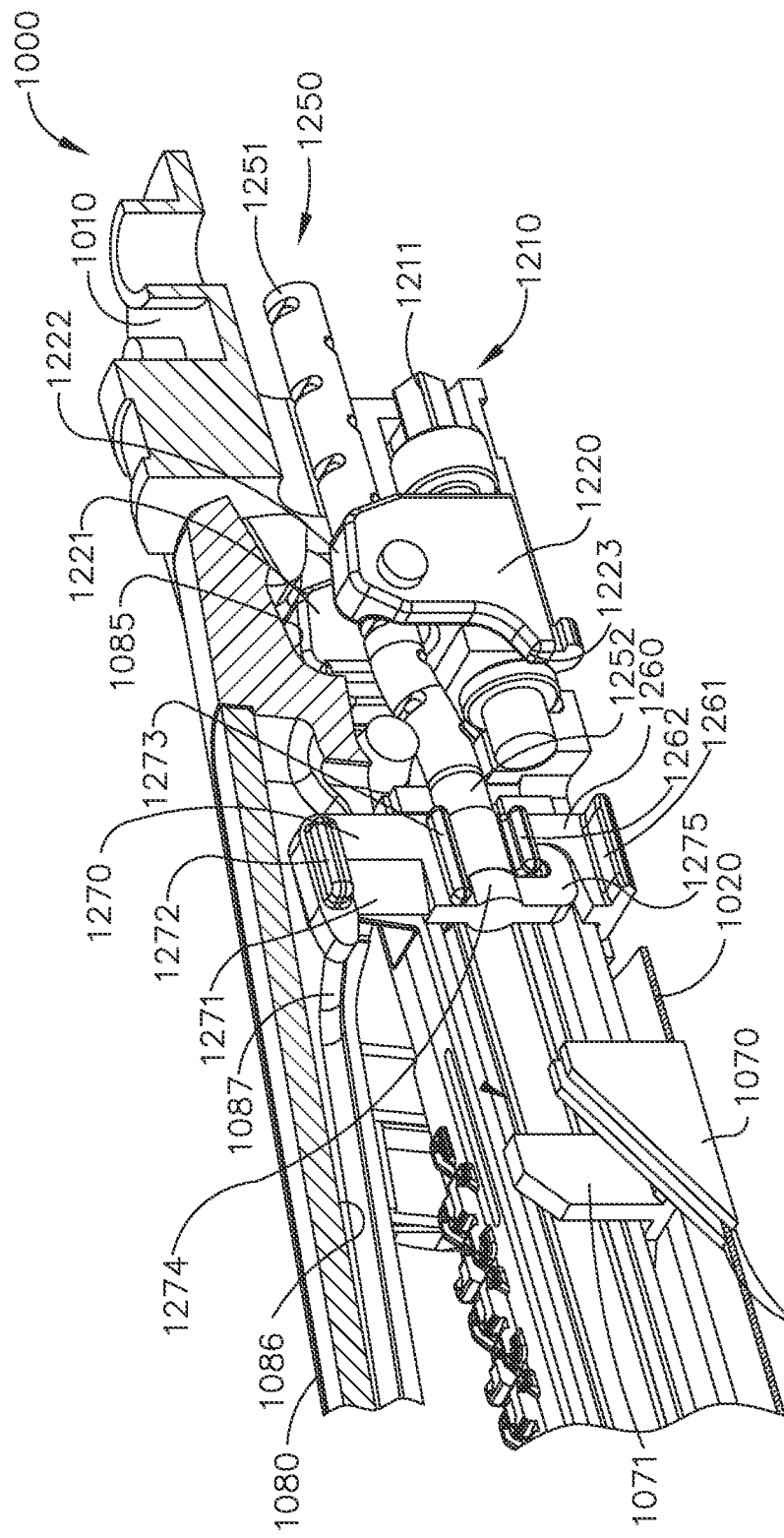
FIG. 26 is a partial cross-sectional perspective view of the end effector assembly of FIG. 24, wherein the end effector assembly comprises a firing drive configured to deploy staples from the staple cartridge and a closure drive configured to open and close the anvil relative to the channel, in accordance with at least one aspect of the present disclosure.
Figure 27:
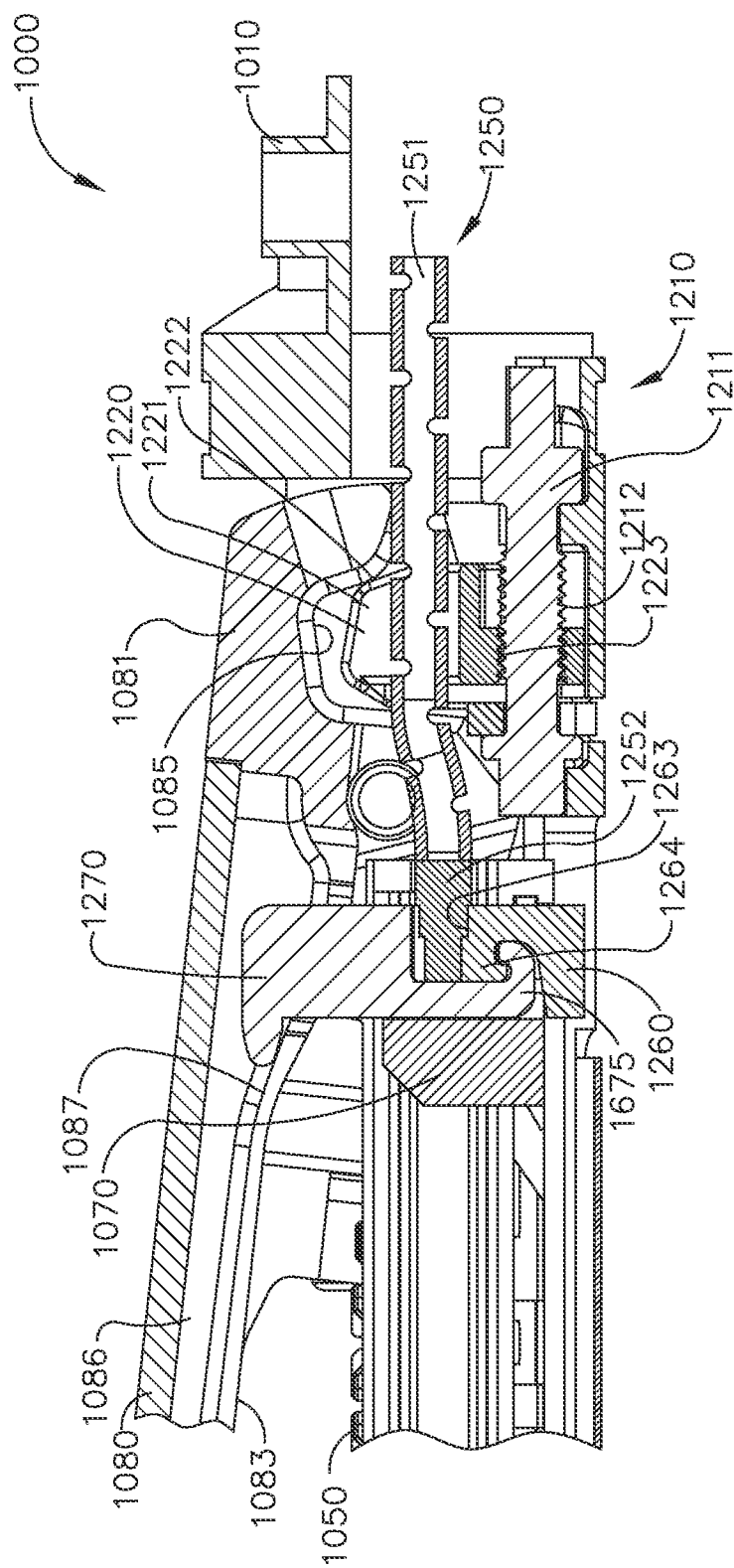
FIG. 27 is a cross-sectional elevation view of the end effector assembly of FIG. 24, in accordance with at least one aspect of the present disclosure.
Figure 28:
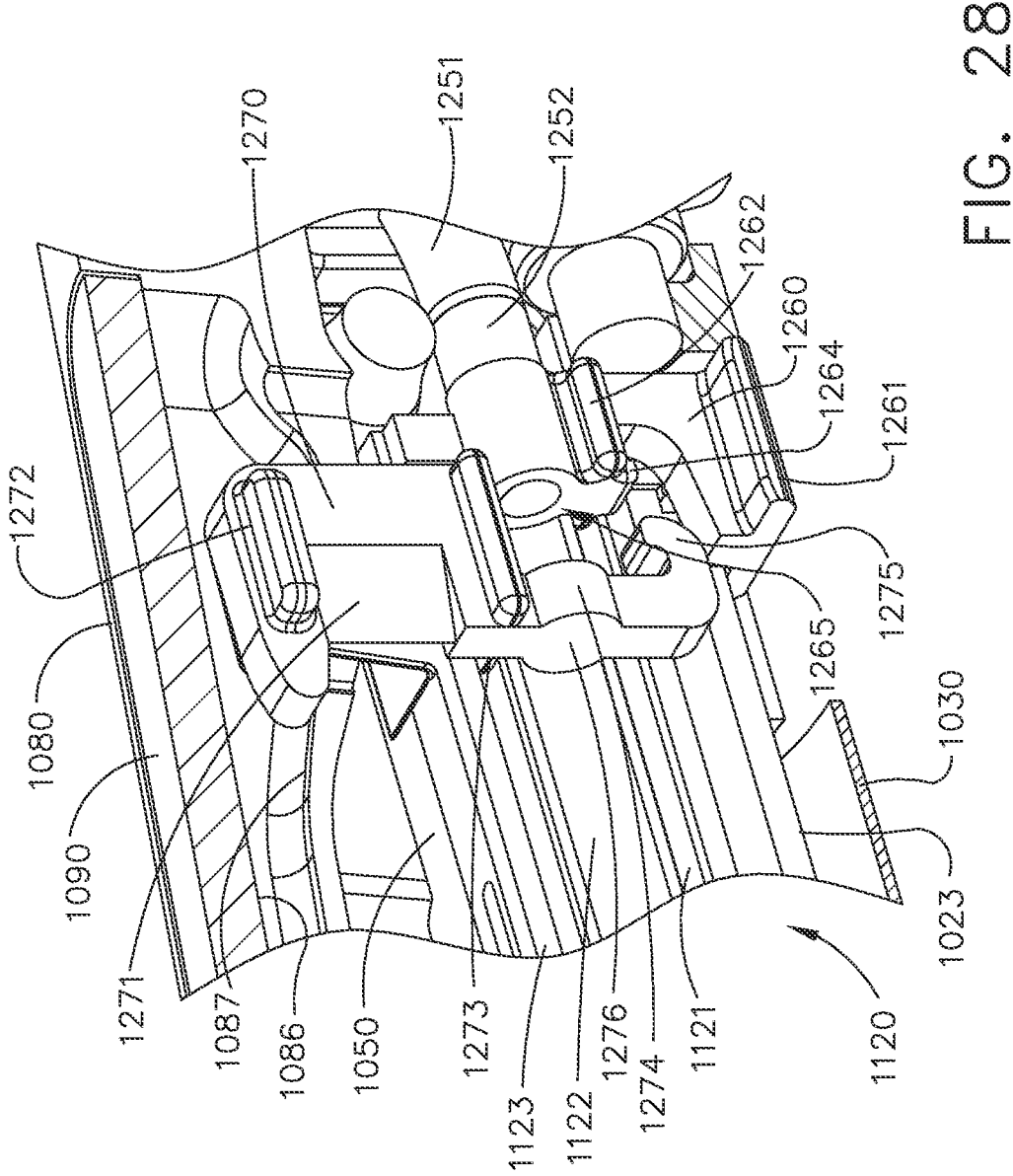
FIG. 28 is a partial cross-sectional perspective view of the end effector assembly of FIG. 24, wherein the end effector assembly comprises a firing assembly comprising an upper firing member and a lower firing member, and wherein the upper firing member is illustrated disengaged from the lower firing member, in accordance with at least one aspect of the present disclosure.
Figure 29:
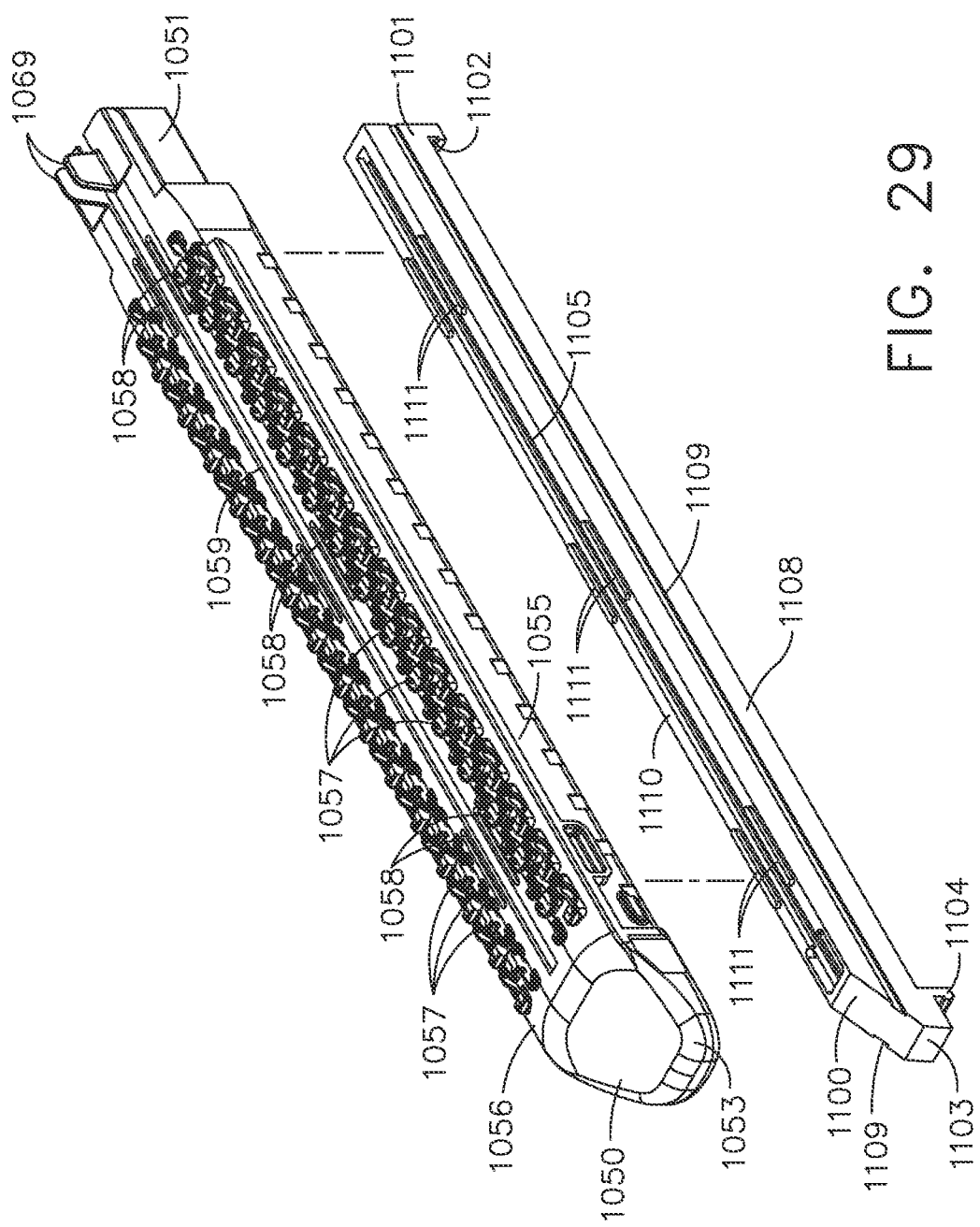
FIG. 29 is an exploded perspective view of the staple cartridge and a support beam of the end effector assembly of FIG. 24, in accordance with at least one aspect of the present disclosure.
Figure 30:
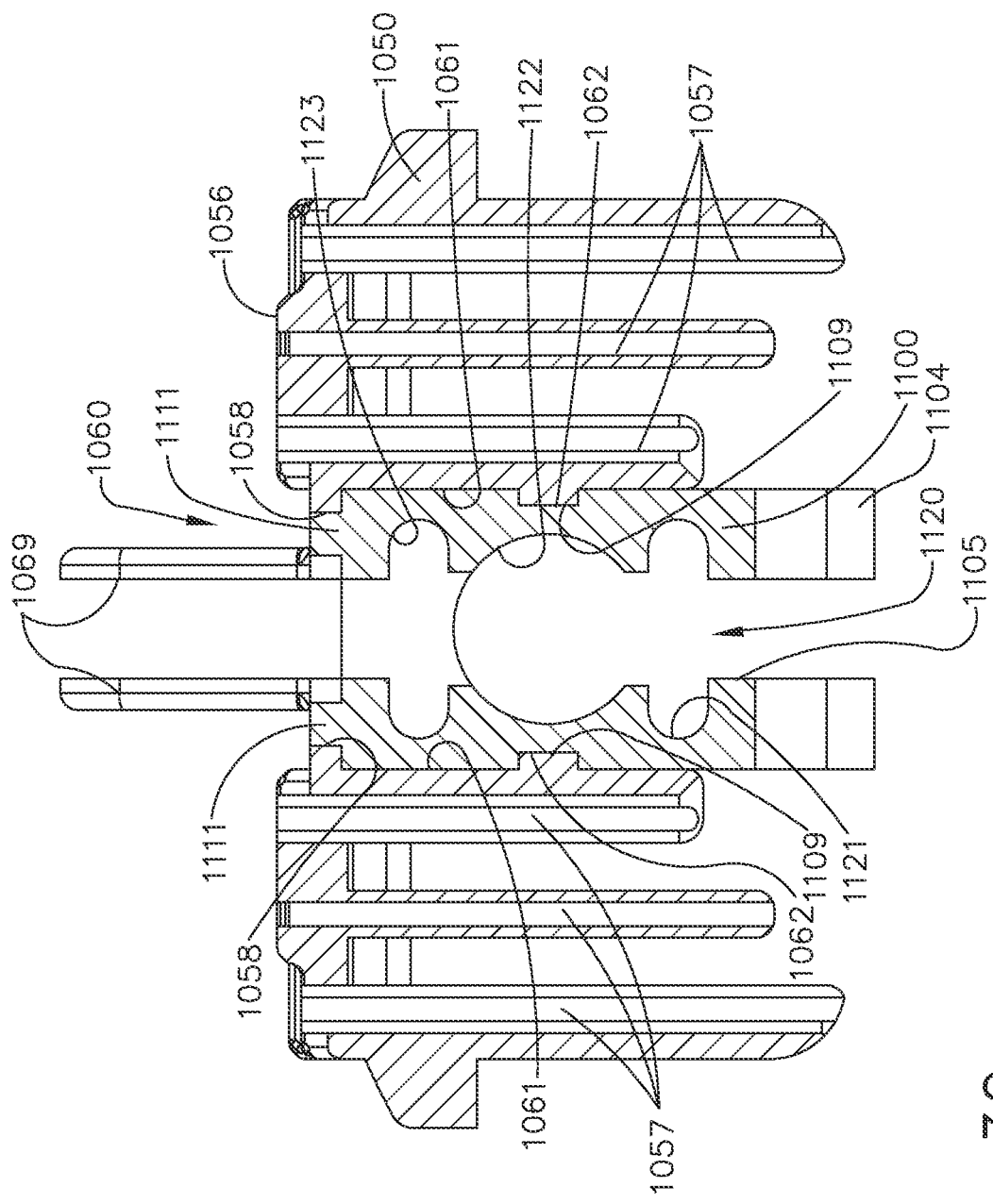
FIG. 30 is a cross-sectional perspective view of the staple cartridge and the support beam of the end effector assembly of FIG. 24, in accordance with at least one aspect of the present disclosure.
Figure 31:
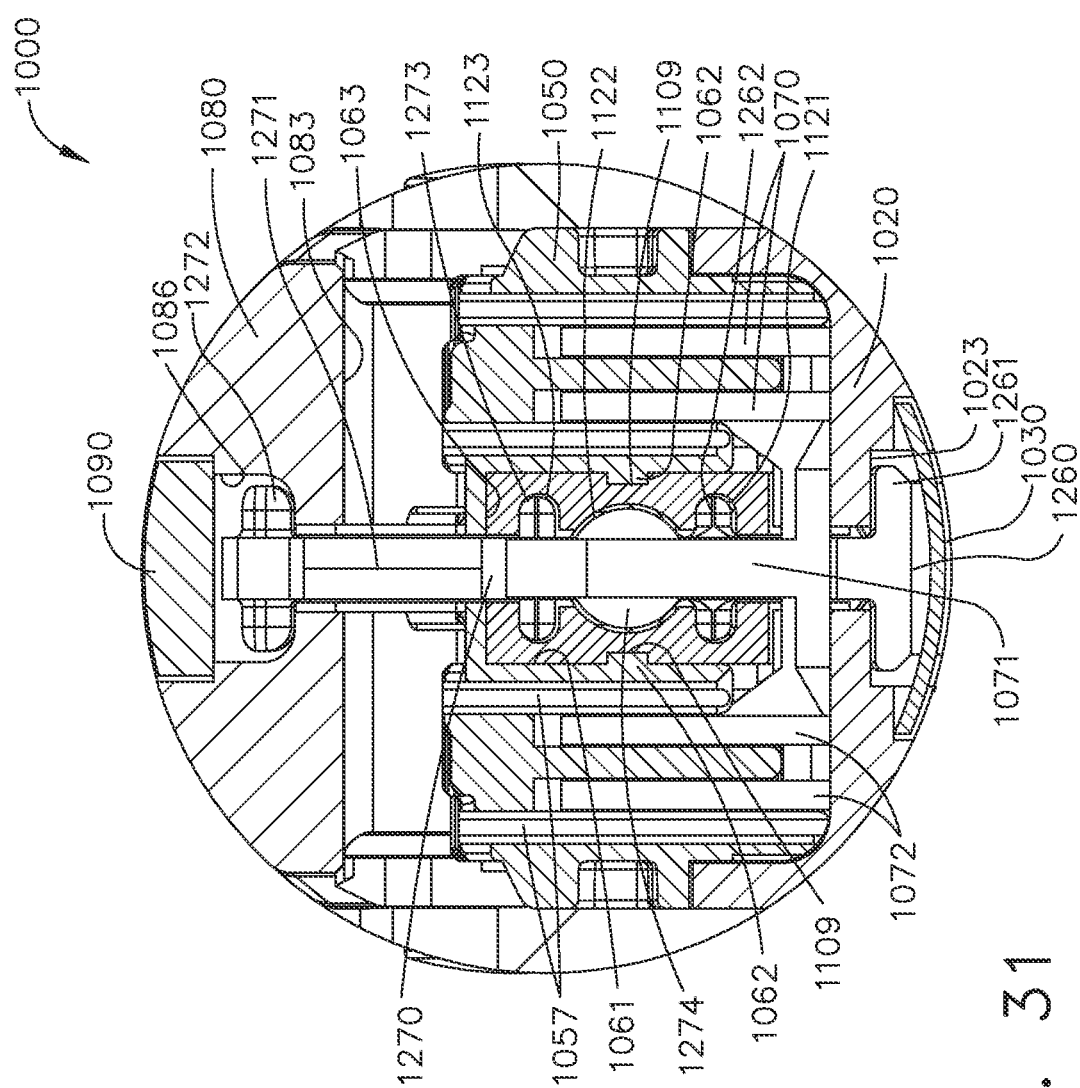
FIG. 31 is a cross-sectional elevation view of the end effector assembly of FIG. 24, in accordance with at least one aspect of the present disclosure.
Figure 32:
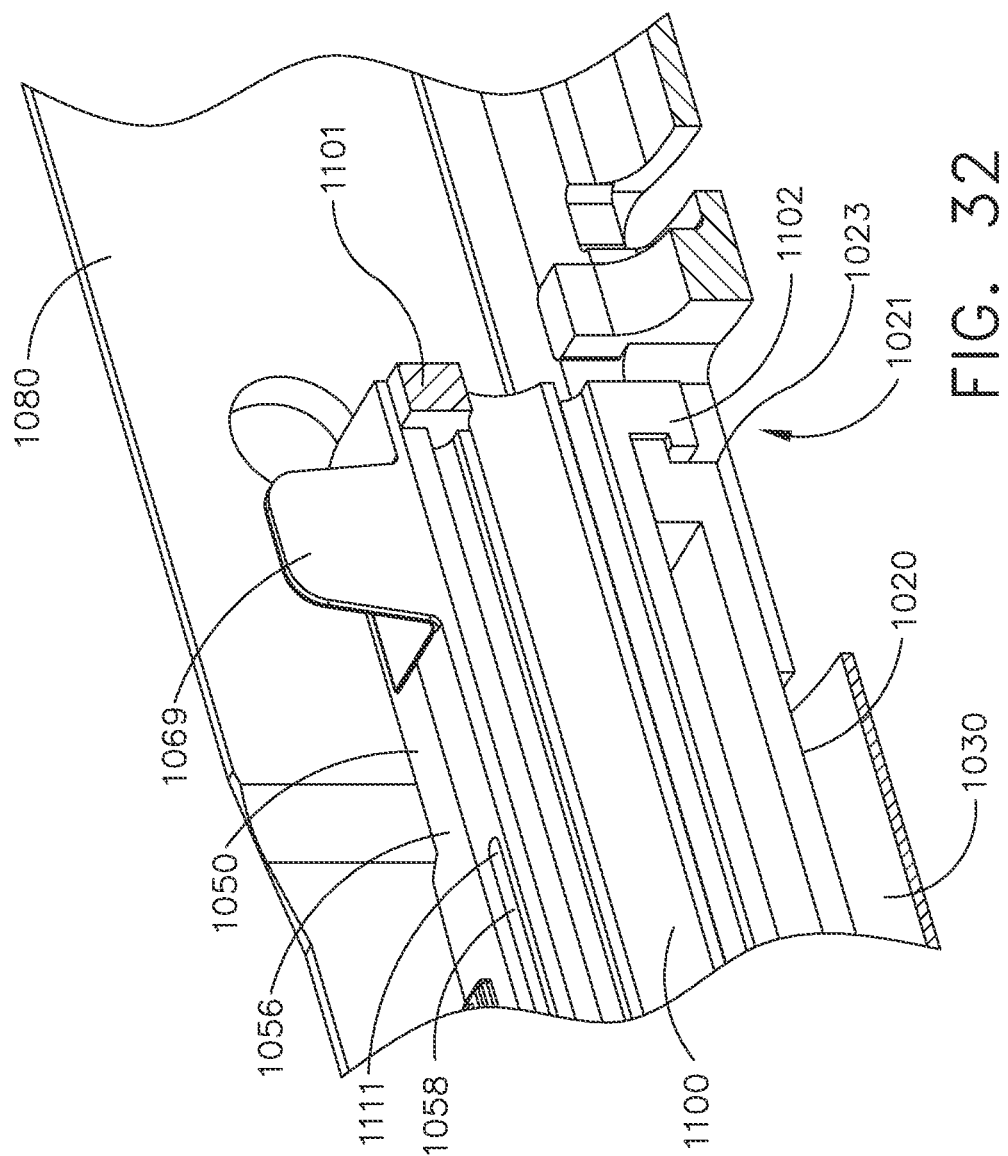
FIG. 32 is a cross-sectional perspective view of a proximal end of the end effector assembly of FIG. 24 with various components not shown for clarity, in accordance with at least one aspect of the present disclosure.
Figure 33:
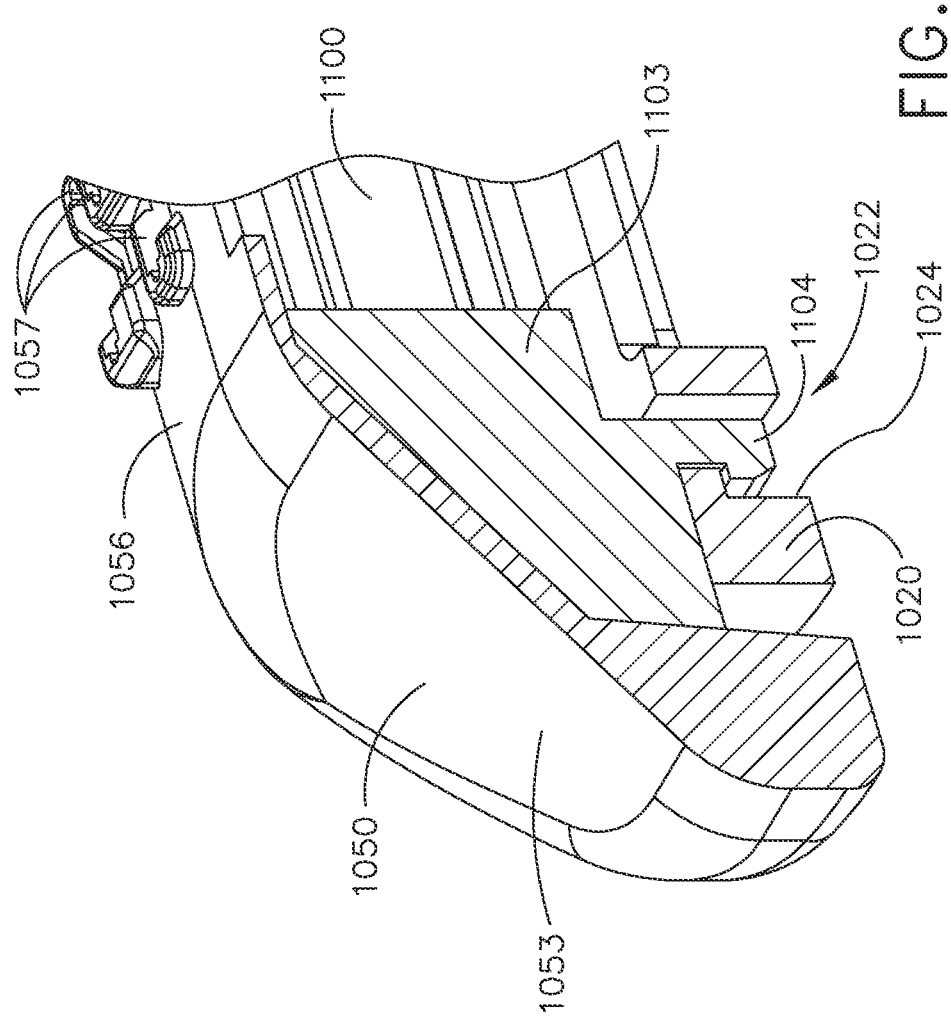
FIG. 33 is a cross-sectional perspective view of a distal end of the end effector assembly of FIG. 24, in accordance with at least one aspect of the present disclosure.

To open and close the anvil 1080 relative to the cartridge channel 1020 and staple cartridge 1050, a closure drive 1210 is provided. Referring to FIGS. 25-27, the closure drive 1210 comprises a rotary closure drive 1211 configured to be actuated by a rotary output shaft of a surgical instrument handle and/or robotic interface, for example. The rotary closure drive 1211 is supported within a proximal end 1021 of the channel 1020 and comprises threads 1212. The closure drive 1210 further comprises a closure wedge 1220 comprising threads 1223 threadably coupled to threads 1212 of the rotary closure drive 1211. Thus, as the rotary closure drive 1211 is rotated, the closure wedge 1220 is configured to translate longitudinally within anvil cavity 1085 defined in a proximal end 1081 of the anvil 1080. The rotary closure drive 1211 can be referred to as a closure screw in various instances.

The closure wedge 1220 comprises an opening cam surface 1222 and closure cam nubs 1223. To close the anvil 1080, the closure wedge 1220 is moved proximally by the rotary closure drive 1221 so that the opening cam surface 1222 defined thereon engages the proximal end 1081 of the anvil 1080 thereby pivoting the anvil 1080 about the pin 1084 toward a closed position. To open the anvil 1080, the closure wedge 1220 is moved distally by the rotary closure drive 1221 so that the closure cam numbs 1223 engage the proximal end 1081 of the anvil 1080 thereby pivoting the anvil 1080 about the pin 1084 toward an open position. The closure wedge 1220 further comprises a u-shaped slot 1221 configured to allow a linearly-actuated firing drive to pass therethrough, discussed in greater detail below.

To fire the end effector assembly 1000, a firing drive 1250 is provided. The firing drive 1250 comprises a flexible firing shaft 1251 configured to be actuated by a linear output shaft of a surgical instrument handle and or robotic interface. The flexible firing shaft 1251 passes through the u-shaped slot 1221 of the closure wedge 1220 toward a firing assembly comprising a lower firing member 1260 and an upper firing member 1270. The firing shaft 1251 comprises a distal end 1252 fixed within a drive slot 1263 defined in a guide portion 1265 of the lower firing member 1260. In at least one instance, the firing shaft 1251 is rotatably supported (e.g. journaled) within the drive slot 1263 such that the firing shaft 1251 may push and pull the lower firing member 1260 while being able to rotate within the drive slot 1263. Such a configuration can permit rotation of the flexible firing shaft 1251 relative to the lower firing member 1260 while maintaining linearly-actuatable engagement. The anvil 1080 further comprises an upper anvil cap 1090 configured to be attached to the anvil 1080. The anvil cap 1090 can be welded to the anvil 1080, for example, and can serve to strengthen the anvil 1080. The channel 1020 can also comprise a channel cap 1030.

The lower firing member 1260 comprises a lower camming flange 1261 extending laterally from the lower firing member 1260, an upper camming flange 1262 extending laterally from the lower firing member 1260, and the guide portion 1265 configured to be received within the support beam 1100, discussed in greater detail below. The lower camming flange 1261 is configured to engage the channel 1020 during a firing stroke to maintain a defined clamped tissue gap between the staple cartridge 1050 and the anvil 1080. The upper camming flange 1262 is configured to engage the support beam 1100 during a firing stroke. Discussed in greater detail below, providing multiple camming flanges within the firing assembly can aid in distributing clamping forces within the end effector assembly 1000. When discussing the camming flanges, it should be understood that, as can be seen in the drawings, the flanges extend laterally outwardly from both sides of the primary body portions of the firing members.

An upper firing member 1270 is also provided. The upper firing member 1270 is configured to be advanced through the firing stroke by the lower firing member 1260. The guide portion 1265 is configured to push a guide portion 1274 of the upper firing member 1270. The upper firing member 1270 comprises an upper camming flange 1272 extending laterally from the upper firing member 1270, a lower camming flange 1273 extending laterally from the upper firing member 1270, and the guide portion 1274 configured to be received within the support beam 1100, discussed in greater detail below. The upper camming flange 1272 is configured to engage the anvil 1080 during a firing stroke. Specifically, the upper camming flange 1272 is configured to apply clamping forces to the anvil 1080 within a slot 1086. At the beginning of a firing stroke, the upper camming flange 1272 is configured to engage a proximal ramp portion 1087 of the slot 1086 to begin applying clamping forces within the end effector assembly 1000.

The lower camming flange 1273 of the upper firing member 1270 is configured to engage the support beam 1100 during a firing stroke. Such a lower camming flange 1273 can provide an additional camming flange within the firing member assembly to help distribute clamping forces within the end effector assembly 1000. The upper firing member 1270 further comprises a cutting edge, or knife, 1271 configured to cut tissue clamped between the staple cartridge 1050 and the anvil 1280. The upper firing member 1270 further comprises a drive surface 1276 defined on the front of the upper firing member 1270. The drive surface 1276 is configured to push a drive flange 1071 of the sled 1070. As the sled 1070 is advanced through the end effector assembly 1000 by the upper firing member 1270, sled rails 1072 of the sled 1070 are configured to engage staple drivers, lift the staple drivers, and eject the staples to staple tissue.

In at least one instance, the upper firing member 1270 is disposable and the lower firing member 1260 is reusable. In such an instance, the upper firing member 1270 is replaced and comes with the staple cartridge 1050 positioned in a ready to install, or ready to fire position. In other words, every time a new staple cartridge is to be installed, the user receives a new upper firing member. Such a configuration can provide a fresh knife with each fresh staple cartridge.

The lower firing member 1260 comprises a receiving hook slot 1264 and the upper firing member 1270 comprises a hook portion 1275 configured to be received within the receiving hook slot 1264. The staple cartridge 1050 including the sled 1070 and the upper firing member 1270 may be installed at an angle similar to that of the anvil 1080 positioned in its open position. Such an angle allows a user to latch, or hook, the upper firing member 1270 into the lower firing member 1260 as the user installs the staple cartridge 1050 into the channel 1020. In at least one instance, the lower firing member 1260 is configured to push and pull the upper firing member 1270 within the end effector assembly 1000 by pushing the guide portion 1274 with the guide portion 1265 and pulling the hook portion 1275 with the hook portion 1264. In certain instances, alignment and/or leveraging features intermediate the staple cartridge 1050 and the channel 1020 are configured to interact to ensure proper alignment and insertion of the staple cartridge 1050.

Because a fresh and disposable knife can be provided each time a staple cartridge is installed, the staple cartridge 1050 further comprises knife guard tabs 1060 extending upwardly from the deck 1056. The knife guard tabs 1060 may protect a user from getting cut by the knife edge 1271 when handling the staple cartridge 1050. The knife guard tabs 1060 may also prevent tissue from being inadvertently cut when tissue is being clamped by the end effector assembly 1000 and prior to the cutting motion. If tissue leaks toward the knife guard tabs 1060 prior to firing, the knife guard tabs 1060 will protect unstapled tissue before firing.

As discussed above, various types of firing and clamping forces are present within the end effector assembly 1000. The support beam 1100 is configured to help distribute the clamping forces within the end effector assembly to various components to reduce the possibility of any single component failing by increasing the distribution of forces within the end effector assembly. In end effectors without a support beam, clamping forces may be primarily applied to a channel and an anvil. The end effector assembly 1000 permits a greater distribution of clamping forces within the end effector assembly 1000.

Referring primarily to FIGS. 28-33, the internal support beam 1100 is positioned within an internal longitudinal channel 1060 of the staple cartridge 1050. The internal support beam 1100 may comprise of a stronger material than the cartridge body 1055. In at least one instance, the support beam 1100 comprises of a metal material and the cartridge body 1055 comprises of a polymer. In such an instance, the support beam 1100 can help distribute clamping forces within the end effector assembly 1100 by making the support beam 1100 of a material which is stronger than the material of the cartridge body 1055.

The support beam 1100 comprises an upper surface 1110 comprising a plurality of protrusions 1111 protruding therefrom and configured to be received within corresponding slots 1058 defined the deck 1056 of the staple cartridge 1050. The protrusions 1111 may provide additional lateral and longitudinal support within the staple cartridge 1050. In other words, the protrusions 1111 can prevent the support beam 1100 from sliding laterally or longitudinally relative to the cartridge body 1055. The protrusions 1111 can also help align the support beam 1100 to the cartridge body 1055 when assembling the support beam 1100 and the cartridge body 1055. In at least one instance, the support beam 1100 is installed in the staple cartridge 1050 prior to packaging. In such an instance, the replaceable staple cartridge 1050 already comprises the support beam 1100. Thus, when the staple cartridge 1050 is replaced, a new support beam is provided.

The support beam 1100 may be slid vertically into the internal longitudinal channel 1060 of the cartridge body 1055 from the bottom of the staple cartridge 1050 opposite the deck 1056. The cartridge body 1055 further comprises lateral rails, or ledges, 1062 defined on channel walls 1061 of the internal longitudinal channel 1060. The rails 1062 are configured to fit within corresponding slots 1109 defined in the sides of the support beam 1100. The rails 1062 are configured to hold the support beam 1100 within the cartridge body 1055 and prevent the support beam 1100 from falling out of the bottom of the cartridge body 1055. The internal longitudinal channel 1060 further comprises an upper surface 1063 defined underneath a thickness of the deck 1056. The upper surface 1110 of the support beam 1100 is configured to abut the upper surface 1063.

In at least one instance, the cartridge body 1055 is overmolded onto the support beam 1100. Such a configuration can provide various internal features otherwise difficult to provide where the parts need to be separately manufactured and assembled after they are manufactured. In at least one instance, the cartridge body 1055 is overmolded and/or insert molded onto the support beam 1100 and the upper firing member 1270. In such instances, the staples, staple drivers, and sled can be assembled into the staple cartridge 1050 and support beam 1100 after the overmolding process is complete. In at least one instance, the support beam 1100 is insert molded into the staple cartridge 1050.

The support beam 1100 further comprises a longitudinal cavity 1120 comprising a lower cam slot 1121, an upper cam slot 1123, and a cylindrical slot 1122. The lower cam slot 1121 is configured to receive the upper camming flange 1262 of the lower firing member 1260. The upper cam slot 1123 is configured to receive the lower camming flange 1273 of the upper firing member 1270. The cylindrical slot 1122 is configured to receive the guide portion 1274, the guide portion 1265, and the flexible firing shaft 1251 as the upper and lower firing members 1270, 1260 are advanced through the end effector assembly 1000. The longitudinal cavity 1120 is also configured to receive the drive flange 1071 of the sled 1070 as the sled 1070 is pushed by the upper firing member 1270. In at least one instance, the flexible firing shaft 1251 is configured to be closely received within the cylindrical slot 1122 such that the cross sectional profile of each substantially matches. In such an instance, the cylindrical slot 1122 can serve to help prevent buckling of the flexible firing shaft 1251 as the flexible firing shaft 1251 is advanced through the cylindrical slot 1122. As compressive forces are experienced by the flexible firing shaft 1251, the cylindrical slot 1122 can support the length of the flexible firing shaft 1251 positioned therein and help to prevent buckling of the flexible firing shaft 1251.

As discussed above, the support beam 1100 is configured to help distribute clamping forces applied to the end effector assembly 1100 by the flanges 1272, 1273, 1262, and 1261. The guide portions 1274, 1265 may also apply vertical clamping forces by way of the flanges 1272, 1273, 1262, and 1261 and can also help distribute the clamping forces through the support beam 1100. As the upper firing member 1270 and the lower firing member 1260 are advanced through the end effector assembly 1000, the flanges 1272, 1273, 1262, and 1261 can apply vertical clamping forces to the anvil 1080, the channel 1020, and the support beam 1100. These forces may be primarily distributed between the anvil 1080, the channel 1020, and the support beam 1100; the components stronger than the staple cartridge 1050 that may primarily consist of metal. Distributing the clamping loads through these components can reduce the vertical crushing forces applied to the cartridge body 1055, itself. Such an arrangement can also reduce the likelihood of any of the flanges 1272, 1273, 1262, and 1261 shearing from their respective firing member body because they can share the vertical clamping forces along the vertical length of the end effector assembly 1000. The support beam 1100 can also provide additional support between the channel 1020 and the anvil 1080 rather than relying on just the channel 1020 and the anvil 1080 to handle all of the clamping forces applied by only a channel flange and an anvil flange.

In at least one instance, the upper and lower firing members 1270, 1260 are referred to as dual I-beams. This configuration can allow for a central longitudinal cavity such as the cylindrical slot 1122 defined in the support beam 1100 positioned between the upper flange 1262 of the lower firing member 1260 and the lower flange 1273 of the upper firing member 1270.

The guide portions 1265, 1274 may also help strengthen the firing members 1260, 1270 by providing a rounded portion engaged with the support beam 1100. The rounded portions can also provide a source of strength to the firing members 1260, 1270 because they can handle significant vertical forces. To fail, they would likely require shear-type failure rather than a bending-type failure making the rounded portions stronger than lateral flanges in certain instances. Having firing members with both lateral flanges and rounded portions can increase the overall strength of the firing assembly as it pertains to vertical clamping forces experienced within the end effector assembly 1000. All of the vertical clamping forces can serve to maintain a predefined tissue gap between the staple cartridge 1050 and the anvil 1080.

Longitudinal loads are also experienced within an end effector assembly 1000. For example, a firing member assembly can experience longitudinal loads applied by tissue on the knife 1271. A firing member assembly can also experience longitudinal loads generated by the clamping forces applied to the channel 1020 and the anvil 1080. Longitudinal loads can also be experienced when the firing member assembly abuts components in its proximal-most position. Longitudinal loads can also be experienced when the firing member assembly and/or sled abuts the distal end of the end effector assembly 1000. In such an instance, the sled and/or firing member assembly components may be pushed distally into the nose of the staple cartridge, anvil, and/or support beam. The end effector assembly 1000 also comprises features to help distribute these longitudinal loads within the end effector assembly 1000.

The support beam 1100 comprises a proximal hook 1102 (FIG. 29) and a distal hook 1104 (FIG. 30) extending downwardly from the support beam 1100. The proximal hook 1102 is configured to be received within a corresponding channel aperture 1023 defined in the proximal end 1021 of the channel 1020. The proximal hook 1102 can be latched into the aperture 1023 as the staple cartridge 1050 and support beam 1100 are installed into the channel 1020. The hook 1102 may be installed with an audible click, for example, to inform a user of successful installation. The hook 1102 may also be visible from underneath the channel 1020 so that a user can see if the hook 1102 has been properly engaged with the channel 1020. The distal hook 1104 is configured to be received within a corresponding channel aperture 1024 defined in the distal end 1022 of the channel 1020. The distal hook 1104 may be snapped into the aperture 1024 by way of the sloped surface 1104' after the proximal hook 1102 is successfully installed into the proximal end 1021 of the channel 1022. The hooks 1102, 1104 may serve to distribute longitudinal loads experienced within the end effector assembly 1000. The distal hook 1104 can cause the firing members 1260, 1270 to apply forces primarily to the channel 1020 instead of the distal end, or nose, 1053 of the staple cartridge 1050 at the end of the firing stroke. Such a configuration may protect the integrity of the nose 1053 of the staple cartridge 1050 which is typically made of a more brittle material than the channel 1020. The channel 1020 can serve to support the distally applied forces by the firing members 1260, 1270 in lieu of the cartridge nose 1053. The distal end 1103 of the support beam 1100 also comprises a fitted profile configured to fit within the nose 1053 of the staple cartridge 1053.

As discussed above, the upper firing member 1270 can be disposable and removed with the staple cartridge 1050 so that a new upper firing member can be installed within a new staple cartridge. In such an instance, the upper firing member 70 can be moved into its proximal-most position after a firing stroke is completed. When the upper firing member 1270 is pulled into its proximal-most position, the anvil 1080 may be pivoted open by the closure drive 1210. As the anvil 1080 is pivoted open, the engagement surface 1087 may tilt the upper firing member proximally relative to the lower firing member 1260 and unlatch the hook 1275. At such point, the staple cartridge 1050 and upper firing member 1270 can be pried and/or unsnapped out of the channel 1020 so that a new staple cartridge, support beam, and upper firing member may be installed in the channel 1020 and the end effector assembly 1000 can be used again.

Figure 34:
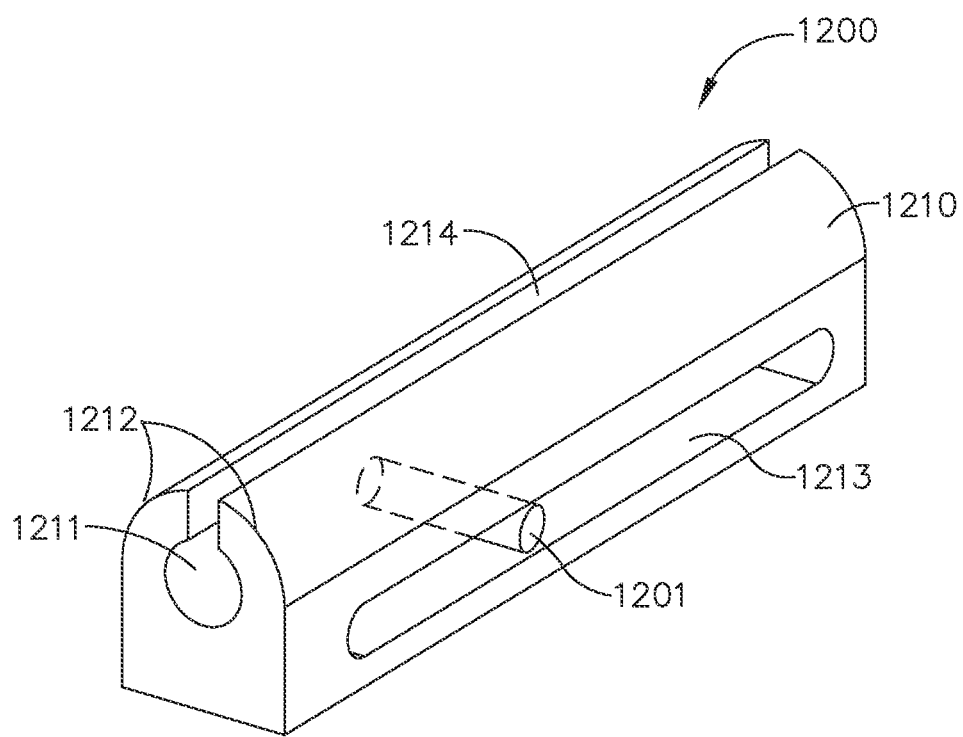
FIG. 34 is a perspective view of a support beam for use with a stapling assembly, in accordance with at least one aspect of the present disclosure.
Figure 35:
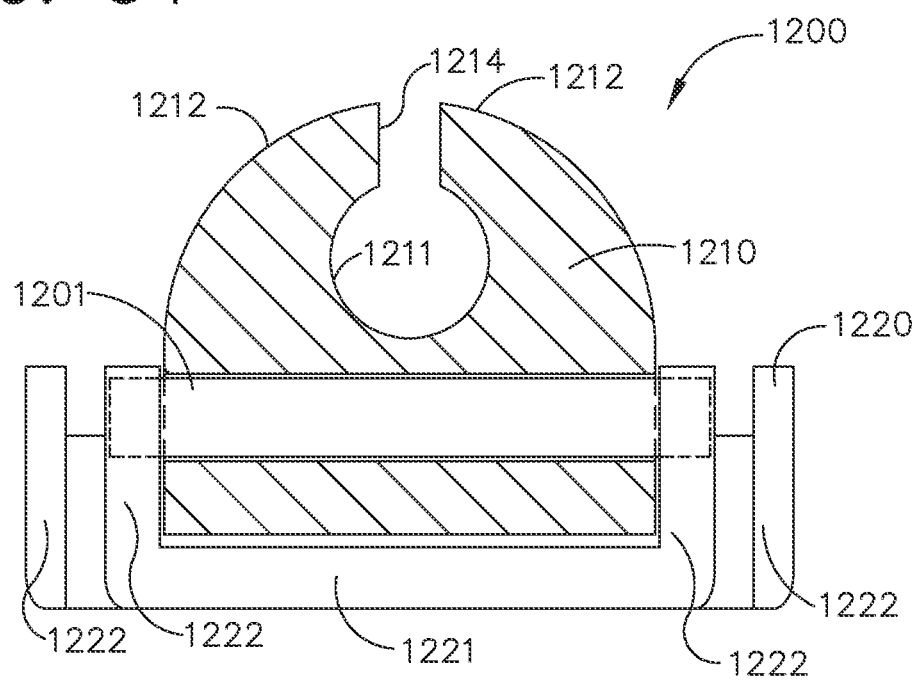
FIG. 35 is an cross-sectional elevation view of the support beam of FIG. 34 with a sled pinned to the support beam, in accordance with at least one aspect of the present disclosure.

FIGS. 34 and 35 depict portions of a stapling assembly 1200 comprising a support beam 1210, a firing member, such as a sled, 1220, and a coupling member 1201 coupling the firing member 1220 to the support beam 1210. The stapling assembly 1200 can be used within any suitable staple cartridge such as those disclosed herein. The support beam 1210 comprises a central drive cavity 1211 configured to receive at least a portion of a firing beam and/or firing member assembly, such as the upper and lower firing members discussed above, an upper slot 1214 configured to receive at least a portion of a firing member assembly, and a pair of horizontal slots 1213 configured to receive the coupling member 1201. The upper slot 1214 may be aligned with a longitudinal slot defined in a deck of a staple cartridge. The coupling member 1201 may comprise of a pin, for example.

The firing member 1220 is configured to eject staples from a staple cartridge as the firing member is advanced through a staple cartridge and the support beam 1210. The support beam 1210 further comprises at least partially curved walls, or flanges, 1212 partially encompassing the central drive cavity 1211. The firing member 1220 comprises drive ramps 1222 configured to push staples and/or staple drivers out of a staple cartridge.

In at least one instance a firing member assembly is configured to push on only the firing member 1220 to advance the firing member 1220 through a staple cartridge and the support beam 1210. Such a configuration can permit the majority of firing force to be applied directly to the firing member 1220. In at least one instance, a firing member assembly is configured push on both the coupling member 1201 and the firing member 1220 to advance the firing member 1220 through a staple cartridge and the support beam 1210. Such a configuration can permit sharing of the applied firing forces and can distribute the applied firing forces throughout the coupling member 1201 and the firing member 1220.

In at least one instance, a firing member assembly is configured to push on only the coupling member 1201 to advance the firing member 1220 through a staple cartridge and the support beam 1210. Such a configuration can permit a more focused firing force application on a component made of metal rather than a component made of a polymer in certain instances. For example, the firing member 1220 may consist of a polymer while the coupling member 1201 may comprise of a metal. In at least one instance, the firing member 1220 and the coupling member 1201 comprise the same material.

Applying the firing forces to a coupling member such as the coupling member 1201, for example, can spread out the application of the firing forces laterally with respect to the longitudinal travel path of the firing member 1220. This lateral distribution can help distribute firing forces throughout the support beam 1210. The firing member 1220 is configured to surround a bottom of the support beam 1210. Such a configuration can permit the use of differently sized sleds within a cartridge channel.

FIGS. 36 and 37 depict a stapling assembly 1300 configured to be used with any suitable staple cartridge disclosed herein. The stapling assembly 1300 comprises a firing assembly 1310 configured to be actuated by a firing shaft, a support beam 1340 configured to be positioned with a staple cartridge, and a sled, or firing member, 1350 configured to eject staples from the staple cartridge. The firing assembly 1310 comprises a lower firing member 1320 and an upper firing member 1330 configured to be actuated by the lower firing member 1320. The lower firing member 1320 comprises a drive portion 1323 configured to drive the upper firing member 1330, a shaft connection cavity 1321 configured to receive a firing shaft therein, and a bottom 1322. The upper firing member 1330 comprises an upper flange 1331 configured to engage an anvil, for example, and a lower flange 1332 configured to engage a portion of the support beam 1340.

The support beam 1340 comprises a longitudinal channel 1343 configured to receive the firing member assembly 1310 therein and flared ledges 1341 configured to support the firing member 1350. The lower flange 1332 is configured to apply camming forces to the support beam 1340 within the longitudinal channel 1343. Collectively, the upper flange 1331 and the lower flange 1332 are configured to maintain a predefined tissue gap between a staple cartridge and an anvil.

The sled 1350 comprises guide arms 1351 configured to be supported by the flared ledges 1341 of the support beam 1340 and drive ramps 1352 configured to eject staples from a staple cartridge. The sled 1350 can be slid onto one end of the support beam 1340 for assembly. The sled 1350 hangs from the flared ledges 1341. Such a configuration can permit use of differently sized sleds for different cartridges and the same support beam 1340. The firing member assembly 1310 is configured to push the sled 1350 through a firing stroke. The flared ledges 1341 can further serve to transfer vertical camming forces applied by the firing member assembly 1310 to the staple cartridge. In at least one instance, the vertical camming forces applied by the firing member assembly 1310 are isolated from the staple cartridge. In such an instance, the support beam 1340 is configured to experience most, if not all, of the vertical clamping forces in addition to the anvil and/or channel, for example. Such a configuration can focus vertical clamping forces onto stronger components such as those components made of metal.

Figure 38:
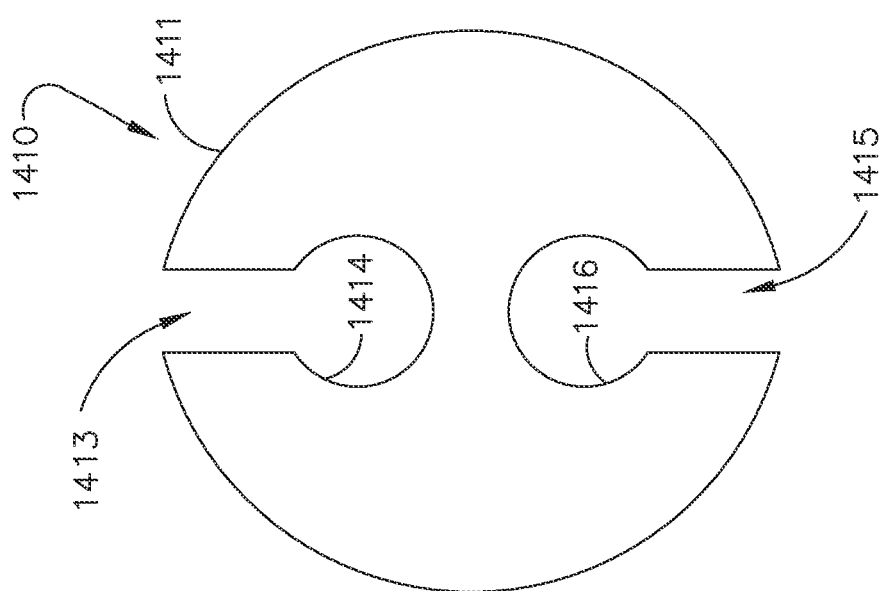
FIG. 38 is an elevation view of a support beam for use with a stapling assembly, in accordance with at least one aspect of the present disclosure.

Alternative support beam geometries are also contemplated. For example, FIG. 38 depicts a support beam 1410 configured to be positioned within a staple cartridge such as those staple cartridges disclosed herein. The support beam 1410 is configured to help distribute vertical clamping forces throughout an end effector assembly. The support beam 1410 comprises a substantially round, oval, or radial outer perimeter 1411 and thus cross-sectional profile. The support beam 1410 further comprises an upper channel 1413 and a lower channel 1415. The channels 1413, 1415 are configured to receive one or more components of a firing member assembly such those disclosed herein. The channel 1413 comprises a cylindrical cavity portion 1414 and can receive a guide portion of an upper firing member, for example. The channel 1415 comprises a cylindrical cavity portion 1416 and can receive a guide portion of a lower firing member, for example. The substantially radial cross-sectional profile of the support beam can serve to strengthen the support beam 1410. In such a configuration, it is less likely that the support beam 1410 will fail due to bending loads applied by vertical clamping forces. Rounded camming flanges can also be used with the support beam 1410. Rounded camming flanges can provide a strengthened flange system within an end effector assembly, as further described herein.

Figure 39:
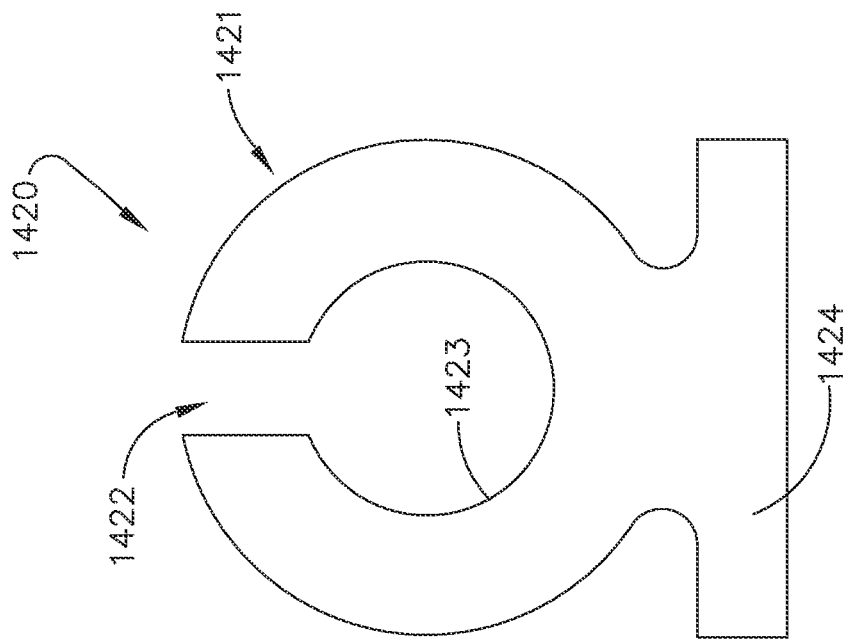
FIG. 39 is an elevation view of a support beam for use with a stapling assembly, in accordance with at least one aspect of the present disclosure.

FIG. 39 depicts a support beam 1420 configured to be positioned within a staple cartridge such as those staple cartridges disclosed herein. The support beam 1420 is configured to help distribute vertical clamping forces throughout an end effector assembly. The support beam 1420 comprises a substantially round, or radial, outer perimeter 1421 and thus cross-sectional profile. The support beam 1410 further comprises a lower flange 1424 extending from the substantially round, or radial, outer perimeter 1421. In at least one instance, the lower flange 1424 is configured to engage the bottom of a staple cartridge, for example, and can comprise one of the flanges in a multi-flange system. In such an instance, a firing member of a firing member assembly may comprise a flange-receiving cavity rather than a laterally extending flange.

The support beam 1420 further comprises an upper channel 1422. The channel 1422 is configured to receive one or more components of a firing member assembly such those disclosed herein. The channel 1422 comprises a cylindrical cavity portion 1423 and can receive a guide portion of an upper firing member, for example.

Figure 40:
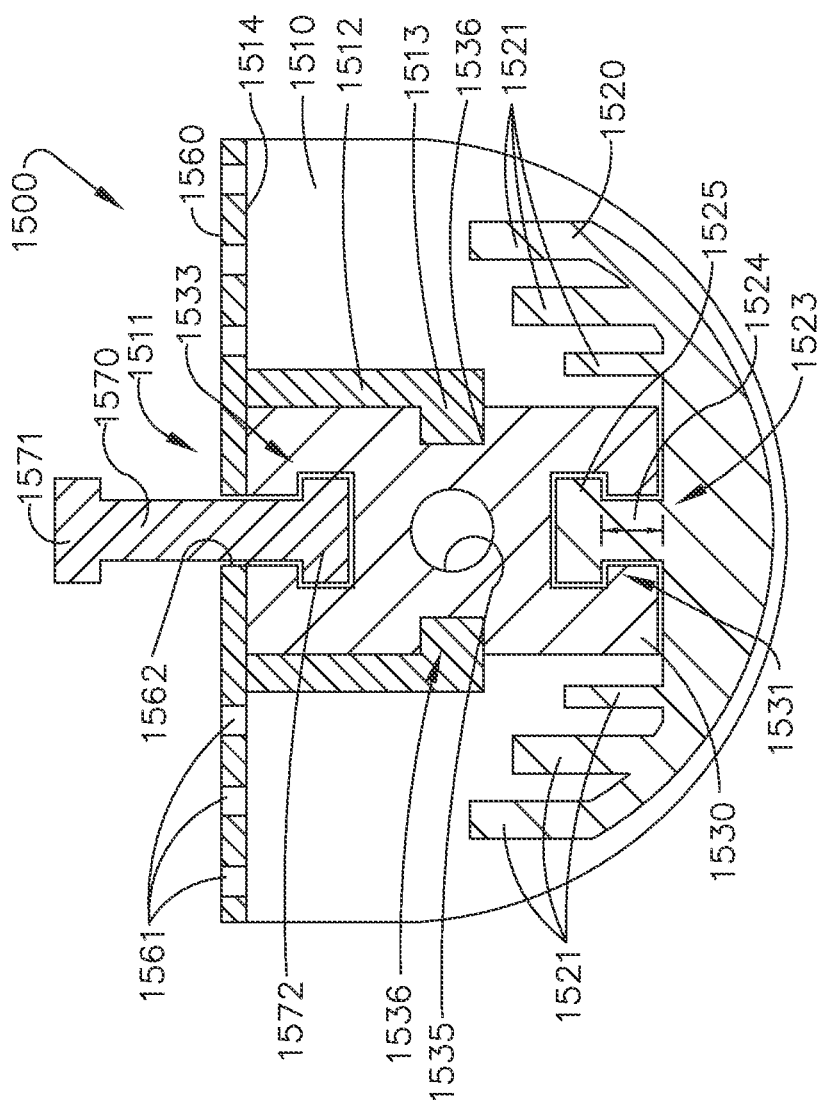
FIG. 40 is a cross-sectional elevation view of a stapling assembly comprising a staple cartridge, a sled, a cartridge support, and an I-beam, in accordance with at least one aspect of the present disclosure.
Figure 41:
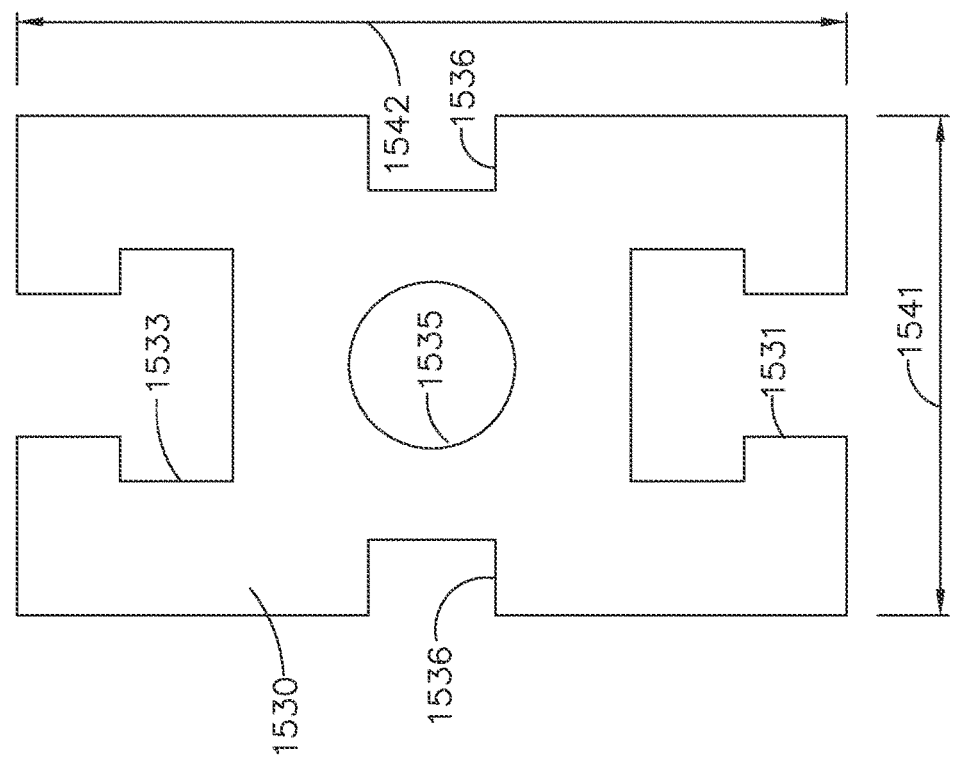
FIG. 41 is an elevation view of the cartridge support of FIG. 40, in accordance with at least one aspect of the present disclosure.

FIGS. 40 and 41 depict a stapling assembly 1500 configured to cut and staple tissue of a patient. The stapling assembly 1500 comprises a staple cartridge 1510 configured to removably store a plurality of staples therein, a sled 1520 comprising drive ramps 1521 configured to eject the staples stored within the staple cartridge 1510, and an I-beam 1570 configured to push the sled 1520 through the staple cartridge 1510. The stapling assembly 1500 further comprises a cartridge support 1530 positioned within a longitudinal channel 1511 of the staple cartridge 1510 defined by inner walls 1512 and ledges 1513. The cartridge support 1530 comprises an upper cam channel 1533 configured to receive a lower camming flange 1572 of the I-beam 1570 and a lower cam channel 1531 configured to receive a camming flange 1523 of the sled 1520.

The camming flange 1523 comprises a support portion 1524 extending upwardly into the cam channel 1531 and a flange 1525. The flange 1525 extends from the support portion 1524 to form a T-shape; however, other geometries are also contemplated. As the sled 1520 is advanced through the staple cartridge 1510 and the cartridge support 1530, the flange 1525 moves through the cam channel 1531. The cartridge support 1530 is configured to support the vertical clamping forces applied within the stapling assembly 1500 by the I-beam 1570 and the sled 1520.

The stapling assembly 1500 further comprises a deck plate 1560 positioned on a deck surface 1514 of the staple cartridge 1510. The deck plate 1560 may help distribute clamping forces within the stapling assembly 1500. The deck plate 1560 may be comprised of a metal material, for example. The deck plate 1560 comprises a plurality of apertures 1561 configured to be aligned with staple cavities defined in the staple cartridge 1510. The deck plate 1560 further comprises a longitudinal slot 1562 aligned with the longitudinal channel 1511. The cartridge support 1530 further comprises a central cylindrical support cavity 1535 configured to receive at least a portion of a firing member assembly. For example, the central cylindrical support cavity 1535 is configured to receive a linear actuator, guide portions of firing member components, and/or a guide portion of a sled, for example.

Referring primarily to FIG. 41, the cartridge support 1530 comprises longitudinal slots 1536 configured to receive ledges 1513 of the staple cartridge 1510. The width 1541 and the height 1542 can be adjusted to accommodate different size cartridges, staples, and/or staple drivers, for example. The width 1541 and height 1542 of the cartridge support 1530 can also be adjusted for different tissue gap distances between the staple cartridge 1510 and an anvil. In at least one instance, the width 1541 and height 1542 can be adjusted to tune the clamping load distribution for different scenarios. For example, a stapling instrument with lower clamping forces may be served better by a cartridge support with a thinner width than the cartridge support 1530.

Figure 42:
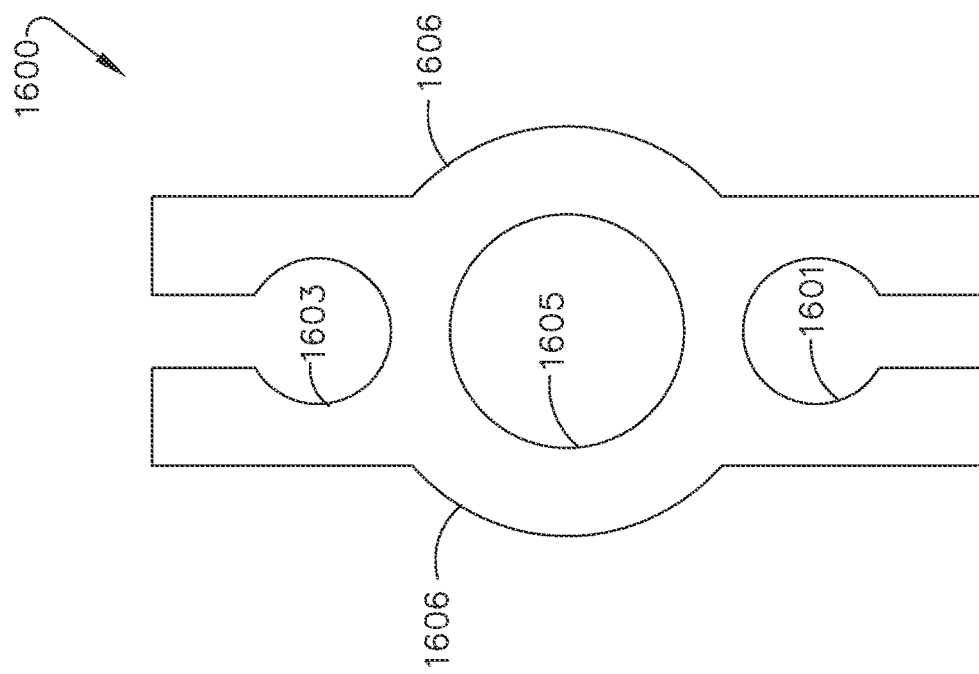
FIG. 42 is an elevation view of a cartridge support for use with a surgical stapling assembly, in accordance with at least one aspect of the present disclosure.

FIG. 42 depicts a cartridge support 1600 configured to be positioned within a staple cartridge such as those staple cartridges disclosed herein. The cartridge support 1600 comprises a cylindrical central portion 1606 defining a central longitudinal guide cavity 1605, an upper cam channel 1603, and lower cam channel 1601 each configured to receive a camming flange. The central longitudinal guide cavity 1605 can be configured to receive guide portions of one or more components a firing assembly such as a sled, upper firing member, or lower firing member. The central longitudinal guide cavity 1605 can also be configured to receive a firing shaft therein. The cam channels 1601, 1603 comprise a radial cross section. Such an arrangement can reduce the likelihood of failure of the respective flanges received therein due to bending loads.

FIG. 43 depicts a stapling assembly 1700 comprising a cartridge support 1710 and a sled 1720. The cartridge support 1710 comprises a longitudinal slot 1711 configured to receive at least a portion of the sled 1720 therethrough during a firing stroke. The sled 1720 comprises a bottom portion 1721 configured to be threadably coupled to a firing drive screw, for example, and a first arm 1722 extending from the bottom portion 1721 upwardly around a first side of the cartridge support 1710. The sled 1720 further comprises a second arm 1723 extending from the bottom portion 1721 upwardly around a second side of the cartridge support 1710. The arms 1722, 1723 each comprise a guide tooth 1724, 1725, respectively, received within corresponding slots 1712, 1713, respectively, of the cartridge support 1710. The engagement features for securing the sled 1720 in the cartridge support 1710 are asymmetric relative to a vertical centerline plane. More specifically, the arms 1722, 1723 comprise different geometries, e.g. different heights, and the guide teeth 1724, 1724 also comprise different geometries, e.g. different lengths and/or shapes. The slots 1712, 1713 comprise a profile similar to the tooth they are configured to receive. Such a configuration can provide a means for ensuring that the sled 1720 is installed in the correct direction. Such a configuration can also allow for fine tuning of loads applied to the sled 1720 through the differently sized arms 1722, 1723.

FIG. 44 depicts a sled 1730 configured to be used with any suitable staple cartridge and/or staple cartridge support discussed herein. Unlike the sled 1720, the sled 1730 comprises arms 1732 comprising the same height and profile. The arms 1732 extend from bottom portion 1731 and comprise teeth 1733 extending outwardly with respect to the sled 1731. Such a sled can be configured to be guided by a cartridge support and/or staple cartridge within internal guide slots defined in the cartridge support and/or staple cartridge owing to the outwardly extending teeth 1733.

FIG. 45 depicts a cartridge support 1740 comprising a central cavity 1741 configured to receive the sled 1730 (FIG. 45), for example, therein. The central cavity 1741 comprises laterally opposed slots 1742 comprising vertical installation portions 1743 configured to receive teeth 1733, for example. A firing member assembly can be configured to push the sled 1730 through the cartridge support 1740 during a firing stroke.

FIG. 46 depicts a stapling assembly 1800 comprising a cartridge jaw 1810, an anvil 1820, a firing member 1840, and a sled 1830 configured to be pushed through the cartridge jaw 1810 by the firing member 1840. The sled 1830 is pinned to the firing member 1840 by way of a pin 1812. As the firing member 1840 is advanced by a firing shaft, for example, the sled 1830 is pushed by way of the pin 1812. The firing member 1840 comprises a bottom flange 1842 configured to be received within a slot 1811 of the cartridge jaw 1810 and an upper flange 1841 configured to be received within a slot 1821 defined in the anvil 1820.

FIG. 47 depicts a surgical stapling assembly 1900 comprising a cartridge channel 1910 and an anvil 1920. The surgical stapling assembly 1900 further comprises a support beam 1940 and a staple cartridge 1970. The surgical stapling assembly 1900 further comprises a firing member 1950 comprising an upper flange 1952 configured to engage the anvil 1920 and a lower flange 1951 configured to engage the support beam 1940. The surgical stapling assembly further comprises a sled 1930 pinned to the staple cartridge 1970 and the support beam 1940 by way of pin 1960.

In various instances, firing member assemblies configured to be driven by firing drive screws positioned within an end effector can bind during the firing stroke. The binding can exist at the threaded coupling engagement between the firing member assembly and the firing drive screw. Such binding can be attributed to the location of the transfer of drive forces from the drive screw to the firing member assembly in certain instances. In various instances, the location of the transfer of drive force occurs immediately adjacent the threads of the firing drive screw and the receiving threads of the firing member assembly. Because the firing drive screw is generally positioned within a cartridge channel jaw, the location of the transfer force is positioned a distance away from the center of mass and/or drive center of the firing member assembly. This application of force can cause a torque load applied to the firing member assembly which may cause the threaded engagement between the firing drive screw and the firing member assembly to bind.

Various firing member assemblies are disclosed herein which may move the location of the transfer force closer to the center of mass and/or drive center of the firing member assembly to reduce incidences of binding. More specifically, these configurations can reduce the likelihood of thread binding between the firing member assembly and the firing drive screw. Such configurations may also provide a more efficient transfer of force from the firing drive screw, to the firing member assembly, to the sled and/or cutting member. A more direct force application to the sled and/or cutting member by the firing member assembly can reduce the over drive force necessary of the firing drive screw. Such a direct force applied near the center of the firing member assembly can also reduce the required drive force to maintain a predefined tissue gap using the upper and lower camming flanges of the firing member assembly. This can be attributed to centering the force application to the firing member assembly at a vertical center, or near the center, of the camming flanges.

FIGS. 48 and 49 depict a firing member assembly 2000 configured to be used within a surgical stapling assembly such as those disclosed herein. The firing member assembly 2000 is configured to be actuated by a firing drive screw to cut and staple tissue. Specifically, the firing member assembly 2000 is configured to push a sled to deploy staples from a staple cartridge. In at least one instance, the sled comprises a cutting member configured to cut tissue as the firing member assembly 2000 is actuated through an end effector. In another instance, the cutting member is part of the firing member assembly. The firing member assembly 2000 is further configured to maintain a predefined tissue gap by providing camming flanges, which engage an upper jaw and lower jaw of an end effector.

The firing member assembly 2000 comprises a primary body portion, or distal head, 2010 and a drive nut 2030 configured to fit within a drive cavity, or receptacle, 2023 of the primary body portion 2010. The primary body portion 2010 comprises an upper portion 2011 comprising a jaw-engaging flange 2012. The upper portion 2011 further comprises a distal nose 2013, which can be used to clamp a jaw from an unclamped position. The primary body portion 2010 comprises a drive surface 2014 configured to push a sled and/or a cutting member, for example. The primary body portion 2010 further comprises a lower portion 2015 comprising a proximal portion 2016 and a distal portion 2019 defining the drive cavity 2023. The proximal portion 2016 comprises a proximal lower flange 2018 extending laterally therefrom and a drive screw duct 2017. The distal portion 2019 comprises a distal lower flange 2021 and a drive screw duct 2020. The drive screw ducts 2017, 2020 are aligned with each other are configured to receive a firing drive screw therethrough; however, the drive screw ducts 2017, 2020 are not threadably coupled with the drive screw. Rather, the drive screw ducts 2017, 2020 can comprise support channels, for example, configured to support the firing drive screw (e.g. firing screw 261 in FIGS. 4 and 5) threadably coupled with the firing member assembly 2000.

The drive nut 2030 is configured to be threadably coupled with a firing drive screw and is configured to apply actuation forces to the primary body portion 2010. The drive nut 2030 is configured to fit within the drive cavity 2023. The drive nut 2030 comprises a lower threaded portion 2035 comprising a camming flange 2031 configured to engage a jaw of an end effector, a threaded channel 2037 configured to be threadably coupled with a firing drive screw, and a proximal protrusion 2036 configured to fit within the drive cavity 2023. The drive nut 2030 further comprises an upper drive portion 2040 extending upwardly from the threaded portion 2035. The drive portion 2040 comprises a proximal drive surface 2041 and a distal drive surface 2043. The proximal drive surface 2041 is configured to push on a proximal drive surface 2025 of the drive cavity 2023 when the firing member assembly 2000 is moved proximally and the distal drive surface 2043 is configured to push on a distal drive surface 2024 of the drive cavity 2023 when the firing member assembly 2000 is moved distally.

As can be seen in FIG. 49, the drive nut 2030 is configured to apply a drive force DF to the primary body portion 2010 off center with respect to a longitudinal screw axis SA. The longitudinal screw axis SA is defined by a longitudinal centerline though a drive screw configured to actuate the firing member assembly 2000. The longitudinal screw axis SA may also be synonymous with a longitudinal centerline defined through the ducts 2017, 2020.

In at least one instance, the drive nut 2030 comprises a substantially similar cross-sectional profile to the primary body portion 2010. The drive portion 2040 is configured to apply an axial drive force to the primary body portion 2010 away from and/or off-axis with respect to the firing drive screw and threads 2037.

Figures 50, 51:
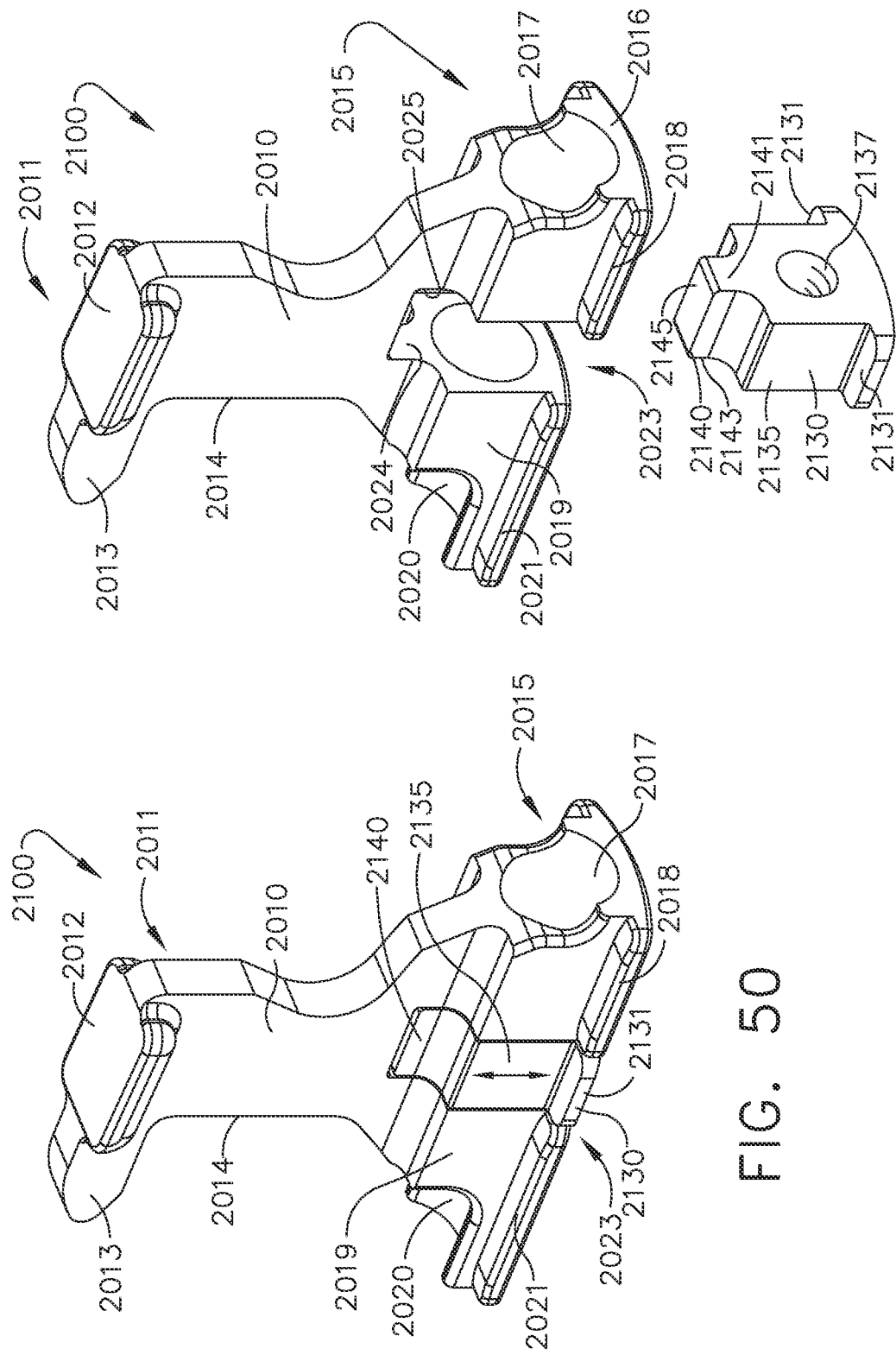
FIG. 50 is a perspective view of a firing member assembly comprising the primary body portion of the firing member assembly of FIG. 48 and a drive nut, in accordance with at least one aspect of the present disclosure.
FIG. 51 is an exploded perspective view of the firing member assembly of FIG. 50, in accordance with at least one aspect of the present disclosure.

FIGS. 50 and 51 depict a firing member assembly 2100 comprising the primary body portion 2010 of the firing member assembly 2000 and a drive nut 2130. The firing member assembly 2100 is similar to the firing member assembly 2000 except for the drive nut 2100. The drive nut 2100 is configured to fit within the drive cavity 2023 of the primary body portion 2010. Unlike the drive nut 2030, the drive nut 2130 does not include a proximal protrusion. The drive nut 2130 comprises a lower threaded portion 2135 comprising a camming flange 2131 configured to engage a jaw of an end effector and a threaded channel 2137 configured to be threadably coupled with a firing drive screw. The drive nut 2130 further comprises an upper drive portion 2140 extending upwardly from the threaded portion 2135. The drive portion 2140 comprises a proximal drive surface 2141 and a distal drive surface 2143. The proximal drive surface 2141 is configured to push on the proximal drive surface 2025 of the drive cavity 2023 when the firing member assembly is moved proximally and the distal drive surface 2043 is configured to push on the distal drive surface 2024 of the drive cavity 2023 when the firing member assembly is moved distally. The drive portion 2140 also comprises an upper surface 2145. The upper surface 2145 does not abut the primary body portion 2010 within the drive cavity 2023. Embodiments are envisioned where the upper surface 2145 abuts the primary body portion 2010 within the drive cavity 2023. In at least one instance, the flange 2131 is configured to prevent the drive nut 2130 from rotating with the firing drive screw during actuation.

Figure 52:
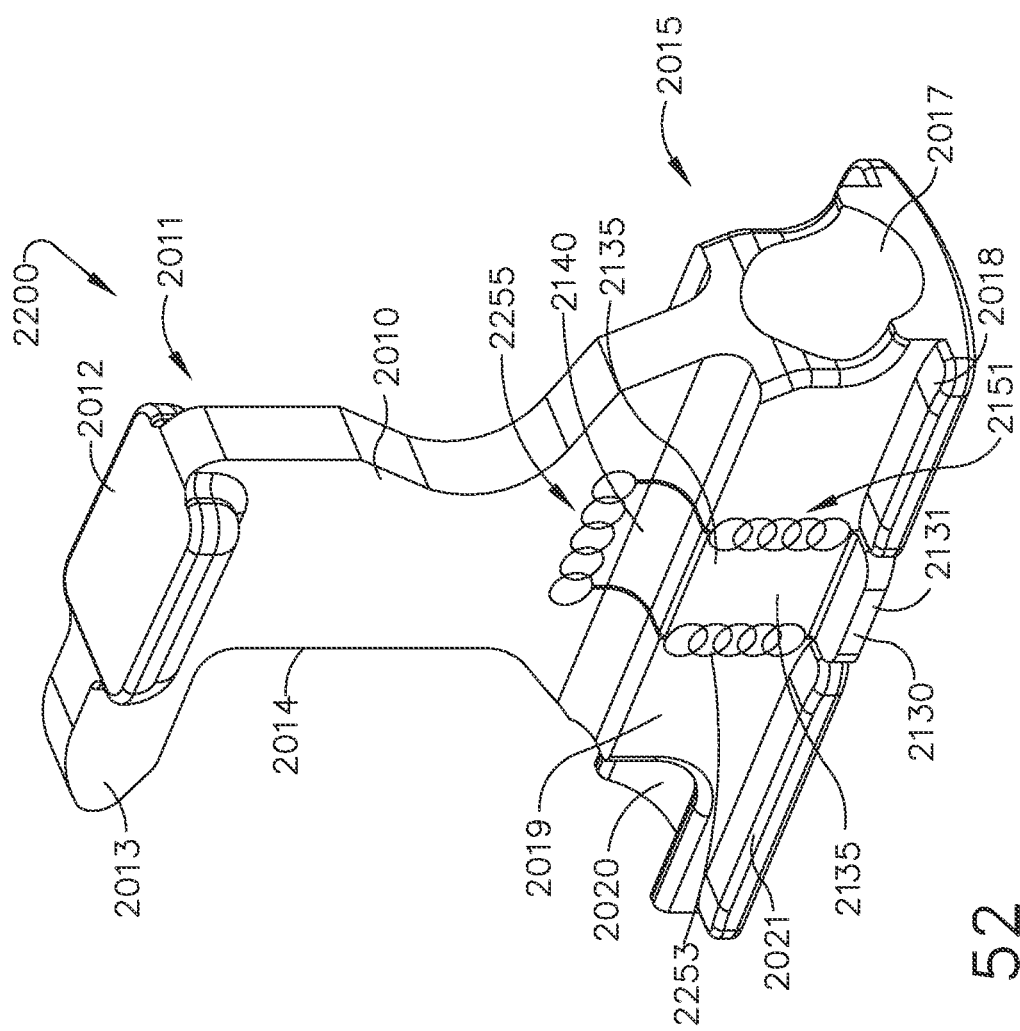
FIG. 52 is a perspective view of the firing member assembly of FIG. 50, wherein the drive nut is welded to the primary body portion, in accordance with at least one aspect of the present disclosure.

FIG. 52 depicts a firing member assembly 2200 comprising the primary body portion 2010 of the firing member assembly 2000 and the drive nut 2130. The firing member assembly 2100 is similar to the firing member assembly 2100 except for welds 2251, 2253, 2255. Unlike the firing member assembly 2100, the welds 2251, 2253, 2255 provide positive attachment mechanisms within the drive cavity 2023 to attach the drive nut 2130 to the primary body portion 2010. Stated differently, the drive nut 2130 is welded to the primary body portion 2010. Welding can take place after the drive nut 2130 is positioned within the drive cavity 2023 and threaded to a firing drive screw. The threaded portion 2135 of the drive nut 2130 is welded to the proximal portion 2016 of the primary body portion 2010 and the distal portion 2019 of the primary body portion 2010. The upper surface 2045 of the drive portion 2140 is also welded to the primary body portion 2010. These welds can provide strength to the firing member assembly 2200.

Figure 53:
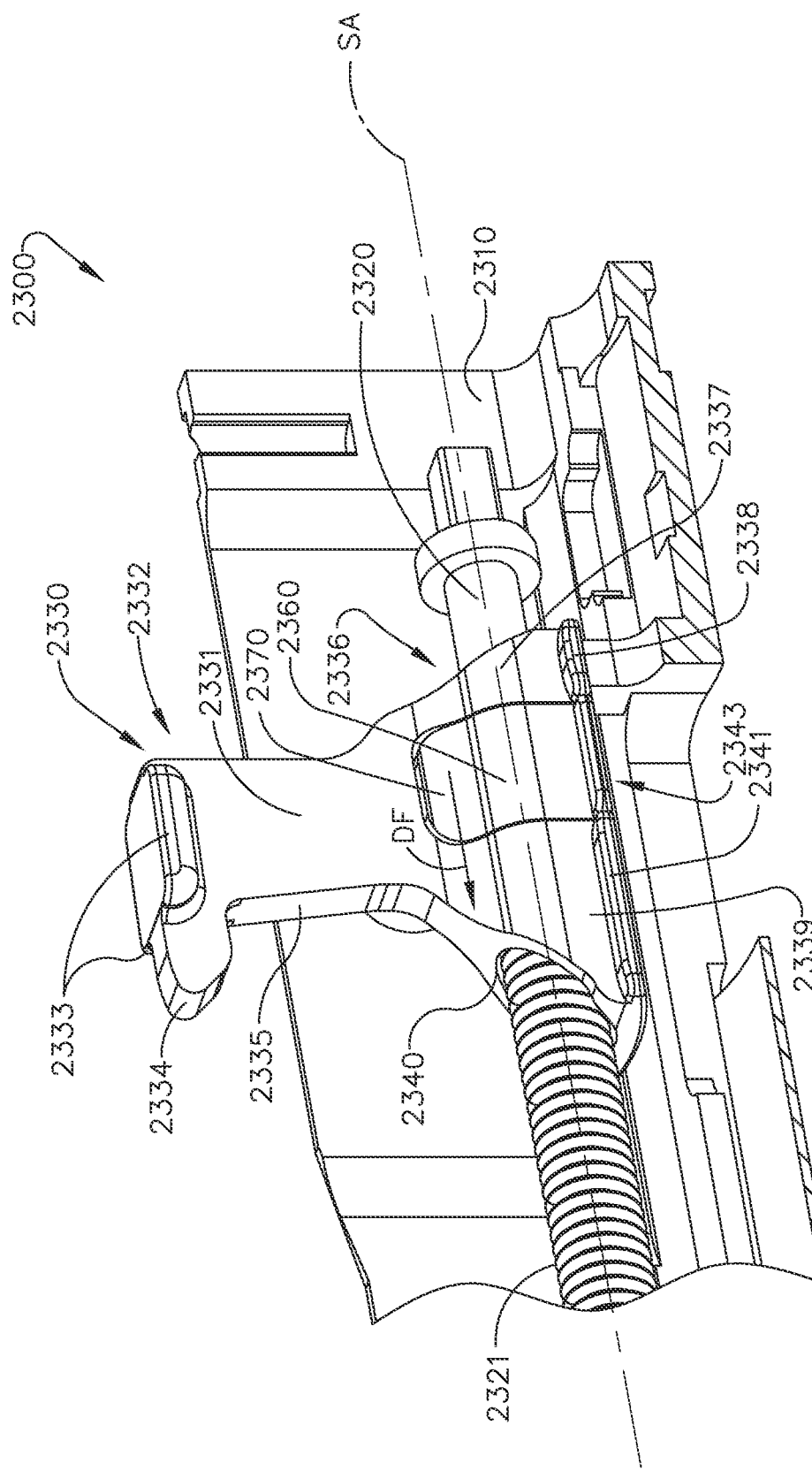
FIG. 53 is a partial cross-sectional, exploded perspective view of a stapling assembly comprising a channel jaw, a drive screw, and a firing member assembly, in accordance with at least one aspect of the present disclosure.
Figure 56:
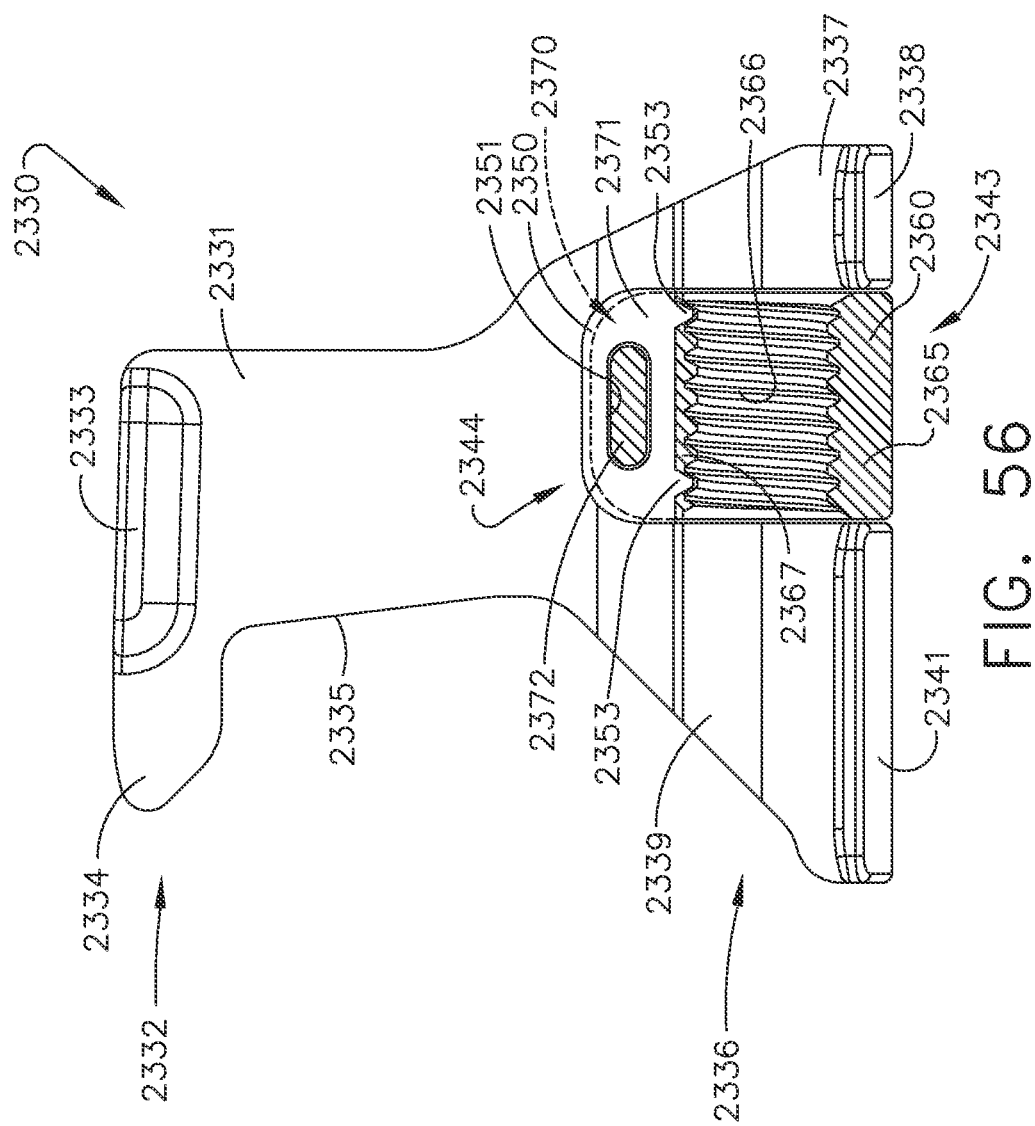
FIG. 56 is a partial cross-sectional elevation view of the firing member assembly of FIG. 53, in accordance with at least one aspect of the present disclosure.
Figure 61:
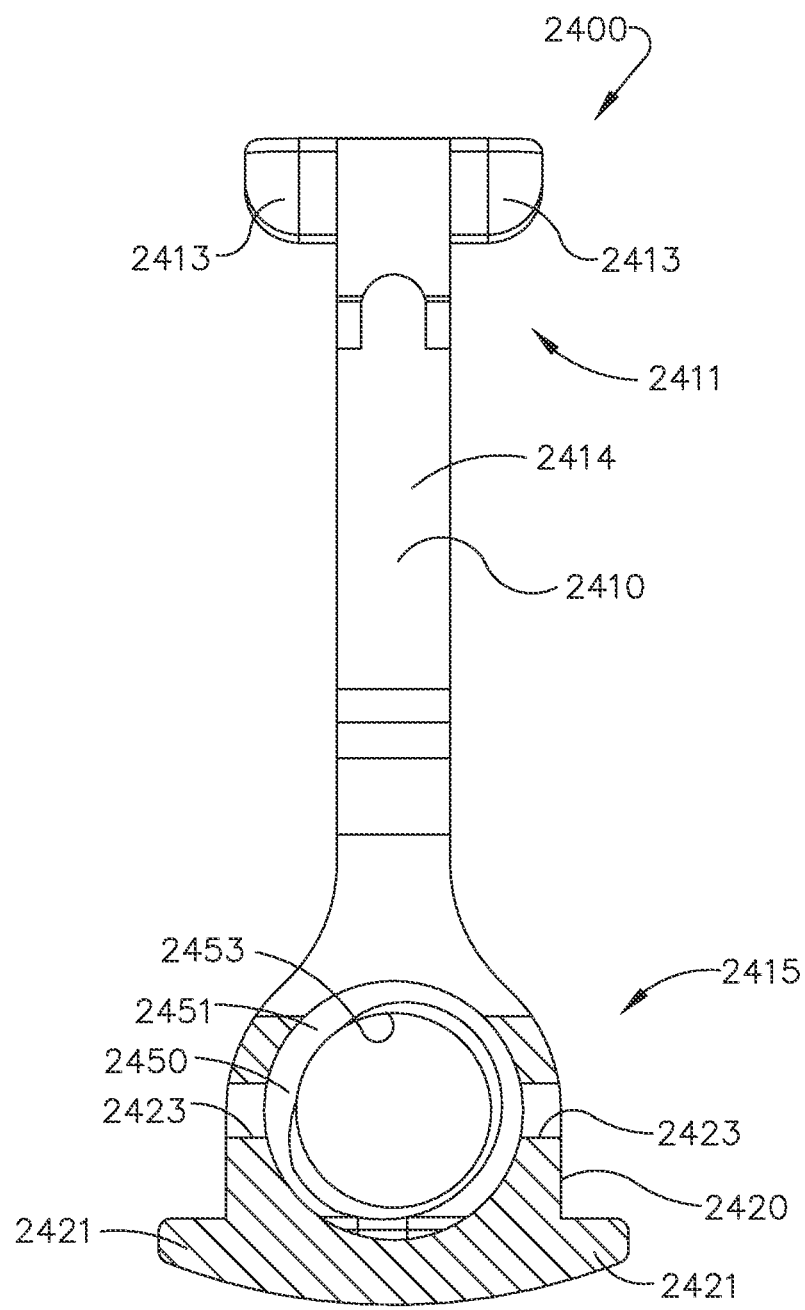
FIG. 61 is another cross-sectional elevation view of the firing member assembly of FIG. 57 taken through distal apertures of the primary body portion, in accordance with at least one aspect of the present disclosure.
Figure 66:
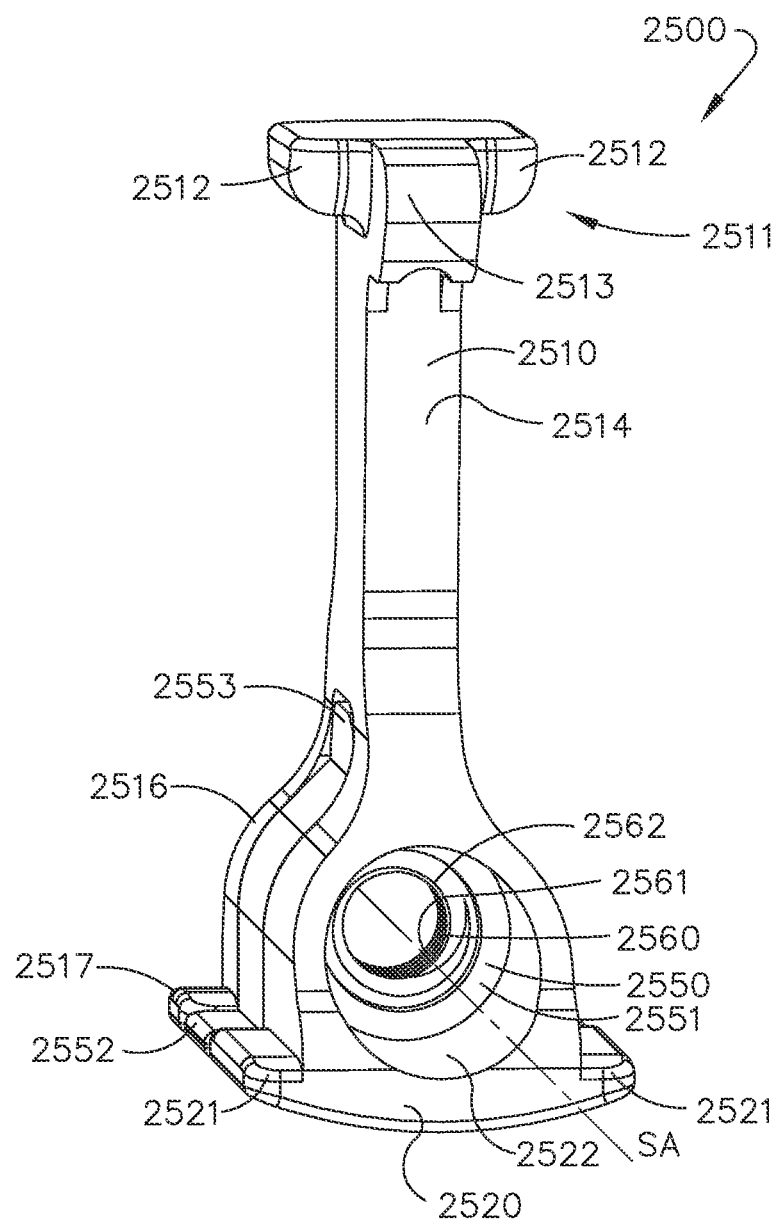
FIG. 66 is a perspective view of the firing member assembly of FIG. 62, in accordance with at least one aspect of the present disclosure.

FIGS. 53-56 depict a stapling assembly 2300 comprising a channel jaw 2310, a firing drive screw, or rotary drive member, 2320 comprising threads 2321, and a firing member assembly 2330. The firing member assembly 2330 is similar to the firing member assemblies discussed above; however, the firing member assembly 2330 comprises a different drive nut and attachment means for attaching the drive nut to the primary body portion. As can be seen in FIG. 53, the firing member assembly 2330 is threadably coupled to the threads 2321 of the firing drive screw 2320. The firing drive screw 2320 is configured to be supported within the channel jaw 2310. The firing member assembly 2330 is configured to be actuated proximally and distally through a firing stroke relative to the channel jaw 2310.

The firing member assembly 2330 comprises a primary body portion 2331 and a drive nut 2360 configured to fit within a drive cavity, or receptacle, 2343 of the primary body portion 2331. The primary body portion 2331 comprises an upper portion 2332 comprising an anvil-engaging flange 2333. The upper portion 2332 further comprises a distal nose 2334 which can be used to clamp an anvil jaw from an unclamped position. The primary body portion 2331 comprises a drive surface 2335 configured to push a sled and/or a cutting member, for example. The primary body portion 2331 further comprises a lower portion 2336 comprising a proximal portion 2337 and a distal portion 2339 defining the drive cavity 2343. The proximal portion 2337 comprises a proximal lower flange 2338 extending laterally therefrom and a drive screw duct. The distal portion 2339 comprises a distal lower flange 2341 and a drive screw duct 2340. The flanges 2338, 2341 are configured to engage the channel jaw 2310 to affirmatively hold a consistent tissue gap between an anvil jaw and the channel jaw 2310. The drive screw duct of the proximal portion 2337 and the drive screw duct 2340 are aligned with each other and are configured to non-threadably receive the firing drive screw 2320 therethrough.

The drive nut 2360 comprises a threaded portion 2365 configured to be threadably coupled with the firing drive screw 2320 by way of threads 2366, and a drive portion 2070. The drive nut 2360 further comprises a lower camming flange 2361 also configured to cammingly engage the channel jaw 2310 during a firing stroke. The drive portion 2370 comprises laterally opposing tabs 2371 extending upwardly from the threaded portion 2365. The drive tabs 2371 are configured to cradle, or straddle, a corresponding drive tab 2350 extending downwardly from the primary body portion 2331 and into the drive cavity 2343. The drive portion 2370 further comprises an internal cross member, or brace, 2372 connecting the tabs 2371 to each other and securing, or attaching, the drive portion 2370 to the drive tab 2350 and, thus, the primary body portion 2331. The cross member 2372 is configured to be received within a drive slot 2351 defined in the drive tab 2350. As the drive nut 2360 is actuated, forces can be applied to the primary body portion 2331 from the cross member 2372 to the drive tab 2350 within the slot 2351. Such a configuration can provide a drive force to the primary body portion 2331 off center with respect to the drive screw 2320 and nearer the center of the firing member assembly 2330. Stated another way, the drive nut 2360 can apply a drive force eccentrically with respect to a longitudinal axis of the drive screw 2320 to the primary body portion 2331. This can be seen in FIG. 53, for example. The drive nut 2360 can apply drive force DF to the primary body portion 2310 off center with respect to longitudinal screw axis SA.

The drive tab 2350 further comprises a pair of drive teeth 2353 extending downwardly therefrom within an internal channel 2367 defined in the drive nut 2360. The drive teeth 2353 are configured to mate with the threads 2321 of the drive screw 2320 directly. The drive teeth 2353 may bolster the threaded engagement of the firing drive screw 2320 and the firing member assembly 2330 as a whole.

In at least one instance, the drive nut 2360 is insert molded over the drive screw 2320. This permits complex shapes of a drive nut and allows for finely tuned engagement features between the drive nut 2360 and the primary body portion 2331. Such an engagement feature comprises the cross member 2372, for example. Once molded over the drive screw 2320 and through the slot 2351, the drive nut 2360 is permanently fixed to the primary body portion 2331 notwithstanding destroying the drive nut 2360 to remove the drive nut 2360 from the primary body portion 2331.

In at least one instance, the drive nut 2360 is snapped to the drive tab 2350. For example, the drive nut 2360 may comprise a degree of flexibility and a manufactured split, or break, in the material corresponding to the internal channel 2367 permitting the drive nut 2360 to be spread around the drive tab 2350 and snapped thereto. In at least one instance, the drive nut 2360 is separated between a drive tab 2350 and one side of the cross member 2372 such that the drive tabs 2359 may be pried apart to position the cross member 2372 into the slot 2351.

In at least one instance, the cross member 2372 is configured to shear off of the drive nut 2360 if a firing force between the drive screw 2320 and the drive nut 2360 exceeds a predetermined threshold. Such a configuration can provide a safety feature so as to not over drive a firing member assembly through a firing stroke when a firing member assembly experiences a higher than normal load.

FIGS. 57-61 depict a firing member assembly 2400. The firing member assembly 2400 is similar to the firing member assemblies discussed above; however, the firing member assembly 2400 comprises a different drive nut and attachment means for attaching the drive nut to the primary body portion. The firing member assembly 2400 also comprises registration features for use with a molding tool. The firing member assembly 2400 is configured to be threadably coupled to a firing drive screw and is configured to be actuated proximally and distally through a firing stroke by way of the firing drive screw.

The firing member assembly 2400 comprises a primary body portion, or distal head, 2410 and a drive nut 2450 configured to fit within a drive cavity, or receptacle, 2430 of the primary body portion 2410. The primary body portion 2410 comprises an upper portion 2411 comprising a jaw-engaging flange 2412. The upper portion 2411 further comprises a distal nose 2413 which can be used to clamp an anvil jaw from an unclamped position. The primary body portion 2410 further comprises a drive surface 2414 configured to push a sled and/or a cutting member, for example. The primary body portion 2410 further comprises a lower portion 2415 comprising a proximal portion 2416 and a distal portion 2420 defining the drive cavity 2430. The proximal portion 2416 comprises a proximal lower flange 2417 extending laterally therefrom and a drive screw duct 2418. The distal portion 2420 comprises a distal lower flange 2421 and a drive screw duct 2422. The flanges 2417, 2421 are configured to engage a jaw of an end effector to affirmatively hold a consistent tissue gap between the jaw and another jaw of the end effector. The drive screw ducts 2418, 2422 aligned with each other are configured to non-threadably receive the firing drive screw therethrough. Discussed in greater detail below, the proximal portion 2416 and the distal portion 2420 each comprise registration apertures 2423 configured for use during an overmolding and/or insert molding process.

The drive nut 2450 comprises a threaded portion, or driven portion, 2451 configured to be threadably coupled with a firing drive screw by way of threads 2453 and comprises a drive portion, or driving portion, 2460. The drive nut 2450 further comprises a lower camming flange 2452 also configured to cammingly engage an end effector jaw during a firing stroke. The drive nut 2450 comprises a substantially trapezoidal shape. Discussed in greater detail below, the firing member assembly 2400 comprises a proximal clearance void, or longitudinal space, 2431 defined between the proximal portion 2416 and a proximal drive surface 2454 of the threaded portion 2451 and a distal clearance void, or longitudinal space, 2455 defined between the distal portion 2420 and a distal drive surface 2455 of the threaded portion 2451.

The drive portion 2460 comprises laterally opposing tabs 2461 extending upwardly from the threaded portion 2451. It should be appreciated that the primary body portion 2410 and the drive nut 2450 is symmetrical relative to vertical plane defined by the primary body portion 2410 but for the threads 2453. The drive tabs 2461 are configured to cradle, or straddle, a corresponding drive tab 2440 extending downwardly from the primary body portion 2410 and into an upper portion 2433 of the drive cavity 2430. The drive portion 2060 further comprises a plurality of internal cross members, or ribs, 2463 extending between the tabs 2461. The ribs 2463 secure, or attach, the drive portion 2460 to the drive tab 2440 and, thus, the primary body portion 2410. The ribs 2463 are configured to be received within a plurality of corresponding apertures 2441 defined in the drive tab 2440. As the drive nut 2450 is actuated, force can be applied to the primary body portion 2410 from the ribs 2463 to the drive tab 2440 within the slots 2441. Such a configuration can provide a drive force to the primary body portion 2331 off center with respect to the drive screw positioned within the threaded channel 2453 and nearer the center of the firing member assembly 2400. As can be seen in FIGS. 57 and 60, the drive nut 2450 can apply a drive force DF to the primary body portion 2410 off center with respect to a longitudinal screw axis SA.

The tabs 2461 of the drive nut 2450 are further configured to apply force to the primary body portion 2410 within the upper portion 2433 of the drive cavity 2430 to proximal drive surface 2443 and distal drive surface 2445. These additional drive surfaces can further center the application of drive force to the primary body portion 2410 nearer the center of the firing member assembly 2400.

As discussed above, the firing member assembly 2400 comprises clearance voids 2431, 2432 positioned between the threaded portion 2451 of the drive nut 2450 and the proximal and distal portions 2416, 2420 of the primary body portion 2410. The clearance voids are configured to further center the application of drive force within the firing member assembly 2400 from the drive nut 2450 to the primary body portion 2410. The clearance voids 2431, 2432 prevent the threaded portion 2451 from contacting the proximal and distal portions 2416, 2420 of the primary body portion 2410 thereby preventing the application of drive force immediately adjacent the drive screw configured to drive the firing member assembly 2400.

The clearance voids 2431, 2432 can also be configured to control overall deflection of the drive nut 2450. In various instances, a firing drive screw can deflect relative to the end effector in which it is positioned. This can be attributed to clamping forces applied to the jaws of an end effector during a firing stroke, among other things. Notably, as the drive screw deflects, the drive nut 2450 will be urged to deflect, or rotate, relative to the primary body portion 2410, along with the drive screw owing to the threaded engagement between the drive nut 2450 and the firing drive screw. The trapezoidal shape and clearance voids 2431, 2432 provide a degree of flexibility, or forgiveness, for the drive nut 2450 to deflect and rotate with the firing drive screw. Permitting this forgiveness within the firing member assembly 2400 can help prevent binding of the threaded engagement between the drive nut 2450 and the firing screw. A rigid firing assembly and drive nut combination, for example, may afford little to no flexibility further increasing the likelihood of thread binding, for example. In certain cases, other components of the firing member assembly such as camming flanges and/or the driving cross members discussed above may elastically deform owing to bending and/or shearing forces within an end effector assembly. In at least one instance, the drive cavity 2430 comprises a trapezoidal shape in addition to or in lieu of the drive nut 2450.

In at least one instance, the drive nut 2450 is insert molded over a drive screw. This permits complex shapes of a drive nut and allows for finely tuned engagement features between the drive nut 2450 and the primary body portion 2410. Such an engagement feature comprises the ribs 2463, for example. In at least one instance, the drive nut 2450 is overmolded onto the primary body portion 2410.

As discussed above, the proximal portion 2416 and the distal portion 2420 each comprise registration apertures 2419, 2423 configured for use during an overmolding and/or insert molding process. The registration apertures 2419, 2423 are configured to hold the primary body portion 2410 within a molding tool and are aligned at the equator, or center, of the ducts 2418, 2020. This positioning can help align the mold used for the drive nut 2450 with the ducts 2418, 2020 for manufacturing so that the drive nut 2450 and, specifically, the threaded portion 2451 is aligned with the ducts 2418, 2020. This alignment ensures that a firing drive screw is aligned within the ducts 2018, 2020 and the threaded portion 2451 upon assembly. In at least one instance, a firing drive screw and the primary body portion 2410 are both presented prior to molding the drive nut 2450. In such an instance, the drive nut 2450 can be molded around the pre-placed primary body portion 2410 and firing drive screw. In at least one instance, only the primary body portion 2410 is presented prior to molding the drive nut 2450.

FIGS. 62-66 depict a firing member assembly 2500. The firing member assembly 2500 is similar to the firing member assemblies discussed above; however, the firing member assembly 2500 comprises a drive nut assembly comprising an external drive portion 2550 and an internal drive nut 2560 positioned within the external drive portion 2550. The firing member assembly 2500 is configured to be threadably coupled to a firing drive screw and is configured to be actuated proximally and distally through a firing stroke by way of the firing drive screw within an end effector assembly.

The firing member assembly 2500 comprises a primary body portion 2510 and a drive nut assembly configured to fit within a drive cavity, or receptacle, 2530 of the primary body portion 25510. The primary body portion 2510 comprises an upper portion 2511 comprising an anvil-engaging flange 2512. The upper portion 2511 further comprises a distal nose 2513 which can be used to clamp an anvil jaw from an unclamped position. The primary body portion 2510 further comprises a drive surface 2514 configured to push a sled and/or a cutting member, for example. The primary body portion 2510 further comprises a lower portion 2515 comprising a proximal portion 2516 and a distal portion 2520 defining the drive cavity 2530. The proximal portion 2516 comprises a proximal lower flange 2517 extending laterally therefrom and a drive screw duct 2518. The distal portion 2520 comprises a distal lower flange 2521 and a drive screw duct 2522. The flanges 2517, 2521 are configured to engage a jaw of an end effector to affirmatively hold a consistent tissue gap between the jaw and another jaw of the end effector. The drive screw ducts 2518, 2522 are aligned with each other are configured to non-threadably receive the firing drive screw therethrough.

As discussed above, the drive nut assembly comprises the external drive portion 2550 and the internal drive nut 2560 positioned within the external drive portion 2550. In at least one instance, the internal drive nut 2560 comprises a stock drive nut comprised of a metallic material, for example. In at least one instance, the external drive portion 2550 comprises of a polymer, for example, and is overmolded and/or insert molded within the firing member assembly 2500. In such an instance, the drive nut assembly comprises a hybrid multi-material drive nut assembly and may have metamaterial properties in certain instances. In at least one instance, the external drive portion 2560 is insert molded to the internal drive nut 2550 and then the drive nut assembly is positioned within the drive cavity 2530 for assembly to a firing drive screw and the primary body portion 2510. Regardless, the drive nut assembly comprises a multi-piece arrangement.

The external drive portion 2550 comprises a lower portion 2551 comprising a flange 2552. The lower portion 2551 is configured to surround and secure the internal drive nut 2560 within the drive nut assembly. The external drive portion 2550 further comprises a drive tab 2553 positioned within an upper portion of the drive cavity 2530. The drive cavity 2530 further comprises a clearance slot 2531 positioned between the drive tab 2553 and the primary body portion 2510. Such a clearance slot 2531 can permit the drive nut assembly to float with the firing drive screw relative to the primary body portion 2510. In such an instance, the primary body portion 2510 can be constrained by various elements of an end effector assembly such as, for example, an anvil jaw and a channel jaw.

As discussed above, the external drive portion 2550 is configured to secure the internal drive nut 2560 therein and in line with a screw axis SA. The screw axis SA is defined as the center of the ducts 2518, 2522 and a primary cylindrical portion 2561 of the internal drive nut 2560. Threads 2562 are defined in the primary cylindrical portion 2561 of the internal drive nut 2560. The threads 2562 are configured to be threadably engaged, or coupled, with threads of a firing drive screw. The internal drive nut 2560 further comprises rows 2563 of gripping features 2564 configured to prevent rotation of the internal drive nut 2560 relative to the external drive portion 2550 during drive screw rotation. The external drive portion 2550 can envelop the internal drive nut 2560 during the molding process. The internal drive nut 2560 further comprises a flared proximal end 2565. The flared proximal end 2565 can aid assembly of the firing member assembly 2500 with a firing drive screw. For example, a firing drive screw can be inserted in through the duct 2518 and guided into the threads 2562 of the internal drive nut 2560 by the flared proximal end 2565.

In at least one instance, the gripping features 2564 can aid in the manufacturing process of the drive nut assembly. For example, the gripping features 2564 may fit into corresponding slots of a mold configured to hold the drive nut 2560 during molding of the external drive portion 2550.

Figure 67:
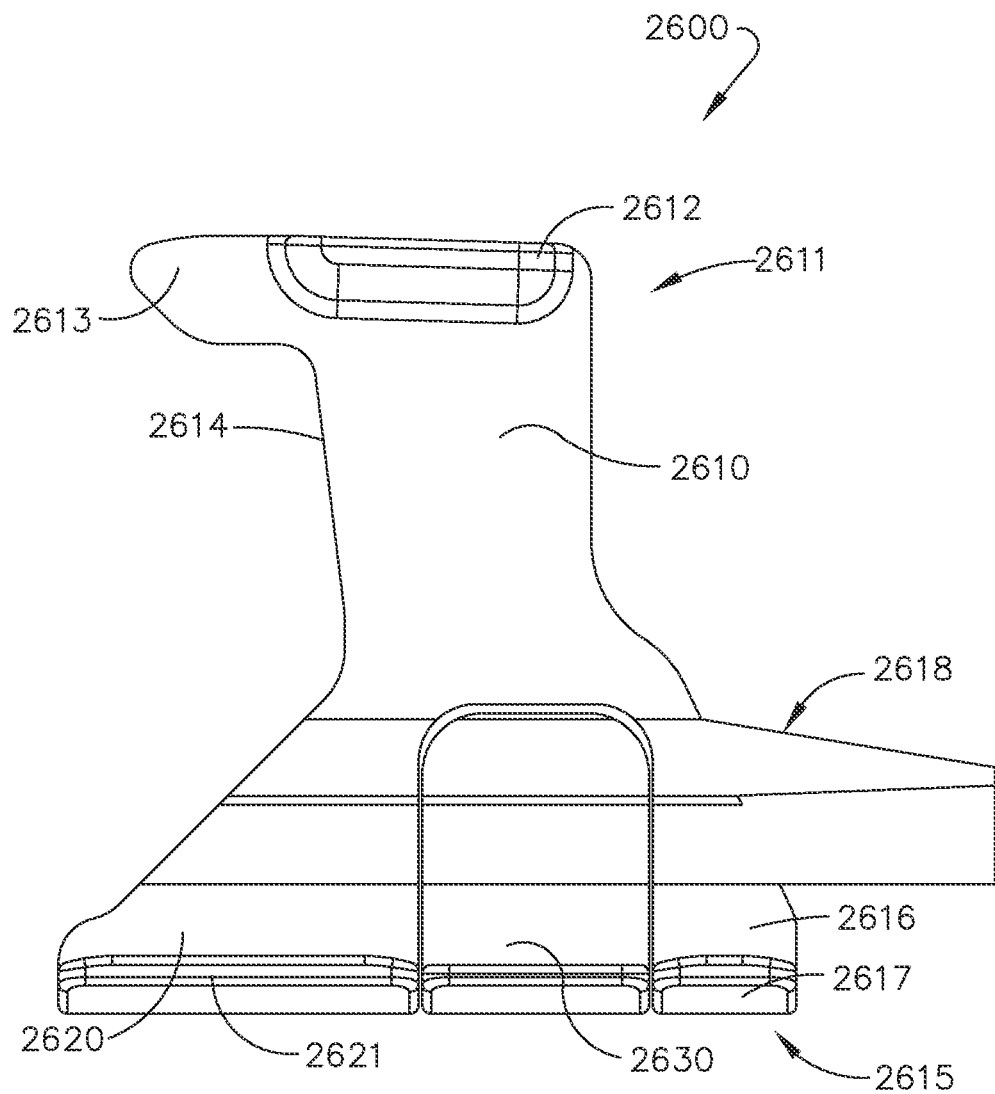
FIG. 67 is an elevation view of a firing member assembly comprising a primary body portion and a drive nut, wherein the primary body portion comprises a proximal tail extension, in accordance with at least one aspect of the present disclosure.
Figure 74:
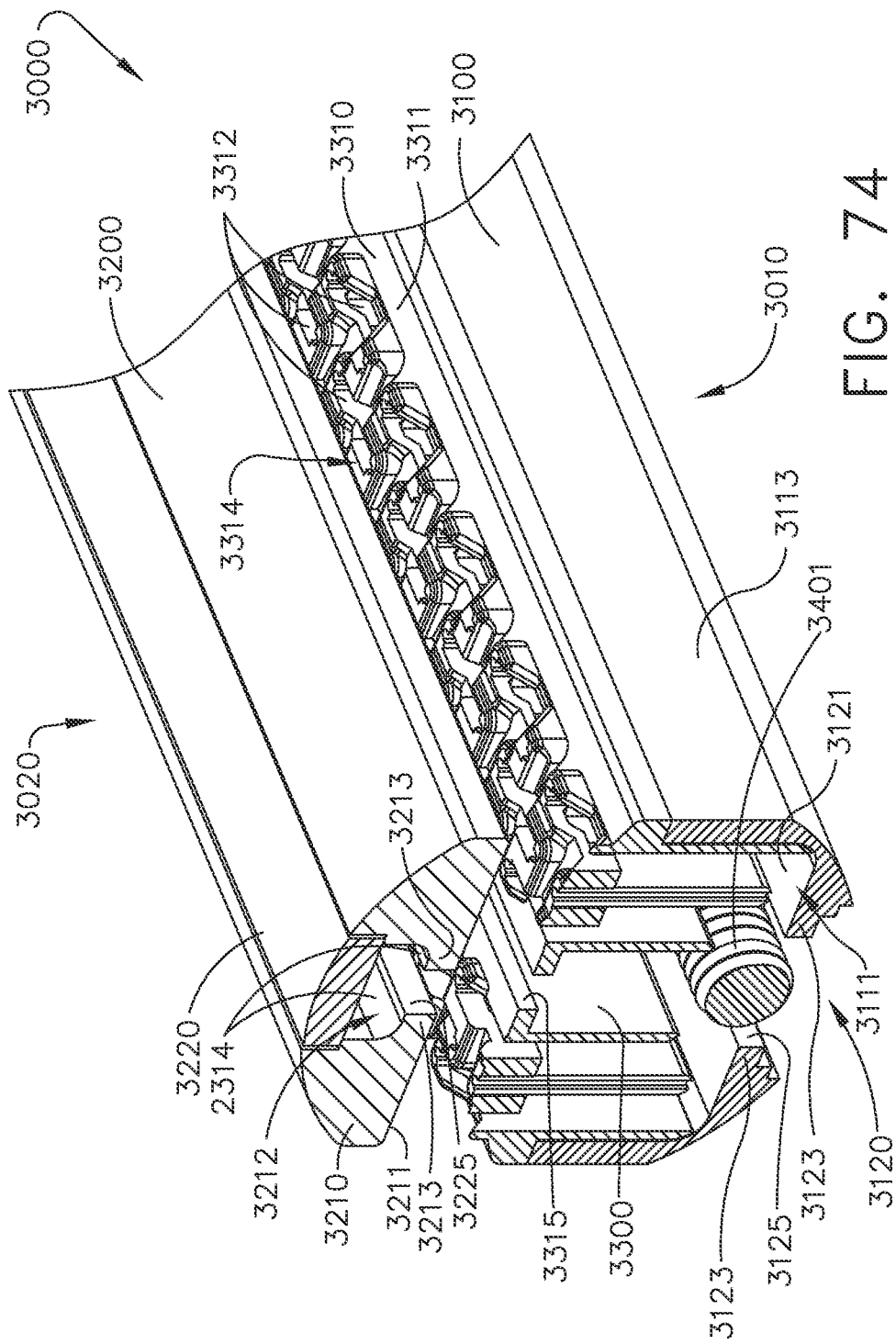
FIG. 74 is a cross-sectional perspective view of an end effector assembly comprising a cartridge channel, a staple cartridge, an anvil, and a firing assembly, in accordance with at least one aspect of the present disclosure.
Figure 75:
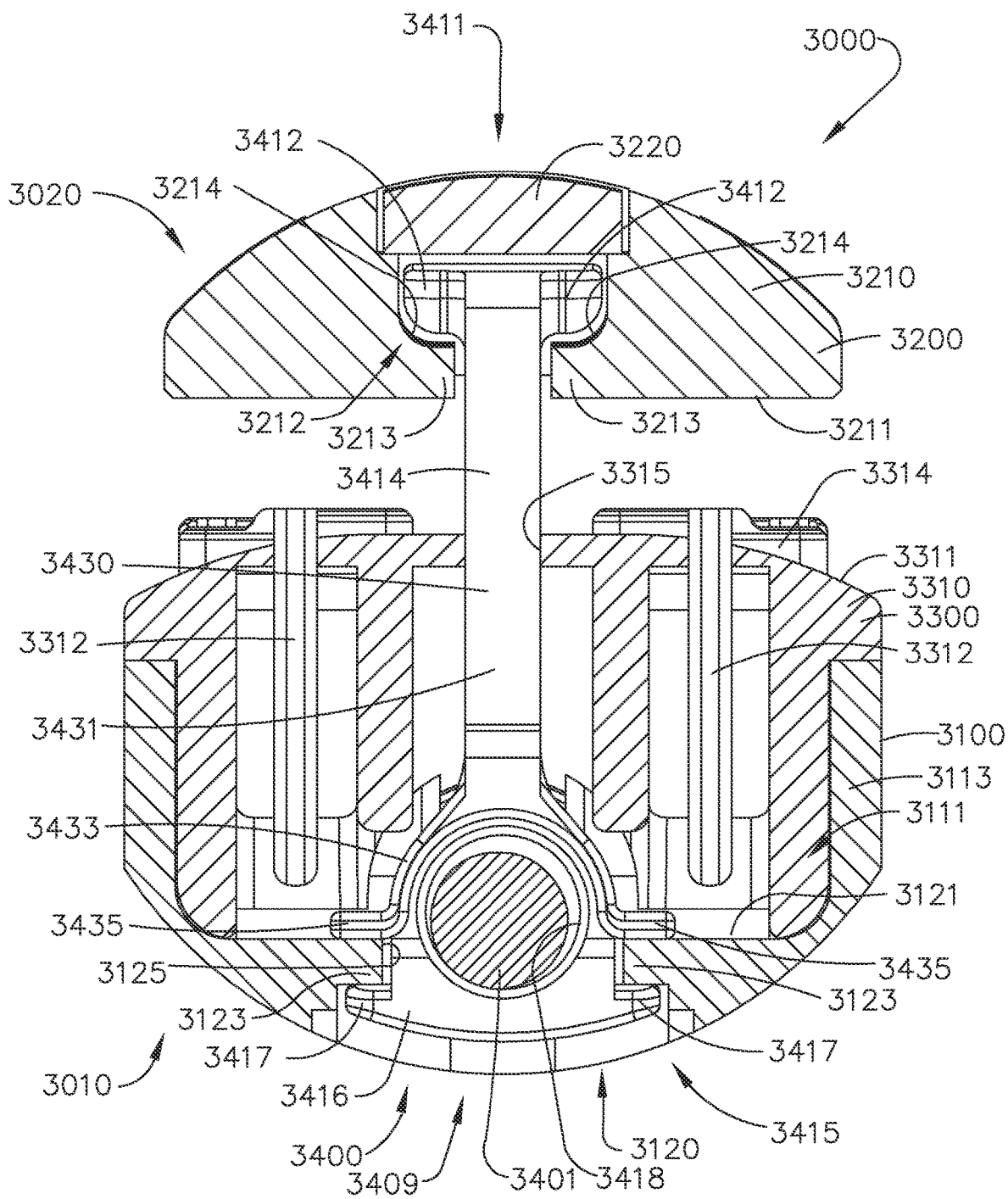
FIG. 75 is a cross-sectional elevation view of the end effector assembly of FIG. 74 viewed from a proximal end of the end effector assembly, in accordance with at least one aspect of the present disclosure.
Figure 76:
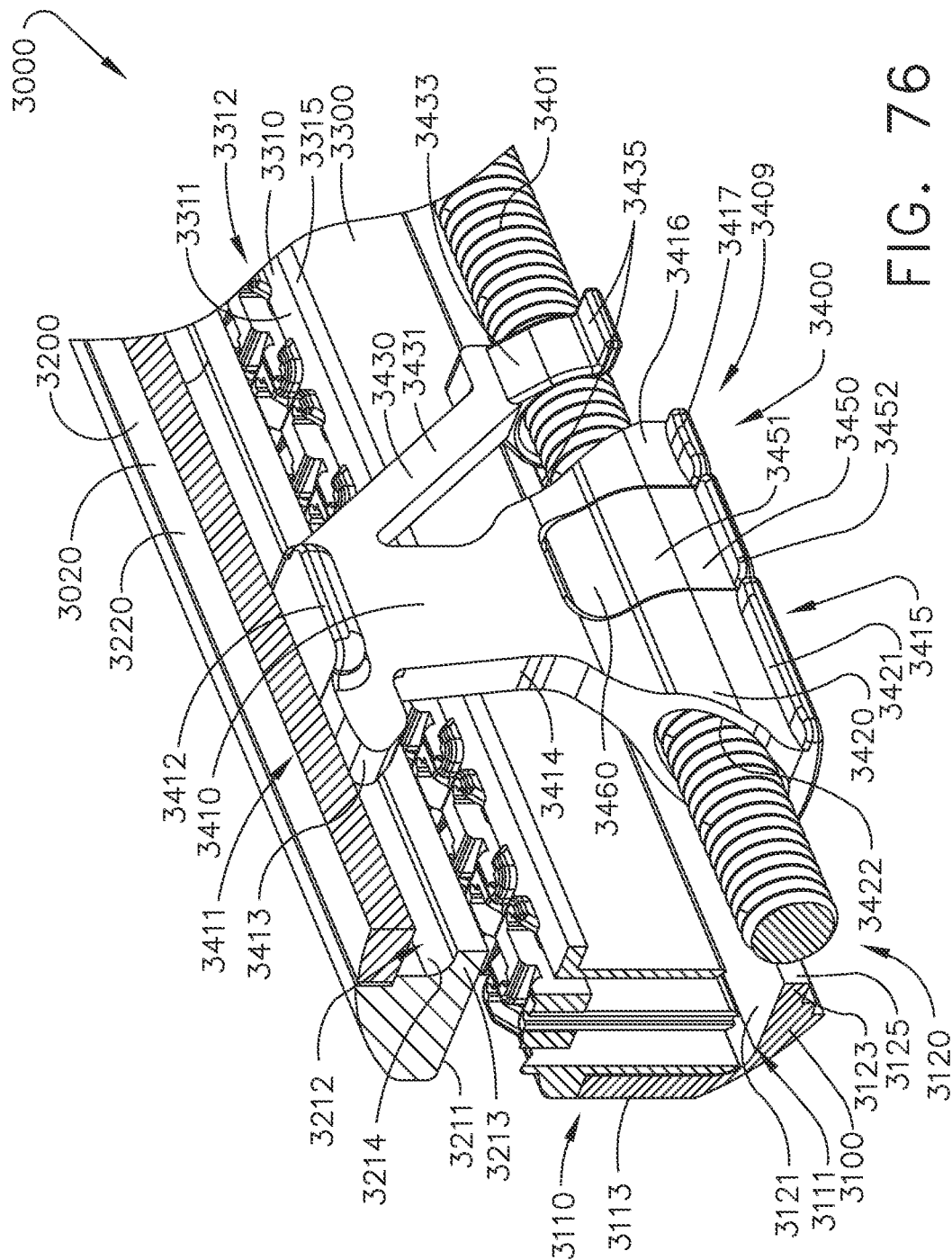
FIG. 76 is a partial cross-sectional perspective view of the end effector assembly of FIG. 74, wherein the firing member assembly comprises a firing drive screw and a firing member assembly, in accordance with at least one aspect of the present disclosure.
Figure 77:
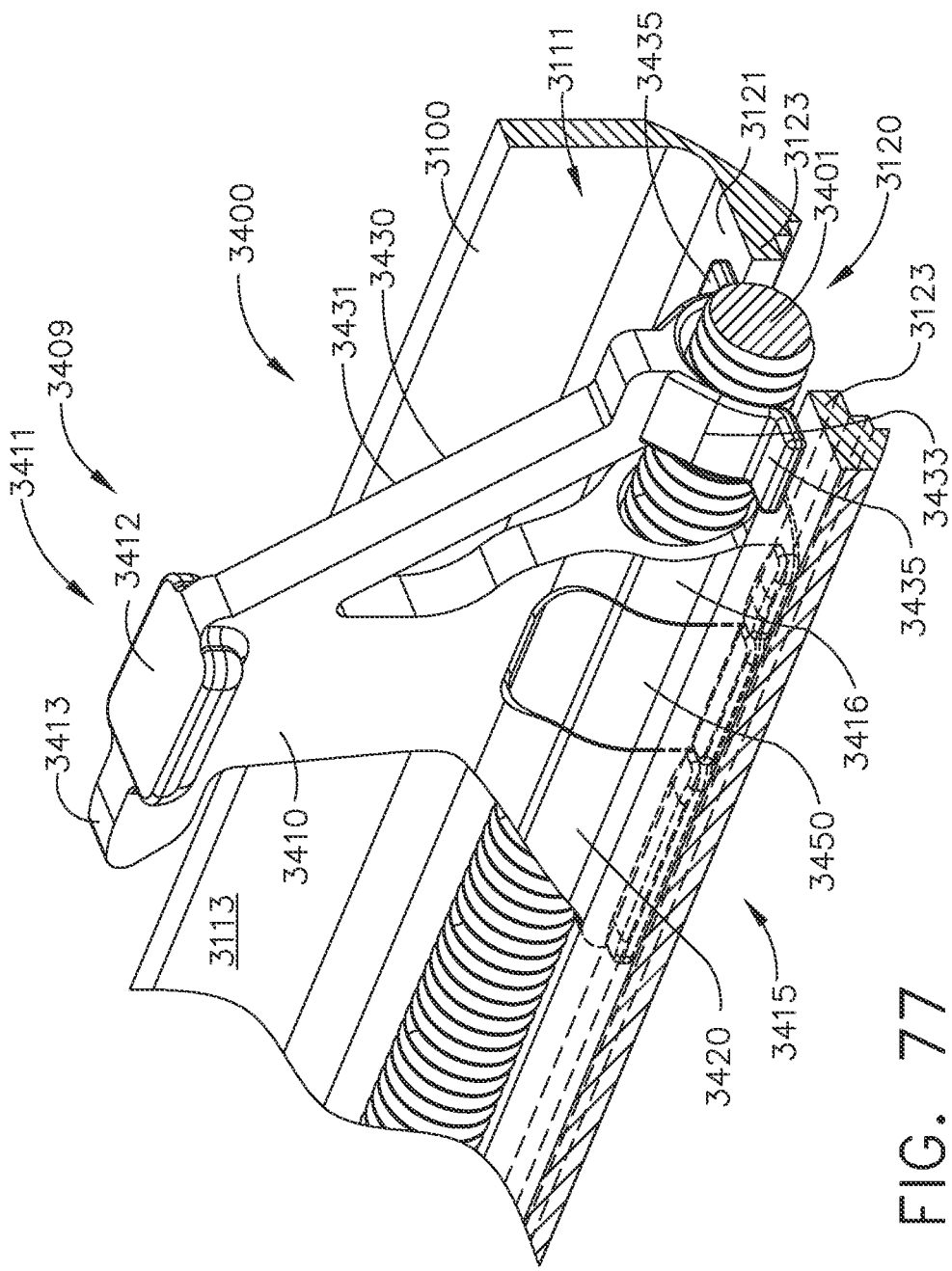
FIG. 77 is a partial cross-sectional perspective view of the channel and the firing assembly of FIG. 74, wherein certain hidden features are shown with dashed lines for illustrative purposes, in accordance with at least one aspect of the present disclosure.

FIG. 67 depicts a firing member assembly 2600. The firing assembly 2600 is similar to the firing member assemblies discussed above; however, the firing member assembly 2600 comprises a proximal tail extension configured to further support the firing member assembly 2600 through a firing stroke. The firing member assembly 2600 is configured to be threadably coupled to a firing drive screw and is configured to be actuated proximally and distally through the firing stroke by way of the firing drive screw within an end effector assembly.

The firing member assembly 2600 comprises a primary body portion 2610 and a drive nut 2630. The primary body portion 2610 comprises an upper portion 2611 and a lower portion 2615. The upper portion 2611 comprises an anvil-camming flange 2612. The upper portion 2611 further comprises a distal nose 2613 configured to close a jaw of an end effector from an open position to a closed position. The primary body portion 2610 further comprises a drive surface 2614 configured to push a sled and/or a cutting member, for example. The lower portion 2615 comprises a proximal portion 2616 comprising a proximal lower flange 2617 and a proximal tail extension 2618. The lower portion 2615 further comprises a distal portion 2620 comprising a distal lower flange 2621. The flanges 2617, 2621, 2612 can be configured to maintain a predefined tissue gap between a staple cartridge and an anvil throughout a firing stroke of the firing member assembly 2600.

The proximal tail extension 2618 is an extension of a screw duct, such as those described above, of the proximal portion 2616. Such a proximal tail extension can further support the firing member assembly 2500 through a firing stroke. Such a proximal tail extension may also resist deflection, or rotation, of the primary body portion 2610 which may cause a threaded engagement between the drive nut 2630 and the firing drive screw to bind.

FIGS. 68-72 depicts a firing member assembly 2700 threadably coupled with a firing drive screw 2701. The firing assembly 2700 is similar to the firing member assemblies discussed above; however, the firing member assembly 2700 comprises a primary body portion 2710 and a drive nut 2750 snappable to the primary body portion 2710. The firing member assembly 2700 is configured to be actuated proximally and distally through a firing stroke by way of the firing drive screw 2701 within an end effector assembly.

The primary body portion 2710 comprises an upper portion 2711 and a lower portion 2715 defining a drive cavity 2730. The drive nut 2750 is configured to be positioned within the drive cavity 2730. The upper portion 2711 comprises a jaw-camming flange 2712. The upper portion 2711 further comprises a distal nose 2713 configured to close a jaw of an end effector from an open position to a closed position. The primary body portion 2710 further comprises a drive surface 2714 configured to push a sled, for example. The lower portion 2715 comprises a proximal portion 2716 comprising a proximal lower flange 2717. The lower portion 2715 further comprises a distal portion 27720 comprising a distal lower flange 2721 and a drive screw duct 2722 defined therein configured to non-threadably receive the firing drive screw 2701. The flanges 2617, 2721, 2712 can be configured to maintain a predefined tissue gap between a staple cartridge and an anvil throughout a firing stroke of the firing member assembly 2700.

In at least one instance, a profile or perimeter of the drive screw duct 2722 and/or a proximal portion of the drive screw duct can be oval shaped and/or oblong or, non-circular, for example. Such a configuration can reduce the likelihood of a deflected drive screw rubbing or interfering inside the screw ducts, which can cause stack-up losses in the event of such drive screw deflection. Stack-up losses can refer to the various problematic engagements of the drive screw and other components within the system that would result in various interferences in a scenario where the drive screw is deflected substantially. For example, if a drive screw is deflected substantially, the deflected drive screw, as discussed above, may rub against a drive screw duct, the deflected drive screw may cause the threads of a drive nut to bind, and/or the deflected drive screw may bind near its connection with a firing output shaft, for example. Providing features to minimize such stack-up losses can prevent premature failure of components and/or reduce the firing forces necessary to drive a firing member assembly, for example.

In at least one instance, the drive screw duct 2722 and/or a proximal portion of the drive screw duct comprises filleted or chamfered edges. Such a configuration can further reduce the likelihood of the ducts contacting and binding with the firing drive screw.

In at least one instance, a screw duct of a primary body portion can provide lateral and/or vertical support to the drive screw such that, should the drive screw be loaded enough to induce bending of the drive screw, the drive screw duct can prevent the drive screw from bending at least near the threaded drive nut. Such a configuration can help prevent binding between the threads of the drive screw and the threaded drive nut.

In at least one instance, a sled of a staple cartridge can comprise a distally extending cradle support feature extending from a distal end of the sled. The cradle support feature may also support the firing drive screw and help prevent bending of the firing drive screw at least near the cradle support feature. In at least one instance, the sled prevents bending of the drive screw in only one direction. In at least one instance, the sled comprises a proximal cradle support feature in addition to or in lieu of the distal cradle support feature.

The drive nut 2750 comprises a jaw-engaging flange 2751, a threaded portion 2755 configured to be threadably coupled with the firing drive screw 2701 by way of threads 2756, and laterally-opposing drive tabs 2760 extending upwardly from the threaded portion 2755. The drive nut 2750 comprises a substantially trapezoidal shape such as those drive nuts comprising a trapezoidal shape discussed herein.

The drive tabs 2760 are configured to cradle, or straddle, a corresponding drive tab 2740 extending downwardly from the primary body portion 2710. The drive tabs 2760 define a slot 2761 therebetween and each comprise a snap nub 2762 protruding inwardly therefrom. The snap nubs 2762 each comprise a sloped upper surface 2763 and a latch surface 2764. As can be seen in FIG. 71, the drive tabs 2760 are configured to snap to the drive tab 2740 of the primary body portion 2710. Specifically, the drive tab 2740 comprises a horizontally extending slot 2741 defined therein and the snap nubs 2762 are configured to widen the drive tabs 2760 during installation of the drive nut 2750 with the primary body portion 2710 enough such that the latch surfaces 2764 clear the drive tab 2740 and can bias inwardly into the slot 2741. In at least one instance, the snap nubs 2762 are not configured to transfer any longitudinal drive forces from the firing drive screw 2701 to the primary body portion 2710. Instead, the drive tabs 2760 are configured to fit within the drive cavity 2730 such that the drive tabs 2760 directly push and pull the primary body portion 2710 relative to the firing drive screw similar to various firing member assemblies discussed herein. Such a configuration can alleviate the reliance on the internal cross members of the drive nut 2750 to transfer firing force from the firing drive screw 2701 to the primary body portion 2710. This can be advantageous in that the drive nut 2750 can remain attached to the primary body portion 2710 through the drive nubs 2762 through higher than normal loads. Like various drive tabs discussed herein, the drive tabs 2760 of the drive nut 2750 are further configured to apply force to the primary body portion 2710 nearer the center of the primary body portion 2710. As can be seen in FIG. 69, the drive nut 2750 is configured to apply a drive force DF to the primary body portion 2710 off axis with respect to a longitudinal screw axis SA.

In at least one instance, the drive nut 2750 is injection molded prior to being snapped onto the primary body portion 2710. In at least one instance, the drive nut 2750 is insert molded onto the primary body portion 2710 and the firing drive screw 2701. In such an instance, the drive nut 2750 may be snapped off and replaced should the drive nut 2750 wear out over time, for example.

FIG. 73 depicts a firing member assembly 2800 comprising a primary body portion 2810 and a drive nut 2850 configured to be threadably coupled to a firing drive screw. The firing member assembly 2800 is similar to various firing member assemblies discussed above; however, the firing member assembly 2800 further comprises a drive cavity 2830 configured to permit the primary body portion 2810 to flex during a firing drive stroke as discussed in greater detail below.

The primary body portion 2810 comprises an upper portion 2811 comprising a flange 2812 extending laterally therefrom and a distal nose 2813 configured to close a jaw from an open position during a closure stroke. The primary body portion 2810 further comprises a drive surface 2814 configured to push a sled and/or a cutting member through a staple firing stroke, for example. Other embodiments are envisioned where various other surfaces on the front of the primary body portion 2810 are configured to drive various components such as a sled and/or a cutting member, for example. The primary body portion 2810 further comprises a lower portion 2815 comprising a proximal portion 2816 comprising a proximal lower flange 2817 and a distal portion 2820 comprising a distal lower flange 2821. Collectively, the flanges 2812, 2817, 2821 are configured to affirmatively space opposing jaws during a firing stroke and maintain a consistent tissue gap between the opposing jaws.

The drive nut 2850 is positioned within the drive cavity 2830 and is configured to be threadably coupled to a firing drive screw. The drive nut 2850 is configured to apply axial drive forces to the primary body portion 2810 as the firing drive screw is actuated to move the firing member assembly 2810 proximally and distally within an end effector. The drive cavity 2830 comprises a lower portion 2833 where the drive nut 2850 is primarily positioned and is configured to float within and comprises an upper triangular portion 2831. The upper triangular portion 2831 is configured to permit the primary body portion 2810 to flex during a firing stroke. For example, under clamping loads, the triangular portion 2831 is configured to permit the proximal portion 2816 to flex longitudinally away from the distal portion 2820. Such flexion can provide forgiveness within the firing member assembly 2800 so as to prevent binding, for example. In addition to flexion of the primary body portion 2810, the drive nut 2850 is configured to float within the drive cavity 2850. Collectively, such an arrangement can reduce binding engagement between the threaded connections and/or binding engagement between the flanges and jaws.

Various drive nuts disclosed herein comprise a laterally extending flange aligned with the proximal and distal lower flanges of the lower portions of the primary body portions. Such a flange can prevent the drive nut from rotating with a firing drive screw. Such a flange can comprise a rounded bottom so as to reduce binding engagement with a corresponding jaw. For example, the proximal and distal lower flanges can be configured to handle the majority of the clamping loads while the drive nut flange is provided for support to the drive nut but not necessarily to handle high clamping loads. Rounding the flange can reduce the overall contact with the corresponding jaw thus reducing the likelihood of the flange from binding against the corresponding jaw. In such an instance, the flange, or lateral fin, of the drive nut is configured to be loose within the corresponding jaw, such as a channel jaw, for example. This loose engagement between the flange and the corresponding jaw can provide the anti-rotation feature without requiring the flange to handle high clamping loads. In at least one instance, the lateral fin is overall thinner and comprises a top edge which is positioned below top edges of corresponding proximal and distal lower flanges of a primary body portion.

In at least one instance, the primary body portions are machined from a metallic material and the drive nuts are injection molded, insert molded, or overmolded from a polymer and/or a plastic material. Such a configuration can reduce manufacturing costs and machining complexity as various molding processes can allow for more complex geometries and shapes. Various molding processes can also allow for various order of component assembly and manufacturing. As discussed above, insert molding allows the multi-material firing member assembly to comprise various materials as well as complex integrated geometries between the different materials. Moreover, insert molding, for example, permits the firing drive screw to be positioned within the firing member assembly prior to molding of the drive nut.

FIGS. 74-78 depict an end effector assembly 3000 configured to cut and staple the tissue of a patient. The end effector assembly 3000 comprises a first jaw 3010 and a second jaw 3020 movable relative to the first jaw 3010. Embodiments are envisioned where the first jaw 3010 is movable relative to the second jaw 3020. The first jaw 3010 comprises a cartridge channel 3100 and a replaceable staple cartridge 3300 configured to be removably positioned within the cartridge channel 3100. The second jaw 3020 comprises an anvil 3200 configured to deform staples removably stored in the staple cartridge 3300 during a staple firing stroke. The second jaw 3020 is movable, or pivotable, relative to the first jaw 3010 to clamp tissue between the anvil 3200 and the staple cartridge 3300. Once tissue is clamped between the anvil 3200 and the staple cartridge 3300, the end effector assembly 3000 is fired to eject staples and cut tissue with a firing assembly 3400 of the end effector assembly 3000.

Discussed in greater detail below, the firing assembly 3400 comprises a firing drive screw 3401 supported within the cartridge channel 3100. The firing assembly 3400 further comprises a firing member assembly 3409 threadably coupled to the firing drive screw 3401 which is configured to push a sled to deploy staples from the staple cartridge 3300 during a firing stroke, push a cutting member to cut tissue during the firing stroke, and maintain a consistent tissue gap between the staple cartridge 3300 and the anvil 3200 during the firing stroke.

The cartridge channel 3100 comprises a longitudinal channel cavity 3111 within which the staple cartridge 3300 is removably positioned. The cartridge channel 3100 also comprises side walls 3113 configured to support the staple cartridge 3300. In at least one instance, the staple cartridge comprises ledges configured to rest on top of the side walls 3113. The cartridge channel 3100 further comprises a base portion 3120. The base portion 3120 comprises an internal bottom surface 3121 and camming ledges 3123. A longitudinal slot 3125 is defined between the camming ledges 3123 and is configured to receive at least a portion of the firing assembly 3400 therethrough.

The anvil 3200 comprises a body portion 3210 and an anvil cap 3220 configured to be attached to the body portion 3210 within a longitudinal channel 3212. The body portion 3210 comprises an anvil surface 3211. The anvil surface 3211 comprises a plurality of staple forming pockets aligned with staple cavities 3312 defined in a deck 3311 of staple cartridge body 3310. The body portion 3210 also comprises camming ledges 3213 extending laterally inwardly into the longitudinal channel 3212 and defining a longitudinal slot 3225 therebetween. Discussed in greater detail below, the camming ledges 3123, 3213 are configured to be cooperatively engaged by corresponding flanges of the firing member assembly 3409 to affirmatively space the jaws 3010, 3020 relative to each other. In at least one instance, a predefined tissue gap is defined between the cartridge deck 3311 and the anvil surface 3211 during a firing stroke by way of the engagement of the flanges of the firing member assembly 3409 with the camming ledges 3213, 3123.

The staple cartridge 3300 further comprises deck protrusions, or pocket extenders, 3314 configured to extend the effective height of each staple cavity 3312. The deck protrusions 3314 can be configured to help grip tissue clamped between the jaws 3010, 3020. The staple cartridge 3300 further comprises a longitudinal slot 3315 configured to receive at least a portion of the firing member assembly 3409 therethrough. As discussed above, a sled and/or cutting member is configured to be advanced through the jaws 3010, 3020 to cut tissue and fire staples during a staple firing stroke with the firing assembly 4400.

The firing assembly 3400 comprises the firing drive screw 3401 and the firing member assembly 3409 threadably coupled to the firing drive screw 3401. The firing member assembly 3409 comprises a primary body portion 3410, a drive nut 3450 configured to be threadably coupled to the firing drive screw 3401, and a rear support brace 3430. The primary body portion 3410 comprises an upper portion 3411 comprising an anvil-engaging flange 3412 and a distal nose portion 3413. The anvil-engaging flange 3412 is configured to move within the longitudinal channel 3212 and, more specifically, configured to apply clamping pressure to the upper surface 3214 of the camming ledges 3213. In at least one instance, the anvil cap 3220 is configured to provide an upper boundary to the anvil-camming flange 3412. Nonetheless, the anvil-camming flange 3412 is configured to move within the longitudinal channel 3212 during a firing stroke to apply camming forces thereto to ensure a consistent tissue gap distance between the cartridge deck 3311 and the anvil surface 3211.

The primary body portion 3410 further comprises a lower portion 3415 comprising a proximal portion 3416 comprising a channel-camming flange 3417 and a screw duct 3418 configured to non-threadably receive the firing drive screw 3401 therethrough. The lower portion 3415 further comprises a distal portion 3420 comprising a channel-camming flange 3421 and a screw duct 3422 configured to non-threadably receive the firing drive screw 3401. The drive nut 3450 is configured to fit between the proximal portion 3416 and the distal portion 3420. The drive nut 3450 comprises a threaded portion 3451 configured to be threadably coupled to the firing drive screw 3401 and comprising a channel-camming flange 3452. In at least one instance, the channel-camming flange 3452 comprises a thickness that is less than the thickness of the channel-camming flanges 3417, 3421. The drive nut 3450 also comprises a drive tab 3460 extending upwardly toward the primary body portion 3410. The drive nut 3450 is configured to apply axial drive forces proximally and distally to the primary body portion 3410 to move the firing member assembly 3409 through jaws 3010, 3020. The channel-camming flanges 3417, 3452, 3421 are configured to apply camming forces to the camming ledges 3123. Collectively, the camming flange 3412 and the flanges 3417, 3452, 3421 are configured to maintain a consistent tissue gap distance between the cartridge deck 3311 and the anvil surface 3211.

Firing member assemblies can be subject to loads which would cause off center moment loading. For example, the anvil ledges engaged with upper camming flanges 3412 can apply an off-center moment load to the firing member 3400 in certain instances, such as when thick and/or tough tissue is clamped between the jaws. It can be advantageous to provide a means for counter-acting such off center moment loading. The firing member assembly 3409 comprises a rear support brace 3430 extending at an angle proximally from the upper portion 3411 of the primary body portion 3410. The rear support brace 3430 comprises a strut member 3431 and an arcuate brace portion 3433 extending from the strut member 3431. The arcuate brace portion 3433 comprises laterally extending flanges 3435 configured to support the rear support brace 3430 and counteract moment loading of the primary body portion 3410. The flanges 3435 are configured to ride against the internal bottom surface 3121. Notably, the flanges 3435 ride above the camming ledges 3123 such that the flanges 3432 of the rear support brace 3430 and the channel-camming flanges 3421 contact opposite sides of the base portion 3120 of the channel 3100.

In at least one instance, should the primary body portion 3410 be loaded and cause rotation in an opposite direction, the flanges 3435 may provide flexibility to lift off of the internal bottom surface 3121 and resist torqueing of the anvil-camming flanges 3412 out of substantially parallel alignment with the longitudinal channel 3214. The rear support brace 3430 can be configured to provide a degree of flexibility so as to permit some flexion of the primary body portion 3410 during loading while preventing a magnitude of flexion that would cause binding if the threaded engagement between the drive nut 3450 and the firing drive screw 3401. In certain instances, the rear support brace 3430 can act as a spring feature for balancing the load.

Embodiments are envisioned where the flanges 3435 are positioned under the ledges 3123. Embodiments are also envisioned where two sets of flanges are provided. One set of flanges can be positioned above the ledges 3123 and one set of flanges can be positioned below the ledges 3123.

In various instances, the rear support brace 3430 acts a spring member for the firing member assembly 3409 to balance various loads experienced by the firing member assembly 3409. Moreover, a clearance is provided between the arcuate brace portion 3433 and the firing drive screw 3401. Such a configuration can prevent I-beam roll, for example, and balance an I-beam, or firing member assembly, throughout a staple firing stroke. Embodiments are envisioned where the arcuate brace portion 3433 is also threaded and threadably coupled to the firing drive screw 3401.

Figure 78:
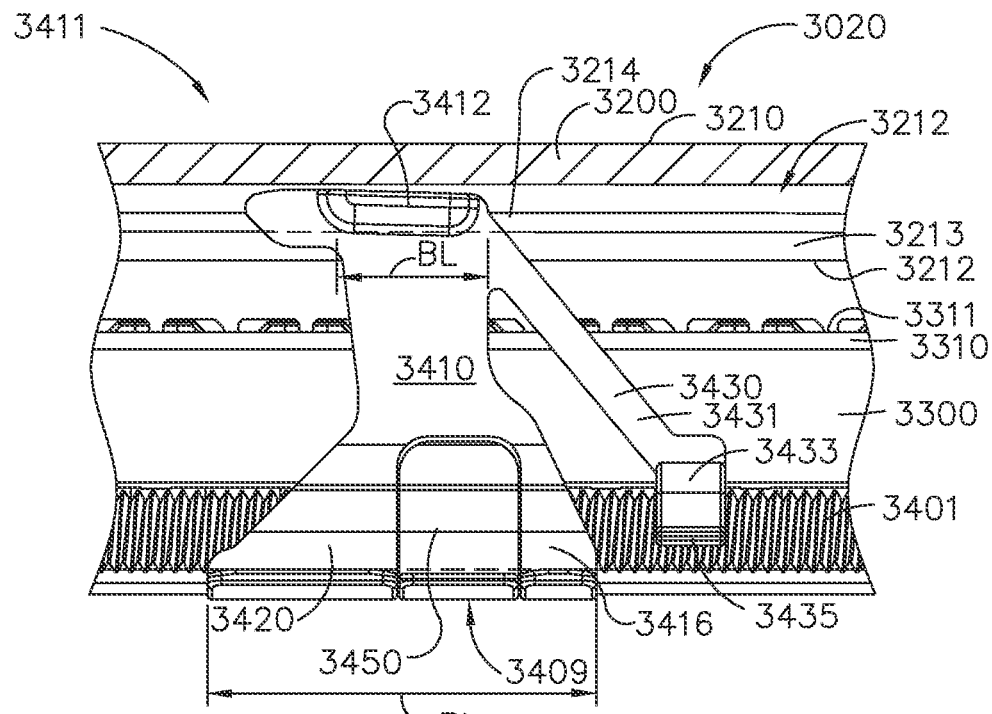
FIG. 78 is a partial cross-sectional elevation view of the end effector assembly of FIG. 74, in accordance with at least one aspect of the present disclosure.

In various instances, the geometries of various firing member components can be optimized. Referring to FIG. 78, for example, the length of a central portion of the primary body portion 3410 is referred to as the body length BL and the length of the lower flanges 3417, 3421, collectively, are referred to as the pin length PL. Generally, the pin length PL is about twice the length of the body length BL. This may also apply to the upper flange 3412. However, in certain instances, the upper flange 3412, for example, may comprise a shorter pin length than twice the body length BL at least because the rear support brace 3430 can help prevent the upper flange 3412 from rotating and/or deflecting under load. In various instances, the longer the pin length, the more likely the corresponding flange is will bind within its slot. In such instances, the clearance slot within which the flange is positioned should be smaller so as to reduce binding between the flange and the clearance slot.

Figure 79:
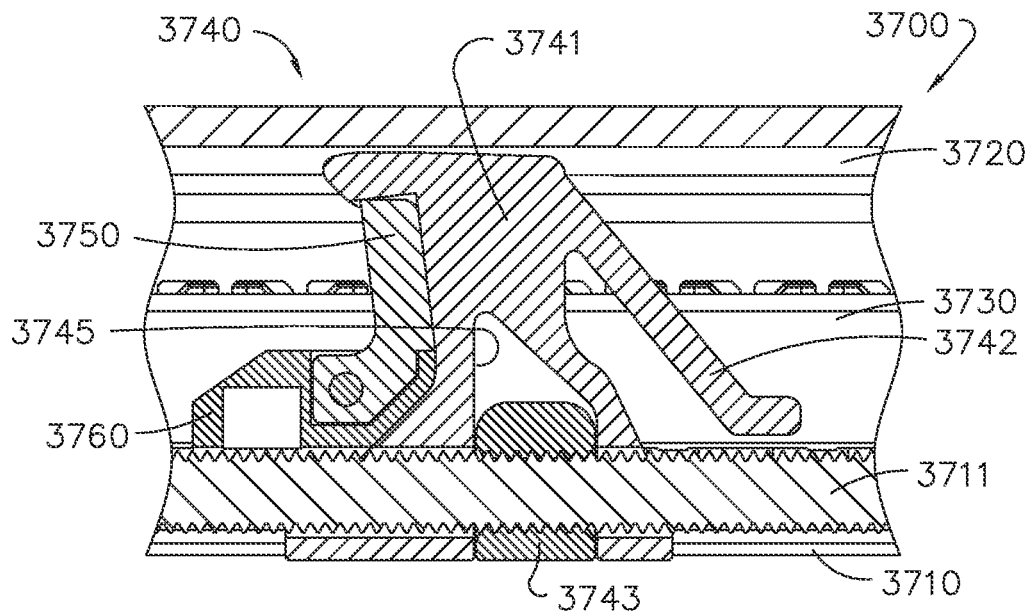
FIG. 79 is a cross-sectional elevation view of a surgical stapling assembly comprising a channel, a staple cartridge, an anvil, and a firing assembly comprising a drive screw, a firing member assembly, and a sled, in accordance with at least one aspect of the present disclosure.
Figure 80:
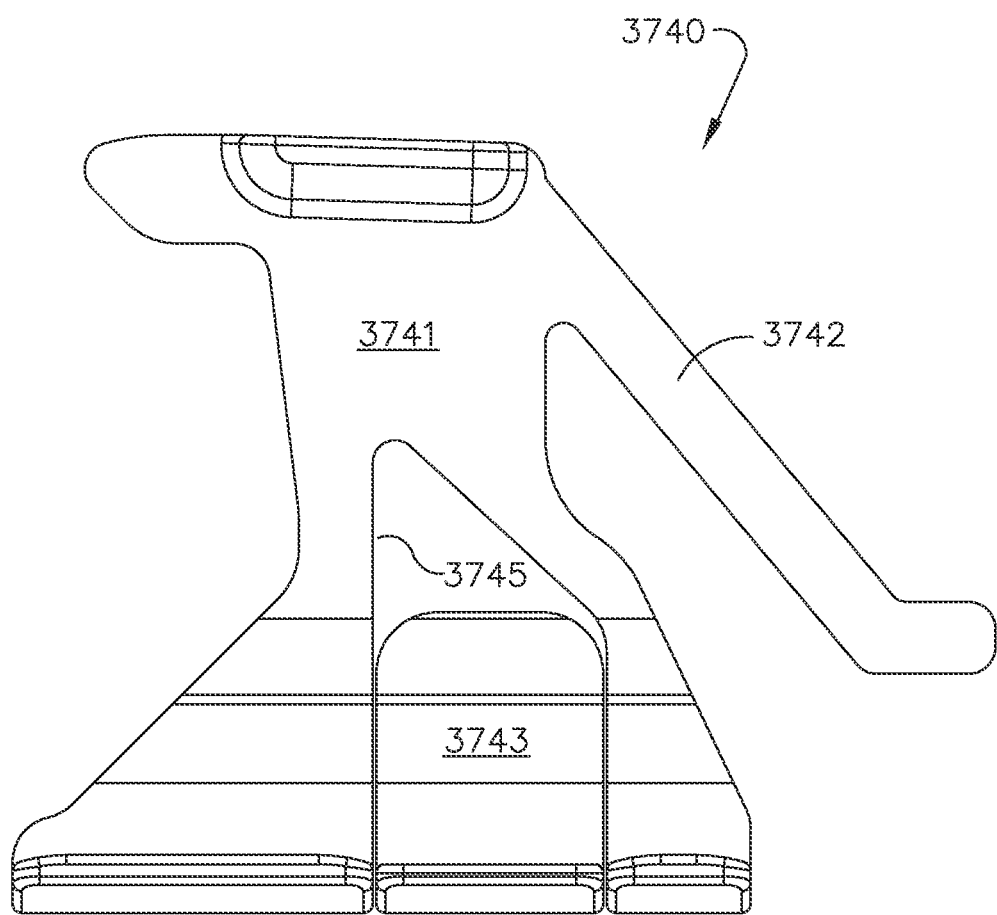
FIG. 80 is an elevation view of the firing member assembly of FIG. 79, in accordance with at least one aspect of the present disclosure.

FIGS. 79 and 80 depict a surgical stapling assembly 3700 similar to those discussed above. However, the surgical stapling assembly 3700 combines a triangular drive cavity cutout in addition to various other features discussed herein. The surgical stapling assembly 3700 comprises a channel jaw 3710, a staple cartridge 3730 configured to be received within the channel jaw 3710, and a firing drive screw 3711 supported within the channel jaw 3710. The surgical stapling assembly 3700 further comprises an anvil jaw 3720 configured to deform staples ejected from the staple cartridge 3730. The surgical stapling assembly further comprises a firing member assembly 3740 configured to be actuated by the firing drive screw 3711 through the jaws 3710, 3720. The firing member assembly 3740 comprises a primary body portion 3741, a rear support brace 3745, and a drive nut 3743 threadably coupled to the firing drive screw 3711. The primary body portion 3741 comprises a triangular drive cavity cutout 3745 configured to provide an additional spring feature within the firing member assembly 3740 configured to balance various loads experienced by the firing member assembly 3740. The surgical stapling assembly 3700 further comprises a knife 3750 configured to cut tissue during a firing stroke and a sled 3760 configured to deploy staples from the staple cartridge 3730. The knife 3750 and the sled 3760 can each experience and transfer loads to the firing member assembly 3740.

The knife 3750 is a component of the sled 3760 and is mounted to the sled 3760 at a pivot. During a distal firing motion, the knife 3750 can assume the upright configuration shown in FIG. 79, in which the knife 3750 protrudes out of the cartridge body and the cutting edge thereof is configured to cut tissue. During a proximal firing motion, the knife 3750 can assume a shielded configuration, in which at least a portion of the cutting edge of the knife 3750 is shielded by the fastener cartridge. The knife 3750 can pivot between the upright configuration and the shielded configuration in response to the firing direction and/or various mechanical lockouts and/or biasing mechanisms in the staple cartridge.

Figure 81:
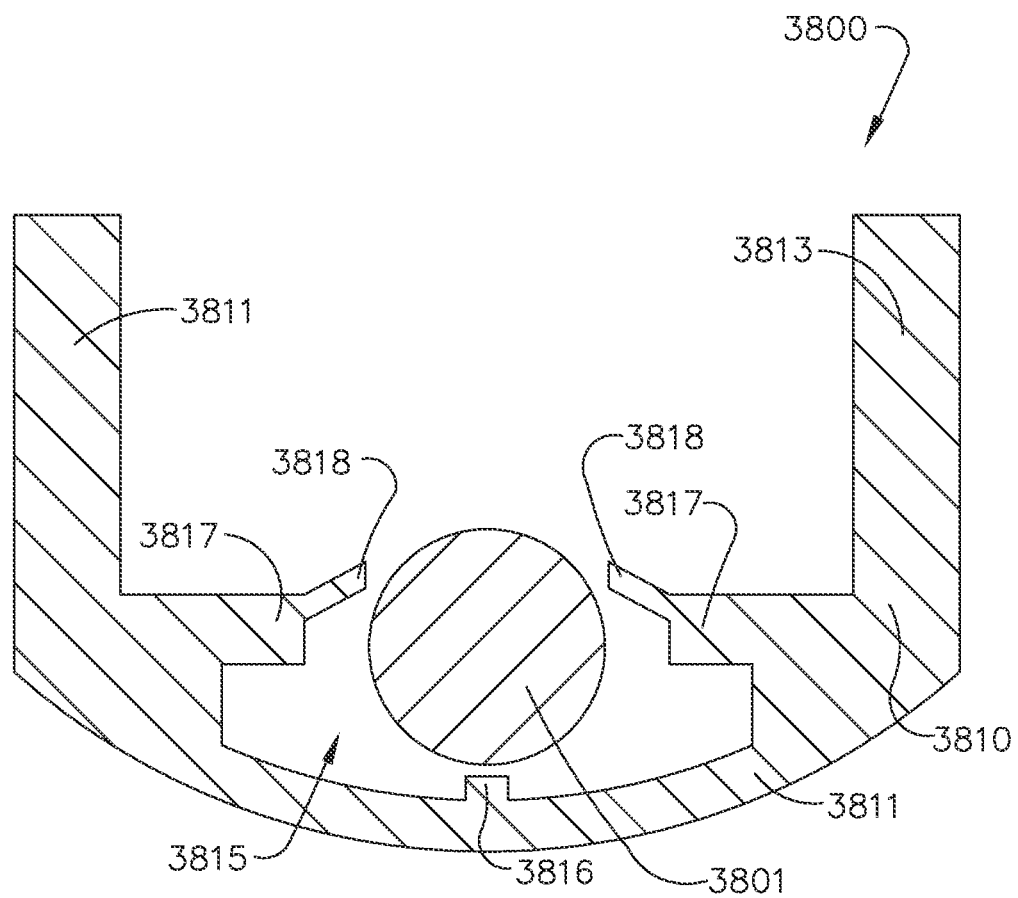
FIG. 81 is a cross-sectional elevation view of a jaw assembly for use with a surgical stapling assembly, wherein the jaw assembly comprises a channel and a firing drive screw, in accordance with at least one aspect of the present disclosure.

FIG. 81 depicts a jaw assembly 3800 configured to support a firing drive screw 3801 therein. Under high loads, a firing drive screw may tend to buckle. The jaw assembly 3800 is configured to prevent buckling of the firing drive screw 3801. The jaw assembly comprises a channel jaw 3810 comprising a bottom 3811 and channel walls 3813 extending from the bottom 3811. The bottom 3811 comprises a drive cavity 3815 configured to receive the firing drive screw 3801 and one or more flanges such as the camming flanges discussed herein. The bottom 3811 further comprises a lower support 3816 and lateral supports 3818 extending from camming ledges 3817. The lower support 3816 and lateral supports 3818 are configured to restrain the firing drive screw 3801 from buckling under high loads. In at least one instance, the supports 3816, 3818 are positioned only near the middle of the firing stroke and channel jaw, for example. Such an arrangement may suffice owing to the fact that, under high loads, the firing drive screw 3801 may tend to buckle near the center of its effective length. In at least one instance, the supports 3816, 3818 may be longitudinal ribs that extend along the majority of the length of the firing drive screw 3801 and channel jaw 3810. The supports 3818 can comprise of metal arms and act as hard stops for the firing drive screw 3801.

In at least one instance, the supports 3818 comprise plastic arms. In such an instance, the supports 3818 can be pried out of the way of a firing member assembly by the firing member assembly as the firing member assembly passes by the supports 3818 during a firing stroke. Such a configuration can be advantageous at least because once the firing member assembly reaches the location of the supports 3818 during the firing stroke, the firing member assembly can then, itself, support the firing drive screw 3801 and prevent buckling thereof.

In various instances, balancing an I-beam, or firing member assembly, can be advantageous so as to optimize loading of the firing member assembly between the anvil camming flanges and channel camming flanges, for example. Various forces are applied to the firing member assembly. These forces are applied by the firing drive screw and/or the drive nut, the anvil camming flanges, the channel camming flanges, the tissue, and/or the sled configured to deploy staples. It may be advantageous to balance these forces such that the driving force provided by the drive screw is driving the firing member assembly at an optimal location. A less than optimal driving force application may result in unnecessary roll, rotation, and/or rocking, of the firing member assembly relative to the firing screw and/or relative to a longitudinal axis defined by the firing screw. Torsional loads may cause such roll, rotation, and/or rocking, for example. Applying the drive force at a location to optimally counteract the predictable torsional loads applied to the firing member assembly can help prevent the roll, rotation, and/or rocking of the firing member assembly.

In various instances, the channel/anvil camming flanges, or pins, comprise width and length that is configured to be tuned relative to their corresponding slots through which they are received. In at least one instance, the greater the length of the flange along the longitudinal axis, the less clearance is required within its corresponding camming slot. In other words, the corresponding camming slot may comprise a geometry to more tightly receive the flange. On the other hand, the lesser the length of the flange along the longitudinal axis, the greater the clearance required within its corresponding camming slot. In other words, the corresponding camming slot may comprise a geometry to more loosely receive the flange. In at least one instance, an ideal length of one or more of the flanges may comprise about twice the width of the primary body portion of the firing member assembly. Notably, the thickness of the of primary body portion is synonymous with the portion of the primary body portion configured to travel through the longitudinal staple cartridge slot.

In various instances, drive nuts disclosed herein are configured to float up and down relative to the primary body portion of the firing member assembly, up and down and side to side relative to the primary body portion of the firing member assembly, and/or side to side relative to the primary body portion of the firing member assembly. The floating of the drive nut can reduce the likelihood of the drive screw binding with various other components. As discussed above, a drive nut may be rigidly welded to a primary body portion in certain instances.

In various instances, the various components of the surgical stapling assemblies disclosed herein can be assembled in a particular order so as to prevent inadvertent disassembly. For example, various components can be introduced during assembly after the firing member assembly is introduced, which would otherwise tend to fall out or be disassembled inadvertently without a holding force in the assembly provided by flanges of the firing member assembly, for example. Components and sub-assemblies in addition to or other than the firing member assembly may also provide assembly holding forces, for example. For example, a drive screw can be pre-loaded, as discussed herein, and can provide an internal assembly holding force during assembly. The drive screw may be installed into the surgical stapling assembly prior to various other components. In certain instances, the above-discussed assembly holding forces could actually encourage inadvertent disassembly of one or more components. In such instances, such components would be installed after certain components so as to ensure that, when such components are installed, the entire assembly at that point in time can maintain an assembled state so as to reduce the likelihood of inadvertent disassembly.

In at least one instance, a plastic and/or metal injection molded (MIM) drive nut of a firing member assembly can first be assembled to the primary body portion of the firing member assembly. Once the drive nut is positioned, then a drive screw can be threaded into the drive nut through corresponding ducts of the primary body portion. Assembling in such a manner allows the drive screw to couple the drive nut and primary body portion of the firing member assembly so as to prevent inadvertent disassembly of the drive nut and the primary body portion.

Further to the above, the drive screw ends can then be coupled to their corresponding supports with their corresponding attachment means. For example, any bearings and/or springs used, for example, can all be assembled at this time. This would prevent the firing member assembly from running off of the proximal end or distal end of the drive screw. Additionally, should the firing member assembly be overdriven, for example, the thrust bearings would already be presented and the firing member assembly would predictably deflect a channel for example, through the thrust bearing and/or channel support flange, for example, rather than abnormally loading only the thrust bearing and or distal head portion of the drive screw, for example. If the firing member assembly is advanced into a thrust bearing and/or distal head portion of the drive screw, the firing member assembly may exert an unexpected load onto the thrust bearing and/or distal head portion of the drive screw and possibly cause premature failure of the thrust bearing and/or distal head portion, for example. This can be attribute to not being assembled to their corresponding channel support flanges, for example, with which the ends of the drive screw are designed to interact and cooperatively load. Without the channel flanges and the channel, for example, a distal head portion of a drive screw can be sheared off if prematurely loaded prior to the installation of the drive screw into the channel support flanges, for example.

In at least one instance, a firing member assembly is advanced beyond its distal-most position during actual operation of a surgical stapling assembly on the drive screw so that the flanges of the firing member assembly can be inserted within their corresponding slots in the anvil, channel, and/or staple cartridge, for example. Once the flanges are aligned with their corresponding slots, the drive screw can be rotated to move the firing member assembly proximally thereby moving the flanges into their corresponding slots. As such point, the drive screw can then be seated within its support flanges, for example. In at least one instance, using such a sequential assembly method can prevent the flanges from coming loose out of their respective slots during assembly, for example.

In at least one instance, the various supports positioned within the proximal end of an end effector assembly are configured to support a proximal end of a firing drive screw and are configured to support a closure drive screw interlock with a cartridge channel, for example. In such an instance, an anvil can be introduced to the end effector assembly and pinned to the cartridge channel with a pivot pin after the various supports are positioned in the cartridge channel. The pivot pin, itself, can prevent vertical decoupling loads from decoupling various components of the end effector assembly. In such an instance, lateral channel walls along with lateral tissue stops, lateral walls of the anvil configured to straddle the lateral channel walls upon clamping tissue, can prevent lateral decoupling loads from decoupling various components of the end effector assembly. In various instances, the end effector assembly is configured such that each component and sub-assembly is assemble-able and disassemble-able in one unique sequential manner. This would ensure that the system can be assembled in only one way which provides support and prevents inadvertent disassembly during assembly.

In various instances, one or more components of surgical stapling assemblies discussed herein can be 3D printed. More specifically, such components can be made using a graphite-based selective laser sintering process, which can be an additive manufacturing process allowing for complex geometries of parts while eliminating the need for expensive tooling. Specifically, thrust bearings and/or drive nuts of firing member assemblies can be manufactured using this process. In various instances, a drive nut can be 3D printed out of graphite and steel, for example. In at least one instance, between about 1% and about 5% of the component comprises graphite and the rest of the component comprises a steel material. In such an instance, the exposed graphite of the drive nut, for example, could provide a degree of lubrication within the threaded connection, for example.

Figure 82:
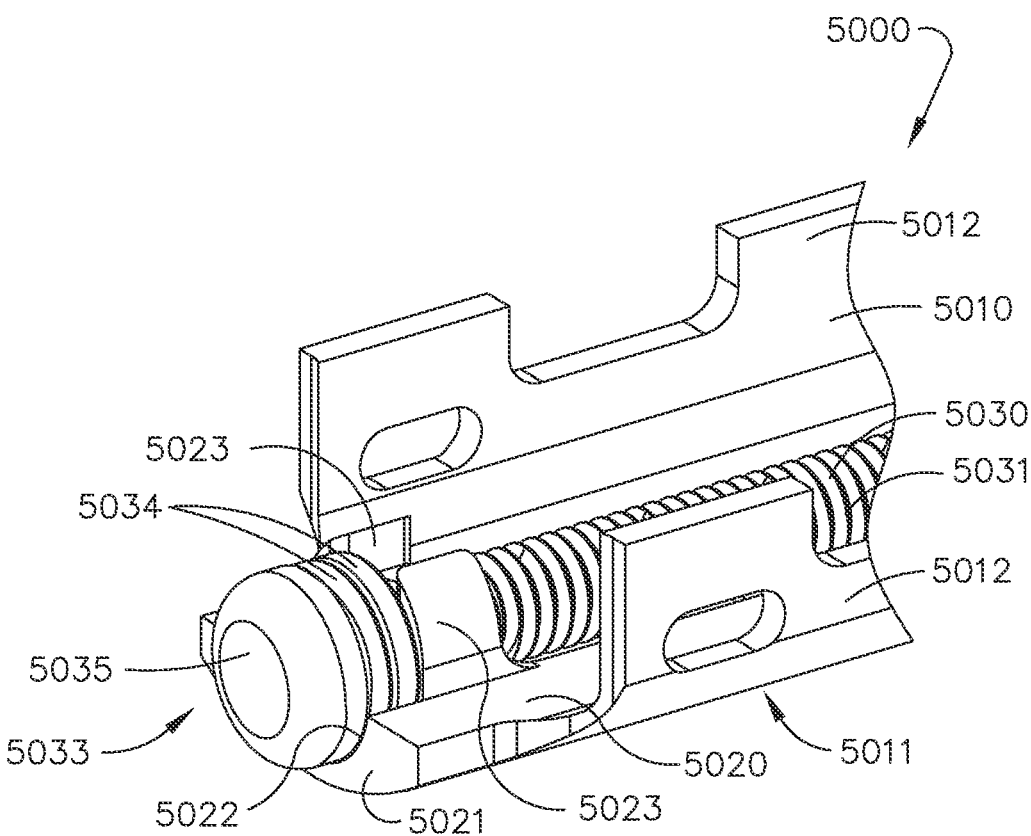
FIG. 82 is a perspective view of a surgical stapling assembly comprising a staple cartridge, a cartridge channel, and a firing drive assembly, wherein the staple cartridge is hidden, in accordance with at least one aspect of the present disclosure.
Figure 83:
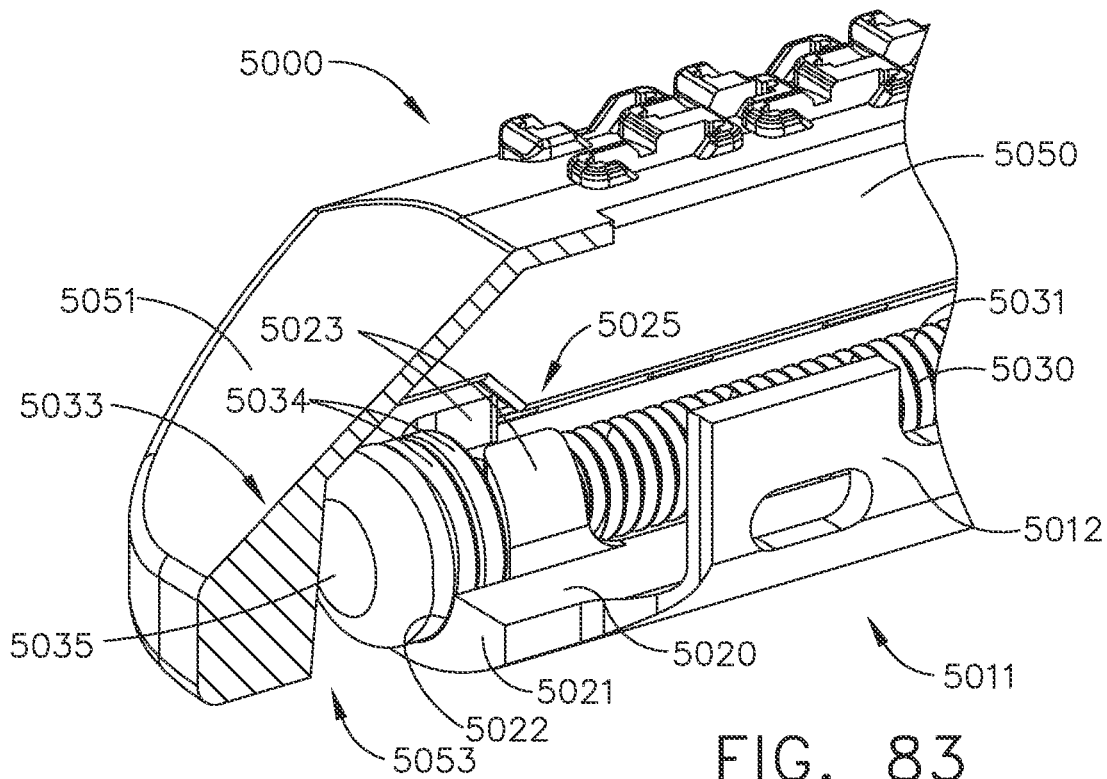
FIG. 83 is a partial cross-sectional perspective view of the surgical stapling assembly of FIG. 82, in accordance with at least one aspect of the present disclosure.
Figure 84:
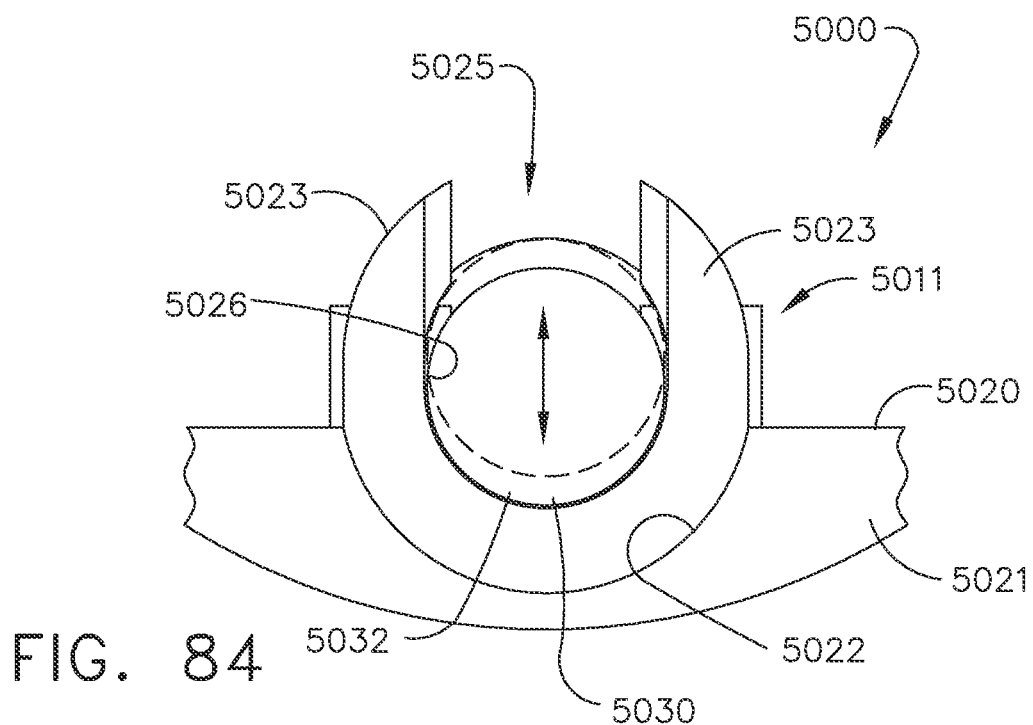
FIG. 84 is an elevation view of a portion of the cartridge channel and the firing member assembly of FIG. 82, wherein a distal support head and pair of bushings are hidden, in accordance with at least one aspect of the present disclosure.

In various instances, firing member assemblies are configured to be driven by firing drive screws positioned within an end effector. The firing member assemblies and/or the firing drive screws can experience various loads during a firing stroke. For example, a firing member assembly can experience loads applied thereto by tissue as the firing member assembly is advanced through a firing stroke. The firing member assembly can be subject to various loads applied thereto by the firing drive screw itself. The firing member assembly can also experience loads generated by the engagement of camming flanges of the firing member assembly with a cartridge channel jaw and/or an anvil jaw. The firing drive screw can also be subject to various loads during various stages of use of an end effector assembly within which the screw is positioned. For example, the firing drive screw may be subject to bending loads owing to camming and/or clamping forces applied within the end effector assembly when the jaws are closed to clamp tissue and/or when tissue is further clamped by flanges of a firing member assembly during a staple firing stroke. Discussed herein are various arrangements configured to manage the various loads experienced by firing member assemblies and firing drive screws. Such arrangements can reduce binding of a firing drive screw with various components, for example. Such arrangements can also be employed with a closure drive system. For example, in various instances, an end effector assembly can comprise a separate closure drive screw configured to open and close a jaw relative to another jaw. In such instances, the closure drive screw can also be subject to various loads which may cause bending and/or binding with various drive components, for example FIGS. 82-84 depict a surgical stapling assembly 5000 comprising a cartridge channel 5010, a staple cartridge 5050 seated within the cartridge channel 5010, and a rotary drive assembly 5030 supported within the channel 5010. The cartridge channel 5010 comprises a distal portion 5011, a bottom 5020, and sidewalls 5012 extending vertically from the bottom 5020. The bottom 5020 comprises a distal end 5021, an annular cradle slot 5022 defined in the distal end 5021 of the bottom, and a pair of arcuate flanges 5023 extending upwardly from the bottom 5020. The arcuate flanges 5023 are configured to floatably support the rotary drive assembly 5030. Various features of the distal end 5021 comprise a distal mount, for example, of the drive screw 5031.

The rotary drive assembly 5030 comprises a threaded screw portion 5031 and a distal end 5033 supported by the distal portion 5011 of the cartridge channel 5010. The distal end 5033 of the rotary drive assembly 5030 comprises two thrust bearings, or bushings, 5034 for example, configured to contact the arcuate flanges 5023. The distal end 5033 further comprises a distal support head 5035 configured to support the thrust bearings 5034 against the arcuate flanges 5023. The distal support head 5035 may be formed using an orbital forming process on a distal end of a firing drive screw, for example. This forming process can take place, for example, after one or more bushings and/or bearings are positioned on the distal end of the firing drive screw.

The arcuate flanges 5023 define a float cavity 5025 therebetween in the distal portion 5011 of the cartridge channel 5010. A portion 5032 of the rotary drive assembly 5030 is configured to be supported within the float cavity 5025 such that the distal end 5033 of the rotary drive assembly 5030 is permitted to float within the float cavity 5025 upon deflection of the cartridge channel 5010, for example. In such an instance where the distal portion 5011 of the cartridge channel 5011 is deflected downwardly, the distal end 5033 of the rotary drive assembly 5030 can remain relatively unloaded by floating within the float cavity 5025. As can be seen in FIG. 84, the float cavity 5025 comprises a vertical slot portion 5026 configured to permit a predefined float distance, or vertical limit of floatation, of the drive assembly 5030 and/or portion 5032 of the rotary drive assembly 5030. The portion 5032 may be limited in its ability to float vertically within the float cavity 5025 by the flanges 5023, for example.

Embodiments are envisioned where there is no vertical limiting feature defined by the bottom 5020 of the cartridge channel 5010. In at least one instance, the annular cradle slot 5022 is configured to support the bushings 5034 and/or the distal support head 5035. In at least one instance, the annular cradle slot 5022 defines a lower vertical limiting feature, or stop, configured to prevent the distal end 5033 of the rotary drive assembly 5030 from floating below a certain threshold defined by contact between the bushings 5034 and/or 5035 with the annular cradle slot 5022, for example. In at least one instance, the vertical slot portion 5026 and the flanges 5023 define an upper vertical limiting feature, or stop, configured to prevent the distal end 5033 of the rotary drive assembly 5030 from floating above a certain threshold defined by contact between the distal end 5033 and the flanges 5023.

As can be seen in FIG. 83, the staple cartridge 5050 comprises a distal nose 5051 defining a nose cavity 5053 therein. The nose cavity 5053 may provide space for the distal end 5033 of the rotary drive assembly to float within.

In at least one instance, a proximal end of the rotary drive assembly 5030 is fixed in place. In at least one instance, the proximal end of the rotary drive assembly 5030 is also configured to float relative to the cartridge channel 5010.

In at least one instance, a spring is provided at a proximal mounting location and/or distal mounting location of a firing drive screw within a cartridge channel, for example. The spring is configured to bias the firing drive screw into a neutral configuration. In at least one instance, the spring is configured to counteract bending loads applied to the firing drive screw. In at least one instance, one or more magnets are provided within a mounting location and a screw magnet of opposite polarity is provided on the firing drive screw at the mounting location. Such a configuration can bias the firing drive screw toward a neutral configuration as well as counteract bending loads applied to the firing drive screw. Such a spring may comprise a vertically deformable bushing, for example. In at least one instance, a coil spring is employed within the mounting location.

In various instances, the flexible floatation mounts described herein are configured to permit a limited vertical range of floatation of the rotary drive assembly relative to the cartridge channel. For example, a vertical floatation range of 0.0002-0.0003 inches can be permitted by the distal mounts described herein. In other instances, a vertical floatation range of 0.001 inches can be permitted and, in certain instances, of up to 0.0015 inches can be permitted by the flexible floatation mounts. The size of the vertical floatation range can be configured to avoid lateral loads being applied to the rotary drive assembly, which is well-suited for tension loads but may result in bending under lateral loads. Instead, the rotary drive assembly can float within the limited vertical range of floatation to ensure the rotary drive assembly is not laterally loaded. Even when thick and/or tough tissue is clamped between the jaws and the anvil is bowed in the clamped configuration, the vertical range of floatation can allow shifting of the rotary drive assembly and avoid lateral loads on the rotary drive assembly.

In at least one instance, flanges of a firing member assembly are configured to define the limited vertical range of floatation of a firing drive screw through the threaded connection between the firing member assembly and the firing drive screw. For example, an anvil-engaging flange may contact an upper portion of an anvil slot and/or a channel-engaging flange may contact an upper portion of a channel slot to provide an upper stop for the firing drive screw. Further to the above, the anvil-engaging flange may contact a lower portion of the anvil slot and/or the channel-engaging flange may contact a lower portion of the channel slot to provide a lower stop for the firing drive screw. In at least one instance, a drive nut cutout, drive cavity, and/or receptacle configured to receive a drive nut is configured to further define the vertical range of flotation of a firing drive screw.

Figure 85:
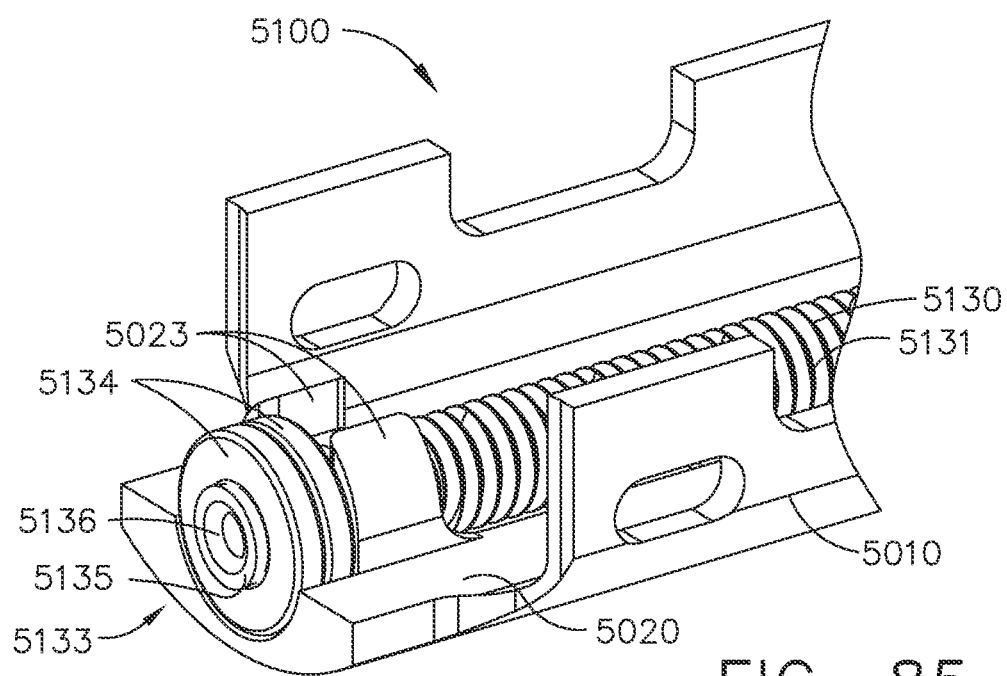
FIG. 85 is a perspective view of a surgical stapling assembly comprising a cartridge channel and a firing member assembly supported by support flanges of the cartridge channel, in accordance with at least one aspect of the present disclosure.

FIG. 85 depicts a surgical stapling assembly 5100 comprising the cartridge channel 5010 of the surgical stapling assembly 5000. The surgical stapling assembly 5100 comprises a rotary drive assembly 5130 comprising a threaded portion 5131 and a distal end 5133. The distal end 5133 comprises one or more bearings 5134 configured to support the distal end 5133 against the flanges 5023. The distal end 5133 further comprises a distal support head 5135 comprising a swaged screw end 5136. The swaged screw end 5136 may be externally swaged and/or internally swaged. The swaged screw end 5136 is configured to provide a distal bearing surface for the one or more bearings 5134. The rotary drive assembly 5130 is configured to float within the cartridge channel 5010 similar to the rotary drive assembly 5030.

Any suitable bushings and/or bearings can be employed with any of the various rotary drive assemblies and/or firing drive screws disclosed herein. In at least one instance, a compression bushing can be used at a proximal or distal end of a firing drive screw within a cartridge channel. Such a compression bushing can provide a compressive pre-load to a firing drive screw, for example, once installed in a cartridge channel. Such a compressive pre-load can prevent the firing drive screw from disengaging from any support elements supporting the firing drive screw in the cartridge channel. For example, a compression bushing can be used at one more ends of the firing drive screw to prevent the proximal end and/or distal end of the firing drive screw from disengaging from a corresponding support such as, for example, arcuate flanges extending from the cartridge channel.

A compressive pre-load can be induced by a spring, a longitudinal screw, and/or a rivet, for example, on a compression bushing. In such an instance, the compression bushing will tend to expand radially under a compressive pre-load. Such radial expansion can fill an annular cradle support and/or float cavity such as those discussed herein. This tendency for the compression bushing to fill such slots and/or cavities, for example, can help prevent the firing drive screw from longitudinally, laterally, and/or vertically de-seating from the support elements such as the arcuate flanges discussed herein.

In at least one instance, a bushing and/or bearing configure to support a rotary drive assembly disclosed herein comprises a flange extending radially outward therefrom. The flange is configure to be positioned on the side of the channel support flange opposite the distal support head of the firing drive screw. The radial flange can then be biased away from the channel support flange and, thus, the distal support head by a spring. In such an instance, the spring would push against the channel support flange and the radial flange of the bushing, for example. In such an instance, the radial flange and the spring can be configured to pull the distal support head into the channel support flange. In at least one instance, this pulling force applied to the distal support head can be configured to seat the distal support head such that the firing drive screw cannot be lifted directly out of the channel support flange without first pulling the firing drive screw distally and overcoming the force applied by the spring. Overcoming the force would then disengage the distal support head from the channel support flange only then allowing the firing drive screw to be lifted out of the channel support flange.

Further to the above, the spring can be compressed by a distal tightening screw configured to pull the distal support head proximally toward the channel support flange relative to the bushing comprising the radial flange, for example. Other embodiments are contemplated where a bearing is positioned distal to the channel support flange and then a nut is threaded onto the drive screw. The nut can then be turned to compress the bearing against the channel support flange.

Figure 86:
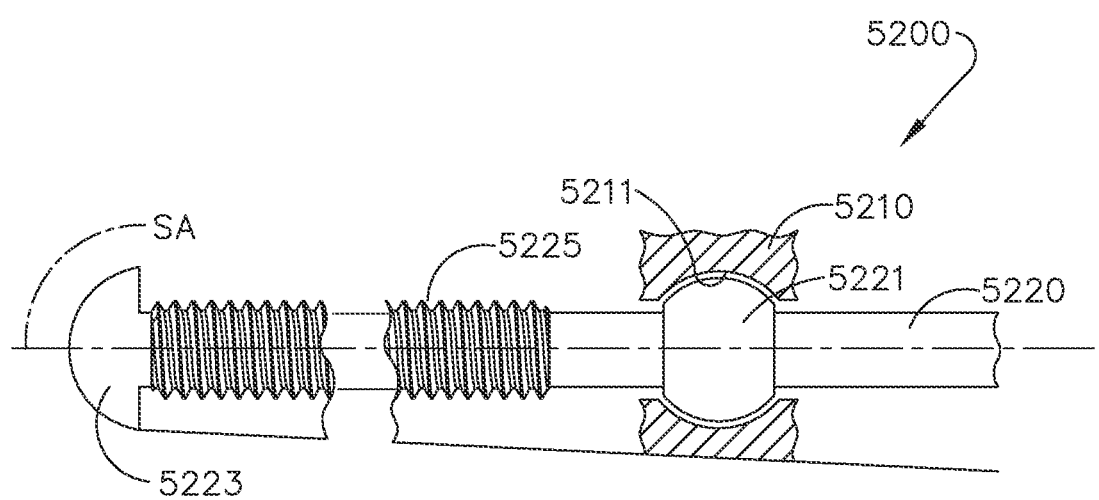
FIG. 86 is an elevation view of a portion of a surgical stapling assembly comprising a firing drive screw and a channel support, wherein a proximal end of the firing drive screw is pivotally mounted at the cartridge support, in accordance with at least one aspect of the present disclosure.
Figure 87:
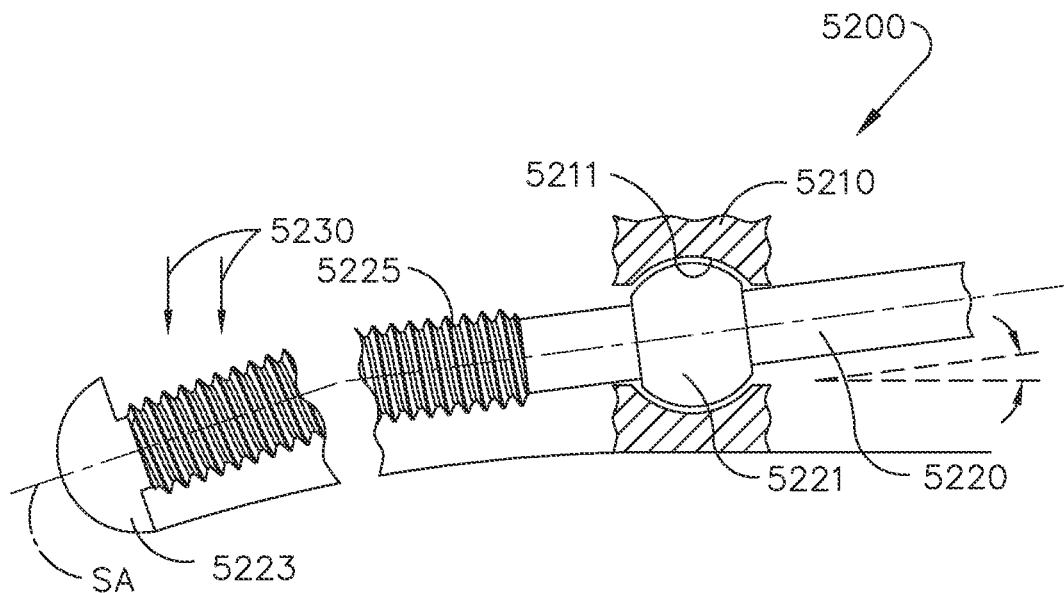
FIG. 87 is an elevation view of the portion of the surgical stapling assembly of FIG. 86, wherein the firing drive screw is illustrated in a loaded configuration, in accordance with at least one aspect of the present disclosure.

FIGS. 86 and 87 depict a surgical stapling assembly 5200 comprising a support channel 5210 and a firing drive screw 5220 configured to actuate a firing member assembly such as the firing member assemblies disclosed herein. The firing drive screw 5220 defines a screw axis SA. As discussed above, firing drive screws used within surgical end effector assemblies can be subject to bending loads. As can be seen in FIG. 87, arrows 5230 indicate a bending load being applied to a distal end 5223 of the firing drive screw 5220. The firing drive screw 5220 comprises a proximal ball joint 25221 mounted within a ball joint socket, or mount, 5211 of a channel support 5211. Such a configuration permits the firing drive screw 5220 to pivot relative to the channel support 5211 upon experiencing a bending load. In at least one instance, the ball joint 5221 and socket 5211 permit the firing drive screw 5220 to pivot without significantly bending the firing drive screw 5220. Bending can cause binding of the threaded portion 5225 and a firing member assembly, for example. The ball and socket joint can be finely tuned to permit a predefined amount of pivot so as to not permit the firing drive screw 5220 to pivot outside of the permitted predefined amount and possibly cause other issues within an end effector assembly. In at least one instance, the proximal mounting location of the firing drive screw 5220 comprises a radial and/or spherical shape to permit a slight rotation of the firing drive screw 5220 relative to the screw axis SA. Such a configuration can also prevent binding and/or gouging of the firing drive screw 5220 within the proximal mounting location.

In at least one instance, a proximal and/or distal end of a drive screw is support within a channel and/or anvil, for example, by way of more than one support flange extending from the channel and/or anvil. For example, the more than one support flange can comprise a plurality of flanges in series with each other. One or more corresponding thrust bearings of the drive screw can be configured to be supported against the more than one support flange. Such a configuration can help support the drive screw should the drive screw want to move proximally and distally, for example. In at least one instance, a separate thrust bearing is provided on the drive screw for each support flange extending from the channel and/or anvil, for example. In at least one instance, each thrust bearing is configured to engage only its corresponding support flange. In other instances, one thrust bearing is provided between two flanges where the one thrust bearing is configured to engage both flanges in a proximal direction and a distal direction. In such an instance, one or more additional thrust bearings can be provided proximal to both support flanges and/or distal to both support flanges. Such arrangements may provide multiple thrust surfaces as opposed to a single thrust surface for a drive screw.

In at least one instance, a thrust surface of a support flange, for example, comprises a recessed inner donut hole, for example. In such an instance, a thrust bearing of a drive screw can be configured to be received within the recessed inner donut hole. In at least one instance, a deformable thrust bearing is compressed into the recessed hole. In at least one instance, the deformable thrust bearing comprises a diameter which is greater than an outer diameter of the recessed hole. Such a configuration can provide additional support to the drive screw. In at least one instance, the deformable thrust bearing comprises a soft, low-density polyethylene washer. In at least one instance, the thrust bearing is compressed using an orbital forming process. In at least one instance, the thrust bearing can comprise a threaded washer, for example.

In various instances, springs and/or magnets can be integrated in various components of an end effector assembly to allow various components of the end effector assembly to float and/or move relative to each other under load. For example, springs and/or magnets can be integrated in proximal and/or distal mount locations where a firing drive screw is supported by a cartridge channel, for example. Another example includes integrating springs and/or magnets in a firing member assembly to permit a drive nut thereof to float relative to a primary body portion, for example.

FIGS. 88-91 depict a firing member assembly 5300 configured to push a sled and/or cutting member through a staple firing stroke within an end effector assembly. The firing member assembly 5300 comprises a primary body portion 5010 and a threaded drive nut 5350 configured to be threadably coupled to a firing drive screw. The drive nut 5350 is configured to apply axial drive forces to the primary body portion 5010 to push and pull the primary body portion 5010 through an end effector assembly. The primary body portion 5010 comprises an upper portion 5311 configured to engage a first jaw of the end effector assembly and a lower portion 5315 configured to engage a second jaw of the end effector assembly. The lower portion 5315 comprises a proximal portion 5316 and a distal portion 5320 each configured to non-threadably receive the firing drive screw therethrough. A drive nut cavity 5330 is defined between the proximal portion 5316 and the distal portion 5320 which is configured to receive the drive nut 5350 therein. The firing member assembly 5300 further comprises magnetic elements 5360 configured to couple the drive nut 5350 to the primary body portion 5310.

The magnetic elements 5360 can comprise cylindrical rods, or pins, and/or rectangular rods, or pins, for example. Nonetheless, one of the magnetic elements 5360 is attached to and spring loaded by a spring 5361 within a proximal channel 5363 defined in the proximal portion 5316. Another one of the magnetic elements 5360 is attached to and spring loaded by a spring 5361 within a distal channel 5365 defined in the distal portion 5320. To mount the drive nut 5350 to the body portion 5310, the magnetic elements 5360 are retracted in their respective channels 5363, 5365 by externally presented magnets 5370 (FIG. 90) which are configured to overcome the spring force applied to the magnetic elements by the springs 5361. Only then can the drive nut 5350 be inserted into the drive nut cavity 5330. Once the drive nut 5350 is in position, the externally presented magnets 5370 may be moved away from the magnetic elements 5360 to allow the springs 5361 to bias the magnetic elements 5360 inwardly toward the drive nut 5350.

Specifically, the magnetic elements 5360 are configured to reside within a corresponding proximal channel 5351 defined in the drive nut 5350 and a corresponding distal channel 5355 defined in the drive nut 5350. The channels 5351, 5355 comprise a width and/or diameter which is greater than the width and/or diameter of the magnetic elements 5360. This difference in size allows the drive nut 5350 to float relative to the primary body portion 5310. The amount of floatation of the drive nut 5350 relative to the primary body portion 5310 may be defined and limited, at least in part, by the difference 5371 in size of the magnetic elements 5360 and the channels 5351, 5355. In at least one instance, one of the width and/or height is substantially the same as the width and/or height of the magnetic elements 5360. Such a configuration will permit floatation of the drive nut in only one plane. For example, if the vertical height of the magnetic elements 5360 and the drive nut channels 5351, 5355 are substantially the same and the width of the drive nut channels 5351, 5355 are greater than the width of the magnetic elements 5360, the drive nut 5350 is permitted to float only horizontally, or laterally, with respect to the primary body portion 5310. On the other hand, where the widths are substantially the same and the vertical heights differ, the drive nut 5350 is permitted to float only vertically with respect to the primary body portion 5310. Any floatation may be ultimately limited by the size of drive screw ducts of the proximal portion 5316 and the distal portion 5320, as discussed in greater detail above.

In at least one instance, the channels, or pockets, 5363, 5365 may be machined into a metal primary body portion. In at least one instance, the channels, or pockets, 5351, 5355 may be part of an injection mold when manufacturing the drive nut 5350. In at least one instance, the magnetic elements 5360 can comprise steel pins, for example. In at least one instance, the arrangement discussed above can reduce the need for exact alignment of an internal threaded channel defined in the drive nut to be coupled with the firing drive screw with corresponding drive screw ducts of the primary body portion. In such an instance, if the internal threaded channel is molded slightly off center with respect to the corresponding drive screw ducts of the primary body portion, the magnetic element arrangement discussed above can permit the drive nut 5350 to float into alignment with the primary body portion 5310. The flotation of the drive nut 5350 may also help prevent binding of the drive nut 5350 and a firing drive screw, for example. In at least one instance, a third degree of motion can be controlled and defined by the proximal portion 5316 and distal portion 5320 which can define the amount flotation, if any, which is permitted along a longitudinal axis relative to the primary body portion 5310.

In various instances, a firing drive screw can be configured so as to provide a compliant drive screw which can accommodate various loads experienced by the firing drive screw and reduce the likelihood of drive screw binding, for example. Such a compliant drive screw can automatically adapt and/or conform under different loaded conditions, for example. Such compliance may result in changing the shape of the drive screw itself, as discussed in greater detail below.

Figure 93:
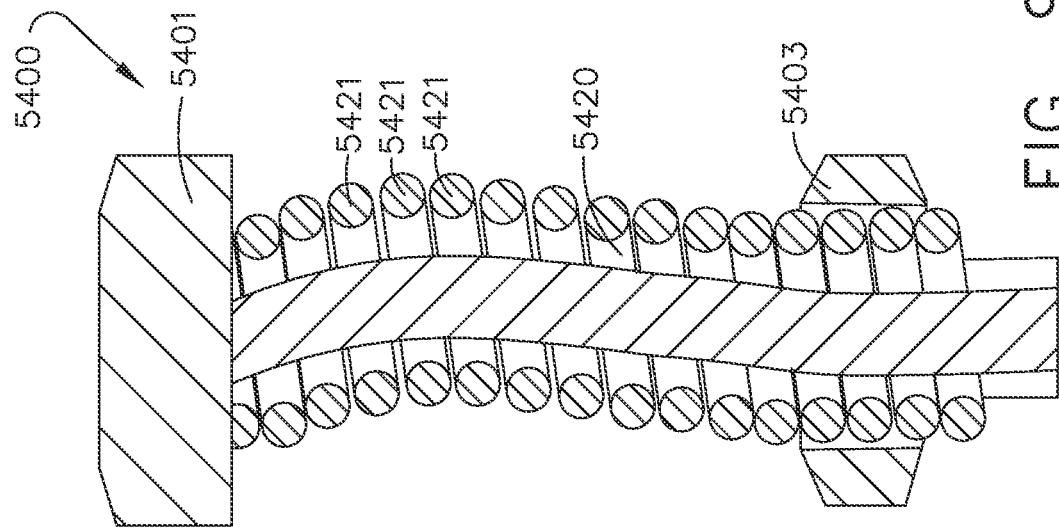
FIG. 93 is a cross-sectional schematic of the flexible firing drive screw of FIG. 92, in accordance with at least one aspect of the present disclosure.
Figure 92:
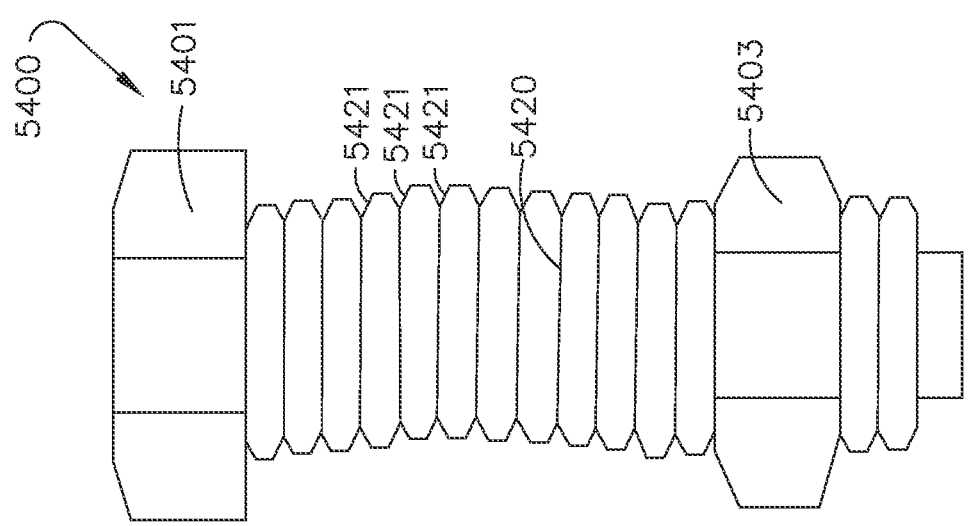
FIG. 92 is an elevation view of a flexible firing drive screw comprising a flexible core member and an outer helical member, in accordance with at least one aspect of the present disclosure.

FIGS. 92 and 93 depict a firing drive screw 5400 configured to automatically adapt under load. The firing drive screw 5400 comprises a cable or primary core member 5410 comprising a proximal end 5401 and a distal end 5403. The distal end 5403 may comprise a flange portion extending directly therefrom and/or a press fit thrust bearing, for example. The firing drive screw 5400 also comprises a spring or helical member 5420 defining individual threaded sections 5421 configured to provide a threaded interface for a threaded firing member assembly, for example. The primary core member 5410 comprises a flexible material such that the primary core member 5410 can flex and adapt its shape under load. Along with the primary core member 5410, the helical member 5420 also comprises a flexible material such that the helical member 5420 can flex along with the primary core member 5410 under load. This flexibility of the core member 5410 and the helical member 5420 allows the individual threaded sections 5421 to shift relative to each other. Each individual threaded section 5421 can shift relative to one another. However, the threaded sections 5421 can be configured to shift semi-independently. Such a configuration can permit slight shifting of each member 5421; however, all of the threaded sections 5421 are part of the single helical member 5420 so shifting of one threaded section 5421 can cause some shifting of one or more adjacent helical members and so on. This can also be referred to as splaying of the threaded sections 5421 when the firing drive screw 5420 is under load. The firing drive screw 5420 can reduce the likelihood of drive screw binding under load. In various instances, the primary core member 5410 and the helical member can comprise different materials. Although the schematic cross-sectional view of FIG. 93 depicts a space or gap between the inside diameter of the helical member 5420 and the outside diameter of the primary core member 5410, in other instances the inside diameter of the helical member 5420 is in contact and/or abutting the outside diameter of the primary core member 5410.

Figure 94:
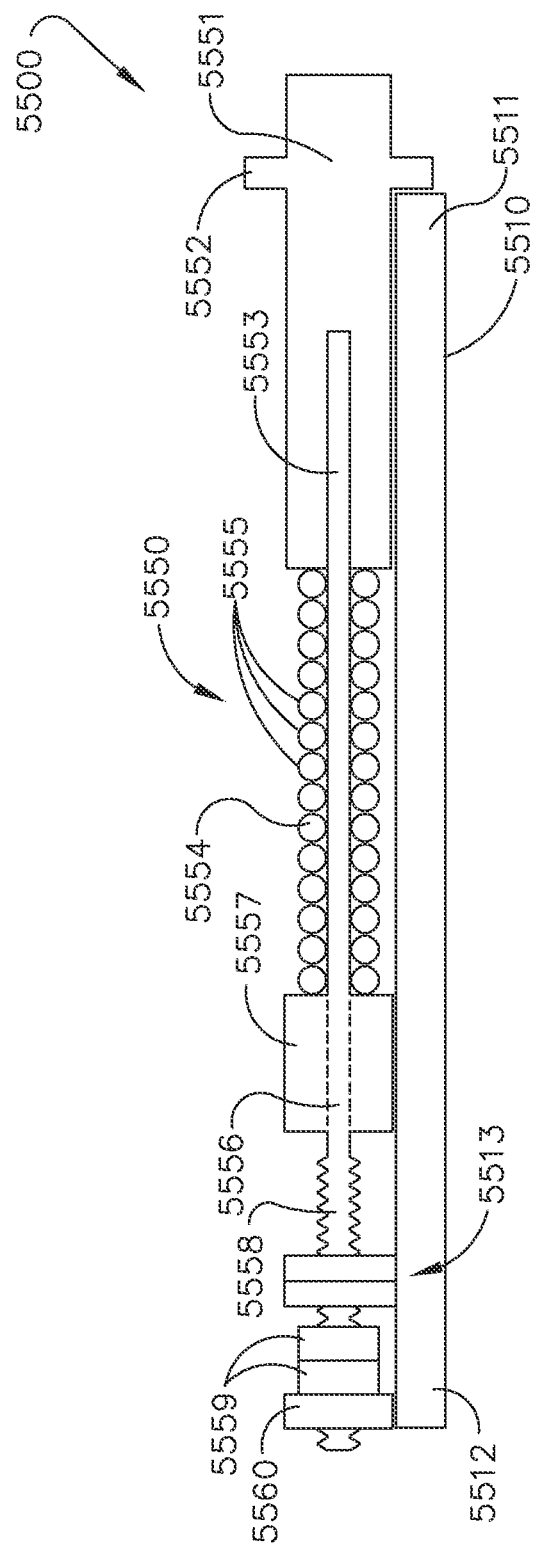
FIG. 94 is a schematic representation of a firing assembly comprising a flexible firing drive screw, in accordance with at least one aspect of the present disclosure.

FIG. 94 is a schematic representation of a firing assembly 5500 comprising a flexible firing drive screw 5550. The firing drive screw 5550 may comprise many similarities to the firing drive screw 5400, for example, among other disclosed herein. The firing assembly 5500 comprises a firing drive screw 5550 mounted to a channel frame 5510. A proximal drive member, or solid bushing, 5551 of the firing drive screw 5550 comprises a flange 5552 configured to be supported by a proximal end 5511 of the channel frame 5510. A distal portion 5556 of the firing drive screw 5550 is configured to be support by a distal support flange 5513 extending from the channel frame 5512. The firing drive screw 5550 further comprises a flexible core member 5556 and a helical member 5554 surrounding the flexible core member 5556 and defining threaded sections, or regions, 5555. The helical member 5554 is attached to the proximal drive member 5551 and a sleeve/plug 5557 is fixedly attached to the distal portion 5556 of the firing drive screw 5550. For example, proximal drive member 5551 can be swaged onto the flexible core member 5556 of the firing drive screw 5556. The distal portion 5556 comprises a threaded section 5558, bushings 5559, and a distal nut 5560 threadably coupled to the threaded section 5558. A pair of bushings 5559 are positioned proximal to the distal nut 5560 in the socket and can sandwiched between the distal nut 560 and the distal support flange 551 (see, e.g. bearings 5034 in FIG. 82).

In at least one instance, the inner diameter of the helical member 5554 is configured to surround and contact an outer diameter of the flexible core member 5553. The helical member 5554 may comprise a type of coil spring, for example. The flexible core member 5553 may comprise a flexible cable, for example. In at least one instance, the helical member 5554 is manufactured with an inner diameter that is less than the outer diameter of the flexible core member 5553. In such an instance, the helical member 5554 can be counter-rotated to increase its inner diameter for assembly onto the flexible core member 5553. Once the helical member 5554 is positioned on the flexible core member 5553, the helical member 5554 can be released. Once the helical member 5554 is released, it will bias back to its neutral, non-loaded configuration and synch, or pinch, itself tightly to the flexible core member 5553. In at least one instance, the helical member 5554 is welded to the flexible core member 5553 at various locations along the length of the flexible core member 5553.

In at least one instance, the nut 5560 is configured to be tightened and/or loosened to provide the desired configuration of the helical member 5554. Tightening and/or loosening the nut 5560 can also allow for adjustment of tension of the flexible core member 5553. Adjusting the tension of the flexible core member 5553 can directly correlate to the amount of deflection permitted of the flexible core member 5553 along its length under load. A tighter cable may permit less flexion than a looser cable, for example. This can be tuned during manufacturing to a desired tension, for example. Embodiments are envisioned where it is tuned differently for different size cartridges and/or surgical stapling systems requiring different firing forces, for example.

In various instances, a firing drive screw is provided that is configured to minimize plastic deformation thereof under various loads. Such a firing drive screw can comprise variations in cross-sectional geometry along its longitudinal length. Such variations can result in a portion of a firing drive screw which is more flexible than an adjacent portion of the firing drive screw. The more flexible portion of the firing drive screw may be subject to greater bending loads than the less flexible portion, for example. Variations of the firing drive screw can be located at a proximal portion, an intermediate portion, a distal portion, or any combination thereof. Locations of variations can depend on application and areas of the firing drive screw subject to the highest loads, for example.

Figure 95:
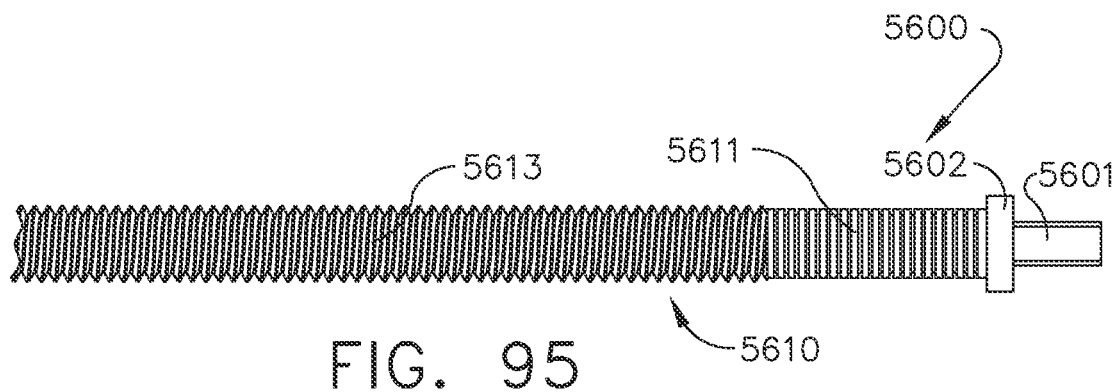
FIG. 95 is an elevation view of a portion of a firing drive screw for use with a surgical stapling assembly, in accordance with at least one aspect of the present disclosure.

FIG. 95 depicts a firing drive screw 5600 configured to be used with a surgical stapling assembly such the surgical stapling assemblies discussed herein. The firing drive screw 5600 comprises a proximal driven end 5601 configured to be attached to a rotary drive shaft. The firing drive screw 5600 also comprises a proximal flange 5602 configured to be supported within a frame component of an end effector assembly, for example. The firing drive screw 5600 comprises a screw shaft 5610 comprising a primary threaded portion 5613 and a proximal necked down portion 5611. The proximal necked down portion 5611 comprises a smaller cross-sectional diameter than the primary threaded portion 5613. Such a variation in the cross-sectional diameter can permit slight bending of the necked down portion 5611 to reduce the over bending effect on the primary threaded portion 5613. Reducing the bending effect on the primary threaded portion 5613, where a firing member assembly is configured to be threadably driven proximally and distally relative thereto, can reduce the likelihood of drive screw binding in the section of the firing drive screw 5600 engaged with the firing member assembly. In at least one instance, a firing member assembly is also configured to threadably travel through the necked down portion 5611; however, in at least one instance, high drive forces may not be required through the length of the stroke that consists of the necked down portion 5611.

Figure 96:
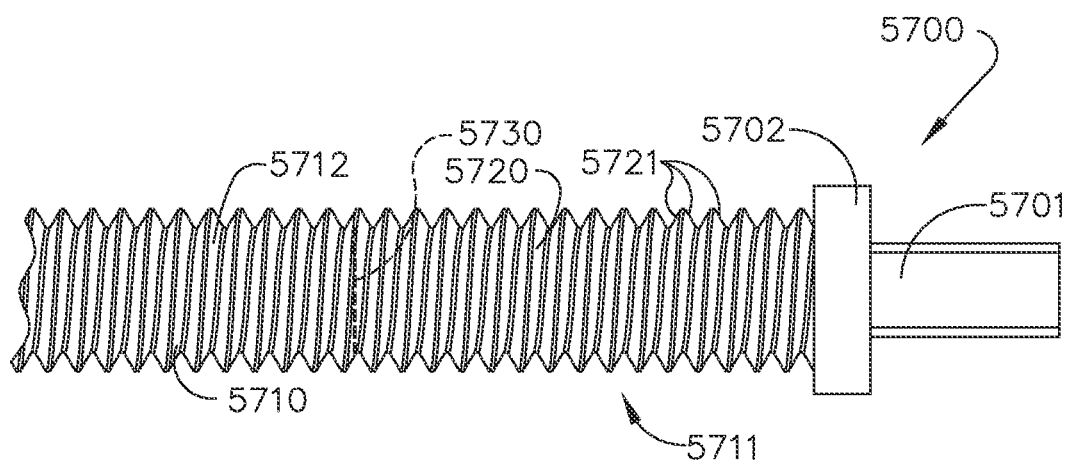
FIG. 96 is an elevation view of a portion of a firing drive screw for use with a surgical stapling assembly, wherein the firing drive screw comprises an overmolded section of threads, in accordance with at least one aspect of the present disclosure.
Figure 97:
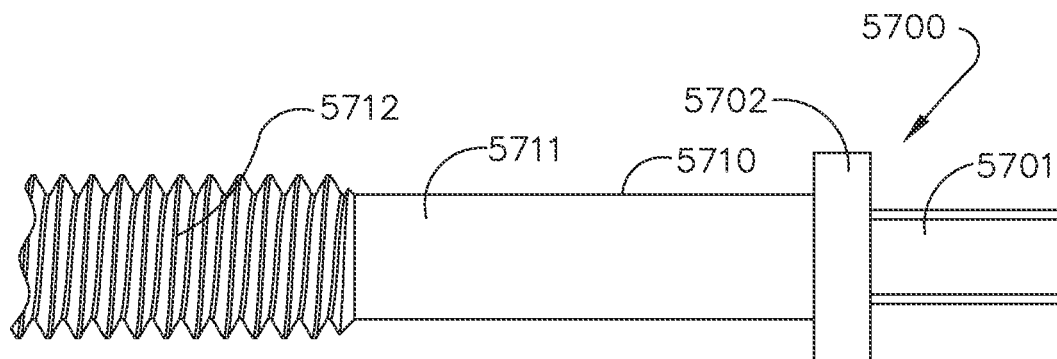
FIG. 97 is an elevation view of a portion of the firing drive screw of FIG. 96, wherein the overmolded section of threads are removed for clarity, in accordance with at least one aspect of the present disclosure.

FIGS. 96 and 97 depict a firing drive screw 5700 comprising a proximal driven end 5701 and a mounting flange 5702. The firing drive screw 5700 further comprises a proximal section 5720 of threads 5721 which is overmolded and/or insert molded, for example, onto a proximal portion 5711 of a primary shaft 5710 of the firing drive screw 5700. The firing drive screw 5700 comprises a primary threaded portion 5712, which comprises a cross-sectional diameter which is greater than the diameter of the proximal portion 5711. As discussed above, the variation in cross-sectional diameter can permit flexion of the primary shaft 5710 and localize the flexion to the proximal portion 5711 specifically so as to reduce the likelihood of drive screw binding with a drive nut of a firing member assembly. The threads 5721 can consist of a polymer material while the primary shaft 5710 consists of a metallic material, for example. The threads 5721 can help maintain a consistent thread pattern along a travel stroke of a firing member assembly threadably coupled to the firing drive screw 5700.

In at least one instance, various portions along the length of a firing drive screw comprise overmolded plastic threaded sections, for example. In at least one instance, various overmolded portions can accommodate manufacturing tolerance differences between a drive nut of a firing assembly and a firing drive screw thread profile and, in certain instances, can provide a more lubricious threaded engagement surface, for example. In at least one instance, a central section, midway through a firing stroke, section of a firing drive screw comprises a varied cross-sectional profile.

FIGS. 98-100 depict various types of shaft couplings 5810, 5820, 5830 that can be used with a firing drive screw such as those firing drive screws disclosed herein. The shaft couplings 5810, 5820, 5830 can be positioned at any location along the length of a firing drive screw to provide a location intended to localize bending of the firing drive screw. The shaft couplings 5810, 5820, 5830 are configured to convert rotary shaft motion from one shaft to another shaft. The shaft couplings 5810 can introduce little to no backlash in the firing drive screw with which it is employed. The shaft couplings 5810, 5820, 5830 can permit a degree of angular misalignment of shafts owing to bending forces applied to a firing drive screw within an end effector, parallel misalignment of shafts, and/or axial movement of shafts, for example.

The shaft coupling 5810 may be a beam coupling, for example. The coupling 5810 comprises a proximal hub 5811 configured to be attached to a distal end of a portion of a firing drive screw, a distal hub 5813 configured to be attached to a proximal end of another portion of a firing drive screw, and helical cutouts 5815 configured to flex during scenarios of shaft misalignment.

The shaft coupling 5820 may be a bellow coupling, for example. The coupling 5820 comprises a proximal hub 5821 configured to be attached to a distal end of a portion of a firing drive screw, a distal hub 5823 configured to be attached to a proximal end of another portion of a firing drive screw, and a flexible corrugation portion 5825 configured to flex during scenarios of shaft misalignment.

The shaft coupling 5830 may be a curved jaw coupling, for example. The coupling 5830 comprises a proximal hub 5831 configured to be attached to a distal end of a portion of a firing drive screw, a distal hub 5833 configured to be attached to a proximal end of another portion of a firing drive screw, and a spider gear comprising teeth 5835. The spider gear can comprise of a softer material configured to flex between the hubs 5831, 5833 while retaining drive engagement between the spider gear, the proximal hub 5831, and the distal hub 5833.

In an end effector assembly, such couplings 5810, 5820, and 5830 can permit bending of a firing drive screw at the coupling itself and reduce bending within the threaded shafts themselves. As discussed herein, bending of a threaded shaft can cause binding of a firing drive screw and a firing member assembly which are threadably coupled to each other.

Figure 101:
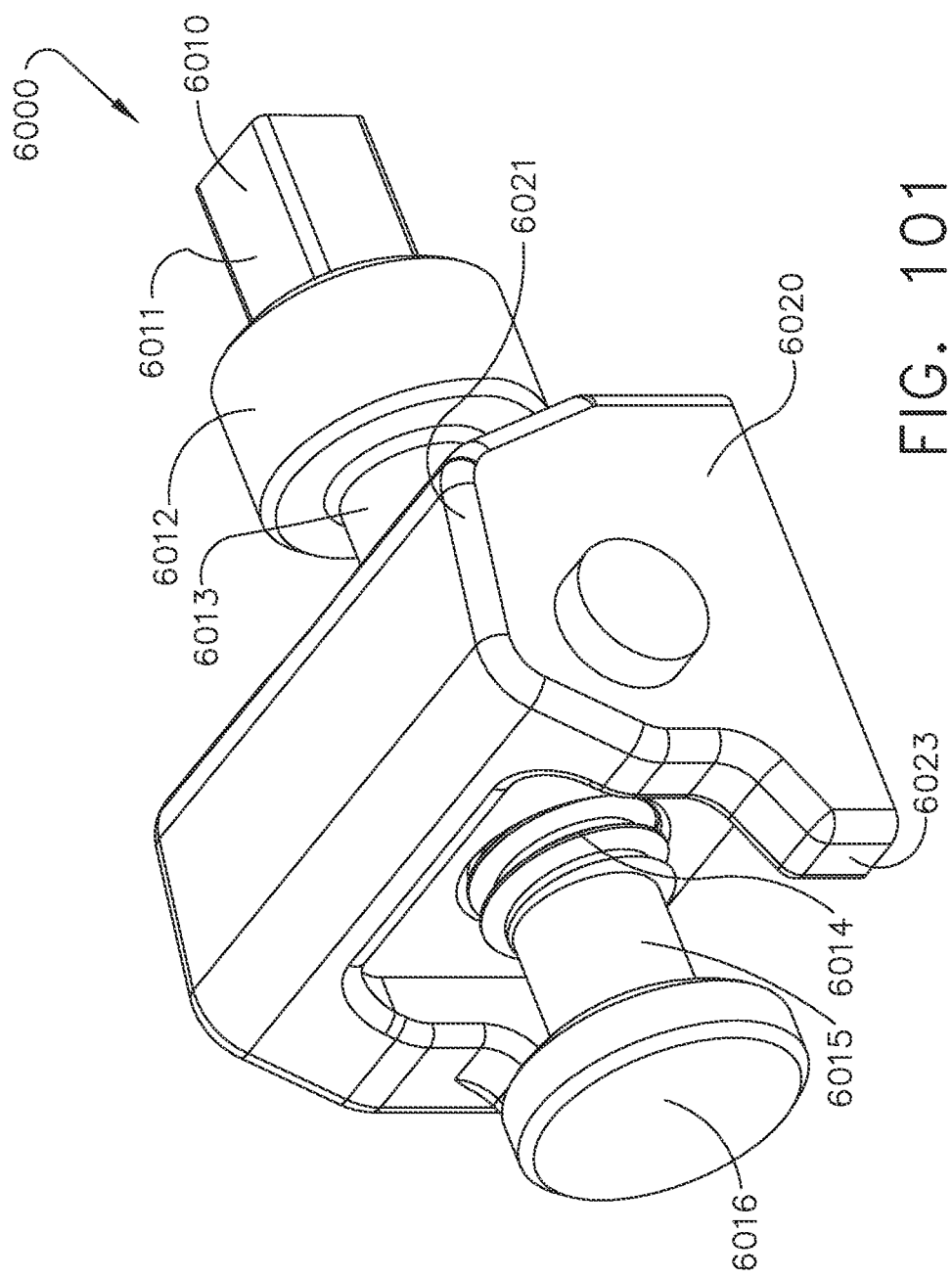
FIG. 101 is a perspective view of a closure drive assembly comprising a closure drive screw and a closure wedge configured to open and close a jaw of an end effector assembly, in accordance with at least one aspect of the present disclosure.
Figure 102:
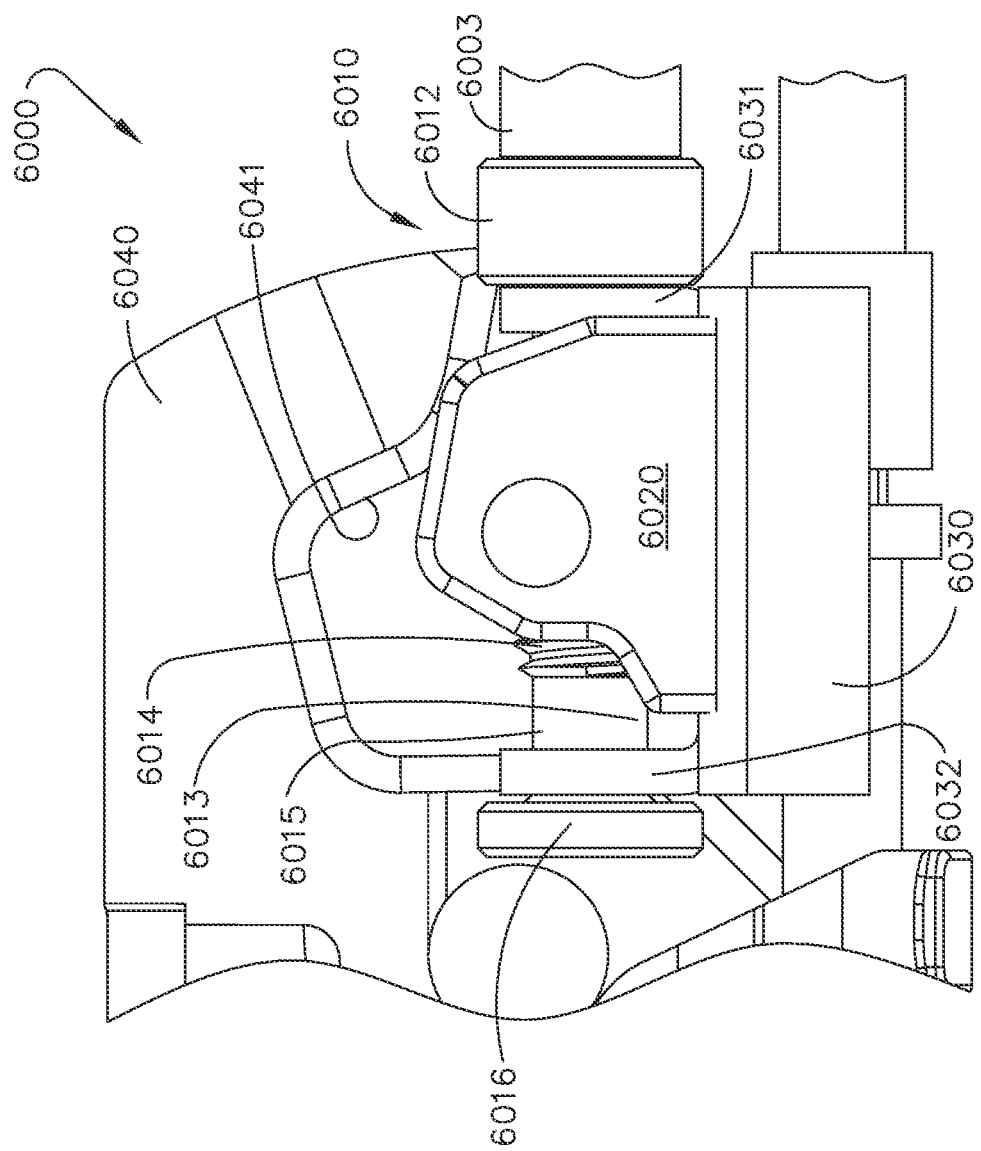
FIG. 102 is an elevation view of the closure drive assembly of FIG. 101 and an anvil, in accordance with at least one aspect of the present disclosure.
Figure 103:
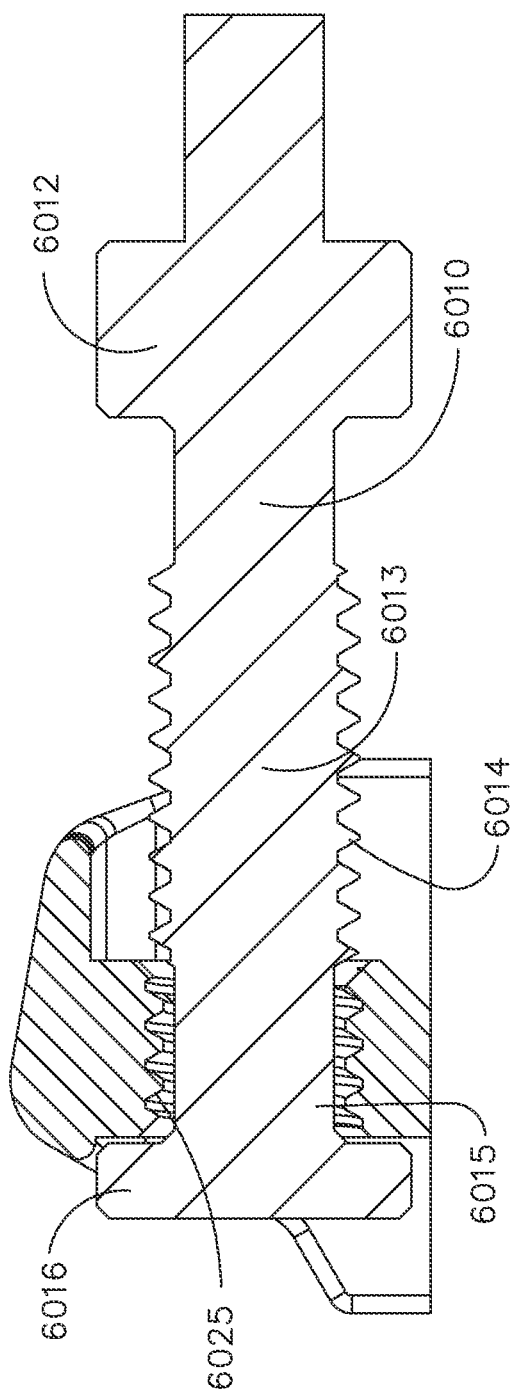
FIG. 103 is a cross-sectional elevation view of the closure drive assembly of FIG. 101, in accordance with at least one aspect of the present disclosure.

FIGS. 101-103 depict a closure drive assembly 6000 comprising a closure drive 6010 and a closure nut, or wedge, 6020 threadably coupled to the closure drive 6010. The closure nut 6010 is configured to open and close a jaw 6040 of the closure drive assembly 6000 relative to an opposing jaw with cam nubs 6023 and cam surface 6021, respectively. The closure drive assembly 6000 comprises a support element 6030 configured to support the closure drive 6010 thereon. The support element 6030 can be fixed to a channel retainer, for example. The support element 6030 comprises shaft seating flanges 6031, 6032 configured to support a closure drive screw 6013 of the closure drive 6010 therein. The closure drive 6010 further comprises a proximal driven portion 6010 configured to be driven by a rotary closure drive shaft, a thrust bearing 6012 configured to abut the flange 6031, and a distal thrust bearing portion 6016 configured to abut the flange 6032.

The closure drive screw 6013 comprises a threaded section 6014 and a distal non-threaded section 6015. The closure nut 6020 further comprises an internal threaded section 6025 configured to be threadably engaged with the threaded section 6014 such that the closure nut can be advanced proximally and distally along the threaded section to open and close the jaw 6003. In at least one instance, the closure nut 6020 is configured to be 3D printed onto the pre-manufactured closure drive 6010. The closure nut 6020 may comprise of a metal material and/or a polymer material, for example. The closure nut 6020 is configured to be printed around the distal non-threaded section 6015. Such an arrangement can allow the internal threaded section 6025 of the closure nut 6020 to be printed with an effective diameter which is slightly smaller than if the closure nut were printed directly around the threaded section 6015. Printed on the closure drive screw 6013, the closure nut 6020 can be effectively trapped between the bearing 6012 and bearing portion 6016 preventing inadvertent disassembly after manufacturing. In at least one instance, the bearing 6012 and the bearing portion 6016 are printed on the drive screw 6013 prior to printing of the closure nut 6020.

In at least one instance, one or more portions of the closure drive 6010 are also 3D printed. In such an instance, the closure drive 6010 can be 3D printed to be a size that is slightly larger than the desired size. For example, the closure drive 6010 can be scaled 0.5% larger than the desired size. In such an instance, various details of the closure drive 6010 requiring precise dimensions can be machined after the closure drive 6010 is printed. Such a manufacturing process can decrease machining waste and reduce the amount of time required to manufacture one or more parts, in certain instances. For example, a closure drive comprising a shaft with a non-threaded section and a threaded section where the non-threaded section comprises a diameter less than or equal to a minor diameter of the threaded section requires at least the removal of a ring of material with a width of the thread depth at the non-threaded section. 3D printing such a closure drive can allow the non-threaded section to be printed much closer to the minor diameter of the threads, albeit slightly larger for the reasons discussed above.

Figure 104:
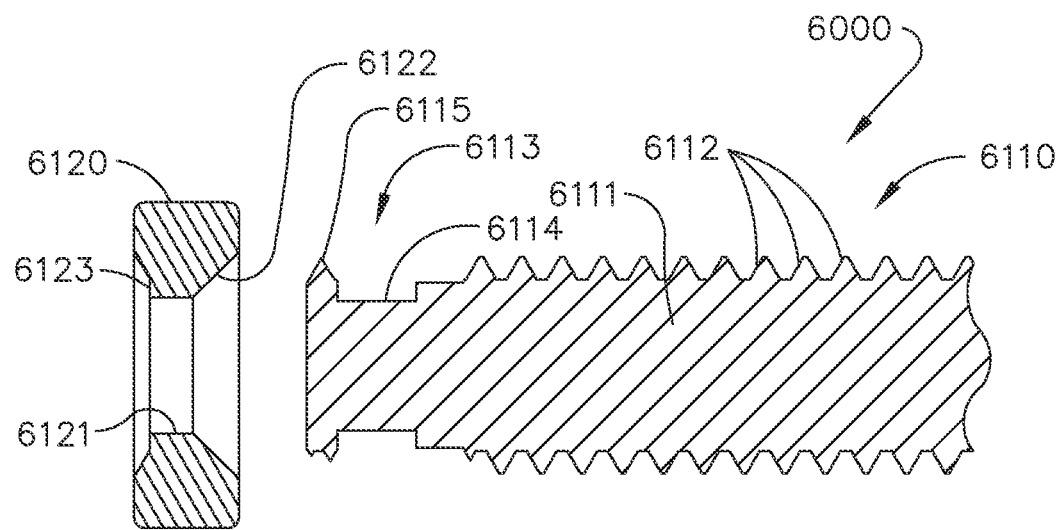
FIG. 104 is a cross-sectional elevation view of a closure drive comprising a drive screw and a restraining collar, wherein the restraining collar is not installed onto the drive screw, in accordance with at least one aspect of the present disclosure.
Figure 105:
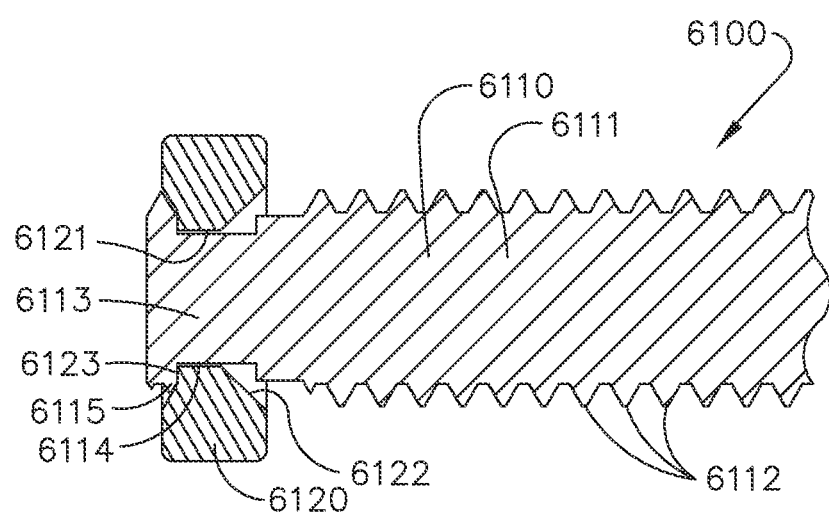
FIG. 105 is a cross-sectional elevation view of the closure drive of FIG. 104, wherein the restraining collar is installed onto the drive screw, in accordance with at least one aspect of the present disclosure.

FIGS. 104 and 105 depict a closure drive 6100 comprising a drive screw 6110 and a restraining collar 6120 configured to be secured to the drive screw 6110. The restraining collar 6120 can be similar to the distal thrust bearing portion 6016 of the closure drive 6010. The restraining collar 6120 can be configured to support the closure drive 6110 against a support flange, for example. The restraining collar 6120 may be referred to as a washer, a nut, and/or a flange, for example. The drive screw 6110 comprises a primary threaded portion 6111 comprising threads 6112. The primary threaded portion 6111 can be configured to drive a closure nut, for example, proximally and distally thereon to open and close a jaw of an end effector.

The drive screw 6110 further comprises a distal end 6113 comprising an annular slot 6114 and a thread 6115. The annular slot 6114 is configured to support the restraining collar 6120 therein. The thread 6115 is configured to permit the installation of the restraining collar 6120 as well as prevent the removal of the restraining collar 6120 from the drive screw 6110. The restraining collar 6120 comprises a proximal ramp surface 6122 defined therein. The proximal ramp surface 6122 is configured to permit the restraining collar 6120 to be screw onto the thread 6115 of the drive screw 6110 such that the restraining collar 6120 can clear the thread 6115 and fit an internal support surface 6121 to the annular slot 6114. Once installed onto the drive screw 6110, the thread 6115 resides distal to a distal, vertical, wall 6123 defined in the restraining collar 6120. The distal wall 6123 is configured to prevent the restraining collar 6120 from being pulled off of the distal end 6113 of the drive screw 6110.

In at least one instance, the drive screw 6110 is machined and/or 3D printed from a metallic material. In at least one instance, the restraining collar 6120 is molded and/or 3D printed from a polymer. In at least one instance, the restraining collar 6120 is constructed from a material which permits a degree of flexibility so as to allow the restraining collar 6120 to flex around and clear the thread 6115. A great degree of force may be required to install the restraining collar 6120 onto the drive screw 6110. In at least one instance, a greater degree of force may be required to remove the restraining collar 6120 from the drive screw 6110 at least owing the distal wall 6123.

In at least one instance, such a restraining collar can be used with a firing drive screw configured to threadably drive a firing member assembly. In various instances, such a restraining collar is used at a proximal end of a drive screw, a distal end of a drive screw, or both ends of a drive screw.

In at least one instance, a restraining collar is installed onto a drive screw with a lock washer. In such an instance, the thread and/or threads that the restraining collar is configured to be installed over can be configured so as to further tighten the locking engagement of the lock washer and the restraining collar when the drive screw is under load, for example. For example, each end of the restraining collar can comprise threads comprising opposite thread directions. For example, a proximal end of the restraining collar can comprise left handed threads and a distal end of the restraining collar can comprise right handed threads or vice-versa. Once installed, the restraining collar can be introduced to the opposite thread pattern such that, as the restraining collar is encouraged off of the distal end of the drive screw, the opposite thread pattern can serve to further tighten the locking engagement of the lock washer and restraining collar.

In at least one instance, a firing drive screw and/or closure drive screw can be 3D printed. In such instances, various features can be printed directly with the drive screw. For example, support flanges, bearings, restraining collars, etc., can be printed directly onto the drive screw. In at least one instance, one or more of these various features can comprise a different material than the drive screw itself. In such instances, the features comprising a material different than the drive screw can be printed directly onto the metal, for example, drive screw. In at least one instance, the various features comprise the same material as the drive screw. In such instances, the various metal, for example, features can be printed onto a metal drive screw using a process called directed energy deposition, for example. In at least one instance, various features can comprise a different material that, after printed, for example, onto the drive screw, can be welded to the drive screw.

In various instances, the use of different material features on the drive screw such as flanges, for example, can provide a lower coefficient of friction between the flange and a support structure as compared to a support structure and flange both comprising a metal material, for example. Manufacturing the features after the primary portion of the drive screw is machined, for example, can also reduce the manufacturing time and cost of the entire closure drive.

Figure 106:
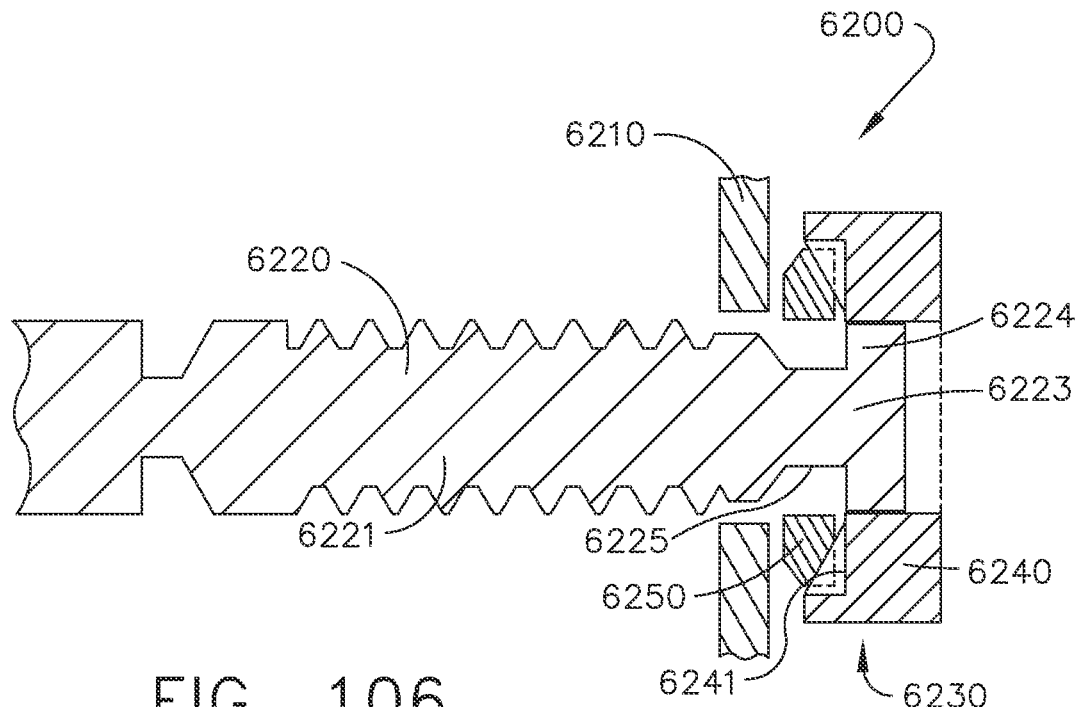
Figure 107:
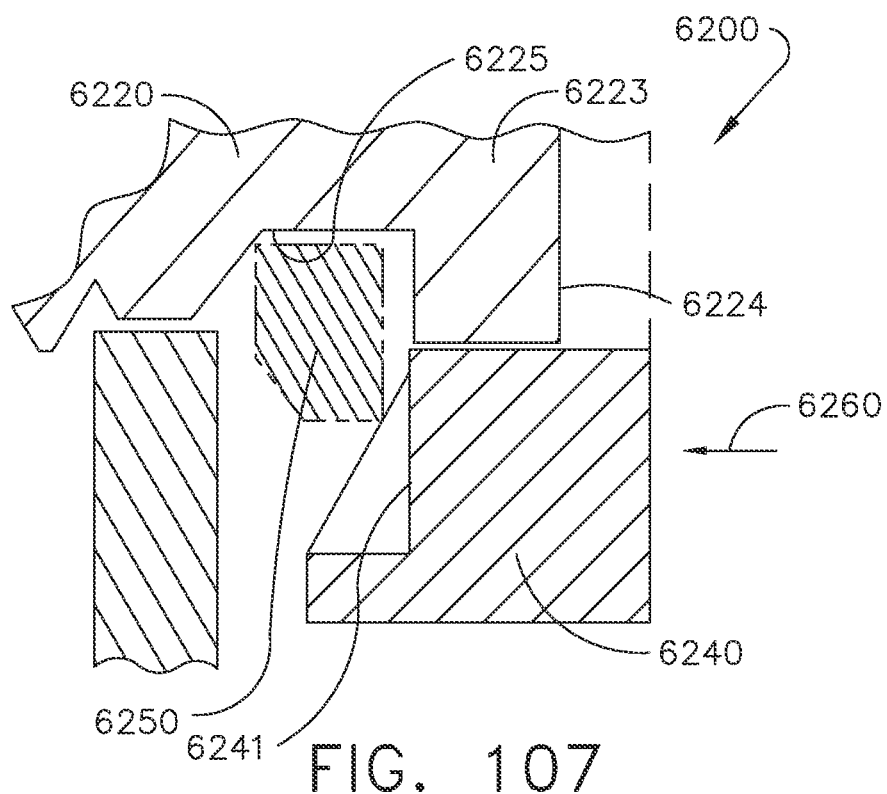

FIGS. 106 and 107 depict a drive assembly 6200 mounted to a channel flange 6210. The drive assembly 6200 comprises a drive screw shaft 6220 comprising a threaded portion configured to be threadably coupled to a firing member of a surgical stapling assembly. The drive screw shaft 6220 further comprises a distal end 6223 comprising a flanged end 6224 and an annular slot 6225. To secure the drive screw shaft 6220 to the channel flange 6210, a locking assembly 6230 is provided. The locking assembly 6230 comprises a distal nut 6240 and a locking member 6250. The locking member 6250 is configured to be locked into the annular slot 6225 to provide an abutment surface for the distal end 6223 of the drive screw shaft 6220 to be secured against. The distal nut 6240 can be threaded onto the distal end 6223 after the locking member 6250 is positioned on the drive screw shaft 6220 against the channel flange 6210. As the distal nut 6240 is tightened, or moved proximally toward the channel flange 6210, the locking member 6250 can comprise a flexible material so as to be urged into the annular slot 6225 by a ramped surface 6241 of the distal nut 6240. In at least one instance, the locking member 6250 is configured to mushroom and/or balloon in shape as pressure is applied thereto by the distal nut 6240. In at least one instance, the distal nut 6240 comprises a metal material. In at least one instance, the locking member 6250 comprises a deformable restraint for the drive screw shaft 6200. As a load is applied to the drive screw shaft in direction 6260, for example, the drive screw shaft 6220 is prevented from pulling proximally relative to the channel flange 6210 because of the expansion of the locking member 6250. The flanged end 6224 can transfer the load to the locking member 6250 which transfers the load to the channel flange 6210.

In at least one instance, a drive screw shaft such as those discussed herein can be manufactured using a subtractive manufacturing process such as, for example, a Swiss screw manufacturing process, for example. Such a manufacturing process can reduce material waste and manufacturing time of the drive screw, for example. Such a manufacturing process can also allow for high precision machining of such a relatively small drive screw where diameters along the length of such a drive screw shaft may vary and comprise relatively small differences in size.

In various instances, a locking member, such as the locking member 6250, for example, comprises a rubber material and/or a low-density polyethylene and/or polypropylene, for example. The material of the locking member can be selected based on its ability to shear under load such that, under a pre-determined threshold load, the locking member may shear to prevent other part failure within the system. Such a locking member can also automatically center a drive screw shaft as the locking member is installed by being uniformly restricted therearound.

In various instances, end effector assemblies such as those disclosed herein can comprise stackable supports configured to support one more drives of the end effector assembly. For example, one or more stackable supports are configured to support a closure drive and a firing drive which are non-concentric. The one or more stackable supports are configured to support one or more drives against a common frame element such as, for example, a channel jaw.

Figure 108:
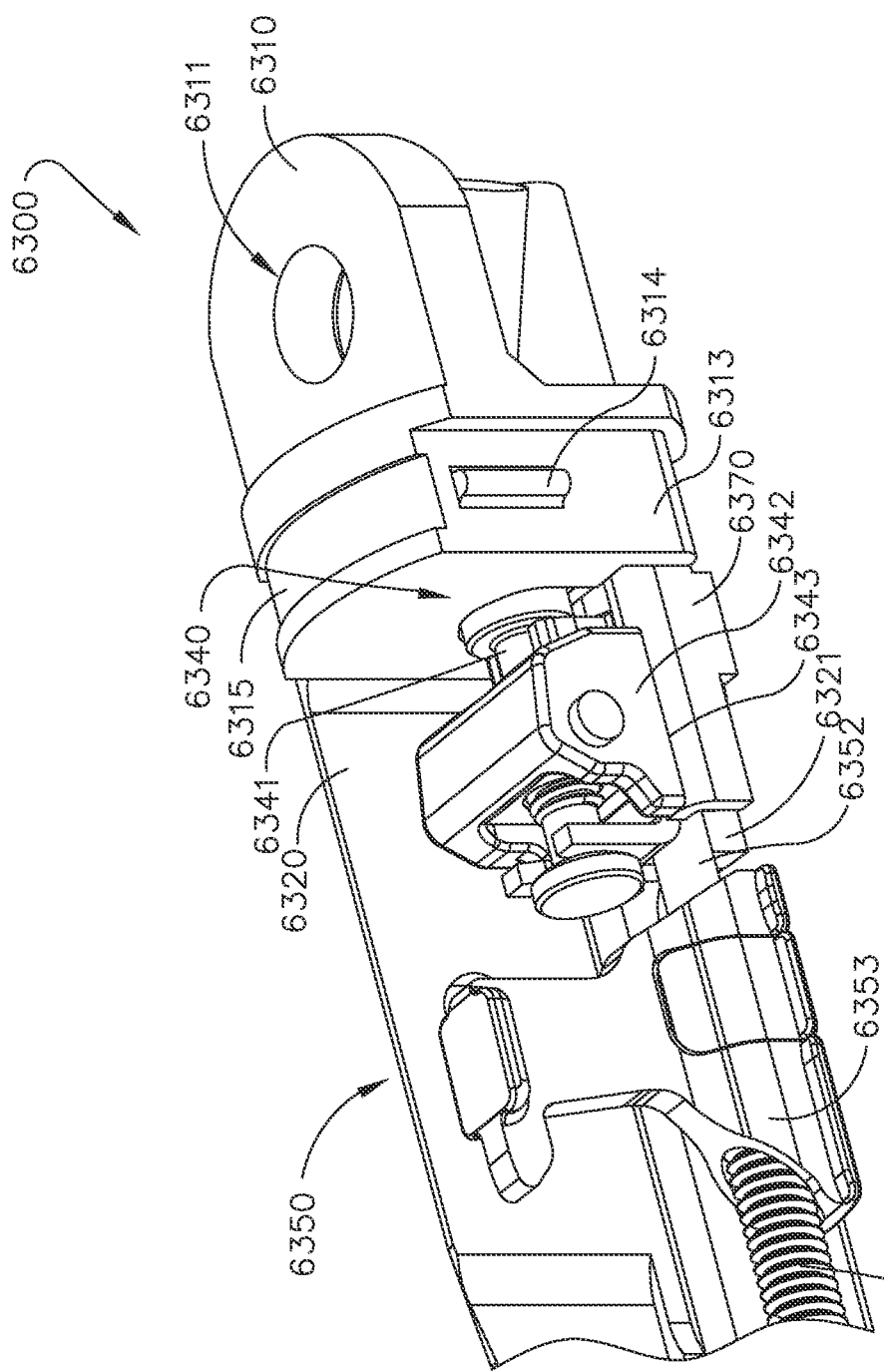
FIG. 108 is a perspective view of a surgical stapling assembly comprising a channel jaw, a closure drive, a firing drive, and support components positioned within the channel jaw and with portions of the surgical stapling assembly hidden for illustrative purposes, in accordance with at least one aspect of the present disclosure.
Figure 109:
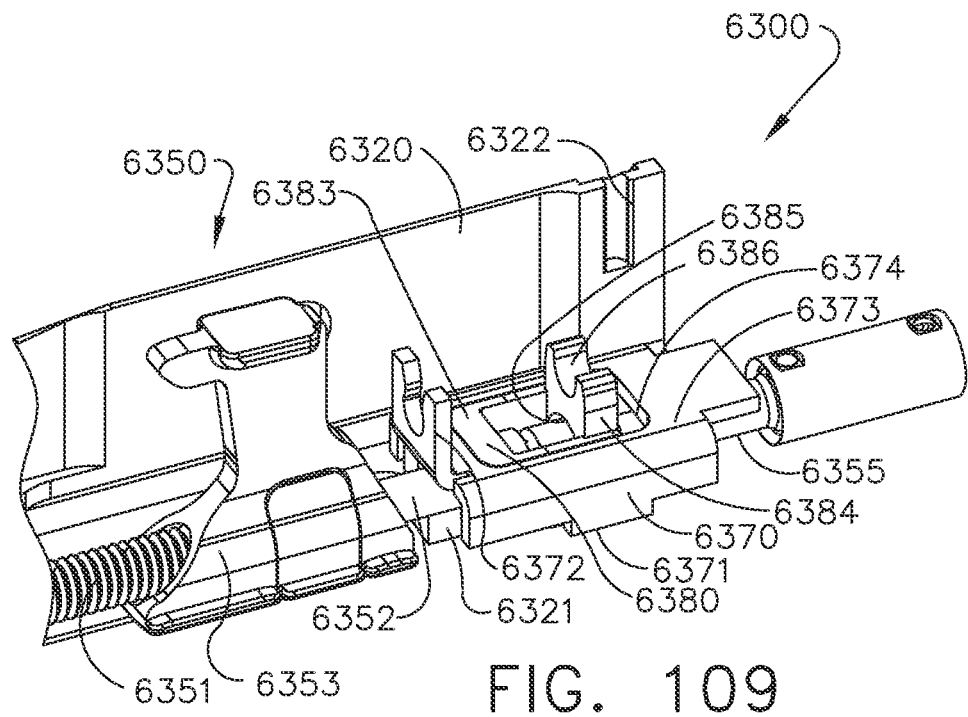
FIG. 109 is a perspective view of the surgical stapling assembly of FIG. 108, wherein various components are hidden for clarity, in accordance with at least one aspect of the present disclosure.
Figure 110:
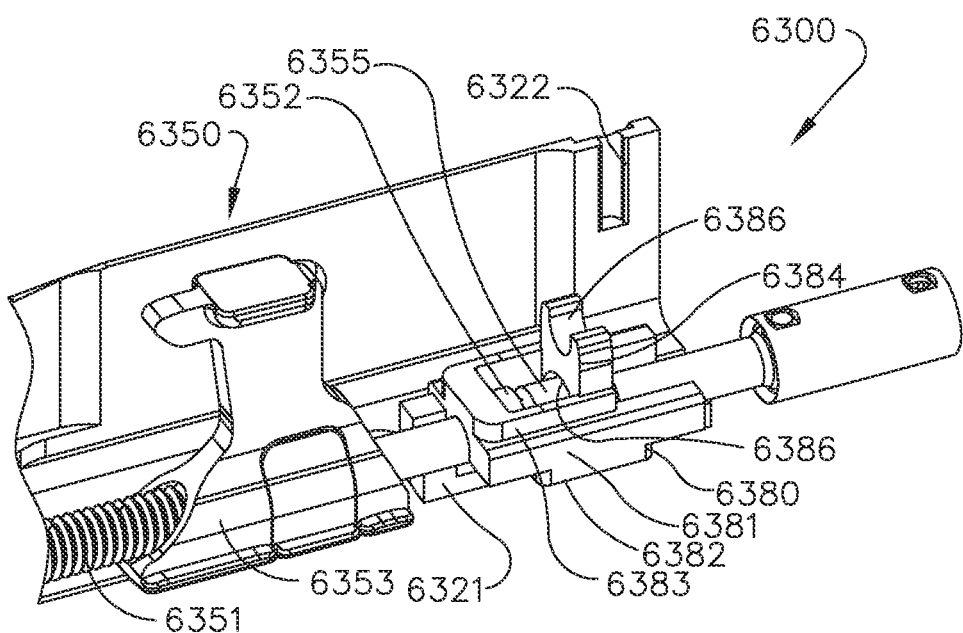
FIG. 110 is a perspective view of the surgical stapling assembly of FIG. 108, wherein various components are hidden for clarity, in accordance with at least one aspect of the present disclosure.

FIGS. 108-110 depict a surgical stapling assembly 6300. The surgical stapling assembly 6300 comprises a joint component 6310 and a channel jaw 6320. The channel jaw 6320 is attached the joint component 6310 by a securement band, or ring, configured to be received within an annular slot 6315 of the joint component 6310. The channel jaw 6320 comprises a bottom 6321 and vertical slots 6322 on each side of the channel jaw 6320 configured to receive tabs 6314 on each side of the joint component 6310. The joint component 6310 defines an articulation pin slot 6311 therein. The channel jaw 6310 may be articulated about an axis defined by the articulation pin slot 6311. The joint component 6310 is configured to receive one or more drive shafts therethrough to drive a closure drive 6340 and a firing drive 6350 of the surgical stapling assembly 6300.

The closure drive 6340 comprises a drive screw 6341 and a closure wedge 6342 threadably coupled to the drive screw 6341. The closure wedge 6342 is configured to be actuated proximally and distally with the drive screw 6341 to open and close a jaw opposing the channel jaw 6320 such as, for example, an anvil jaw. The firing drive 6350 comprises a drive screw 6351 comprising a proximal end 6352 and a firing member assembly 6353 configured to be threadably coupled to the drive screw 6351. The firing drive 6350 is configured to eject staples from a staple cartridge and cut tissue of a patient during a staple firing stroke as the firing member assembly 6350 is actuated along the drive screw 6351.

The closure drive 6340 and the firing drive 6350 are supported within the channel jaw 6320 by a lower support element, or mount, 6380 and an upper support element, or mount, 6370. The support elements 6370, 6380 may be stackable and support one or more elements of the closure drive 6340 and firing drive 6350. The lower support element 6380 comprises a lower portion 6381 and an upper portion 6383. The lower portion 6381 comprises a key 6382 configured to be received within a corresponding slot defined in the channel jaw 6320. Such a key and slot configuration can prevent the lower support element 6380 from moving relative to the channel jaw 6320. The upper portion 6383 comprises a shaft support 6384 comprising a lower arcuate support portion 6385 and an upper arcuate support portion 6386. The lower arcuate support portion 6385 is configured to receive an input shaft 6355 of the firing drive 6350 which is configured to couple and drive the proximal end 6352 of the drive screw 6351. The upper arcuate support portion 6386 is configured to receive and support the drive screw 6341 of the closure drive 6340.

The upper support element 6370 can be received on top of the lower support element 6380 in a track-like manner. For example, a corresponding cavity defined in the upper support element 6370 can be configured to receive the upper portion 6383 of the lower support element 6370 such that the upper support element 6370 fits and surrounds the upper portion 6383 upon installation. The upper support element 6370 further comprises a key 6371 configured to be received within a corresponding slot defined in the channel jaw 6320. The upper support element 6370 further comprises a top surface 6373 and a distal support tab 6372 configured to receive and support a portion of the drive screw 6341 therein. The top surface 6373 is configured to support a bottom surface 6343 of the closure wedge 6342 thereon. In at least one instance, a closure wedge track is defined on the top surface 6373, and the closure wedge 6342 can mate with and ride along the closure wedge track during proximal and distal travel. The upper support element 6370 further comprises a window 6374 configured to receive the upper portion 6383. Both the upper support element 6370 and the lower support element 6380 can be supported by the bottom 6321 of the channel jaw 6320.

In at least one instance, the upper and/or lower support elements 6370, 6380 can be supported within corresponding tracks defined in the channel jaw 6320 such that the upper and lower support elements 6370, 6380 are permitted a degree of longitudinal travel while still being supported by the channel jaw 6320. This can help during clamping, unclamping, and/or articulation of an end effector assembly where various drive shaft components are required to lengthen or shorten owing to the clamping, unclamping, and/or articulation motions and associated forces of the end effector assembly.

In at least one instance, the upper and/or lower support elements 6370, 6380 are manufactured from a single material into a single component. Such a configuration can be achieved using a metal machining process, for example. In at least one instance, the upper and/or lower support elements 6370, 6380 are manufactured separately. In such an instance, one of the upper and lower support elements 6370, 6380 comprises a machined component and the other of the upper and lower support elements 6370, 6380 comprises a sheet stamped component, for example. In at least one instance, both of the upper and lower support elements 6370, 6380 are stamped.

Various types of closure wedges and/or nuts are disclosed herein. The closure wedges can comprise a camming surface configured to close a jaw and one or more camming surfaces configured to open the jaw. In various instance, angles of the corresponding cam surfaces can comprise steeper angles relative to the engaging surface of the jaw which they cammingly engage. The camming surfaces can be tuned such that the drive force required from a corresponding closure drive screw is minimal while maintaining more than sufficient closure drive cam forces.

Figure 111:
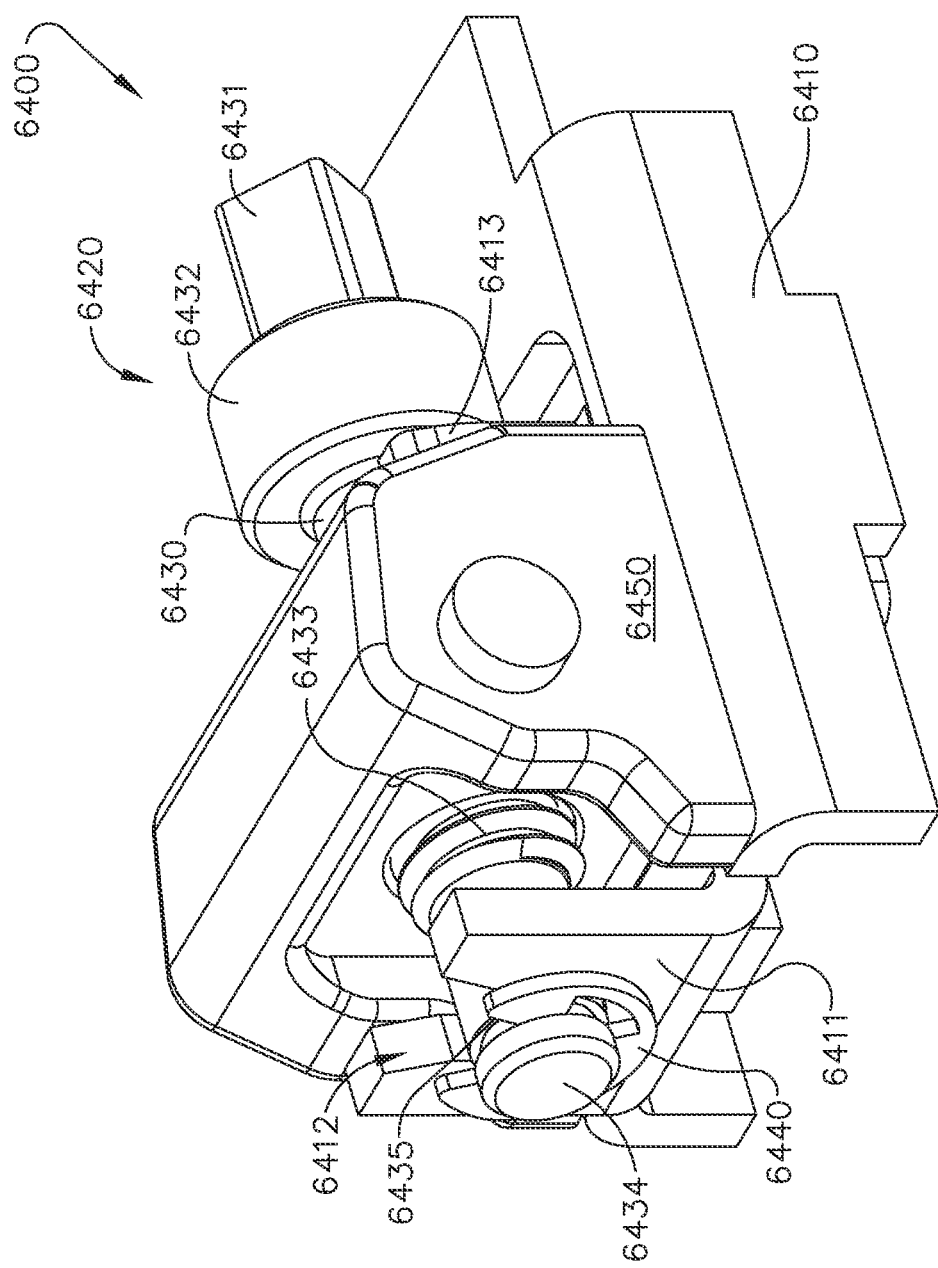
FIG. 111 is a perspective view of a closure drive assembly comprising a closure drive and a support element, in accordance with at least one aspect of the present disclosure.
Figure 112:
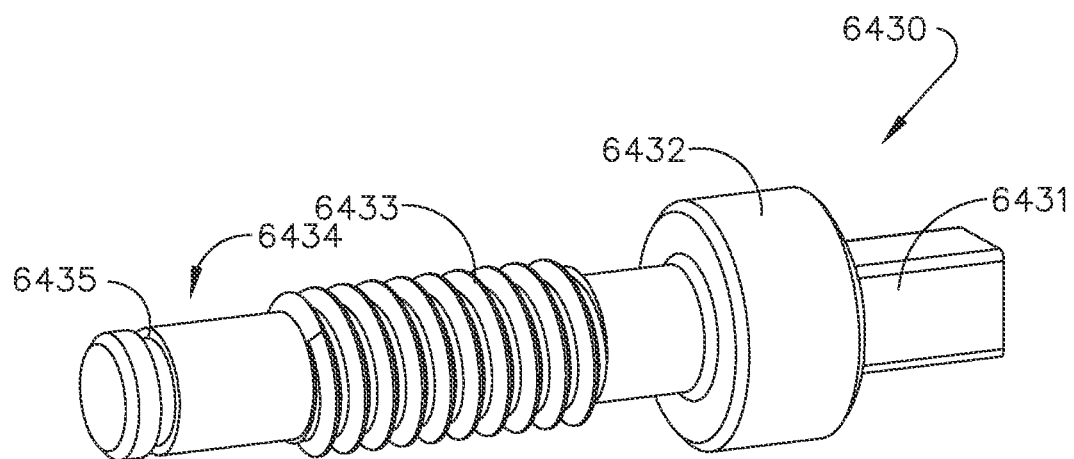
FIG. 112 is a perspective view of a drive screw shaft of the closure drive assembly of FIG. 111, in accordance with at least one aspect of the present disclosure.
Figure 113:
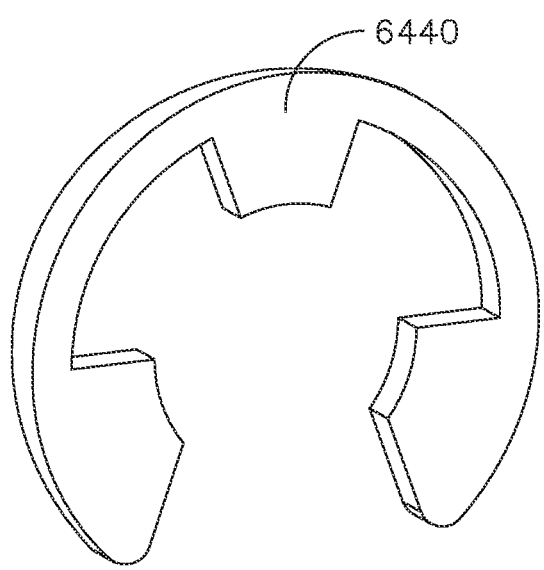
FIG. 113 is a perspective view of a retention clip of the closure drive assembly of FIG. 111, in accordance with at least one aspect of the present disclosure.
Figure 114:
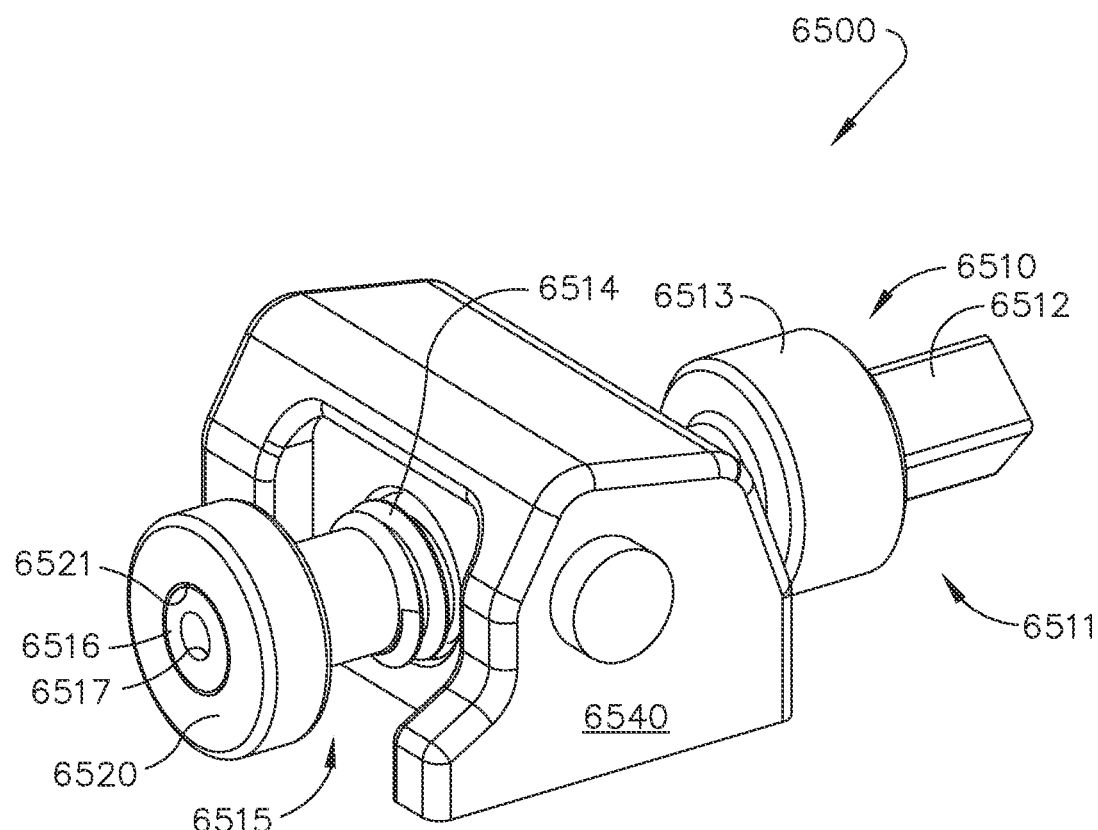
FIG. 114 is a perspective view of a closure drive comprising a drive screw shaft and a closure drive nut, in accordance with at least one aspect of the present disclosure.
Figure 115:
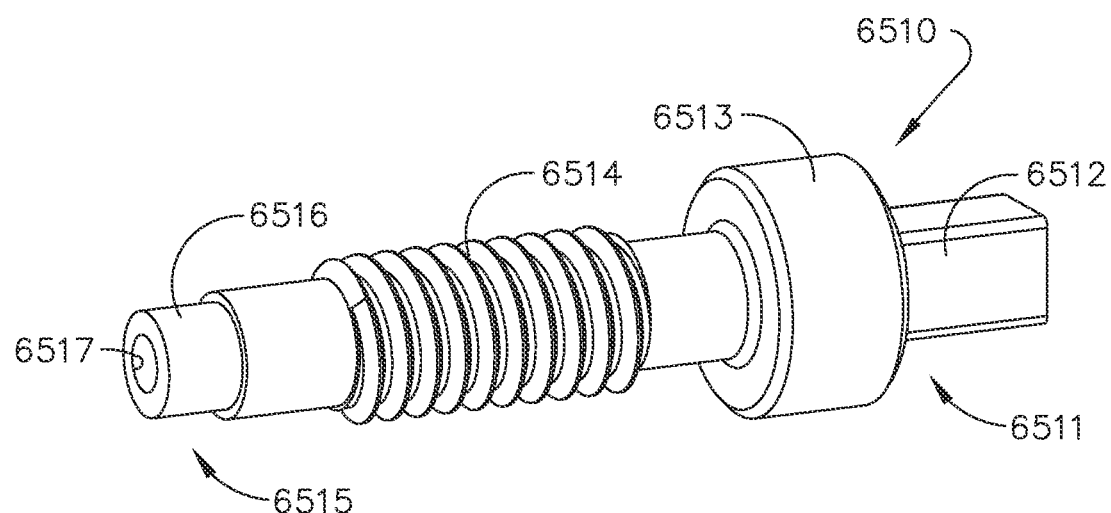
FIG. 115 is a perspective view of the drive screw shaft of FIG. 114, in accordance with at least one aspect of the present disclosure.

FIGS. 111-113 depict a closure drive assembly 6400 configured to open and close a jaw of an end effector assembly. The closure drive assembly 6400 comprises a jaw support element 6410 and a closure drive 6420 supported by support flanges 6411, 6413 of the jaw support element 6410. The closure drive 6420 comprises a drive screw shaft 6430 comprising a proximal end 6431 configured to be rotated by a rotary drive shaft, a proximal bearing portion 6432 configured to prevent the drive screw shaft 6430 from moving distally relative to the flange 6413, and a threaded portion 6433 configured to be threadably coupled to a closure wedge 6450. The drive screw shaft 6430 further comprises a distal end 6434 supported within flange support slot 6412 of the flange 6411 and secured to the flange 6411 by way of a clip 6440. The clip 6440 is configured to be received within a clip slot 6435 defined in the distal end 6435 of the drive screw shaft 6430. The clip 6440 is configured to prevent the drive screw shaft 6430 from moving proximally relative to the flange 6411. The clip 6440 may comprise an e-clip, for example. However, any suitable clip, retention clip, and/or retention ring, may be used. In at least one instance, the closure wedge 6450 may be threaded onto the drive screw shaft 6430 from the distal end 6434.

FIGS. 114-117 depict a closure drive 6500 comprising a drive screw shaft 6510 and a closure drive nut, or wedge, 6540 configured to open and close a jaw of an end effector assembly. The drive screw shaft 6510 comprises a proximal end 6511 and a distal end 6515. The proximal end 6511 comprises a driven portion 6512 configured to be rotated by a rotary drive shaft, a proximal bearing portion 6513, and a threaded portion 6514 configured to be threadably coupled to the closure wedge 6540. The distal end 6515 comprises an attachment section 6516 comprising a diameter less than the diameter of the drive screw shaft 6510 immediately proximal to the attachment section 6516. The attachment section 6516 is configured to receive a locking member, or radial washer 6520, thereon.

Figure 116:
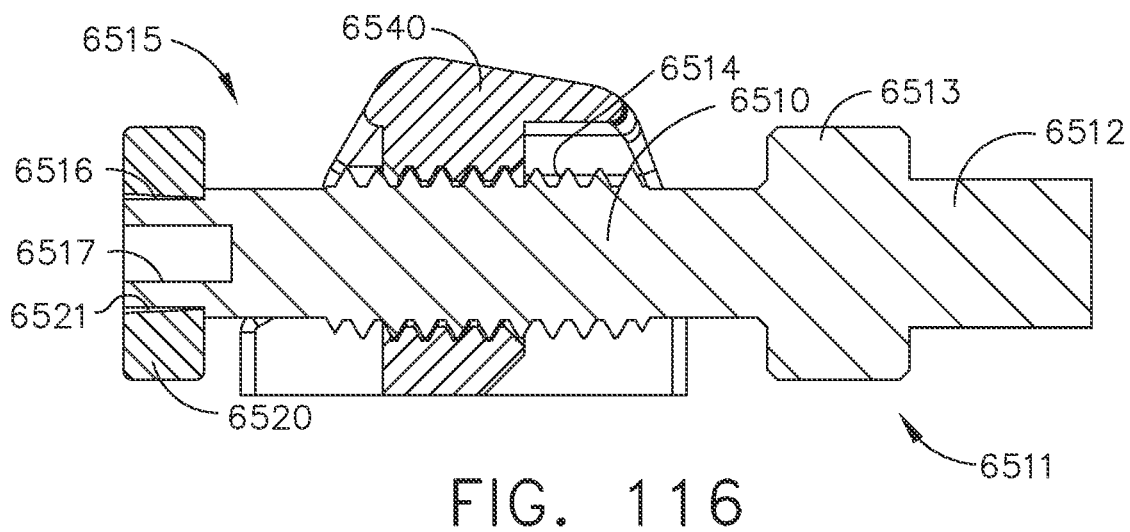
FIG. 116 is a cross-sectional elevation view of the closure drive of FIG. 114, wherein a distal end of the drive screw shaft is illustrated in a pre-formed configuration, in accordance with at least one aspect of the present disclosure.
Figure 117:
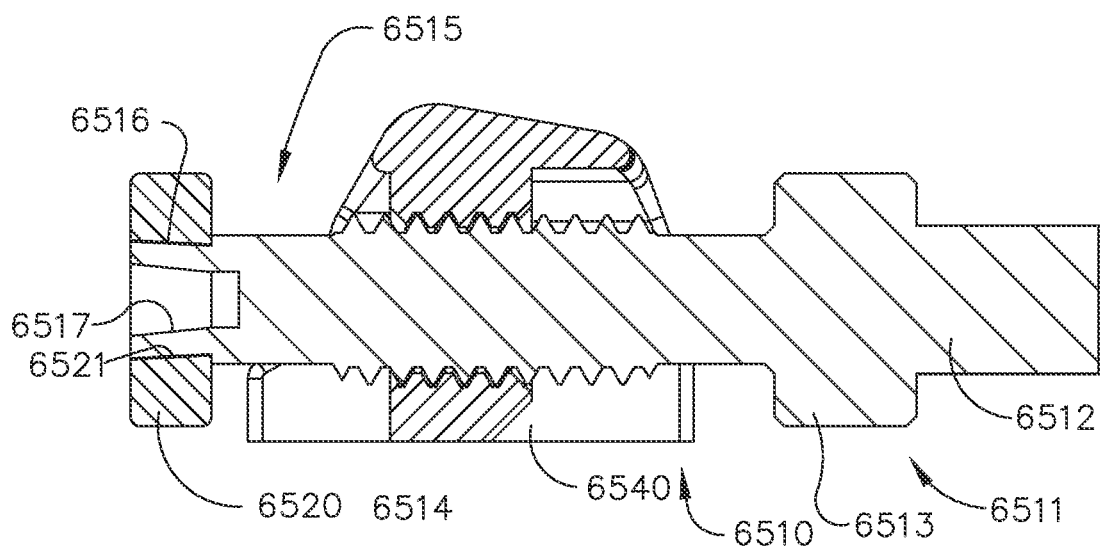
FIG. 117 is a cross-sectional elevation view of the closure drive of FIG. 114, wherein the distal end of the drive screw shaft is illustrated in a formed configuration, in accordance with at least one aspect of the present disclosure.
Figure 118:
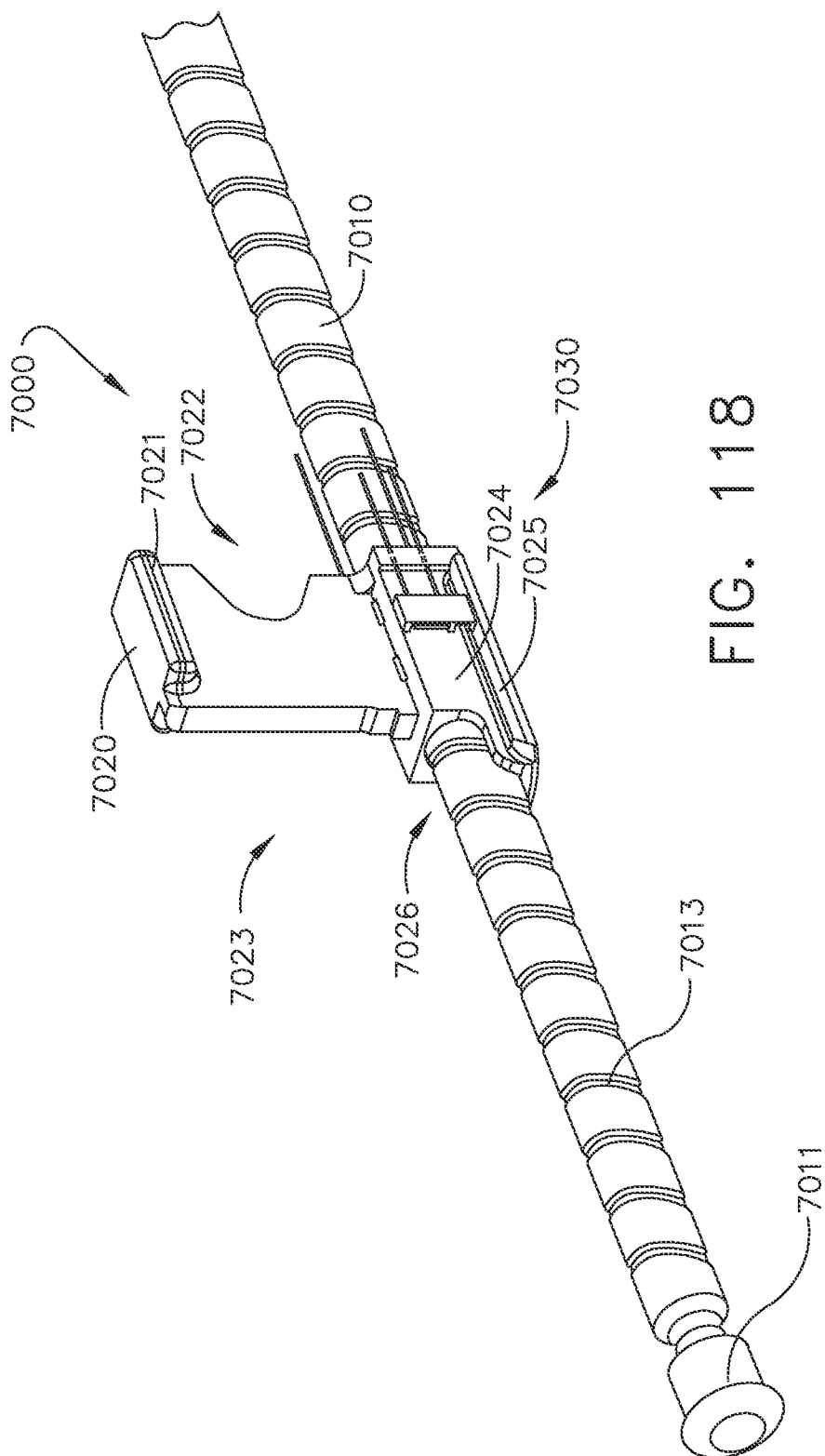
FIG. 118 is a perspective view of a firing drive assembly comprising a rotary firing shaft, a firing member threadably coupled to the rotary firing shaft, and a bailout configured to disengage the threaded engagement between the rotary firing shaft and the firing member, in accordance with at least one aspect of the present disclosure.
Figure 119:
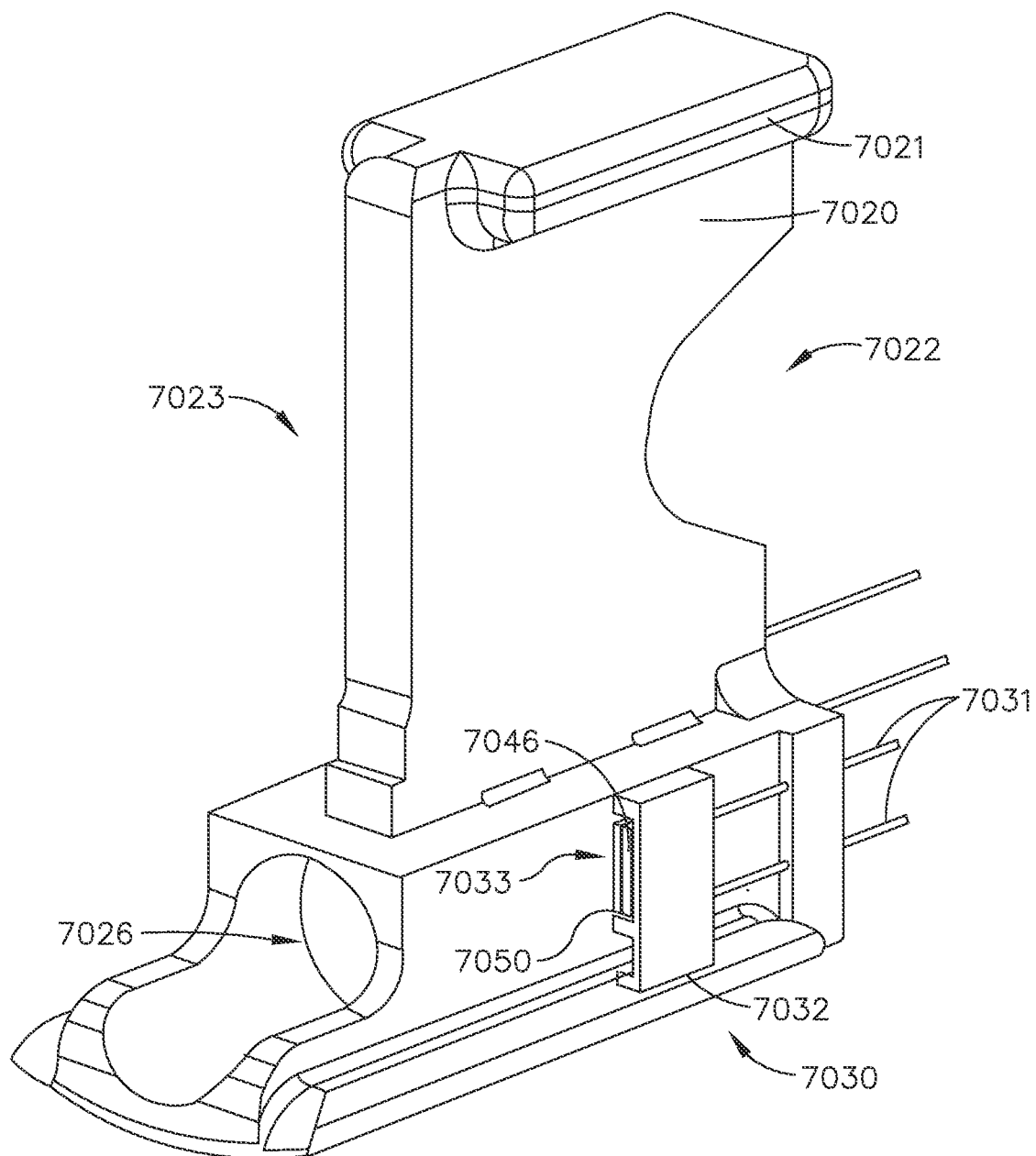
Figure 120:
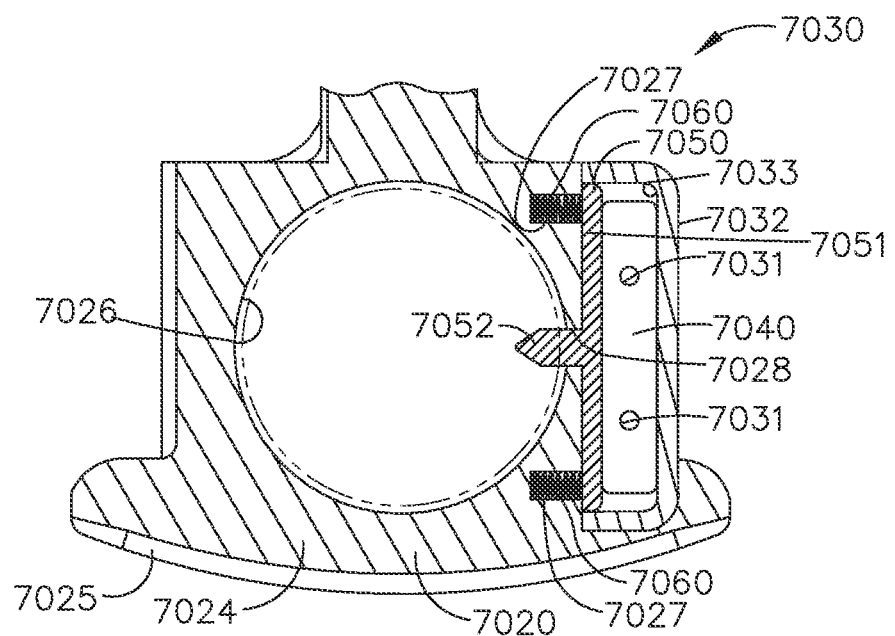
Figure 121:
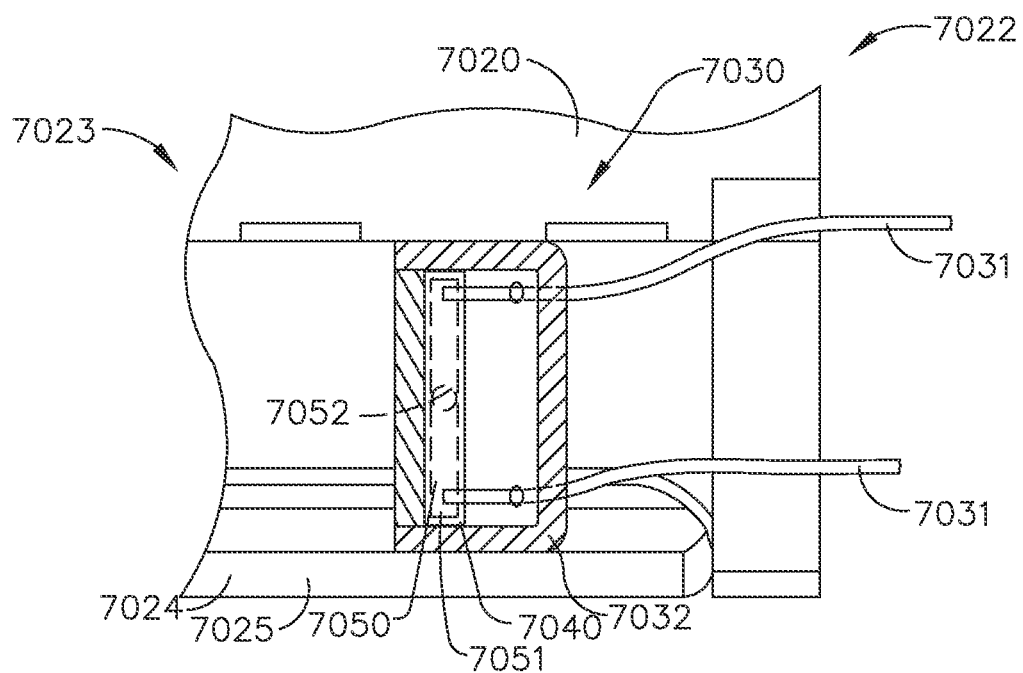
Figure 122:
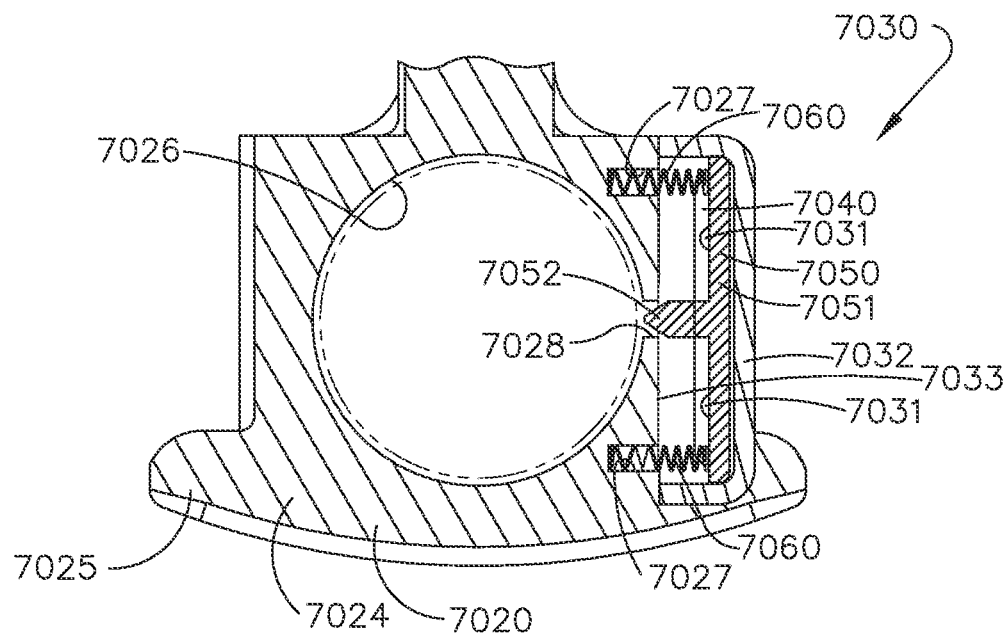
Figure 123:
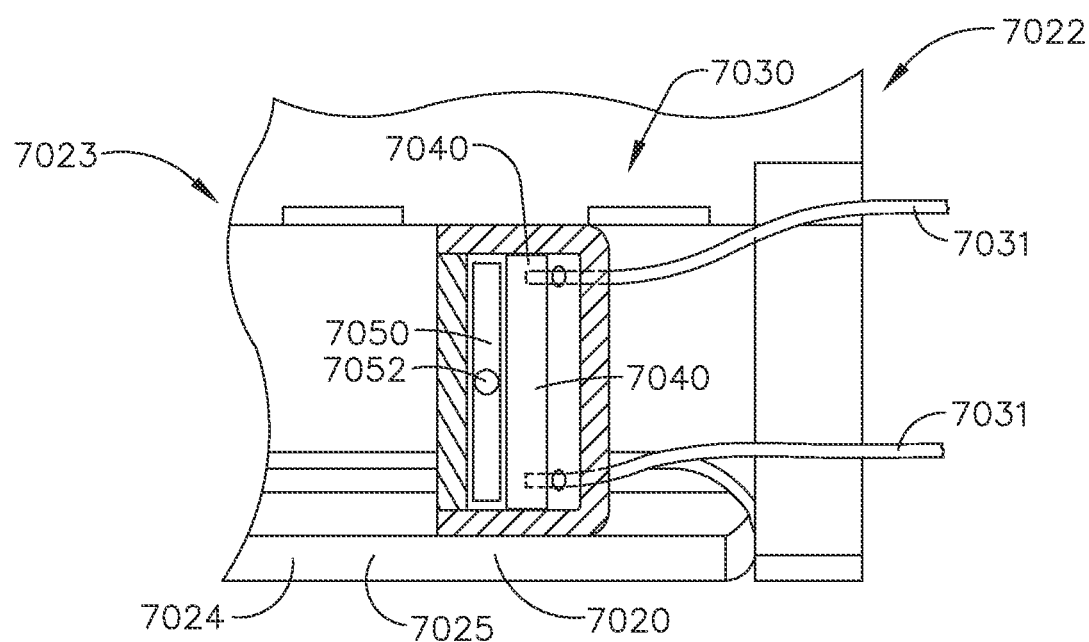
Figure 124:
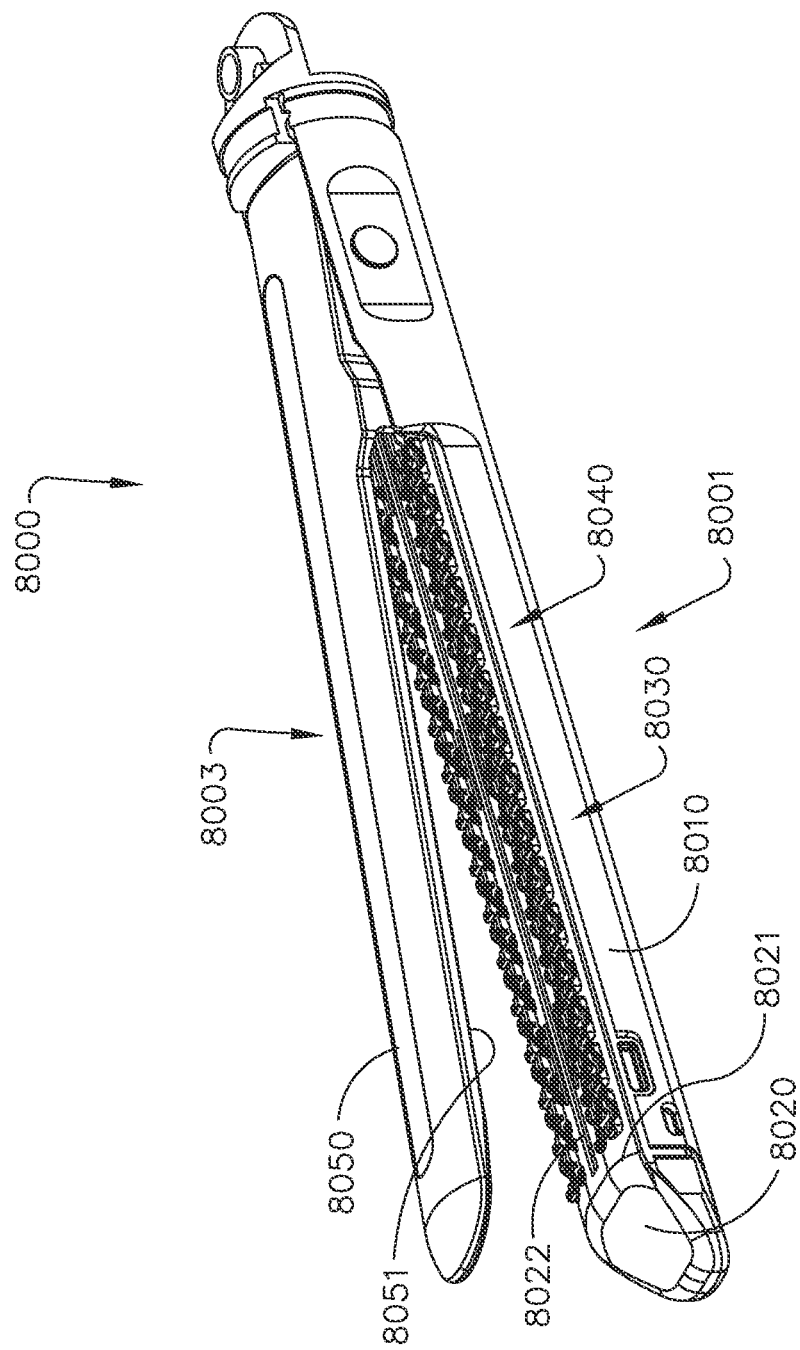

Turning now to FIGS. 116 and 117, installation of the locking member 6520 will now be described. The distal end 6515 may be swaged, for example, to radially expand the attachment section 6516. This radial expansion can provide a frictional holding engagement between the locking member 6520 and the attachment section 6516. A central slot 6517 is provided. The slot 6517 can be used to insert a swaging tool therein to expand the attachment section 6516 to lock the locking member 6520 in place. In at least one instance, the locking member 6520 is deformable and swaging of the attachment section 6516, for example, is configured to deform the locking member 6520 into an installed configuration.

In at least one instance, the locking member 6520 is pinned to the attachment section 6516 in addition to or in lieu of the swaging process discussed above. In at least one instance, the locking member 6520 further comprises an annular groove and the attachment section 6516 further comprises a corresponding annular slot defined on the outside thereof configured to receive the annular groove of the locking member 6520. In at least one instance, a hole is machined in the drive screw and a dowel pin is configured to be inserted into the hole to retain a closure wedge on the drive screw.

In at least one instance, a high density polyethylene washer is positioned proximal to the locking member 6520. The high density polyethylene washer may also comprise a deformable support flange such that the washer is deformed when the locking member 6520 is assembled to the drive screw shaft 6510, for example.

In at least one instance, a deformable washer used herein comprises a grooved and/or knurled face. Such a grooved and/or knurled face can be used to compensate for tolerance stack-ups of various components within a drive system. For example, such a grooved and/or knurled face can wear slightly after a first stage of actuation after assembly so as to compensate for tolerance stack-ups.

FIGS. 118-123 depict a firing drive assembly 7000 comprising a rotary drive shaft 7010, a firing member 7020 threadably coupled to the rotary drive shaft 7010, and a bailout assembly 7030 configured to threadably couple the firing member 7020 to the rotary drive shaft 7010 and permit the bailing out of and/or disengagement of the threaded engagement between the rotary drive shaft 7010 and firing member 7020. The rotary drive shaft 7010 comprises a distal end 7011 and a threaded, or grooved, section 7013. The firing member 7020 comprises an upper flange, a proximal edge 7022, and a distal edge 7023. The firing member 7020 further comprises a lower portion 7024 comprising a drive shaft duct 7026 configured to receive the rotary drive shaft 7010 therethrough. The lower portion 7024 further comprises a lower flange 7025.

The bailout assembly 7030 comprises bailout actuators, or cables, 7031 and a housing 7032 defining a housing cavity 7033. The bailout assembly 7030 further comprises a biasing plate 7040 and an actuator plate 7050. The actuator plate 7050 comprises a primary plate portion 7051 and a point, or pin, 7052 extending inwardly therefrom to be received and driven by the threaded section 7013 of the rotary drive shaft 7013. The pin 7052 is configured to be received within a pin slot 7028 defined in the lower portion 7024 to drivingly engage the threaded, or grooved, section 7013. The actuator plate 7050 is spring loaded against the lower portion 7024 with springs 7060 positioned within spring slots 7027 defined in the lower portion 7024. The springs 7060 are configured to bias the actuator plate 7050 out of threaded engagement with the rotary drive shaft 7010.

To hold the actuator plate 7050 in threaded engagement with the rotary drive shaft 7010, the biasing plate 7040 is positioned, or wedged, between the housing 7032 and the primary plate portion 7051 within the housing cavity 7033. This wedging engagement overcomes the spring force applied to the actuator plate 7050 by the springs 7060 and keeps the pin 7052 engaged with the threaded section 7013 of the rotary drive shaft 7010. In various instances, the firing drive assembly 7000 may become stuck or jammed within an end effector assembly due to a variety of circumstances. The bailout assembly 7030 allows for the firing member 7020 to be disengaged from the rotary drive shaft 7010 and pulled proximally independently of the rotary drive shaft 7010 to overcome a stuck or jammed scenario.

To bailout the firing drive assembly 7000, the pin 7052 is moved from an inward-most position (FIG. 120, FIG. 121) to an outward-most position (FIG. 122, FIG. 123) disengaging the pin 7052 and, thus, the firing member 7020, from the rotary drive shaft 7010. To achieve this motion, the biasing plate 7040 is pulled proximally by the actuators 7031 to move the biasing plate 7040 out of the way of the actuator plate 7050 so as to allow the springs 7060 to push the primary plate portion 7051 and, thus, the pin 7052 out of threaded engagement with the threaded section 7013 of the rotary drive shaft 7010. At such point, the actuators 7031 can continue to be pulled proximally to apply a pulling force to the firing member 7020 through the biasing plate 7040. The housing cavity 7033 comprises a proximal limit wall configured to transfer the pulling force from the biasing plate 7040 to the firing member 7050. Once the firing member 7020 is pulled into its proximal most position the end effector assembly may be opened and removed from a surgical site, for example.

In at least one instance, the firing drive assembly 7000 and end effector assembly employing the firing drive assembly 7000 may not be usable again due to the nature of the bailout assembly 7030. For example, the bailout assembly 7030 may not be able to be reset back into threaded engagement with the rotary drive shaft 7010. In at least one instance, the bailout assembly 7030 may be capable of being reset and reused. In at least one instance, another pin 7052 and corresponding structure is provided on the other side of the firing member 7020. The same, or separate, cables may be provided to actuate the other pin in such an instance.

In at least one instance, the actuators, or cables, may be controlled using a geared pulley system. In at least one instance, the cables may be motor driven. In at least one instance, the cables are manually actuatable. In at least one instance, the cables may be manually actuatable and motor driven. For example, during a power failure, the manual actuation method could be used where the motor driven system is temporarily down. In at least one instance, the cables are permitted to lengthen as the firing member is actuated so as to not prematurely actuate the bailout assembly. The cables may be passively moved or actively moved to accommodate movement of the firing member.

In various instances, surgical stapling arrangements are provided which are configured to form staples, such as traditional wire staples, differently within a single staple cartridge. More specifically, a staple cartridge may store staples with identical unformed heights, size, and shape, for example. In such an instance, different features are provided so as to form the same unformed staples into different final formed configurations. In at least one instance, the varied forming of staples varies progressively along the lateral width of the staple cartridge. More specifically, an inner row of staples may be formed into a planar, or 2D, formed configuration while an intermediate row of staples and/or an outer row of staples may be formed into a non-planar, or 3D, formed configuration. Such an arrangement can provide varied stapled tissue compression along the lateral width of the staple cartridge.

Further to the above, such surgical stapling arrangements can comprise tissue gripping features, or staple cavity extensions, defined on a deck of the staple cartridge. Such tissue gripping features can vary in shape and/or size, for example, laterally across the staple cartridge. The deck of the staple cartridge may comprise a curved surface where an apex of such a curved deck is defined at a longitudinal slot of the staple cartridge. The deck of the staple cartridge may also comprise one or more flat surfaces either providing a single flat surface in which all of the staple rows are defined or a stepped deck arrangement where various stepped portions of the deck comprise one or more corresponding staple rows defined therein.

The tissue gripping features may also be interconnected along the lateral width of the staple cartridge. For example, on each side of a longitudinal slot of the staple cartridge, the staple cartridge may comprise three rows of staple cavities and, thus, three rows of staples removably stored therein. The tissue gripping features, or deck protrusions, may be positioned around each cavity of each row; however, the tissue gripping features can be interconnected between one or more of the staple cavity rows while still varying in shape and/or size, for example. Such tissue gripping features can provide varied tissue compression along the lateral width of a staple cartridge. The varying size tissue gripping features can be advantageous when forming certain rows of staples into a non-planar, 3D configuration, and certain rows of staples into a planar, 2D configuration. Such features can be tuned specifically for the corresponding staple configuration of the staples to be formed through tissue gripped by the features. For example, gripping features configured to grip tissue to be stapled between an anvil and a row of staple cavities comprising staples configured to be formed into a non-planar configuration can comprise a first profile and gripping features configured to grip tissue to be stapled between an anvil and a row of staple cavities comprising staples configured to be formed into a planar configuration can comprise a second profile, wherein the first profile is different than second profile. In certain instances, the gripping features aligned with the rows of 3D staples can include cutouts in the areas where curved, formed legs would interfere. For example, the rows aligned with 2D staples can include full gripping features surrounding the staple cavity, and the rows aligned with the 3D staples can include gripping features with cutouts therearound to accommodate the staple legs during the 3D formation thereof.

In various instances, staples formed into a planar configuration and staples formed into a non-planar configuration may result in different formed compression heights. This can be attributed to a distance required to be traveled by legs of each staple to their corresponding staple forming pocket defined in an anvil. For example, legs of staples formed into a non-planar configuration may have to travel on a diagonal to a corresponding staple forming pocket. Without altering any other features of the stapling assembly, this distance may be farther than the distance required to be traveled by legs of staples formed into a planar configuration to a corresponding staple forming pocket.

In various instances, the distance which each leg must travel to be formed into its corresponding configuration, non-planar or planar, may be tuned by altering one or more features of a surgical stapling assembly. In at least one instance, the depths of staple forming pockets defined in the anvil are adjusted corresponding to the formed configuration of the staple to be formed thereby. In at least one instance, the unformed length of the staples are configured to be adjusted corresponding to the formed configuration of the staple to be formed thereby. In at least one instance, a corresponding driver height is adjusted corresponding to the formed configuration of the staple to be formed thereby. In at least one instance, one or more of these adjustments are combined together to accommodate 2D formed staples and 3D formed staples.

FIGS. 124-128 depict a surgical stapling assembly 8000. The surgical stapling assembly 8000 comprises a cartridge jaw 8001 comprising a cartridge channel 8010 and a staple cartridge 8020. The surgical stapling assembly 8000 also comprises an anvil jaw 8003 comprising an anvil 8050. The staple cartridge 8020 comprises a plurality of staple cavities 8030 and a longitudinal slot 8022 defined in a cartridge deck 8021. The staple cartridge 8020 also comprises and a plurality of tissue-gripping features, or cavity extensions, 8040 defined on the deck 8021. The staple cavities 8030 are aligned in longitudinal rows offset with respect to each other. In this instance, the staple cartridge 8020 comprises three rows of staple cavities on each side of the longitudinal slot; however, any suitable number of rows of staple cavities can be employed. The staple cavities 8030 are configured to removably store staples which are configured to be ejected toward staple forming pockets defined in an anvil surface 8051 of the anvil 8050.

Referring to FIGS. 125 and 126, the anvil 8050 comprises an anvil slot 8052 defined in the anvil surface 8051. The anvil 8050 further comprises a pair of inner staple forming pocket rows 8061, a pair of intermediate staple forming pocket rows 8063, and a pair of outer staple forming pocket rows 8065. The rows 8061, 8063, 8065 are aligned with corresponding rows of the staple cavities 8030. The inner staple row 8081 comprises staples 8070 which are configured to be formed by the staple forming pocket rows 8061, the intermediate staple row 8082 comprises staples 8070 which are configured to be formed by the staple forming pocket rows 8063, and the outer staple row 8083 comprises staples 8075 which are configured to be formed by the staple forming pocket rows 8065. The staple tip entry location of the pockets in the stapling forming pocket row 8065 is aligned, or substantially aligned, with the tips of the staples in the outer staple row 8065; however, the staple tip exit location of those pockets can be laterally offset from the staples positioned in the outer staple row 8065. The staples 8070, 8075 comprise traditional wire staples. The staples 8070, 8075 comprise the same unformed height. The staples 8070 are formed into a planar configuration while the staples 8075 are formed into a non-planar configuration.

Each pair of forming pockets of the row 8061 comprises a proximal forming pocket 8061A and a distal forming pocket 8061B. Each pair of forming pockets of the row 8063 comprises a proximal forming pocket 8063A and a distal forming pocket 8063B. Each pair of forming pockets of the row 8065 comprises a proximal forming pocket 8065A and a distal forming pocket 8065B. The forming pockets 8061A, 8061B comprise centerline axes, or longitudinal pocket axes, which are aligned with each other along the row 8061. Similarly, the forming pockets 8063A, 8063B comprise centerline axes, or longitudinal pocket axes, which are aligned with each other along the row 8063. The forming pockets 8065A, 8065B comprise centerline axes, or transverse pocket axes, which are transverse with respect to the centerline axes of the pockets 8061A, 8061B and the centerline axes of the pockets 8063A, 8063B. The centerline axes of the pockets 8065A, 8065B may be substantially parallel to each other. Further to the above, a proximal leg of one of the staples 8070 is configured to enter the proximal forming pocket 8065A and a distal leg of the staple is configured to enter the distal forming pocket 8065B. The forming pockets 8065A, 8065B are configured to direct the legs of the staple 8075 laterally away from a crown of the staple or, laterally away from each other (see FIG. 126). This variance in 2D formed staples and 3D formed staples laterally along the width of the stapling assembly 8000 with respect to a longitudinal axis defined thereby can provide varied tissue compression on the stapled tissue. For example, the outer 3D staples may provide less tissue compression as compared to the inner 2D formed staples near the cut line of the tissue.

As can be seen in FIG. 125, a gap is defined longitudinally between each pair of forming pockets 8061A, 8061B, a gap is defined longitudinally between each pair of forming pockets 8063A, 8063B, and a gap is defined between each pair of forming pockets 8065A, 8065B. The gap defined between the forming pockets 8061A, 8061B may be substantially the same and/or similar to the gap defined between the forming pockets 8063A, 8063B. The gap defined between the forming pockets 8065A, 8065B is larger than the gap defined between the forming pockets 8061A, 8061B and the gap defined between the forming pockets 8063A, 8063B. The gap defined between the forming pockets 8065A, 8065B may be defined as the space intermediate the forming pockets 8065A, 8065B.

Figure 127:
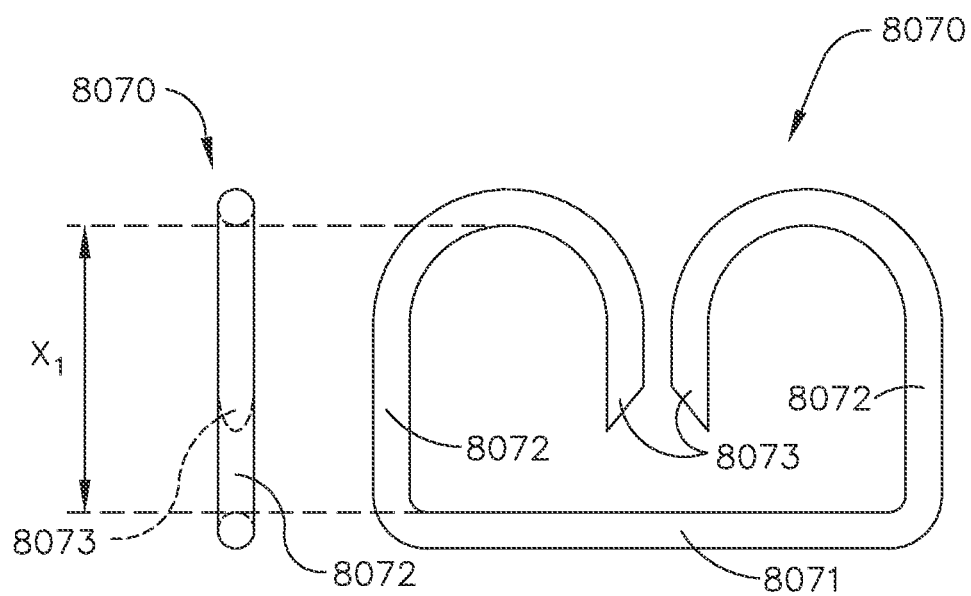
Figure 128:
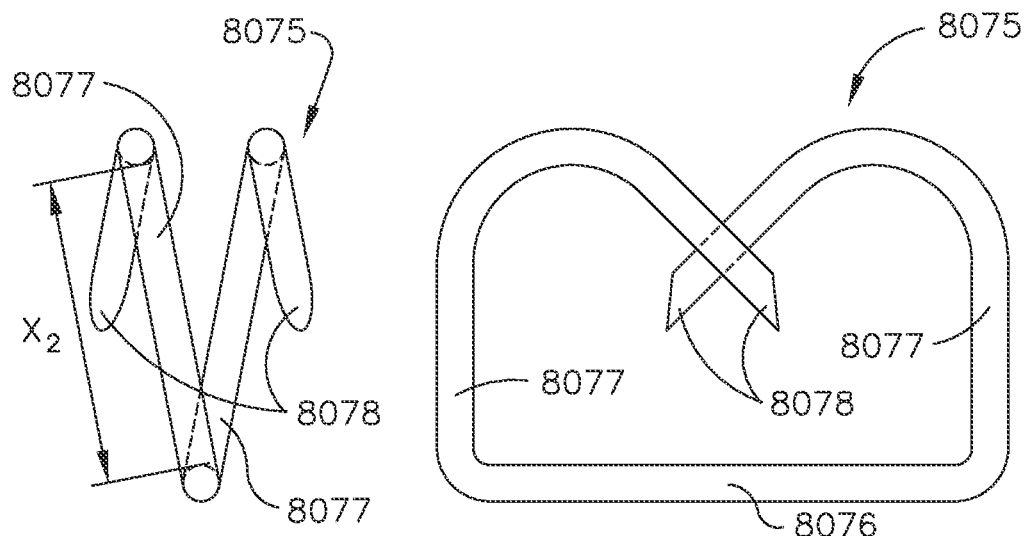

As can be seen in FIGS. 127 and 128, the staples 8070 are formed into a planar configuration and the staples 8075 are formed into a non-planar configuration. The staple 8070 comprises a crown 8071 and legs 8072 extending from the crown 8071. The legs 8072 further comprise staple tip portions 8073 configured to pierce tissue and enter corresponding forming pockets. The staples 8070 define a formed compression height "$X_1$" which is the effective height of tissue compression captured by the staple 8070. The staple 8075 comprises a crown 8076 and legs 8077 extending from the crown 8076. The legs 8077 further comprise staple tip portions 8078 configured to pierce tissue and enter corresponding forming pockets. The staples 8075 define a formed compression height "$X_2$" which is the effective height of tissue compression captured by the staple 8075. Because of the non-planar formed configuration of the staple 8075, the formed compression height $X_2$ is taller than the formed compression height $X_1$. In at least one instance, this is desirable and can provide a progressive reduction in compression as the staple lines move laterally away from the cut line. For example, a tighter formed compression height near the cut line may provide adequate tissue sealing pressure and a looser formed compression height away from the cut line progressively reduces pressure on the tissue as the staple lines move laterally outwardly with respect to the cut line.

In at least one instance, the legs 8077 are formed at different angles away from the crown 8076 with respect to each other. For example, a proximal leg can be formed away from the crown at a first angle and the distal leg can be formed away from the crown in the opposite direction at a second angle. The first angle is different than the second angle. This would allow for a narrow footprint of the corresponding staple forming pockets. Moreover, when stamping these pocket shapes into the anvil, the different angles and/or narrower footprint can ensure that the wall between adjacent rows of forming pockets is sufficiently maintained, which can prevent bleeding or washout of features in one row into those in an adjacent row during the stamping process.

3D staples can be intermixed within and/or across longitudinal rows, which can maximum use of the anvil surface and further nest the pockets and allow a narrower footprint. In certain instances, intermixing of 3D staple pockets can improve tissue pressure dispersion along the anvil. In at least one instance, the 3D staple pockets can be positioned along an outermost row of pockets to further ease and/or taper the tissue pressure along the edges of the staple line farthest from the cut line.

In various instances, the gripping features 8040 and the curved deck 8021 can provide laterally varying tissue gaps. More specifically, the gap for tissue to be captured between each corresponding row of staple cavities and staple forming pockets is varied between each row. The outer-most row comprises the tallest gripping features as compared to the inner row and intermediate row. This may provide additional tissue compression in a row where the 3D staples are configured to be formed. This may provide greater stability during staple forming owing to the additional cavity extension length of the outer staple cavities. The taller gripping features can maintain a similar compression profile between the gripping features and the corresponding forming pockets; however, the portion of the deck surface 8021 that the outer row of staple cavities are defined in is further away from the anvil than the portion of the deck surface 8021 that the inner row of staple cavities and the intermediate row of staple cavities are defined in due to the lateral curvature of the deck. Collectively, the taller gripping features and the lower deck surface can provide a more stable platform for 3D formed staples in certain instances.

In various instances, flat form, or stamped, staples can be used in addition to or in lieu of wire staples. In various instances, two of the three rows of staples on each side of a cartridge are configured to be formed into a non-planar configuration while the other one of the three rows on that side of the cartridge is configured to be formed into a planar configuration. In at least one instance, the same longitudinal row of staples comprises both planar formed staples as well as non-planar formed staples. In at least one instance, the unformed height of staples within the same row is varied. In at least one instance, the unformed height of staples within different rows is varied. In at least one instance, planar staples and non-planar staples are varied along axes transverse to a longitudinal slot of a staple cartridge to spread staple pressure. In at least one instance, staple legs of non-planar formed staples are formed laterally on one side of the crown rather than opposite directions relative to the crown away from each other. In such an instance, the row gap between each row can be substantially similar at least because the legs, although forming away from the crown upon ejection, can be formed back toward the crown to tighten the staple lines. Such a configuration can help maintain a consistent lateral row gap between each row of staple forming pockets.

Figure 129:
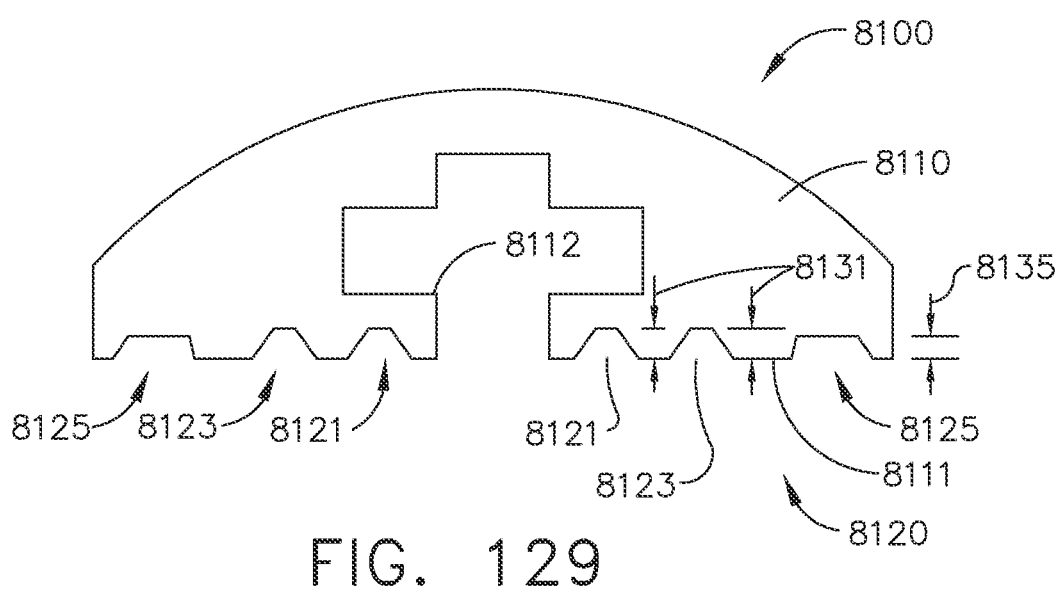

As discussed above, one or more adjustments can be made to vary the final formed height and/or compression height of the staples as there form can vary laterally, row-to-row, for example. FIG. 129 depicts an anvil 8100 configured to deform staples ejected from a staple cartridge. The anvil 8100 comprises an anvil body 8110 comprising an anvil surface 8111 and a firing member slot 8112 defined in the anvil body 8110. The anvil surface 8111 comprises a plurality of staple forming pocket rows comprising inner rows 8121, intermediate rows 8123, and outer rows 8125. The inner and intermediate rows 8121, 8123 are configured to form staples into a planar configuration and the outer rows 8125 are configured to form staples into a non-planar configuration. As can be seen in FIG. 129, the inner and intermediate rows 8121, 8123 define a pocket depth 8131 and the outer rows define a pocket depth 8135 which is shallower than the pocket depth 8131. This shallower pocket depth can accommodate for loss in compression or final formed height owing to the diagonal forming path of the non-planar staples. In at least one instance, the pocket depths are tuned so that the final compression height is the same between non-planar staples and planar staples. In another instance, the pocket depths are tuned so that the final compression heights between non-planar staples and planar staples are different.

Figure 130:
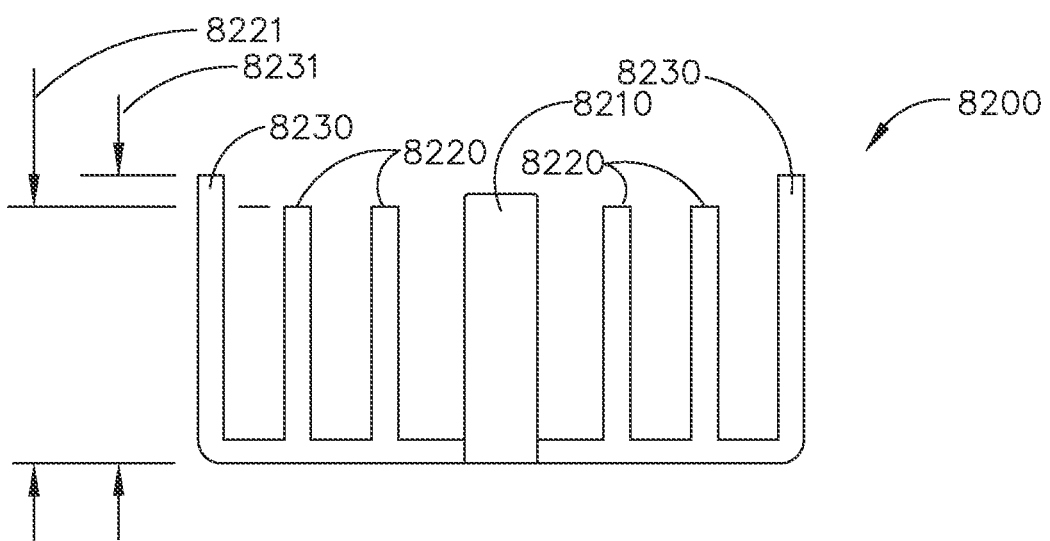

FIG. 130 depicts a sled 8200 comprising inner ramps 8220 and outer ramps 8230. The inner ramps are configured to lift staples a height 8221 and the outer ramps 8230 are configured to lift staples a height 8231. The ramps 8220 are configured to lift staples to be formed into a planar configuration and the ramps 8230 are configured to lift staples to be formed into a non-planar configuration. The height 8231 may accommodate for loss in compression or final formed height owing to the diagonal forming path of the non-planar staples.

FIG. 131 depicts staples 8300 to be used with a surgical stapling assembly. The staples 8300 comprise a first staple 8310 comprising a first unformed height 8311 and a second staple 8320 comprising a second unformed height 8321. The first unformed height 8311 is less than the second unformed height 8321. The different unformed heights can accommodate for loss in compression or final formed height owing to the diagonal forming path of the non-planar staples. The second staple 8320 can be configured to be formed into a non-planar configuration while the first staple 8310 can be configured to be formed into a planar configuration.

FIGS. 132 and 133 depict staples 8410, 8420. The staple 8410 formed into a planar configuration defines a final compression height 8411 and the staple 8420 formed into a non-planar configuration defines final compression height 8421. The final compression height 8421 is less than the compression height 8411; however, the staple 8420 defines a distance 8422 defined between the apex of each formed leg and the crown. The distance 8422 may be substantially equal to the final compression height 8411. The distance 8422 may be the effective compression height of the staple 8420.

In various instances, surgical stapling assemblies are provided which are configured to overdrive staples from a staple cartridge. The amount of staple overdrive may vary from row to row. In various instances, staple drivers can comprising varying amounts of support from a corresponding staple cartridge support wall. More specifically, inner staple drivers can be supported less by a staple cartridge support wall than outer staple drivers owing to the geometry of the cartridge body and firing assembly and/or drive screw therein. In various instances, a tissue gap can be varied from row to row while maintaining a similar, or the same, driving distance between the rows.

FIGS. 134-136 depict a surgical stapling assembly 8500. The surgical stapling assembly 8500 comprises a lower jaw 8501 and an upper jaw 8502. The lower jaw 8501 comprises a cartridge channel 8510 and a staple cartridge 8520 configured to be received within the cartridge channel 8510. The upper jaw 8502 comprises an anvil 8530 comprising an anvil body 8531. The anvil body 8531 comprises an anvil surface 8532 and a plurality of forming pockets defined in the anvil surface 8532. The anvil surface 8532 comprises inner forming pockets 8533, intermediate forming pockets 8534, and outer forming pockets 8535. The staple cartridge comprises a plurality of staple cavities 8522 comprising inner staple cavities 8522A aligned with inner forming pockets 8533, intermediate staple cavities 85228 aligned with intermediate forming pockets 8534, and outer cavities 8522C aligned with outer forming pockets 8534. The staple cavities 8522 are configured to store a corresponding driver and staple therein to be ejected to the forming pockets aligned therewith.

The staple cartridge 8520 comprises a curved cartridge deck 8529 comprising a plurality of staple cavities 8522 defined therein and a plurality of tissue gripping features, or cavity extensions, 8523, 8524, 8525 extending from the cartridge deck 8529. The staple cartridge 8520 also comprises a sled 8550 comprising ramps 8551, 8552. The staple cartridge 8520 comprises a plurality of drivers 8540 sequentially aligned to eject rows of staples from the staple cavities when lifted by ramps 8551, 8552. Each driver 8540 comprises an inner row support, or inner support column, 8541 configured to support and drive a staple to be stored and ejected from an inner staple cavity 8522A, an intermediate row support, or intermediate support column, 8542 configured to support and drive a staple to be stored and ejected from an intermediate staple cavity 85228, and an outer row support, or outer support column, 8543 configured to support and drive a staple to be stored and ejected from an outer staple cavity 8522C.

As can be seen in FIG. 135, the staple cartridge 8520 comprises inner support walls 8526A configured to support inner row support 8541 as the driver 8540 is lifted by sled 8550, intermediate support walls, or columns, 8526B configured to support intermediate row support 8542 as the driver 8540 is lifted by sled 8550, and outer support walls 8526c configured to support outer row support 8543 as the driver 8540 is lifted by sled 8550. As can be seen in FIG. 135, the level of support contact between each support 8541, 8542, 8543 and its corresponding support wall 8526A, 8526B, 8526C varies from row to row. In an unfired position, the outer support 8541 has the most support contact, the intermediate support 8542 has less support contact than the outer support 8541, and the inner support 8541 has the least amount of support contact. As can also be seen in FIG. 135, the supports 8541, 8542, 8543 are overdriven to the same limit resulting in the same driving forming distance of each staple supported by the supports 8541, 8542, 8543; however, the amount of overdrive relative to their corresponding gripping feature 8523, 8524, 8525 varies from row to row. The outer row is overdriven past its gripping features the most, and the inner row is overdrive past its gripping features the least.

As discussed herein, staple cartridges can be replaced within a surgical stapling assembly. In various instances, anvil plates are provided which can also be replaced. In such instances, the anvil plate may come with a corresponding staple cartridge such that a fresh staple cartridge and anvil plate are packaged together and are replaced within the surgical stapling assembly together. In such instances, various features of the anvil plates and corresponding staple cartridge can be tuned specifically for each other. For example, different anvil plates can comprise staple forming pockets with different patterns, staple forming pockets with different forming depths, and/or varied staple forming pocket types from row to row, for example, among other things.

A universal fitment profile can be used for a variety of anvil plates such that the stapling assembly may receive several different anvil plates. Replacing an anvil plate can also provide fresh staple forming pockets. The anvil plate and staple cartridge can be paired based on staple leg length, types of staples stored in the staple cartridge, and/or desired formed height of the staples. In such instances, an anvil jaw configured to receive the anvil plate can be manufactured with or without staple forming pockets defined directly thereon. This may reduce manufacturing costs because the anvil jaw can be reused in different scenarios rather than introducing an entirely different surgical stapling instrument with different types of forming pockets.

FIGS. 137-139 depict a surgical stapling assembly 8600 comprising a first jaw 8601 and a second jaw 8603 movable relative to the first jaw 8601 to clamp tissue therebetween. The surgical stapling assembly 8600 is configured to cut and staple tissue captured between the jaws 8601, 8603. The first jaw 8601 comprises a replaceable staple cartridge 8620 configured to removably store a plurality of staples in a plurality of staple cavities 8622 therein defined in a deck surface 8621 of the staple cartridge 8620. The first jaw 8601 further comprises a cartridge channel 8610 configured to receive the replaceable staple cartridge 8620 therein. As discussed above, various different types of staple cartridges can be installed within the cartridge channel 8610. Various differences between replaceable staple cartridges can include different unformed staple leg height and/or orientation, different cartridge length, and/or different staple diameter, for example.

The second jaw 8603 comprises a replaceable anvil plate 8640 comprising an anvil surface 8641 and a plurality of forming pockets 8642 defined in the anvil surface 8641. The second jaw 8603 further comprises an upper anvil jaw portion 8630 configured to receive the replaceable anvil plate 8640 therein. In at least one instance, the replaceable anvil plate 8640 is slid into a distal end of the anvil jaw portion 8630. In at least one instance, the replaceable anvil plate 8640 is configured to be snapped into the anvil jaw portion 8630. In at least one instance, the anvil jaw portion 8630 comprises deformable arms made of a metallic material, for example, hanging from the perimeter of the anvil jaw portion 8630. The deformable arms can be configured to deform upon clamping of the jaws 8601, 8603 together after positioning the anvil plate 8640. Upon attaining a fully clamped position, the deformable arms are deformed and, in their deformed configuration, are configured to grasp and retain the anvil plate 8640 to the anvil jaw portion 8630. In at least one instance, a clampable member is configured to be clamped by the jaws 8601, 8603 to affix the anvil plate 8640 to the anvil jaw portion 8630. In such an instance, the clampable member can be responsible for deforming the deformable arms. After the anvil plate 8640 is secured to the anvil jaw portion 8630, the clampable member may be removed and discarded before the surgical stapling assembly 8600 is used. In at least one instance, the deformable members are part of the anvil plate 8630 and are configured to be secured to the anvil jaw portion 8630.

In at least one instance, an anvil cap is configured to be positioned on a distal end of the anvil jaw portion 8630. The anvil cap is configured to secure the anvil plate 8640 to the anvil jaw portion 8630. In at least one instance, the anvil plate 8640 is slid into the anvil jaw portion 8630 and, without the anvil cap, can only be removed by pulling the anvil plate 8640 distally from the distal end of the anvil jaw portion 8630. Such an anvil cap can secure the anvil plate 8640 at the distal end of the anvil jaw portion 8630. In at least one instance, the distal end of the anvil jaw portion 8630 comprises threads and the anvil cap comprises corresponding threads configured to be threaded onto the threads on the distal end of the anvil jaw portion 8630 to secure the anvil cap to the anvil jaw portion 8630. In at least one instance, the anvil cap comprises a polymer material. In at least one instance, the anvil cap is snapped onto the distal end of the anvil jaw portion 8630 and unsnapped from the distal of anvil jaw portion 8630 to replace the anvil plate 8640. In various instances, a user can install and uninstall the anvil cap. In other instances, a specific tool is required to install and/or uninstall the anvil cap from the anvil jaw portion 8630. In at least one instance, the specific tool is provided with the replaceable anvil plate 8640 and/or replaceable staple cartridge 8620. As discussed above, a replaceable anvil plate and a replaceable staple cartridge can come as a single replaceable unit to be installed within a surgical stapling assembly. In various instances, a user can mix and match anvil plates and replaceable staple cartridges to tune the type of staple line, tissue compression, and/or gripping pressure, for example, desired fora particular use. This can be based on the targeted tissue and/or type of operation, for example. For example, the one or more rows of forming pockets 8642 in certain anvil plates 8640 can include forming pockets having transverse pocket axes and configured to form 3D or non-planar staples, as further described herein, while other rows of forming pockets 8642 include forming pockets having aligned pocket axes and configured to form 2D or planar staples. Additionally or alternatively, the anvil plate can include a stepped and/or contoured surface to optimize the tissue gap for certain applications.

Various aspects of the subject matter described herein are set out in the following examples.

Example Set 1

Example 1—A surgical stapling assembly comprising an anvil and a staple cartridge. The anvil comprises an anvil surface, a first row of forming pockets defined in the anvil surface, and a second row of forming pockets defined in the anvil surface. The staple cartridge comprises a deck surface, a longitudinal slot defining a first cartridge side and a second cartridge side of the staple cartridge, and a first row of staple cavities defined in the deck surface of the first cartridge side, wherein the first row of staple cavities is positioned a first lateral distance from the longitudinal slot. The staple cartridge further comprises a first row of tissue gripping features extending from the deck surface, wherein the first row of tissue gripping features is aligned with the first row of staple cavities and the first row of forming pockets, and wherein the first row of tissue gripping features comprises a first profile, a second row of staple cavities defined in the deck surface of the first cartridge side, wherein the second row of staple cavities is positioned a second lateral distance from the longitudinal slot, wherein the second lateral distance is greater than the first lateral distance, and a second row of tissue gripping features extending from the deck surface, wherein the second row of tissue gripping features is aligned with the second row of staple cavities and the second row of forming pockets, wherein the second row of tissue gripping features comprises a second profile, and wherein the second profile and the first profile are different geometries. The staple cartridge further comprises a plurality of staples removably stored within the first row of staple cavities and the second row of staple cavities, wherein the staples removably stored within the first row of staple cavities are configured to be formed into a planar staple configuration by the first row of forming pockets, and wherein the staples removably stored within second row of staple cavities are configured to be formed into a nonplanar staple configuration by the second row of forming pockets.

Example 2—The surgical stapling assembly of Example 1, wherein each forming pocket of the first row of forming pockets defines a longitudinal pocket axis, and wherein the longitudinal pocket axes are aligned.

Example 3—The surgical stapling assembly of Example 2, wherein each forming pocket of the second row of forming pockets defines a transverse pocket axis, and wherein the transverse pocket axes are transverse to the longitudinal pocket axes.

Example 4—The surgical stapling assembly of any one of Examples 1, 2, and 3, wherein the anvil further comprises a third row of forming pockets defined in the anvil surface, wherein the staple cartridge further comprises a third row of staple cavities defined in the deck surface of the first cartridge side, wherein the third row of staple cavities is positioned a third lateral distance from the longitudinal slot, and wherein the third lateral distance is less than the first lateral distance and the second lateral distance.

Example 5—The surgical stapling assembly of any one of Examples 1, 2, 3, and 4, wherein at least one of the anvil and the staple cartridge is movable to reposition the surgical stapling assembly in a clamped configuration, wherein a first tissue gap distance is defined between the first row of staple cavities and the first row of forming pockets in the clamped configuration, wherein a second tissue gap distance is defined between the second row of staple cavities and the second row of forming pockets in the clamped configuration, and wherein the first tissue gap distance and the second tissue gap distance are different distances.

Example 6—The surgical stapling assembly of any one of Examples 1, 2, 3, 4, and 5, wherein the plurality of staples comprise wire staples.

Example 7—The surgical stapling assembly of Example 6, wherein the plurality of staples comprise a uniform unformed height.

Example 8—The surgical stapling assembly of any one of Examples 1, 2, 3, 4, 5, 6, and 7, wherein at least one of the anvil and the staple cartridge is movable to reposition the surgical stapling assembly in a clamped configuration, wherein the staple cartridge further comprises a plurality of first staple drivers positioned within the first row of staple cavities and a plurality of second staple drivers positioned within the second row of staple cavities, wherein a first forming distance is defined between the first row of forming pockets and the first staple drivers in the clamped configuration, wherein a second forming distance is defined between the second row of forming pockets and the second staple drivers in the clamped configuration, and wherein the first forming distance and the second forming distance are different forming distances.

Example 9—The surgical stapling assembly of any one of Examples 1, 2, 3, 4, 5, 6, 7, and 8, wherein the deck surface comprises a laterally curved profile.

Example 10—A surgical stapling assembly comprising an anvil and a staple cartridge. The anvil comprises an anvil surface, a first row of forming pockets defined in the anvil surface, and a second row of forming pockets defined in the anvil surface. The staple cartridge comprises a deck surface comprising a first row of deck protrusions and a second row of deck protrusions. The staple cartridge further comprises a longitudinal slot defining a first cartridge side and a second cartridge side, a first row of staple cavities defined in the deck surface of the first cartridge side positioned a first lateral distance from the longitudinal slot, wherein the first row of deck protrusions is aligned with the first row of staple cavities, and a second row of staple cavities defined in the deck surface positioned a second distance from the longitudinal slot, wherein the second distance is greater than the first distance, wherein the second row of deck protrusions is aligned with the second row of staple cavities. The staple cartridge further comprises a plurality of staples removably stored within the first row of staple cavities and the second row of staple cavities, wherein the first row of forming pockets are configured to form the staples removably stored within the first row of staple cavities into a planar staple configuration, and wherein the second row of forming pockets are configured to form the staples removably stored within second row of staple cavities into a nonplanar staple configuration.

Example 11—The surgical stapling assembly of Example 10, wherein the first profile comprises a first height, wherein the second profile comprises a second height, and wherein the first height and the second height are different heights.

Example 12—The surgical stapling assembly of any one of Examples 10 and 11, wherein each staple in the plurality of staples comprises a crown, a proximal leg extending from the crown, and a distal leg extending from the crown, wherein, in the planar staple configuration, the proximal leg and the distal leg define a leg plane which is coplanar with the crown.

Example 13—The surgical stapling assembly of Example 12, wherein, in the nonplanar staple configuration, the proximal leg defines a proximal leg plane and the distal leg defines a distal leg plane, and wherein the proximal leg plane is transverse to the distal leg plane.

Example 14—The surgical stapling assembly of any one of Examples 10, 11, 12, and 13, wherein each staple of the plurality of staples comprises the same unformed height.

Example 15—The surgical stapling assembly of any one of Examples 10, 11, 12, 13, and 14, wherein the deck surface comprises a laterally curved profile.

Example 16—The surgical stapling assembly of any one of Examples 10, 11, 12, 13, 14, and 15, wherein the plurality of staples comprise wire staples.

Example 17—The surgical stapling assembly of any one of Examples 10, 11, 12, 13, 14, 15, and 16, wherein each forming pocket of the first row of forming pockets defines a longitudinal pocket axis, wherein the longitudinal pocket axes are aligned, wherein each forming pocket of the second row of forming pockets defines a transverse pocket axis, and wherein the transverse pocket axes are transverse to the longitudinal pocket axes.

Example 18—A surgical stapling assembly comprising a shaft and an end effector attached to the shaft. The end effector comprises an anvil and a staple cartridge. The anvil comprises an anvil surface, a first row of forming pockets defined in the anvil surface, and a second row of forming pockets defined in the anvil surface. The staple cartridge comprises a deck surface, a longitudinal slot defining a first cartridge side and a second cartridge side, and a first row of staple cavities defined in the deck surface of the first cartridge side positioned a first lateral distance from the longitudinal slot, wherein the deck surface comprises a plurality of first tissue gripping features aligned with the first row of staple cavities. The staple cartridge further comprises a second row of staple cavities defined in the deck surface of the second cartridge side positioned a second distance from the longitudinal slot, wherein the second distance is greater than the first distance, wherein each staple cavity of the second row of staple cavities comprises a plurality of second tissue gripping features aligned with the second row of staple cavities, wherein the first tissue gripping features and the second tissue gripping features define different geometries, a plurality of first staples removably stored within the first row of staple cavities wherein the first row of forming pockets are configured to form the first staples into a planar staple configuration with a formed height, and a plurality of second staples removably stored within the second row of staple cavities, wherein the second row of forming pockets are configured to form the second staples into a nonplanar staple configuration with the formed height.

Example 19—The surgical stapling assembly of Example 18, wherein each forming pocket of the first row of forming pockets comprises a first pocket depth and each forming pocket of the second row of forming pockets comprises a second pocket depth, and wherein the second pocket depth is less than the first pocket depth.

Example 20—The surgical stapling assembly of Example 19, wherein a first forming distance is defined by forming pockets of the first row of forming pockets and a second forming distance is defined by forming pockets of the second row of forming pockets, and wherein the first forming distance and the second forming distance are different forming distances.

Example 21—The surgical stapling assembly of any one of Examples 18, 19, and 20, wherein the staple cartridge further comprises a plurality of first staple driver bodies configured to support the first staples, wherein a first forming distance is defined between the first staple driver bodies and the forming pockets of the first row of forming pockets, and a plurality of second staple driver bodies configured to support the second staples, wherein a second forming distance is defined between the second staple driver bodies and the forming pockets of the second row of forming pockets.

Example 22—The surgical stapling assembly of Example 21, wherein the first forming distance and the second forming distance are different forming distances.

Example 23—The surgical stapling assembly of any one of Examples 18, 19, 20, 21, and 22, wherein the staple cartridge further comprises a sled comprising a first rail configured to eject the first staples, wherein the first rail comprises a first rail drive height, and a second rail configured to eject the second staples, wherein the second rail comprises a second rail drive height, and wherein the first rail drive height defines a first forming distance of the first staples and the second rail drive height defines a second forming distance of the second staples.

Example 24—The surgical stapling assembly of Example 23, wherein the first forming distance and the second forming distance are different forming distances.

Example Set 2

Example 1—A surgical stapling assembly comprising a staple cartridge assembly and a firing member assembly. The staple cartridge assembly comprises a sled, a cartridge body comprising a plurality of staple cavities and a longitudinal slot, a longitudinal support beam positioned within the cartridge body, and a plurality of staples removably stored within the staple cavities. The firing member assembly is configured to move through the staple cartridge assembly, wherein the firing member assembly is configured to push the sled through a firing stroke to eject the staples from the cartridge body, and wherein the firing member assembly comprises a first firing member comprising a first camming flange positioned outside the cartridge body, and a second camming flange configured to apply a camming force to the longitudinal support beam. The firing member assembly further comprises a second firing member comprising a third camming flange positioned outside the cartridge body, and a fourth camming flange configured to apply a camming force to the longitudinal support beam.

Example 2—The surgical stapling assembly of Example 1, wherein the cartridge body comprises a first material, wherein the longitudinal support beam comprises a second material, and wherein the first material and the second material are different materials.

Example 3—The surgical stapling assembly of any one of Examples 1 and 2, wherein the longitudinal support beam comprises a cylindrical cavity configured to receive a firing drive shaft therethrough during the firing stroke.

Example 4—The surgical stapling assembly of Example 3, wherein the first firing member comprises a first cylindrical guide, wherein the second firing member comprises a second cylindrical guide, and wherein the first cylindrical guide and the second cylindrical guide are configured to longitudinally translate within the cylindrical cavity.

Example 5—The surgical stapling assembly of any one of Examples 1, 2, 3, and 4, wherein the longitudinal support beam is positioned between the first camming flange and the third camming flange.

Example 6—The surgical stapling assembly of any one of Examples 1, 2, 3, 4, and 5, wherein the first firing member is part of the staple cartridge assembly, wherein the staple cartridge assembly is replaceable, and wherein the first firing member comprises a hook couplable to the second firing member upon installation of the staple cartridge assembly in a cartridge channel.

Example 7—The surgical stapling assembly of any one of Examples 1, 2, 3, 4, 5, and 6, wherein the cartridge body further comprises lateral opposing walls and lateral support ledges extending from the laterally opposing walls, and wherein the lateral support ledges are configured to be received within corresponding lateral support slots defined in the longitudinal support beam.

Example 8—The surgical stapling assembly of any one of Examples 1, 2, 3, 4, 5, 6, and 7, wherein the second firing member is configured to push the first firing member.

Example 9—The surgical stapling assembly of any one of Examples 1, 2, 3, 4, 5, 6, 7, and 8, wherein the longitudinal support beam comprises a proximal hook and a distal hook configured to be engaged with a cartridge channel, and wherein the proximal hook and the distal hook are configured to longitudinally restrain the longitudinal support beam relative to the cartridge channel.

Example 10—The surgical stapling assembly of any one of Examples 1, 2, 3, 4, 5, 6, 7, 8, and 9, wherein the longitudinal support beam comprises a first camming channel defined therein and configured to receive the second camming flange, and a second camming channel defined therein and configured to receive the fourth camming flange.

Example 11—The surgical stapling assembly of any one of Examples 1, 2, 3, 4, 5, 6, 7, 8, 9, and 10, wherein the first firing member comprises a knife protruding out of the cartridge body.

Example 12—A replaceable staple cartridge configured to be installed into a surgical stapling assembly, wherein the replaceable staple cartridge comprises a cartridge body comprising an internal longitudinal support channel, a plurality of staples removably stored within the cartridge body, and an internal longitudinal support positioned within the internal longitudinal support channel. The internal longitudinal support comprises a first camming channel defining a first upper limit and a first lower limit, a second camming channel defining a second upper limit and a second lower limit, and a guide cavity configured to receive a corresponding guide portion of a firing member assembly.

Example 13—The replaceable staple cartridge of Example 12, wherein the internal longitudinal support is configured to transfer camming forces applied thereto to the cartridge body.

Example 14—The replaceable staple cartridge of any one of Examples 12 and 13, wherein the guide cavity is configured to receive a flexible firing drive shaft therethrough during a firing stroke.

Example 15—The replaceable staple cartridge of any one of Examples 12, 13, and 14, wherein the cartridge body further comprises a cartridge deck and a cartridge bottom, and wherein the internal longitudinal support is positioned between the cartridge deck and the cartridge bottom.

Example 16—The replaceable staple cartridge of any one of Examples 12, 13, 14, and 15, further comprising a firing member comprising a knife and a hook couplable to a reusable portion of the firing member assembly upon installation of the replaceable staple cartridge into the surgical stapling assembly.

Example 17—A replaceable staple cartridge configured to be installed into a cartridge channel of a surgical stapling assembly. The replaceable staple cartridge comprises a sled, a cutting member comprising a knife and a camming portion, and a cartridge body comprising a cartridge deck, a plurality of staple cavities defined in the cartridge deck, and a longitudinal support channel. The replaceable staple cartridge further comprises a plurality of staples removably stored within the staple cavities, and a metal support body positioned within the longitudinal support channel. The metal support body comprises a first longitudinal cam channel configured to receive the camming portion of the cutting member during a firing stroke, a second longitudinal cam channel substantially parallel to the first longitudinal cam channel, and a cylindrical guide cavity between the first longitudinal cam channel and the second longitudinal cam channel.

Example 18—The replaceable staple cartridge of Example 17, wherein the cylindrical guide cavity is configured to receive a flexible firing drive shaft therethrough during the firing stroke.

Example 19—The replaceable staple cartridge of any one of Examples 17 and 18, wherein the cartridge body further comprises longitudinally-extending support ledges extending laterally inward from opposing walls of the cartridge body, and wherein the support ledges are configured to be received within corresponding longitudinal support slots defined in the metal support body.

Example 20—The replaceable staple cartridge of any one of Examples 17, 18, and 19, wherein the cutting member further comprises a hook configured to releasable engage an instrument firing member in the surgical stapling assembly upon installation of the replaceable staple cartridge into the surgical stapling assembly.

Example Set 3

Example 1—A surgical stapling assembly comprising a first jaw, a second jaw movable relative to the first jaw, a firing screw, and a firing assembly configured to be actuated by the firing screw through a firing stroke. The firing assembly comprises a body portion and a nut. The body portion comprises a first cam configured to engage the first jaw during the firing stroke, a second cam configured to engage the second jaw during the firing stroke, a passage configured to non-threadably receive the firing screw, and a driven surface. The nut is configured to transmit a drive force from the firing screw to the body portion during the firing stroke. The nut comprises a driven portion comprising a passage threadably coupled to the firing screw, wherein a clearance is defined between the driven portion and the body portion, and a driving portion extending from the driven portion, wherein the driving portion is configured to transmit the drive force to the driven surface off center from the firing screw during the firing stroke.

Example 2—The surgical stapling assembly of Example 1, wherein the drive force is applied eccentrically with respect to a longitudinal axis defined by the firing screw.

Example 3—The surgical stapling assembly of any one of Examples 1 and 2, wherein the clearance comprises a first longitudinal space situated between a proximal end of the nut and the body portion, and wherein a second longitudinal space is situated between a distal end of the nut and the body portion.

Example 4—The surgical stapling assembly of any one of Examples 1, 2, and 3, wherein one of the first jaw and the second jaw is configured to receive a fastener cartridge comprising a plurality of fasteners.

Example 5—The surgical stapling assembly of any one of Examples 1, 2, 3, and 4, wherein the nut comprises a polymer material and the body portion comprises a metallic material.

Example 6—The surgical stapling assembly of any one of Examples 1, 2, 3, 4, and 5, wherein the nut is insert molded within the firing assembly.

Example 7—The surgical stapling assembly of any one of Examples 1, 2, 3, 4, 5, and 6, wherein the nut comprises an anti-rotation flange configured to prevent the nut from rotating with the firing screw, and wherein the anti-rotation flange is engaged with one of the first jaw and the second jaw.

Example 8—The surgical stapling assembly of any one of Examples 1, 2, 3, 4, 5, 6, and 7, wherein the driven portion comprises a metallic nut, wherein the driving portion comprises a polymer, and wherein the metallic nut is insert molded within the driving portion.

Example 9—The surgical stapling assembly of Example 8, wherein the metallic nut comprises securement features configured to secure the metallic nut relative to the driving portion.

Example 10—The surgical stapling assembly of any one of Examples 1, 2, 3, 4, 5, 6, 7, 8, and 9, wherein the nut comprises an internal cross brace extending between a first side of the nut and a second side of the nut.

Example 11—The surgical stapling assembly of Example 10, wherein the body portion of the firing assembly comprises a horizontally extending slot configured to receive the internal cross brace.

Example 12—A surgical stapling assembly comprising a first jaw, a second jaw movable relative to the first jaw, a drive screw defining a longitudinal axis, and a firing assembly configured to be actuated by the drive screw through a firing stroke. The firing assembly comprises a body portion and a nut. The body portion comprises a first cam configured to engage the first jaw during the firing stroke, a second cam configured to engage the second jaw during the firing stroke, a drive screw passage dimensioned to receive the drive screw, an engagement portion, and a receptacle, wherein the engagement portion extends into the receptacle. The nut is installed in the receptacle, wherein the nut comprises a driven portion threadably coupled to the drive screw, and a driving portion extending from the driven portion, wherein the driving portion comprises a brace mounted to the engagement portion, wherein the nut is configured to transfer a drive force to the body portion at the brace and off center from the drive screw as the nut is moved distally and proximally by the drive screw.

Example 13—The surgical stapling assembly of Example 12, wherein the firing assembly further comprises a clearance gap defined between the driven portion and the body portion, and wherein the engagement portion is positioned above the clearance gap.

Example 14—The surgical stapling assembly of any one of Examples 12 and 13, wherein the nut comprises a trapezoidal shape.

Example 15—The surgical stapling assembly of any one of Examples 12, 13, and 14, wherein the nut comprises a polymer material and the body portion comprises a metallic material.

Example 16—The surgical stapling assembly of any one of Examples 12, 13, 14, and 15, wherein the nut is insert molded within the firing assembly.

Example 17—The surgical stapling assembly of any one of Examples 12, 13, 14, 15, and 16, wherein the nut comprises an anti-rotation flange configured to prevent the nut from rotating with the drive screw.

Example 18—The surgical stapling assembly of any one of Examples 12, 13, 14, 15, 16, and 17, wherein the brace comprises a plurality of crossbars.

Example 19—A surgical end effector assembly comprising an anvil, a staple cartridge comprising a sled and a plurality of staples, a rotary drive screw, and a firing member assembly configured to be actuated by the rotary drive screw through a firing stroke to advance the sled through the staple cartridge along a longitudinal axis. The firing member assembly comprises a distal head and a nut. The distal head comprises a sled drive surface configured to push the sled distally within the staple cartridge, a drive member channel, wherein the rotary drive screw is positioned within the drive member channel, a first drive surface, and a cavity defined in the distal head along a cavity axis oriented transverse to the longitudinal axis, wherein the cavity comprises a second drive surface. The nut comprises a driven portion drivingly coupled to the rotary drive screw, and a driving portion extending from the driven portion. The driving portion comprises a first driving surface abutting the first drive surface, and a lateral cross member extending into the cavity, wherein the lateral cross member comprises a second driving surface abutting the second drive surface.

Example 20—The surgical end effector assembly of Example 19, wherein the nut is configured to apply an axial drive force to the distal head eccentrically with respect to the rotary drive screw.

Example 21—The surgical end effector assembly of any one of Examples 19 and 20, wherein the firing member assembly further comprises a clearance gap defined between the driven portion and the distal head, and wherein the first driven surface and the second driven surface are positioned above the clearance gap.

Example 22—The surgical end effector assembly of any one of Examples 19, 20, and 21, wherein the nut generally defines a trapezoidal shape.

Example 23—The surgical end effector assembly of any one of Examples 19, 20, 21, and 22, wherein the nut is insert molded within the firing member assembly.

Example 24—A surgical stapling assembly comprising a first jaw, a second jaw movable relative to the first jaw, a rotary drive member configured to rotate about a drive axis, and a firing assembly coupled to the rotary drive member. The firing assembly comprises a body portion comprising a first cam configured to engage the first jaw during a firing stroke, and a second cam configured to engage the second jaw during the firing stroke. The firing assembly further comprises a driven portion drivingly coupled to the rotary drive member, and a driving portion extending eccentrically from the driven portion, wherein the driving portion is configured to transfer a drive force from the rotary drive member to the body portion off axis with respect to the drive axis during the firing stroke.

Example Set 4

Example 1—A surgical stapling assembly comprising an anvil, a cartridge channel configured to receive a staple cartridge therein, and a firing assembly. The firing assembly comprises a firing member, a firing drive screw, wherein the firing member is threadably coupled to the firing drive screw, and wherein a rotation of the firing drive screw is configured to move the firing member longitudinally within the surgical stapling assembly, and a mount configured to support the firing drive screw within the cartridge channel, wherein the mount is configured to permit the firing drive screw to float within a limited vertical range of floatation relative to the cartridge channel.

Example 2—The surgical stapling assembly of Example 1, wherein the mount comprises an upper stop and a lower stop defining the limited vertical range of floatation of the firing drive screw between the upper stop and the lower stop.

Example 3—The surgical stapling assembly of any one of Examples 1 and 2, wherein the firing member comprises an upper flange configured to engage the anvil, and a lower flange configured to engage the cartridge channel, wherein the upper flange and the lower flange define the limited vertical range of floatation of the firing drive screw.

Example 4—The surgical stapling assembly of any one of Examples 1, 2, and 3, wherein the firing member comprises a drive nut cutout, and wherein the drive nut cutout defines the limited vertical range of floatation.

Example 5—The surgical stapling assembly of any one of Examples 1, 2, 3, and 4, wherein the cartridge channel comprises a proximal end portion and a distal end portion, wherein the firing drive screw is mounted within the cartridge channel at the proximal end portion and the distal end portion, and wherein the mount is positioned at the distal end portion.

Example 6—The surgical stapling assembly of Example 5, wherein the mount comprises a first mount, wherein the cartridge channel further comprises a second mount positioned at the proximal end portion, and wherein the second mount comprises a ball joint mount.

Example 7—The surgical stapling assembly of any one of Examples 1, 2, 3, 4, 5, and 6, further comprising a biasing member configured to bias the firing drive screw toward a neutral position within the mount.

Example 8—The surgical stapling assembly of any one of Examples 1, 2, 3, 4, 5, 6, and 7, wherein the mount comprises a recessed flange and a clip.

Example 9—The surgical stapling assembly of any one of Examples 1, 2, 3, 4, 5, 6, 7, and 8, wherein the firing drive screw comprises a proximal end and a distal end, and wherein the distal end is swaged.

Example 10—The surgical stapling assembly of any one of Examples 1, 2, 3, 4, 5, 6, 7, 8, and 9, further comprising the staple cartridge comprising a plurality of staples.

Example 11—The surgical stapling assembly of any one of Examples 1, 2, 3, 4, 5, 6, 7, 8, 9, and 10, wherein the limited vertical range of floatation comprises a range between about 0.0002 inches and about 0.0003 inches.

Example 12—The surgical stapling assembly of any one of Examples 1, 2, 3, 4, 5, 6, 7, 8, 9, 10, and 11, wherein the limited vertical range of floatation comprises a range of about 0.0001 inches.

Example 13—A surgical end effector assembly comprising a first jaw, a second jaw movable relative to the first jaw, an anvil, a cartridge channel configured to receive a staple cartridge therein, wherein the cartridge channel comprises a drive member support, and a firing assembly. The firing assembly comprises a firing member comprising an upper flange configured to engage the anvil, and a lower flange configured to engage the cartridge channel. The firing assembly further comprises a rotary drive screw, wherein the firing member is threadably coupled to the rotary drive screw such that a rotation of the rotary drive screw is configured to move the firing member within the surgical end effector assembly through a firing stroke, and wherein the drive member support is configured to support the rotary drive screw and permit the rotary drive screw to float vertically relative to the drive member support as the firing member is advanced through the firing stroke.

Example 14—The surgical end effector assembly of Example 13, wherein the drive member support comprises an upper stop and a lower stop defining a limited vertical range of floatation of the rotary drive screw between the upper stop and the lower stop.

Example 15—The surgical end effector assembly of any one of Examples 13 and 14, wherein the upper flange and the lower flange define a limited vertical range of floatation.

Example 16—The surgical end effector assembly of any one of Examples 13, 14, and 15, wherein the cartridge channel comprises a proximal end portion and a distal end portion, wherein the rotary drive screw is supported by the cartridge channel at the proximal end portion and the distal end portion, and wherein the drive member support is positioned at the distal end portion.

Example 17—The surgical end effector assembly of Example 16, wherein the drive member support comprises a first drive member support, wherein the surgical end effector assembly further comprises a second drive member support positioned at the proximal end portion, wherein the rotary drive screw comprises a proximal mount end, and wherein the proximal mount end comprises a ball joint portion mounted within the second drive member support.

Example 18—The surgical end effector assembly of any one of Examples 13, 14, 15, 16, and 17, further comprising a biasing member configured to bias the rotary drive screw toward a neutral position within the drive member support.

Example 19—The surgical end effector assembly of any one of Examples 13, 14, 15, 16, 17, and 18, wherein the drive member support comprises a recessed flange and a clip.

Example 20—The surgical end effector assembly of any one of Examples 13, 14, 15, 16, 17, 18, and 19, further comprising the staple cartridge comprising a plurality of staples.

Example 21—A surgical stapling assembly comprising a shaft and an end effector. The end effector comprises a first jaw, a second jaw movable relative to the first jaw, an anvil, a cartridge channel, and a firing assembly. The firing assembly comprises a firing drive screw and a firing member comprising a drive nut threadably coupled to the firing drive screw, wherein a rotary actuation of the firing drive screw is configured to move the firing member longitudinally within the end effector through a firing stroke, and wherein the drive nut is configured to float relative to the firing member during the firing stroke.

Example 22—The surgical stapling assembly of Example 21, wherein the drive nut is configured to float relative to the firing member laterally and vertically with respect to the firing stroke.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The Entire Disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent application Publication No. 2014/0263552;

U.S. Patent application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by a cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical stapling assembly, comprising:
   a staple cartridge assembly, comprising:
      a sled;
      a cartridge body, comprising:
         a plurality of staple cavities; and
         a longitudinal slot;
      a longitudinal support beam positioned within said cartridge body; and
      a plurality of staples removably stored within said staple cavities; and
   a firing member assembly configured to move through said staple cartridge assembly, wherein said firing member assembly is configured to push said sled through a firing stroke to eject said staples from said cartridge body, and wherein said firing member assembly comprises:
      a first firing member, comprising:
         a first camming flange positioned outside said cartridge body; and
         a second camming flange configured to apply a camming force to said longitudinal support beam; and
      a second firing member, comprising:
         a third camming flange positioned outside said cartridge body; and
         a fourth camming flange configured to apply a camming force to said longitudinal support beam.

2. The surgical stapling assembly of claim 1, wherein said cartridge body comprises a first material, wherein said longitudinal support beam comprises a second material, and wherein said first material and said second material are different materials.

3. The surgical stapling assembly of claim 1, wherein said longitudinal support beam comprises a cylindrical cavity configured to receive a firing drive shaft therethrough during the firing stroke.

4. The surgical stapling assembly of claim 3, wherein said first firing member comprises a first cylindrical guide, wherein said second firing member comprises a second cylindrical guide, and wherein said first cylindrical guide and said second cylindrical guide are configured to longitudinally translate within said cylindrical cavity.

5. The surgical stapling assembly of claim 1, wherein said longitudinal support beam is positioned between said first camming flange and said third camming flange.

6. The surgical stapling assembly of claim 1, wherein said first firing member is part of said staple cartridge assembly, wherein said staple cartridge assembly is replaceable, and wherein said first firing member comprises a hook couplable to said second firing member upon installation of said staple cartridge assembly in a cartridge channel.

7. The surgical stapling assembly of claim 1, wherein said cartridge body further comprises lateral opposing walls and lateral support ledges extending from said laterally opposing walls, and wherein said lateral support ledges are configured to be received within corresponding lateral support slots defined in said longitudinal support beam.

8. The surgical stapling assembly of claim 1, wherein said second firing member is configured to push said first firing member.

9. The surgical stapling assembly of claim 1, wherein said longitudinal support beam comprises a proximal hook and a distal hook configured to be engaged with a cartridge channel, and wherein said proximal hook and said distal hook are configured to longitudinally restrain said longitudinal support beam relative to the cartridge channel.

10. The surgical stapling assembly of claim 1, wherein said longitudinal support beam comprises:
   a first camming channel defined therein and configured to receive said second camming flange; and
   a second camming channel defined therein and configured to receive said fourth camming flange.

11. The surgical stapling assembly of claim 10, wherein said first firing member comprises a knife protruding out of the cartridge body.

12. The surgical stapling assembly of claim 1, wherein said longitudinal support beam comprises a protrusion, wherein said cartridge body comprises a cartridge deck, wherein a slot is defined in said cartridge deck, and wherein said slot is configured to receive said protrusion.

13. A replaceable staple cartridge configured to be installed into a surgical stapling assembly, wherein the replaceable staple cartridge comprises:
   a cartridge body comprising an internal longitudinal support channel;
   a plurality of staples removably stored within said cartridge body; and
   an internal longitudinal support positioned within said internal longitudinal support channel, wherein said internal longitudinal support comprises:
      a first camming channel defining a first upper limit and a first lower limit;
      a second camming channel defining a second upper limit and a second lower limit; and
      a guide cavity configured to receive a corresponding guide portion of a firing member assembly.

14. The replaceable staple cartridge of claim 13, wherein said internal longitudinal support is configured to transfer camming forces applied thereto to said cartridge body.

15. The replaceable staple cartridge of claim 13, wherein said guide cavity is configured to receive a flexible firing drive shaft therethrough during a firing stroke.

16. The replaceable staple cartridge of claim 13, wherein said cartridge body further comprises a cartridge deck and a cartridge bottom, and wherein said internal longitudinal support is positioned between said cartridge deck and said cartridge bottom.

17. The replaceable staple cartridge of claim 13, further comprising a firing member, comprising:
   a knife; and
   a hook couplable to a reusable portion of the firing member assembly upon installation of said replaceable staple cartridge into the surgical stapling assembly.

18. The replaceable staple cartridge of claim 13, wherein said internal longitudinal support comprises a protrusion, wherein said cartridge body comprises a cartridge deck, wherein a slot is defined in said cartridge deck, and wherein said slot is configured to receive said protrusion.

19. The replaceable staple cartridge of claim 13, wherein said cartridge body comprises a first material, wherein said internal longitudinal support comprises a second material, and wherein said first material and said second material are different materials.

20. The replaceable staple cartridge of claim 13, wherein said internal longitudinal support channel comprises a ledge, and wherein said internal longitudinal support defines a slot configured to receive said ledge.

21. The replaceable staple cartridge of claim 13, wherein said internal longitudinal support comprises a proximal hook and a distal hook configured to be engaged with a cartridge channel, and wherein said proximal hook and said distal hook are configured to longitudinally restrain said internal longitudinal support relative to the cartridge channel.

22. A replaceable staple cartridge configured to be installed into a cartridge channel of a surgical stapling assembly, wherein the replaceable staple cartridge comprises:
   a sled;
   a cutting member comprising a knife and a camming portion;
   a cartridge body, comprising:
      a cartridge deck;
      a plurality of staple cavities defined in said cartridge deck; and
      a longitudinal support channel;
   a plurality of staples removably stored within said staple cavities; and
   a metal support body positioned within said longitudinal support channel, wherein said metal support body comprises:
      a first longitudinal cam channel configured to receive the camming portion of the cutting member during a firing stroke;
      a second longitudinal cam channel substantially parallel to the first longitudinal cam channel; and
      a cylindrical guide cavity between the first longitudinal cam channel and the second longitudinal cam channel.

23. The replaceable staple cartridge of claim 22, wherein said cylindrical guide cavity is configured to receive a flexible firing drive shaft therethrough during the firing stroke.

24. The replaceable staple cartridge of claim 22, wherein said cartridge body further comprises longitudinally-extending support ledges extending laterally inward from opposing walls of said cartridge body, and wherein said support ledges are configured to be received within corresponding longitudinal support slots defined in said metal support body.

25. The replaceable staple cartridge of claim 22, wherein said cutting member further comprises a hook configured to releasable engage an instrument firing member in the surgical stapling assembly upon installation of the replaceable staple cartridge into the surgical stapling assembly.

26. The replaceable staple cartridge of claim 22, wherein said metal support body comprises a protrusion, wherein a slot is defined in said cartridge deck, and wherein said slot is configured to receive said protrusion.

27. The replaceable staple cartridge of claim 22, wherein said metal support body comprises a proximal hook and a distal hook configured to be engaged with the cartridge channel, and wherein said proximal hook and said distal hook are configured to longitudinally restrain said metal support body relative to the cartridge channel.

28. A staple cartridge configured to be installed into a cartridge channel of a surgical stapling instrument, wherein the surgical stapling instrument comprises a first firing member comprising a first flange, wherein the first firing member is configured to move through the staple cartridge during a firing stroke, wherein the staple cartridge comprises:

a cartridge body, defining:
  a support channel; and
  a staple cavity;
a staple removably stored in said staple cavity;
a second firing member comprising a second flange; and
a support beam positioned in said support channel, wherein said support beam defines:
  a first slot configured to receive the first flange during the firing stroke; and
  a second slot configured to receive said second flange during the firing stroke.

29. The staple cartridge of claim 28, wherein said second firing member comprises a third flange, wherein said third flange translates outside said support beam during the firing stroke.

30. The staple cartridge of claim 28, wherein said support beam comprises a protrusion, and wherein said cartridge body further defines a slot configured to receive said protrusion.

31. The staple cartridge of claim 28, wherein said cartridge body comprises a first material, wherein said support beam comprises a second material, and wherein said first material and said second material are different materials.

32. The staple cartridge of claim 28, wherein said support channel comprises a ledge, and wherein said support beam defines a slot configured to receive said ledge.

33. The staple cartridge of claim 28, wherein said support beam comprises a proximal hook and a distal hook configured to be engaged with the cartridge channel, and wherein said proximal hook and said distal hook are configured to longitudinally restrain said support beam relative to the cartridge channel.

34. The staple cartridge of claim 28, wherein:
  said support beam defines a cylindrical cavity;
  the first firing member comprises a first cylindrical guide;
  said second firing member comprises a second cylindrical guide; and
  said first cylindrical guide and said second cylindrical guide are configured to longitudinally translate within said cylindrical cavity during the firing stroke.

35. The staple cartridge of claim 28, wherein said second firing member comprises a hook, and wherein the first firing member comprises a slot configured to receive said hook upon installation of said staple cartridge in the cartridge channel.

36. The staple cartridge of claim 28, wherein said second firing member comprises a knife.

* * * * *